US010842853B2

(12) United States Patent
Horling et al.

(10) Patent No.: US 10,842,853 B2
(45) Date of Patent: Nov. 24, 2020

(54) VIRAL VECTORS ENCODING RECOMBINANT FIX WITH INCREASED EXPRESSION FOR GENE THERAPY OF HEMOPHILIA B

(71) Applicants: Baxalta Incorporated, Bannockburn, IL (US); Baxalta GmbH, Glattpark (CH)

(72) Inventors: Franziska Horling, Gaenserndorf (AT); Johannes Lengler, Vienna (AT); Falko-Gunter Falkner, Orth/Donau (AT); Hanspeter Rottensteiner, Vienna (AT); Friedrich Scheiflinger, Vienna (AT)

(73) Assignees: Baxalta Incorporated, Bannockburn, IL (US); Baxalta GmbH

( * ) Notice: Subject to any disclaimer, the term of this patent is extended or adjusted under 35 U.S.C. 154(b) by 0 days.

(21) Appl. No.: 15/986,350

(22) Filed: May 22, 2018

(65) Prior Publication Data

US 2018/0339026 A1 Nov. 29, 2018

Related U.S. Application Data

(60) Provisional application No. 62/509,616, filed on May 22, 2017.

(51) Int. Cl.

| | | |
|---|---|---|
| C07H 21/04 | (2006.01) |
| C12N 15/86 | (2006.01) |
| A61K 38/48 | (2006.01) |
| A61K 48/00 | (2006.01) |
| C07K 14/745 | (2006.01) |
| A61P 7/04 | (2006.01) |
| A61K 31/7088 | (2006.01) |
| A61K 35/76 | (2015.01) |
| C07K 14/005 | (2006.01) |
| C12N 15/62 | (2006.01) |
| C12N 15/85 | (2006.01) |

(52) U.S. Cl.
CPC ...... *A61K 38/4846* (2013.01); *A61K 31/7088* (2013.01); *A61K 35/76* (2013.01); *A61K 48/0058* (2013.01); *A61K 48/0066* (2013.01); *A61P 7/04* (2018.01); *C07K 14/005* (2013.01); *C07K 14/745* (2013.01); *C12N 15/62* (2013.01); *C12N 15/85* (2013.01); *C12N 15/86* (2013.01); *C12N 2750/14143* (2013.01); *C12N 2800/22* (2013.01); *C12N 2830/008* (2013.01); *C12N 2830/42* (2013.01)

(58) Field of Classification Search
CPC ............... A61K 38/4846; C12N 15/86; C12N 15/8645; C12N 2750/14143; C12N 2800/22; C07H 21/04
USPC .............................. 435/320.1; 536/23.5, 24.1
See application file for complete search history.

(56) References Cited

U.S. PATENT DOCUMENTS

| | | |
|---|---|---|
| 4,797,368 A | 1/1989 | Carter et al. |
| 5,139,941 A | 8/1992 | Muzyczka et al. |
| 5,786,464 A | 7/1998 | Seed |
| 5,866,552 A | 2/1999 | Wilson et al. |
| 5,935,935 A | 8/1999 | Connelly et al. |
| 6,093,392 A | 7/2000 | High et al. |
| 6,114,148 A | 9/2000 | Seed et al. |
| 6,238,914 B1 | 5/2001 | Boyce |
| 6,391,858 B2 | 5/2002 | Podsakoff et al. |
| 6,531,298 B2 | 3/2003 | Stafford et al. |
| 6,670,176 B1 | 12/2003 | Samulski et al. |
| 6,924,365 B1 | 8/2005 | Miller et al. |
| 7,943,374 B2 | 5/2011 | Hildinger |
| 8,778,870 B2 | 7/2014 | Madison et al. |
| 9,249,405 B2 | 2/2016 | Simioni |
| 2016/0201088 A1 | 7/2016 | Gao et al. |

FOREIGN PATENT DOCUMENTS

| | | |
|---|---|---|
| EP | 1 316 319 A1 | 6/2003 |
| EP | 2 438 931 A1 | 4/2012 |
| WO | WO 00/074688 A1 | 12/2000 |
| WO | WO 03/052051 A2 | 6/2003 |
| WO | WO 2006/036502 A2 | 4/2006 |
| WO | WO 2009/130208 A1 | 10/2009 |
| WO | WO 2010/029178 A1 | 3/2010 |
| WO | WO 2013/078400 A1 | 5/2013 |
| WO | WO 2013/123503 A1 | 8/2013 |
| WO | WO 2014/063753 A1 | 5/2014 |
| WO | WO 2014/064277 A1 | 5/2014 |
| WO | WO 2016/146757 A1 | 9/2016 |
| WO | WO 2016/210170 A1 | 12/2016 |

OTHER PUBLICATIONS

Asokan, A, et al., "The AAV Vector Toolkit: Poised at the Clinical Crossroads." *Mol. Ther.*, 20(4):699-708 (2012).
Chuah, M.K. et al., "Liver-Specific Transcriptional Modules Identified by Genome-Wide in Silico Analysis Enable Efficient Gene Therapy in Mice and Non-Human Primates" *Mol Ther.*, 22(9):1605-13 (2014).
Chuah, M.K., et al., "Gene therapy for hemophilia." *J Thromb Haemost.*, 11 Suppl 1:99-110 (2013).
Chuah, M.K., et al., "Platelet-directed gene therapy overcomes inhibitory antibodies to factor VIII." *J Thromb Haemost.*, 10(8):1566-69 (2012).
Chuah, M.K. et al., "Recent progress in gene therapy for hemophilia." *Hum Gene Ther.*, 23(6):557-65 (2012).

(Continued)

*Primary Examiner* — Shin Lin Chen
(74) *Attorney, Agent, or Firm* — Morgan, Lewis & Bockius LLP

(57) ABSTRACT

Codon-altered polynucleotides encoding Factor IX variants for expression in mammalian cells are provided, including sequences with high nucleotide sequence identity to the CS02, CS03, CS04, CS05, and CS06 sequences. Mammalian gene therapy vectors, such as adeno-associated viral vectors, and methods for treating hemophilia B using those vectors are also provided.

25 Claims, 23 Drawing Sheets

Specification includes a Sequence Listing.

(56) References Cited

OTHER PUBLICATIONS

Cotton, M. et al., "High-efficiency receptor-mediated delivery of small and large (48 kilobase gene constructs using the endosome-disruption activity of defective or chemically inactivated adenovirus particles." *PNAS USA*, 89(13):6094-6098 (1992).
Curiel, D.T., "High-efficiency gene transfer employing adenovirus-polylysine-DNA complexes." *Nat Immun*, 13(2-3):141-64 (1994).
Fath, S., et al., "Multiparameter RNA and Codon Optimization: A Standardized Tool to Assess and Enhance Autologous Mammalian Gene Expression." *PLoS. One*, 6, e17596, pp. 1-14, (2011).
Faust, S.M. et al., "CpG-depleted adeno-associated virus vectors evade immune detection" *J. Clin. Invest.* 2013; 123, 2994-3001.
Gardiner-Garden M. et al., "CpG Islands in vertebrate genomes" *J Mol Biol.*, 196(2):261-82 (1987).
GenBank NM_000133.3 "*Homo sapiens* coagulation factor IX (F9), transcript variant 1, mRNA," 2008, 7 pages.
Giangrande, P., "The Future of Hemophilia Treatment: Longer-Acting Factor Concentrates versus Gene Therapy," *Semin Thromb Hemost.* 42(5):513-17 (2016).
Gray, S.J. et al., "Optimizing Promoters for Recombinant Adeno-Associated Virus-Mediated Gene Expression in the Peripheral and Central Nervous System Using Self-Complementary Vectors" *Human Gene Therapy* 22:1143-53 (2011).
Grote, A. et al., "JCat: a novel tool to adapt codon usage of a target gene to its potential expression host." *Nucleic Acids Research*, 33 (Web Server issue), W526-W531 (2005).
Haas, J. et al., "Codon usage limitation in the expression of HIV-1 envelope Glycoprotein." *Curr. Biol.*, 6, 315-324 (1996).
Haut, D.D. et al., "Intron Definition Is Required for Excision of the Minute Virus of Mice Small Intron and Definition of the Upstream Exon" *J Virol* 72(3):1834-43 (1998).
Herzog, R.W. et al., "Adeno-associated virus-mediated gene transfer of factor IX for treatment of hemophilia B by gene therapy." *Thromb Haemost* Aug. 1999; 82(2):540-6.
High, K.A., "The gene therapy journey for hemophilia: are we there yet?" *Blood*, 120(23):4482-87 (2012).
Hsieh, J-L. et al., "Transthyretin-driven oncolytic adenovirus suppresses tumor growth in orthotopic and ascites models of hepatocellular carcinoma." *Cancer Sci.*, 100(3):537-45 (2009).
International Search Report and Written Opinion for International Application No. PCT/US2018/033866, 14 pages.
Kay, M. et al., "Evidence for gene transfer and expression of factor IX in haemophilia B patients treated with an AAV vector." *Nat Genet.* 24(3):257-61 (2000).
Kelleher, Z.T. et al., "Long-term episomal gene delivery in human lymphoid cells using human and avian adenoviral-assisted transfection." *Biotechniques*, 17(6):1110-17 (1994).
Kotin, R.M., "Large-scale recombinant adeno-associated virus production." *Hum. Mol. Genet.*, 20(R1):R2-6 (2011).
Kudla, G. et al., "High Guanine and Cytosine Content Increases mRNA Levels in Mammalian Cells" *PLoS Biol.*, 4(6):80 (2006).
Manno, C.S., et al., "Successful transduction of liver in hemophilia by AAV-Factor IX and limitation imposed by the host immune response," *Nat Med.*, 12(3):342-47 (2006).
Mátrai, J. et al., "Preclinical and clinical progress in hemophilia gene therapy." *Curr Opin Hematol.*, 17(5):387-92 (2010).
Mátrai, J. et al., "Recent Advances in Lentiviral Vector Development and Applications." *Mol Ther.*, 18(3):477-90 (2010).
McCarty, D., "Self-complementary AAV Vectors; Advances and Applications." *Mol. Ther.*, (16):1648-56 (2008).
Mingozzi, F. et al., "CD8(+) T-cell responses to adeno-associated virus capsid in humans." *Nat Med.* 13(4):419-22 (2007).
Mirsafian, H. et al., "A Comparative Analysis of Synonymous Codon Usage Bias Pattern in Human Albumin Superfamily." *Scientific World Journal*, 639682, pp. 1-7, (2014).
Monahan, P.E. et al., "Employing a Gain-of-Function Factor IX Variant R338L to Advance the Efficacy and Safety of Hemophilia B Human Gene Therapy: Preclinical Evaluation Supporting an Ongoing Adeno-Associated Virus Clinical Trial" *Hum Gene Ther.*, 26(2):69-81 (2015).
Muzyczka, N., "Use of adeno-associated virus as a general transduction vector for mammalian cells." *Curr Top Microbiol Immunol*, 158:97-129 (1992).
Nair, N. et al., "Computationally designed liver-specific transcriptional modules and hyperactive factor IX improve hepatic gene therapy." *Blood*, 123:3195-99 (2014).
Pechmann, S., et al., "Evolutionary conservation of codon optimality reveals hidden signatures of co-translational folding." *Nat Struct Mol Biol.*, 20(2):237-43 (2013).
Schuettrumpf, J. et al., "Factor IX variants improve gene therapy efficacy for hemophilia B" *Blood*, 105(6):2316-23 (2005).
Sichler, K. et al., "Physiological fIXa Activation Involves a Cooperative Conformational Rearrangement of the 99-Loop" *J Biol Chem.* 278(6):4121-26 (2003).
Simioni, P. et al., "X-Linked Thrombophilia with a Mutant Factor IX (Factor IX Padua)" *N Engl J Med.* 361(17):1671-1675 (2009).
Tats, A. et al., "Preferred and avoided codon pairs in three domains of life." *BMC Genomics*, 9:463, pp. 1-15, (2008).
Uhlén, M. et al., "Proteomics. Tissue-based map of the human proteome." *Science*, 347:6220, 11 pages (2015).
Vandendriessche, T. et al., "Clinical progress in gene therapy: sustained partial correction of the bleeding disorder in patients suffering from severe hemophilia B." *Hum Gene Ther.*, 23(1):4-6 (2012).
Wu, Z. et al., "Optimization of Self-complementary AAV Vectors for Liver-directed Expression Results in Sustained Correction of Hemophilia B at Low Vector Dose" *Mol Ther.*, 16(2):280-9 (2008).

FIX-FL-NA

```
ATGCAGCGCGTGAACATGATCATGGCAGAATCACCAGGCCTCATCACCATCTGCCTTTTAGGATATC
TACTCAGTGCTGAATGTACAGTTTTTCTTGATCATGAAAACGCCAACAAAATTCTGAATCGGCCAAA
GAGGTATAATTCAGGTAAATTGGAAGAGTTTGTTCAAGGGAACCTTGAGAGAGAATGTATGGAAGAA
AAGTGTAGTTTTGAAGAAGCACGAGAAGTTTTTGAAAACACTGAAAGAACAACTGAATTTTGGAAGC
AGTATGTTGATGGAGATCAGTGTGAGTCCAATCCATGTTTAAATGGCGGCAGTTGCAAGGATGACAT
TAATTCCTATGAATGTTGGTGTCCCTTTGGATTTGAAGGAAAGAACTGTGAATTAGATGTAACATGT
AACATTAAGAATGGCAGATGCGAGCAGTTTTGTAAAAATAGTGCTGATAACAAGGTGGTTTGCTCCT
GTACTGAGGGATATCGACTTGCAGAAAACCAGAAGTCCTGTGAACCAGCAGTGCCATTTCCATGTGG
AAGAGTTTCTGTTTCACAAACTTCTAAGCTCACCCGTGCTGAGACTGTTTTTCCTGATGTGGACTAT
GTAAATTCTACTGAAGCTGAAACCATTTTGGATAACATCACTCAAAGCACCCAATCATTTAATGACT
TCACTCGGGTTGTTGGTGGAGAAGATGCCAAACCAGGTCAATTCCCTTGGCAGGTTGTTTTGAATGG
TAAAGTTGATGCATTCTGTGGAGGCTCTATCGTTAATGAAAAATGGATTGTAACTGCTGCCCACTGT
GTTGAAACTGGTGTTAAAATTACAGTTGTCGCAGGTGAACATAATATTGAGGAGACAGAACATACAG
AGCAAAAGCGAAATGTGATTCGAATTATTCCTCACCACAACTACAATGCAGCTATTAATAAGTACAA
CCATGACATTGCCCTTCTGGAACTGGACGAACCCTTAGTGCTAAACAGCTACGTTACACCTATTTGC
ATTGCTGACAAGGAATACACGAACATCTTCCTCAAATTTGGATCTGGCTATGTAAGTGGCTGGGGAA
GAGTCTTCCACAAAGGGAGATCAGCTTTAGTTCTTCAGTACCTTAGAGTTCCACTTGTTGACCGAGC
CACATGTCTTCGATCTACAAAGTTCACCATCTATAACAACATGTTCTGTGCTGGCTTCCATGAAGGA
GGTAGAGATTCATGTCAAGGAGATAGTGGGGGACCCCATGTTACTGAAGTGGAAGGGACCAGTTTCT
TAACTGGAATTATTAGCTGGGGTGAAGAGTGTGCAATGAAAGGCAAATATGGAATATATACCAAGGT
ATCCCGGTATGTCAACTGGATTAAGGAAAAAACAAAGCTCACTTAA   (SEQ ID NO:1)
```

Figure 2

FIX-FL-AA

```
MQRVNMIMAE SPGLITICLL GYLLSAECTV FLDHENANKI LNRPKRYNSG
KLEEFVQGNL ERECMEEKCS FEEAREVFEN TERTTEFWKQ YVDGDQCESN
PCLNGGSCKD DINSYECWCP FGFEGKNCEL DVTCNIKNGR CEQFCKNSAD
NKVVCSCTEG YRLAENQKSC EPAVPFPCGR VSVSQTSKLT RAETVFPDVD
YVNSTEAETI LDNITQSTQS FNDFTRVVGG EDAKPGQFPW QVVLNGKVDA
FCGGSIVNEK WIVTAAHCVE TGVKITVVAG EHNIEETEHT EQKRNVIRII
PHHNYNAAIN KYNHDIALLE LDEPLVLNSY VTPICIADKE YTNIFLKFGS
GYVSGWGRVF HKGRSALVLQ YLRVPLVDRA TCLRSTKFTI YNNMFCAGFH
EGGRDSCQGD SGGPHVTEVE GTSFLTGIIS WGEECAMKGK YGIYTKVSRY
VNWIKEKTKL T   (SEQ ID NO:2)
```

Figure 3A

FIX2-FL-AA

```
mqrvnmimae spgliticll gyllsaectv fldhenanki lnrpkrynsg kleefvqgnl
erecmeekcs feearevfen terttefwkq yvdvtcnikn grceqfckns adnkvvcsct
egyrlaenqk scepavpfpc grvsvsqtsk ltraetvfpd vdyvnsteae tildnitqst
qsfndftrvv ggedakpgqf pwqvvlngkv dafcggsivn ekwivtaahc vetgvkitvv
agehnieete hteqkrnvir iiphhnynaa inkynhdial leldeplvln syvtpiciad
keytniflkf gsgyvsgwgr vfhkgrsalv lqylrvplvd ratclrstkf tiynnmfcag
fheggrdscq gdsggphvte vegtsfltgi iswgeecamk gkygiytkvs ryvnwikekt
klt   (SEQ ID NO:3)
```

Figure 3B

FIXp-FL-AA

MQRVNMIMAE SPGLITICLL GYLLSAECTV FLDHENANKI LNRPKRYNSG
KLEEFVQGNL ERECMEEKCS FEEAREVFEN TERTTEFWKQ YVDGDQCESN
PCLNGGSCKD DINSYECWCP FGFEGKNCEL DVTCNIKNGR CEQFCKNSAD
NKVVCSCTEG YRLAENQKSC EPAVPFPCGR VSVSQTSKLT RAETVFPDVD
YVNSTEAETI LDNITQSTQS FNDFTRVVGG EDAKPGQFPW QVVLNGKVDA
FCGGSIVNEK WIVTAAHCVE TGVKITVVAG EHNIEETEHT EQKRNVIRII
PHHNYNAAIN KYNHDIALLE LDEPLVLNSY VTPICIADKE YTNIFLKFGS
GYVSGWGRVF HKGRSALVLQ YLRVPLVDRA TCLLSTKFTI YNNMFCAGFH
EGGRDSCQGD SGGPHVTEVE GTSFLTGIIS WGEECAMKGK YGIYTKVSRY
VNWIKEKTKL T   (SEQ ID NO:4)

Figure 4

CS02-FL-NA atgcagagggtgaacatgatcatggctgagagccctggcctgatcaccatctgcctgctgggctac
ctgctgtcagcagagtgcacagtgttcctggaccatgagaatgccaacaagatcctgaacaggccc
aagagatacaactcaggcaagctggaggagtttgtgcagggcaacctggagagggagtgcatggag
gagaagtgcagctttgaggaggccagagaggtgtttgagaacacagagaggaccacagagttctgg
aagcagtatgtggatggagaccagtgtgagagcaaccccttgcctgaatggaggcagctgcaaggat
gacatcaacagctatgagtgctggtgccctttggctttgagggcaagaactgtgagctggatgtg
acctgcaacatcaagaatggcaggtgtgagcagttctgcaagaactcagctgacaacaaagtggtg
tgtagctgcacagagggctacagactggctgagaaccagaagagctgtgagcctgctgtgcccttc
ccctgtggcagagtgtcagtgtcccagaccagcaagctgaccagagctgagacagtgttccctgat
gtggactatgtgaatagcacagaggctgagaccatcctggacaacatcacccagagcacccagtcc
ttcaatgacttcaccagagttgtgggaggagaggatgccaagcctggccagttcccctggcaggtg
gtgctgaatggcaaagtggatgccttctgtggaggcagcattgtgaatgagaagtggattgtgaca
gctgcccactgtgtggagacaggagtgaagatcacagtggtggctggagaacacaatattgaggag
acagagcacacagagcagaagaggaatgtcatcaggattatcccccaccacaactacaatgctgcc
atcaacaagtacaaccatgacattgccctgctggagctggatgagcctctggtgctgaatagctat
gtgaccccatctgcattgctgacaaggagtacaccaacatcttcctgaagtttggctcaggctat
gtgtcaggctggggcagagtgttccacaagggcagatcagccctggtgctgcagtacctgagagtg
cccctggtggacagagccacctgcctgttgagcaccaagttcaccatctacaacaacatgttctgt
gctggcttccatgagggaggcagagacagctgccagggagactcaggaggacccccatgtgacagaa
gtggagggcaccagcttcctgacaggcatcatcagctggggagaggagtgtgccatgaagggcaag
tatggcatctacaccaaagtgagcagatatgtgaactggatcaaggagaaaaccaagctgacctga
(SEQ ID NO:5)

```
atgcagagggtgaacatgatcatggctgagagccctggcctgatcaccatctgcctgctgggctac
ctgctgtctgctgagtgcactgtgttcctggaccatgagaatgccaacaagatcctgaacaggccc
aagagatacaactctggcaagctggaggagtttgtgcagggcaacctggagagggagtgcatggag
gagaagtgcagctttgaggaggccagggaagtgtttgagaacactgagaggaccactgagttctgg
aagcagtatgtggatggggaccagtgtgagagcaaccctgcctgaatgggggcagctgcaaggat
gacatcaacagctatgagtgctggtgccccttttggctttgagggcaagaactgtgagctggatgtg
acctgcaacatcaagaatggcaggtgtgagcagttctgcaagaactctgctgacaacaaagtggtg
tgtagctgcactgagggctacagactggctgagaaccagaagagctgtgagcctgctgtgcccttc
ccctgtggcagagtgtctgtgtcccagaccagcaagctgaccagagctgagactgtgttccctgat
gtggactatgtgaatagcactgaggctgagaccatcctggacaacatcacccagagcacccagtcc
ttcaatgacttcaccagagtggtggggggggaggatgccaagcctggccagttcccctggcaggtg
gtgctgaatggcaaagtggatgccttctgtggggcagcattgtgaatgagaagtggattgtgact
gctgcccactgtgtggagactggggtgaagatcactgtggtggctggggaacacaatattgaggag
actgagcacactgagcagaagaggaatgtcatcaggattatcccccaccacaactacaatgctgcc
atcaacaagtacaaccatgacattgccctgctggagctggatgagcctctggtgctgaatagctat
gtgacccccatctgcattgctgacaaggagtacaccaacatcttcctgaagtttggctctggctat
gtgtctggctggggcagagtgttccacaagggcaggtctgccctggtgctgcagtacctgagagtg
cccctggtggacagagccacctgcctgctgagcaccaagttcaccatctacaacaacatgttctgt
gctggcttccatgagggggcagagacagctgccaggggactctggggcccccatgtgactgaa
gtggaGggcaccagcttcctgactggcatcatcagctgggggaggagtgtgccatgaagggcaag
tatggcatctacaccaaagtgagcaggtatgtgaactggatcaaggagaaaaccaagctgacctga
(SEQ ID NO:6)
```

Figure 6

CS04-FL-NA atgcagagggtgaacatgattatggctgagagccctggcctgatcaccatctgcctgctgggctac
ctgctgtctgctgagtgcacagtgttcctggaccatgagaatgccaacaagatcctgaacaggccc
aagagatacaactctggcaagctggaggagtttgtgcagggcaacctggagagggagtgcatggag
gagaagtgcagctttgaggaggccagggaggtgtttgagaacacagagaggaccacagagttctgg
aagcagtatgtggatggtgaccagtgtgagagcaacccttgcctgaatggaggcagctgcaaggat
gacatcaacagctatgagtgctggtgccttttggctttgagggcaagaactgtgagctggatgtg
acctgcaacatcaagaatggcaggtgtgagcagttctgcaagaactctgctgacaacaaggtggtg
tgtagctgcacagagggctacagactggctgagaaccagaagagctgtgagcctgctgtgcccttc
ccctgtggcagagtgtctgtgtcccagaccagcaagctgaccagagctgagacagtgttccctgat
gtggactatgtgaacagcacagaggctgagaccatcctggacaacatcacccagagcacccagtcc
ttcaatgacttcaccagagtggtgggaggagaggatgccaagcctggccagttcccctggcaggtg
gtgctgaatggcaaggtggatgccttctgtggaggcagcattgtgaatgagaagtggattgtgaca
gctgcccactgtgtggagacaggagtgaagatcacagtggtggctggagagcacaacattgaggag
acagagcacacagagcagaagaggaatgtgatcaggatcatccctcaccacaactacaatgctgcc
atcaacaagtacaaccatgacattgccctgctggagctggatgagcctctggtgctgaacagctat
gtgacccctatctgcattgctgacaaggagtacaccaacatcttcctgaagtttggctctggctat
gtgtctggctggggcagagtgttccacaagggcaggtctgccctggtgctgcagtacctgagagtg
cccctggtggacagagccacctgcctgttgagcaccaagttcaccatctacaacaacatgttctgt
gctggcttccatgagggaggcagagacagctgccagggtgactctggaggaccccatgtgacagag
gtggaGggcaccagcttcctgacaggcatcatcagctggggagaggagtgtgccatgaagggcaag
tatggcatctacaccaaagtgagcagatatgtgaactggatcaaggagaagaccaagctgacctga
(SEQ ID NO:7)

```
atgcagagggtgaacatgattatggctgagagccctggcctgatcaccatctgcctgctgggctac
ctgctgtctgctgagtgcactgtgttcctggaccatgagaatgccaacaagatcctgaaccgcccc
aagcgctacaactctggcaagctggaggagtttgtgcagggcaacctggagagggagtgcatggag
gagaagtgcagctttgaggaggccagggaggtgtttgagaacactgagcgcaccactgagttctgg
aagcagtatgtggatggggaccagtgtgagagcaacccctgcctgaatgggggagctgcaaggat
gacatcaacagctatgagtgctggtgccccttggctttgagggcaagaactgtgagctggatgtg
acctgcaacatcaagaatggccgctgtgagcagttctgcaagaactctgctgacaacaaggtggtg
tgctcttgcactgagggctaccgcctggctgagaaccagaagagctgtgagcctgctgtgcccttc
ccctgtggcagggtgtctgtgagccagaccagcaagctgaccagggctgagactgtgttccctgac
gtggactatgtgaacagcactgaggctgagaccatcctggacaacatcacccagagcacccagagc
ttcaatgacttcaccagggtggtgggaggagaggatgccaagcctggccagttcccctggcaggtg
gtgctgaatggcaaggtggatgccttctgtggaggcagcattgtgaatgagaagtggattgtgacc
gctgcccactgtgtggagactggagtgaagatcactgtggtggctggggagcacaacattgaggag
acagagcacacagagcagaagcgcaatgtgatcaggatcatcccccaccacaactacaatgctgcc
atcaacaagtacaaccatgacattgccctgctggagctggatgagcccctggtgctgaacagctac
gtgacccccatctgcattgcagacaaggagtacaccaacatcttcctgaagtttggctctggctat
gtgtctggctggggcagggtgttccacaagggcaggtctgccctggtgctgcagtacctgagggtg
cccctggtggacagggccacctgcctgctgagcaccaagttcaccatctacaacaacatgttctgc
gctggcttccatgagggaggaagggacagctgccagggagactctggaggcccccatgtgacagag
gtggagggcaccagcttcctgacaggcatcatcagctgggggggaggagtgtgccatgaagggcaag
tatggcatctacaccaaagtgtcccgctatgtgaactggatcaaggagaagaccaagctgacctga
(SEQ ID NO:8)
```

Figure 8

CS06-FL-NA atgcagagggtcaacatgatcatggctgagtccctggcctcatcaccatctgcctgctgggctac
ctgctgtctgctgagtgcactgtcttcctggaccatgagaatgccaacaagatcctcaacaggccc
aagagatacaactctggcaaactggaggagtttgtccagggcaacctggagagggagtgcatggag
gagaagtgctcctttgaggaggccagggaggtctttgagaacactgagcgcaccactgagttctgg
aaacagtatgtggatggggaccagtgtgagtccaaccctgcctgaatgggggcagctgcaaggat
gacatcaacagctatgagtgctggtgcccctttggctttgagggcaagaactgtgagctggatgtg
acctgcaacatcaagaatggcagatgtgagcagttctgcaagaactctgctgacaacaaggtggtg
tgctcctgcactgagggctaccgcctggctgagaaccagaagagctgtgagcctgctgtgccattc
ccatgtggcagagtctctgtgagccagaccagcaagctcaccagggctgagactgtgttccctgat
gtggactatgtgaacagcactgaggctgaaaccatcctggacaacatcacccagagcacccagagc
ttcaatgacttcaccagagtggtgggaggagaggatgccaagcctggccagttccctggcaagtg
gtgctcaatggcaaggtggatgccttctgtgggggctccattgtgaatgagaagtggattgtcact
gctgcccactgtgtggagactggggtcaagatcactgtggtggctggggagcacaacattgaggag
actgagcacactgagcagaagcgcaatgtgatcaggatcatcccccaccacaactacaatgctgcc
atcaacaagtacaaccatgacattgccctgctggagctggatgagccctggcctcaacagctat
gtgaccccatctgcattgctgacaaggagtacaccaacatcttcctcaagtttggctctggctat
gtctctggctggggcagagtgttccacaaaggcaggtctgccctggtgctccagtacctgagagtg
cccctggtggacagggccacctgcctcttgagcaccaagttcaccatctacaacaacatgttctgt
gctggcttccatgagggaggaagagacagctgccagggggactctggaggaccccatgtcactgag
gtggagggcacctccttcctcactggcatcatctcctggggagaggagtgtgccatgaaaggcaaa
tatggcatctacaccaaagtctccagatatgtcaactggatcaaggagaagaccaagctgacctga
(SEQ ID NO:9)

Figure 9

FIX-MP-AA

YNSG KLEEFVQGNL ERECMEEKCS FEEAREVFEN TERTTEFWKQ YVDGDQCESN
PCLNGGSCKD DINSYECWCP FGFEGKNCEL DVTCNIKNGR CEQFCKNSAD
NKVVCSCTEG YRLAENQKSC EPAVPFPCGR VSVSQTSKLT RAETVFPDVD
YVNSTEAETI LDNITQSTQS FNDFTRVVGG EDAKPGQFPW QVVLNGKVDA
FCGGSIVNEK WIVTAAHCVE TGVKITVVAG EHNIEETEHT EQKRNVIRII
PHHNYNAAIN KYNHDIALLE LDEPLVLNSY VTPICIADKE YTNIFLKFGS
GYVSGWGRVF HKGRSALVLQ YLRVPLVDRA TCLRSTKFTI YNNMFCAGFH
EGGRDSCQGD SGGPHVTEVE GTSFLTGIIS WGEECAMKGK YGIYTKVSRY
VNWIKEKTKL T   (SEQ ID NO:10)

Figure 11A

FIX2-MP-AA ynsg kleefvqgnl erecmeekcs feearevfen terttefwkq yvdvtcnikn
grceqfckns adnkvvcsct egyrlaenqk scepavpfpc grvsvsqtsk ltraetvfpd
vdyvnsteae tildnitqst qsfndftrvv ggedakpgqf pwqvvlngkv dafcggsivn
ekwivtaahc vetgvkitvv agehnieete hteqkrnvir iiphhnynaa inkynhdial
leldeplvln syvtpiciad keytniflkf gsgyvsgwgr vfhkgrsalv lqylrvplvd
ratclrstkf tiynnmfcag fheggrdscq gdsggphvte vegtsfltgi iswgeecamk
gkygiytkvs ryvnwikekt klt   (SEQ ID NO:11)

Figure 11B

FIXp-MP-AA

```
YNSG KLEEFVQGNL ERECMEEKCS FEEAREVFEN TERTTEFWKQ YVDGDQCESN
PCLNGGSCKD DINSYECWCP FGFEGKNCEL DVTCNIKNGR CEQFCKNSAD
NKVVCSCTEG YRLAENQKSC EPAVPFPCGR VSVSQTSKLT RAETVFPDVD
YVNSTEAETI LDNITQSTQS FNDFTRVVGG EDAKPGQFPW QVVLNGKVDA
FCGGSIVNEK WIVTAAHCVE TGVKITVVAG EHNIEETEHT EQKRNVIRII
PHHNYNAAIN KYNHDIALLE LDEPLVLNSY VTPICIADKE YTNIFLKFGS
GYVSGWGRVF HKGRSALVLQ YLRVPLVDRA TCLLSTKFTI YNNMFCAGFH
EGGRDSCQGD SGGPHVTEVE GTSFLTGIIS WGEECAMKGK YGIYTKVSRY
VNWIKEKTKL T   (SEQ ID NO:12)
```

```
tacaactcag gcaagctgga ggagtttgtg cagggcaacc tggagaggga gtgcatggag
gagaagtgca gctttgagga ggccagagag gtgtttgaga acacagagag gaccacagag
ttctggaagc agtatgtgga tggagaccag tgtgagagca acccttgcct gaatggaggc
agctgcaagg atgacatcaa cagctatgag tgctggtgcc cttttggctt tgagggcaag
aactgtgagc tggatgtgac ctgcaacatc aagaatggca ggtgtgagca gttctgcaag
aactcagctg acaacaaagt ggtgtgtagc tgcacagagg ctacagact ggctgagaac
cagaagagct gtgagcctgc tgtgcccttc ccctgtggca gagtgtcagt gtcccagacc
agcaagctga ccagagctga gacagtgttc cctgatgtgg actatgtgaa tagcacagag
gctgagacca tcctggacaa catcacccag agcacccagt ccttcaatga cttcaccaga
gttgtgggag gagaggatgc caagcctggc cagttcccct ggcaggtggt gctgaatggc
aaagtggatg ccttctgtgg aggcagcatt gtgaatgaga agtggattgt gacagctgcc
cactgtgtgg agacaggagt gaagatcaca gtggtggctg gagaacacaa tattgaggag
acagagcaca cagagcagaa gaggaatgtc atcaggatta tcccccacca caactacaat
gctgccatca acaagtacaa ccatgacatt gccctgctgg agctggatga gcctctggtg
ctgaatagct atgtgacccc catctgcatt gctgacaagg agtacaccaa catcttcctg
aagtttggct caggctatgt gtcaggctgg ggcagagtgt ccacaaggg cagatcagcc
ctggtgctgc agtacctgag agtgcccctg gtggacagag ccacctgcct gttgagcacc
aagttcacca tctacaacaa catgttctgt gctggcttcc atgagggagg cagagacagc
tgccagggag actcaggagg accccatgtg acagaagtgg agggcaccag cttcctgaca
ggcatcatca gctggggaga ggagtgtgcc atgaagggca agtatggcat ctacaccaaa
gtgagcagat atgtgaactg gatcaaggag aaaaccaagc tgacctga
(SEQ ID NO:13)
```

```
tacaactctg gcaagctgga ggagtttgtg cagggcaacc tggagaggga gtgcatggag
gagaagtgca gctttgagga ggccagggaa gtgtttgaga acactgagag gaccactgag
ttctggaagc agtatgtgga tggggaccag tgtgagagca acccttgcct gaatgggggc
agctgcaagg atgacatcaa cagctatgag tgctggtgcc cttttggctt tgagggcaag
aactgtgagc tggatgtgac ctgcaacatc aagaatggca ggtgtgagca gttctgcaag
aactctgctg acaacaaagt ggtgtgtagc tgcactgagg gctacagact ggctgagaac
cagaagagct gtgagcctgc tgtgcccttc ccctgtggca gagtgtctgt gtcccagacc
agcaagctga ccagagctga gactgtgttc cctgatgtgg actatgtgaa tagcactgag
gctgagacca tcctggacaa catcacccag agcacccagt ccttcaatga cttcaccaga
gtggtggggg gggaggatgc caagcctggc cagttcccct ggcaggtggt gctgaatggc
aaagtggatg ccttctgtgg gggcagcatt gtgaatgaga agtggattgt gactgctgcc
cactgtgtgg agactggggt gaagatcact gtggtggctg gggaacacaa tattgaggag
actgagcaca ctgagcagaa gaggaatgtc atcaggatta tcccccacca caactacaat
gctgccatca acaagtacaa ccatgacatt gccctgctgg agctggatga gcctctggtg
ctgaatagct atgtgacccc catctgcatt gctgacaagg agtacaccaa catcttcctg
aagtttggct ctggctatgt gtctggctgg ggcagagtgt ccacaaggg caggtctgcc
ctggtgctgc agtacctgag agtgcccctg gtggacagag ccacctgcct gctgagcacc
aagttcacca tctacaacaa catgttctgt gctggcttcc atgagggggg cagagacagc
tgccaggggg actctggggg cccccatgtg actgaagtgg agggcaccag cttcctgact
ggcatcatca gctgggggga ggagtgtgcc atgaagggca agtatggcat ctacaccaaa
gtgagcaggt atgtgaactg gatcaaggag aaaaccaagc tgacctga
(SEQ ID NO:14)
```

```
tacaactctg gcaagctgga ggagtttgtg cagggcaacc tggagaggga gtgcatggag
gagaagtgca gctttgagga ggccagggag gtgtttgaga acacagagag gaccacagag
ttctggaagc agtatgtgga tggtgaccag tgtgagagca acccttgcct gaatggaggc
agctgcaagg atgacatcaa cagctatgag tgctggtgcc cttttggctt tgagggcaag
aactgtgagc tggatgtgac ctgcaacatc aagaatggca ggtgtgagca gttctgcaag
aactctgctg acaacaaggt ggtgtgtagc tgcacagagg gctacagact ggctgagaac
cagaagagct gtgagcctgc tgtgcccttc ccctgtggca gagtgtctgt gtcccagacc
agcaagctga ccagagctga gacagtgttc cctgatgtgg actatgtgaa cagcacagag
gctgagacca tcctggacaa catcacccag agcacccagt ccttcaatga cttcaccaga
gtggtgggag gagaggatgc caagcctggc cagttcccct ggcaggtggt gctgaatggc
aaggtggatg ccttctgtgg aggcagcatt gtgaatgaga agtggattgt gacagctgcc
cactgtgtgg agacaggagt gaagatcaca gtggtggctg gagagcacaa cattgaggag
acagagcaca cagagcagaa gaggaatgtg atcaggatca tccctcacca caactacaat
gctgccatca acaagtacaa ccatgacatt gccctgctgg agctggatga gcctctggtg
ctgaacagct atgtgacccc tatctgcatt gctgacaagg agtacaccaa catcttcctg
aagtttggct ctggctatgt gtctggctgg ggcagagtgt ccacaaggg caggtctgcc
ctggtgctgc agtacctgag agtgcccctg gtggacagag ccacctgcct gttgagcacc
aagttcacca tctacaacaa catgttctgt gctggcttcc atgagggagg cagagacagc
tgccagggtg actctggagg accccatgtg acagaggtgg agggcaccag cttcctgaca
ggcatcatca gctggggaga ggagtgtgcc atgaagggca agtatggcat ctacaccaaa
gtgagcagat atgtgaactg gatcaaggag aagaccaagc tgacctga
(SEQ ID NO:15)
```

```
tacaactctg gcaagctgga ggagtttgtg cagggcaacc tggagaggga gtgcatggag
gagaagtgca gctttgagga ggccagggag gtgtttgaga acactgagcg caccactgag
ttctggaagc agtatgtgga tggggaccag tgtgagagca acccctgcct gaatgggggg
agctgcaagg atgacatcaa cagctatgag tgctggtgcc cctttggctt tgagggcaag
aactgtgagc tggatgtgac ctgcaacatc aagaatggcc gctgtgagca gttctgcaag
aactctgctg acaacaaggt ggtgtgctct tgcactgagg gctaccgcct ggctgagaac
cagaagagct gtgagcctgc tgtgcccttc ccctgtggca gggtgtctgt gagccagacc
agcaagctga ccagggctga gactgtgttc cctgacgtgg actatgtgaa cagcactgag
gctgagacca tcctggacaa catcacccag agcacccaga gcttcaatga cttcaccagg
gtggtgggag gagaggatgc caagcctggc cagttcccct ggcaggtggt gctgaatggc
aaggtggatg ccttctgtgg aggcagcatt gtgaatgaga agtggattgt gaccgctgcc
cactgtgtgg agactggagt gaagatcact gtggtggctg gggagcacaa cattgaggag
acagagcaca cagagcagaa gcgcaatgtg atcaggatca tcccccacca caactacaat
gctgccatca acaagtacaa ccatgacatt gccctgctgg agctggatga gcccctggtg
ctgaacagct acgtgacccc catctgcatt gcagacaagg agtacaccaa catcttcctg
aagtttggct ctggctatgt gtctggctgg ggcagggtgt tccacaaggg caggtctgcc
ctggtgctgc agtacctgag ggtgcccctg gtggacaggg ccacctgcct gctgagcacc
aagttcacca tctacaacaa catgttctgc gctggcttcc atgagggagg aagggacagc
tgccagggag actctggagg cccccatgtg acagaggtgg agggcaccag cttcctgaca
ggcatcatca gctgggggga ggagtgtgcc atgaagggca gtatggcat ctacaccaaa
gtgtcccgct atgtgaactg gatcaaggag aagaccaagc tgacctga
(SEQ ID NO:16)
```

```
tacaactctg gcaaactgga ggagtttgtc cagggcaacc tggagaggga gtgcatggag
gagaagtgct cctttgagga ggccagggag gtctttgaga acactgagcg caccactgag
ttctggaaac agtatgtgga tggggaccag tgtgagtcca acccctgcct gaatgggggc
agctgcaagg atgacatcaa cagctatgag tgctggtgcc cctttggctt tgagggcaag
aactgtgagc tggatgtgac ctgcaacatc aagaatggca gatgtgagca gttctgcaag
aactctgctg acaacaaggt ggtgtgctcc tgcactgagg gctaccgcct ggctgagaac
cagaagagct gtgagcctgc tgtgccattc ccatgtggca gagtctctgt gagccagacc
agcaagctca ccagggctga gactgtgttc cctgatgtgg actatgtgaa cagcactgag
gctgaaacca tcctggacaa catcacccag agcacccaga gcttaatga cttcaccaga
gtggtgggag gagaggatgc caagcctggc cagttccct ggcaagtggt gctcaatggc
aaggtggatg ccttctgtgg gggctccatt gtgaatgaga agtggattgt cactgctgcc
cactgtgtgg agactggggt caagatcact gtggtggctg gggagcacaa cattgaggag
actgagcaca ctgagcagaa gcgcaatgtg atcaggatca tcccccacca caactacaat
gctgccatca acaagtacaa ccatgacatt gccctgctgg agctggatga gccctggtc
ctcaacagct atgtgacccc catctgcatt gctgacaagg agtacaccaa catcttcctc
aagtttggct ctggctatgt ctctggctgg ggcagagtgt tccacaaagg caggtctgcc
ctggtgctcc agtacctgag agtgccctg gtggacaggg ccacctgcct cttgagcacc
aagttcacca tctacaacaa catgttctgt gctggcttcc atgagggagg aagagacagc
tgccaggggg actctggagg accccatgtc actgaggtgg agggcacctc cttcctcact
ggcatcatct cctggggaga ggagtgtgcc atgaaaggca aatatggcat ctacaccaaa
gtctccagat atgtcaactg gatcaaggag aagaccaagc tgacctga
```

(SEQ ID NO:17)

Figure 17

FIX-PPP-NA atgcagcgcg tgaacatgat catggcagaa tcaccaggcc tcatcaccat ctgcctttta
ggatatctac tcagtgctga atgtacagtt tttcttgatc atgaaaacgc caacaaaatt
ctgaatcggc caaagagg   (SEQ ID NO:18)

CS02-PPP-NA atgcagaggg tgaacatgat catggctgag agccctggcc tgatcaccat ctgcctgctg
ggctacctgc tgtcagcaga gtgcacagtg ttcctggacc atgagaatgc caacaagatc
ctgaacaggc ccaagaga   (SEQ ID NO:19)

CS03-PPP-NA atgcagaggg tgaacatgat catggctgag agccctggcc tgatcaccat ctgcctgctg
ggctacctgc tgtctgctga gtgcactgtg ttcctggacc atgagaatgc caacaagatc
ctgaacaggc ccaagaga   (SEQ ID NO:20)

CS04-PPP-NA atgcagaggg tgaacatgat tatggctgag agccctggcc tgatcaccat ctgcctgctg
ggctacctgc tgtctgctga gtgcacagtg ttcctggacc atgagaatgc caacaagatc
ctgaacaggc ccaagaga   (SEQ ID NO:21)

CS05-PPP-NA atgcagaggg tgaacatgat tatggctgag agccctggcc tgatcaccat ctgcctgctg
ggctacctgc tgtctgctga gtgcactgtg ttcctggacc atgagaatgc caacaagatc
ctgaaccgcc ccaagcgc   (SEQ ID NO:22)

CS06-PPP-NA atgcagaggg tcaacatgat catggctgag tcccctggcc tcatcaccat ctgcctgctg
ggctacctgc tgtctgctga gtgcactgtc ttcctggacc atgagaatgc caacaagatc
ctcaacaggc ccaagaga   (SEQ ID NO:23)

Figure 18

FIX-SP-NA atgcagcgcg tgaacatgat catggcagaa tcaccaggcc tcatcaccat ctgccttta
ggatatctac tcagtgctga atgt   (SEQ ID NO:24)

CS02-SP-NA atgcagaggg tgaacatgat catggctgag agccctggcc tgatcaccat ctgcctgctg
ggctacctgc tgtcagcaga gtgc   (SEQ ID NO:25)

CS03-SP-NA atgcagaggg tgaacatgat catggctgag agccctggcc tgatcaccat ctgcctgctg
ggctacctgc tgtctgctga gtgc   (SEQ ID NO:26)

CS04-SP-NA atgcagaggg tgaacatgat tatggctgag agccctggcc tgatcaccat ctgcctgctg
ggctacctgc tgtctgctga gtgc   (SEQ ID NO:27)

CS05-SP-NA atgcagaggg tgaacatgat tatggctgag agccctggcc tgatcaccat ctgcctgctg
ggctacctgc tgtctgctga gtgc   (SEQ ID NO:28)

CS06-SP-NA atgcagaggg tcaacatgat catggctgag tccctggcc tcatcaccat ctgcctgctg
ggctacctgc tgtctgctga gtgc   (SEQ ID NO:29)

Figure 19

FIX-PP-NA acagttttc ttgatcatga aaacgccaac aaaattctga atcggccaaa gagg
(SEQ ID NO:30)

CS02-PP-NA acagtgttcc tggaccatga gaatgccaac aagatcctga acaggcccaa gaga
(SEQ ID NO:31)

CS03-PP-NA actgtgttcc tggaccatga gaatgccaac aagatcctga acaggcccaa gaga
(SEQ ID NO:32)

CS04-PP-NA acagtgttcc tggaccatga gaatgccaac aagatcctga acaggcccaa gaga
(SEQ ID NO:33)

CS05-PP-NA actgtgttcc tggaccatga gaatgccaac aagatcctga accgccccaa gcgc
(SEQ ID NO:34)

CS06-PP-NA actgtcttcc tggaccatga gaatgccaac aagatcctca acaggcccaa gaga
(SEQ ID NO:35)

Figure 20

FIX-PPP-AA

MQRVNMIMAE SPGLITICLL GYLLSAECTV FLDHENANKI LNRPKR  (SEQ ID NO:36)

Figure 21

FIX-SP-AA

MQRVNMIMAE SPGLITICLL GYLLSAEC  (SEQ ID NO:37)

Figure 22

FIX-PP-AA

TV FLDHENANKI LNRPKR  (SEQ ID NO:38)

Figure 23

CRM8 gggggaggctgctggtgaatattaaccaaggtcaccccagttatcggaggagcaaacagggctaag
tccac  (SEQ ID NO:39)

Figure 24

CS06-CRM8.3-ssV

```
ttggccactccctctctgcgcgctcgctcgctcactgaggccgggcgaccaaaggtcgcccgacgcc
cgggctttgcccgggcggcctcagtgagcgagcgagcgcgcagagagggagtggccaactccatcac
taggggttcctgagtttaaacttcgtcgacggggggaggctgctggtgaatattaaccaaggtcaccc
cagttatcggaggagcaaacaggggctaagtccaccggggggaggctgctggtgaatattaaccaagg
tcaccccagttatcggaggagcaaacaggggctaagtccaccgggggaggctgctggtgaatattaa
ccaaggtcaccccagttatcggaggagcaaacaggggctaagtccaccgagggcactgggaggatgt
tgagtaagatggaaaactactgatgacccttgcagagacagagtattaggacatgtttgaacagggg
ccgggcgatcagcaggtagctctagaggatccccgtctgtctgcacatttcgtagagcgagtgttcc
gatactctaatctccctaggcaaggttcatatttgtgtaggttacttattctccttttgttgactaa
gtcaataatcagaatcagcaggtttggagtcagcttggcagggatcagcagcctgggttggaaggag
ggggtataaaagccccttcaccaggagaagccgtcacacagactaggcgcgccctaaggtaagttgg
cgccgtttaaggatggttggttggtggggtattaatgtttaattacctttttttacaggcctgaaga
tctgccaccatgcagagggtcaacatgatcatggctgagtcccctggcctcatcaccatctgcctgc
tgggctacctgctgtctgctgagtgcactgtcttcctggaccatgagaatgccaacaagatcctcaa
caggcccaagagatacaactctggcaaactggaggagtttgtccagggcaacctggagagggagtgc
atggaggagaagtgctcctttgaggaggccagggaggtctttgagaacactgagcgcaccactgagt
tctggaaacagtatgtggatggggaccagtgtgagtccaaccccctgcctgaatgggggcagctgcaa
ggatgacatcaacagctatgagtgctggtgcccctttggctttgagggcaagaactgtgagctggat
gtgacctgcaacatcaagaatggcagatgtgagcagttctgcaagaactctgctgacaacaaggtgg
tgtgctcctgcactgagggctaccgcctggctgagaaccagaagagctgtgagcctgctgtgccatt
cccatgtggcagagtctctgtgagccagaccagcaagctcaccagggctgagactgtgttccctgat
gtggactatgtgaacagcactgaggctgaaaccatcctggacaacatcacccagagcacccagagct
tcaatgacttcaccagagtggtgggaggagaggatgccaagcctggccagttcccctggcaagtggt
gctcaatggcaaggtggatgccttctgtggggctccattgtgaatgagaagtggattgtcactgct
gcccactgtgtggagactggggtcaagatcactgtggtggctggggagcacaacattgaggagactg
agcacactgagcagaagcgcaatgtgatcaggatcatcccccaccacaactacaatgctgccatcaa
caagtacaaccatgacattgccctgctggagctggatgagcccctggtcctcaacagctatgtgacc
cccatctgcattgctgacaaggagtacaccaacatcttcctcaagtttggctctggctatgtctctg
gctggggcagagtgttccacaaaggcaggtctgccctggtgctccagtacctgagagtgcccctggt
ggacagggccacctgcctcttgagcaccaagttcaccatctacaacaacatgttctgtgctggcttc
catgagggaggaagagacagctgccaggggactctggaggaccccatgtcactgaggtggagggca
cctccttcctcactggcatcatctcctggggagaggagtgtgccatgaaggcaaatatggcatcta
caccaaagtctccagatatgtcaactggatcaaggagaagaccaagctgacctgatgagcatgccta
gagctcgctgatcagcctcgactgtgccttctagttgccagccatctgttgtttgcccctcccccgt
gccttccttgaccctggaaggtgccactcccactgtccttcctaataaaatgaggaaattgcatcg
cattgtcTgagtaggtgtcattctattctggggggtggggtggggcaggacagcaaggggggaggatt
gggaagacaatagcaggcatgctggggaattaattaagctcgcgaaggaaccccctagtgatggagtt
```

```
ggccactccctctctgcgcgctcgctcgctcactgaggccgggcgaccaaaggtcgcccgacgcccg
ggctttgcccgggcggcctcagtgagcgagcgagcgcgcagagagggagtggccaagacgatttaaa
tgacaagcttggcgtaatcatggtcatagctgtttcctgtgtgaaattgttatccgctcacaattcc
acacaacatacgagccggaagcataaagtgtaaagcctggggtgcctaatgagtgagctaactcaca
ttaattgcgttgcgctcactgcccgctttccagtcgggaaacctgtcgtgccagctgcattaatgaa
tcggccaacgcgcggggagaggcggtttgcgtattgggcgctcttccgcttcctcgctcactgactc
gctgcgctcggtcgttcggctgcggcgagcggtatcagctcactcaaaggcggtaatacggttatcc
acagaatcaggggataacgcaggaaagaacatgtgagcaaaaggccagcaaaaggccaggaaccgta
aaaaggccgcgttgctggcgtttttccataggctccgcccccctgacgagcatcacaaaaatcgacg
ctcaagtcagaggtggcgaaacccgacaggactataaagataccaggcgtttccccctggaagctcc
ctcgtgcgctctcctgttccgaccctgccgcttaccggatacctgtccgcctttctcccttcgggaa
gcgtggcgctttctcatagctcacgctgtaggtatctcagttcggtgtaggtcgttcgctccaagct
gggctgtgtgcacgaaccccccgttcagcccgaccgctgcgccttatccggtaactatcgtcttgag
tccaacccggtaagacacgacttatcgccactggcagcagccactggtaacaggattagcagagcga
ggtatgtaggcggtgctacagagttcttgaagtggtggcctaactacggctacactagaagaacagt
atttggtatctgcgctctgctgaagccagttaccttcggaaaaagagttggtagctcttgatccggc
aaacaaaccaccgctggtagcggtggtttttttgtttgcaagcagcagattacgcgcagaaaaaaag
gatctcaagaagatcctttgatcttttctacggggtctgacgctcagtggaacgaaaactcacgtta
agggattttggtcatgagattatcaaaaggatcttcacctagatcctttaaattaaaaatgaagt
tttaaatcaatctaaagtatatatgagtaaacttggtctgacagttaccaatgcttaatcagtgagg
cacctatctcagcgatctgtctatttcgttcatccatagttgcctgactccccgtcgtgtagataac
tacgatacgggagggcttaccatctggccccagtgctgcaatgataccgcgagacccacgctcaccg
gctccagatttatcagcaataaaccagccagccggaagggccgagcgcagaagtggtcctgcaactt
tatccgcctccatccagtctattaattgttgccgggaagctagagtaagtagttcgccagttaatag
tttgcgcaacgttgttgccattgctacaggcatcgtggtgtcacgctcgtcgtttggtatggcttca
ttcagctccggttcccaacgatcaaggcgagttacatgatccccatgttgtgcaaaaaagcggtta
gctccttcggtcctccgatcgttgtcagaagtaagttggccgcagtgttatcactcatggttatggc
agcactgcataattctcttactgtcatgccatccgtaagatgcttttctgtgactggtgagtactca
accaagtcattctgagaatagtgtatgcggcgaccgagttgctcttgcccggcgtcaatacggata
ataccgcgccacatagcagaactttaaaagtgctcatcattggaaaacgttcttcggggcgaaaact
ctcaaggatcttaccgctgttgagatccagttcgatgtaacccactcgtgcacccaactgatcttca
gcatcttttactttcaccagcgtttctgggtgagcaaaaacaggaaggcaaaatgccgcaaaaaagg
gaataagggcgacacggaaatgttgaatactcatactcttcctttttcaatattattgaagcattta
tcagggttattgtctcatgagcggatacatatttgaatgtatttagaaaaataaacaatagggggtt
ccgcgcacatttccccgaaaagtgccacctgacgtctaagaaaccattattatcatgacattaacct
ataaaaataggcgtatcacgaggccctttcgtctcgcgcgtttcggtgatgacggtgaaaacctctg
acacatgcagctcccggagacggtcacagcttgtctgtaagcggatgccgggagcagacaagcccgt
cagggcgcgtcagcgggtgttggcggtgtcggggctggcttaactatgcggcatcagagcagattg
tactgagagtgcaccatatgcggtgtgaaataccgcacagatgcgtaaggagaaaataccgcatcag
gcgccattcgccattcaggctgcgcaactgttgggaagggcgatcggtgcgggcctcTtcgctatta
cgccagctggcgaaggggggatgtgctgcaaggcgattaagttgggtaacgccagggttttcccagt
cacgacgttgtaaaacgacggccagtgaattcctcgagatttaaatgacg
```

(SEQ ID NO:40)

Figure 25B

SEQUENCE LISTING

<160> NUMBER OF SEQ ID NOS: 64

<210> SEQ ID NO 1
<211> LENGTH: 1386
<212> TYPE: DNA
<213> ORGANISM: Artificial Sequence
<220> FEATURE:
<223> OTHER INFORMATION: FIX-FL-NA

<400> SEQUENCE: 1
atgcagcgcg tgaacatgat catggcagaa tcaccaggcc tcatcaccat ctgccttta        60 ggatatctac tcagtgctga atgtacagtt tttcttgatc atgaaaacgc caacaaaatt      120

```
ctgaatcggc caaagaggta taattcaggt aaattggaag agtttgttca agggaacctt    180
gagagagaat gtatggaaga aaagtgtagt tttgaagaag cacgagaagt ttttgaaaac    240
actgaaagaa caactgaatt ttggaagcag tatgttgatg gagatcagtg tgagtccaat    300
ccatgtttaa atggcggcag ttgcaaggat gacattaatt cctatgaatg ttggtgtccc    360
tttggatttg aaggaaagaa ctgtgaatta gatgtaacat gtaacattaa gaatggcaga    420
tgcgagcagt tttgtaaaaa tagtgctgat aacaaggtgg tttgctcctg tactgaggga    480
tatcgacttg cagaaaacca gaagtcctgt gaaccagcag tgccatttcc atgtggaaga    540
gtttctgttt cacaaacttc taagctcacc cgtgctgaga ctgtttttcc tgatgtggac    600
tatgtaaatt ctactgaagc tgaaaccatt ttggataaca tcactcaaag cacccaatca    660
tttaatgact tcactcgggt tgttggtgga gaagatgcca aaccaggtca attcccttgg    720
caggttgttt tgaatggtaa agttgatgca ttctgtggag gctctatcgt taatgaaaaa    780
tggattgtaa ctgctgccca ctgtgttgaa actggtgtta aaattacagt tgtcgcaggt    840
gaacataata ttgaggagac agaacataca gagcaaaagc gaaatgtgat tcgaattatt    900
cctcaccaca actacaatgc agctattaat aagtacaacc atgacattgc ccttctggaa    960
ctggacgaac ccttagtgct aaacagctac gttacaccta tttgcattgc tgacaaggaa   1020
tacacgaaca tcttcctcaa atttggatct ggctatgtaa gtggctgggg aagagtcttc   1080
cacaaaggga atcagctttt agttcttcag taccttagag ttccacttgt tgaccgagcc   1140
acatgtcttc gatctacaaa gttcaccatc tataacaaca tgttctgtgc tggcttccat   1200
gaaggaggta gagattcatg tcaaggagat agtgggggac cccatgttac tgaagtggaa   1260
gggaccagtt tcttaactgg aattattagc tggggtgaag agtgtgcaat gaaaggcaaa   1320
tatggaatat ataccaaggt atcccggtat gtcaactgga ttaaggaaaa aacaaagctc   1380
acttaa                                                              1386
```

<210> SEQ ID NO 2
<211> LENGTH: 461
<212> TYPE: PRT
<213> ORGANISM: Artificial Sequence
<220> FEATURE:
<223> OTHER INFORMATION: FIX-FL-AA

<400> SEQUENCE: 2

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125
```

```
Glu Leu Asp Val Thr Cys Asn Ile Lys Asn Gly Arg Cys Glu Gln Phe
    130                 135                 140
Cys Lys Asn Ser Ala Asp Asn Lys Val Val Cys Ser Cys Thr Glu Gly
145                 150                 155                 160
Tyr Arg Leu Ala Glu Asn Gln Lys Ser Cys Glu Pro Ala Val Pro Phe
                165                 170                 175
Pro Cys Gly Arg Val Ser Val Ser Gln Thr Ser Lys Leu Thr Arg Ala
            180                 185                 190
Glu Thr Val Phe Pro Asp Val Asp Tyr Val Asn Ser Thr Glu Ala Glu
        195                 200                 205
Thr Ile Leu Asp Asn Ile Thr Gln Ser Thr Gln Ser Phe Asn Asp Phe
    210                 215                 220
Thr Arg Val Val Gly Gly Glu Asp Ala Lys Pro Gly Gln Phe Pro Trp
225                 230                 235                 240
Gln Val Val Leu Asn Gly Lys Val Asp Ala Phe Cys Gly Gly Ser Ile
                245                 250                 255
Val Asn Glu Lys Trp Ile Val Thr Ala Ala His Cys Val Glu Thr Gly
            260                 265                 270
Val Lys Ile Thr Val Val Ala Gly Glu His Asn Ile Glu Glu Thr Glu
        275                 280                 285
His Thr Glu Gln Lys Arg Asn Val Ile Arg Ile Ile Pro His His Asn
    290                 295                 300
Tyr Asn Ala Ala Ile Asn Lys Tyr Asn His Asp Ile Ala Leu Leu Glu
305                 310                 315                 320
Leu Asp Glu Pro Leu Val Leu Asn Ser Tyr Val Thr Pro Ile Cys Ile
                325                 330                 335
Ala Asp Lys Glu Tyr Thr Asn Ile Phe Leu Lys Phe Gly Ser Gly Tyr
            340                 345                 350
Val Ser Gly Trp Gly Arg Val Phe His Lys Gly Arg Ser Ala Leu Val
        355                 360                 365
Leu Gln Tyr Leu Arg Val Pro Leu Val Asp Arg Ala Thr Cys Leu Arg
    370                 375                 380
Ser Thr Lys Phe Thr Ile Tyr Asn Asn Met Phe Cys Ala Gly Phe His
385                 390                 395                 400
Glu Gly Gly Arg Asp Ser Cys Gln Gly Asp Ser Gly Gly Pro His Val
                405                 410                 415
Thr Glu Val Glu Gly Thr Ser Phe Leu Thr Gly Ile Ile Ser Trp Gly
            420                 425                 430
Glu Glu Cys Ala Met Lys Gly Lys Tyr Gly Ile Tyr Thr Lys Val Ser
        435                 440                 445
Arg Tyr Val Asn Trp Ile Lys Glu Lys Thr Lys Leu Thr
    450                 455                 460

<210> SEQ ID NO 3
<211> LENGTH: 423
<212> TYPE: PRT
<213> ORGANISM: Artificial Sequence
<220> FEATURE:
<223> OTHER INFORMATION: FIX2-FL-AA

<400> SEQUENCE: 3

Met Gln Arg Val Asn Met Ile Met Ala Glu Ser Pro Gly Leu Ile Thr
1               5                   10                  15
Ile Cys Leu Leu Gly Tyr Leu Leu Ser Ala Glu Cys Thr Val Phe Leu
            20                  25                  30
```

```
Asp His Glu Asn Ala Asn Lys Ile Leu Asn Arg Pro Lys Arg Tyr Asn
            35                  40                  45

Ser Gly Lys Leu Glu Glu Phe Val Gln Gly Asn Leu Glu Arg Glu Cys
 50                  55                  60

Met Glu Glu Lys Cys Ser Phe Glu Glu Ala Arg Glu Val Phe Glu Asn
 65                  70                  75                  80

Thr Glu Arg Thr Thr Glu Phe Trp Lys Gln Tyr Val Asp Val Thr Cys
                 85                  90                  95

Asn Ile Lys Asn Gly Arg Cys Glu Gln Phe Cys Lys Asn Ser Ala Asp
                100                 105                 110

Asn Lys Val Val Cys Ser Cys Thr Glu Gly Tyr Arg Leu Ala Glu Asn
                115                 120                 125

Gln Lys Ser Cys Glu Pro Ala Val Pro Phe Pro Cys Gly Arg Val Ser
    130                 135                 140

Val Ser Gln Thr Ser Lys Leu Thr Arg Ala Glu Thr Val Phe Pro Asp
145                 150                 155                 160

Val Asp Tyr Val Asn Ser Thr Glu Ala Glu Thr Ile Leu Asp Asn Ile
                165                 170                 175

Thr Gln Ser Thr Gln Ser Phe Asn Asp Phe Thr Arg Val Val Gly Gly
                180                 185                 190

Glu Asp Ala Lys Pro Gly Gln Phe Pro Trp Gln Val Val Leu Asn Gly
    195                 200                 205

Lys Val Asp Ala Phe Cys Gly Gly Ser Ile Val Asn Glu Lys Trp Ile
210                 215                 220

Val Thr Ala Ala His Cys Val Glu Thr Gly Val Lys Ile Thr Val Val
225                 230                 235                 240

Ala Gly Glu His Asn Ile Glu Glu Thr Glu His Thr Glu Gln Lys Arg
                245                 250                 255

Asn Val Ile Arg Ile Ile Pro His His Asn Tyr Asn Ala Ala Ile Asn
                260                 265                 270

Lys Tyr Asn His Asp Ile Ala Leu Leu Glu Leu Asp Glu Pro Leu Val
    275                 280                 285

Leu Asn Ser Tyr Val Thr Pro Ile Cys Ile Ala Asp Lys Glu Tyr Thr
290                 295                 300

Asn Ile Phe Leu Lys Phe Gly Ser Gly Tyr Val Ser Gly Trp Gly Arg
305                 310                 315                 320

Val Phe His Lys Gly Arg Ser Ala Leu Val Leu Gln Tyr Leu Arg Val
                325                 330                 335

Pro Leu Val Asp Arg Ala Thr Cys Leu Arg Ser Thr Lys Phe Thr Ile
                340                 345                 350

Tyr Asn Asn Met Phe Cys Ala Gly Phe His Glu Gly Gly Arg Asp Ser
    355                 360                 365

Cys Gln Gly Asp Ser Gly Gly Pro His Val Thr Glu Val Glu Gly Thr
370                 375                 380

Ser Phe Leu Thr Gly Ile Ile Ser Trp Gly Glu Glu Cys Ala Met Lys
385                 390                 395                 400

Gly Lys Tyr Gly Ile Tyr Thr Lys Val Ser Arg Tyr Val Asn Trp Ile
                405                 410                 415

Lys Glu Lys Thr Lys Leu Thr
                420

<210> SEQ ID NO 4
<211> LENGTH: 461
<212> TYPE: PRT
```

<213> ORGANISM: Artificial Sequence
<220> FEATURE:
<223> OTHER INFORMATION: FIXp-FL-AA

<400> SEQUENCE: 4

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
                20                  25                  30

Asp His Glu Asn Ala Asn Lys Ile Leu Asn Arg Pro Lys Arg Tyr Asn
            35                  40                  45

Ser Gly Lys Leu Glu Glu Phe Val Gln Gly Asn Leu Glu Arg Glu Cys
50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Leu
370                 375                 380

Ser Thr Lys Phe Thr Ile Tyr Asn Asn Met Phe Cys Ala Gly Phe His
```

```
                  385                 390                 395                 400
Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
                420                 425                 430

Glu Glu Cys Ala Met Lys Gly Lys Tyr Gly Ile Tyr Thr Lys Val Ser
                435                 440                 445

Arg Tyr Val Asn Trp Ile Lys Glu Lys Thr Lys Leu Thr
                450                 455                 460

<210> SEQ ID NO 5
<211> LENGTH: 1385
<212> TYPE: DNA
<213> ORGANISM: Artificial Sequence
<220> FEATURE:
<223> OTHER INFORMATION: CS02-FL-NA

<400> SEQUENCE: 5
atgcagaggg tgaacatgat catggctgag agccctggcc tgatcaccat ctgcctgctg      60
ggctacctgc tgtcagcaga gtgcacagtg ttcctggacc atgagaatgc caacaagatc    120
ctgaacaggc ccaagagata caactcaggc aagctggagg agtttgtgca gggcaacctg    180
gagagggagt gcatggagga gaagtgcagc tttgaggagg ccagagaggt gtttgagaac    240
acagagagga ccacagagtt ctggaagcag tatgtggatg gagaccagtg tgagagcaac    300
ccttgcctga atggaggcag ctgcaaggat gacatcaaca gctatgagtg ctggtgccct    360
tttggctttg agggcaagaa ctgtgagctg gatgtgacct gcaacatcaa gaatggcagg    420
tgtgagcagt tctgcaagaa ctcagctgac aacaaagtgg tgtgtagctg cacagagggc    480
tacagactgg ctgagaacca gaagagctgt gagcctgctg tgcccttccc ctgtggcaga    540
gtgtcagtgt cccagaccag caagctgacc agagctgaga cagtgttccc tgatgtggac    600
tatgtgaata gcacagaggc tgagaccatc ctggacaaca tcacccagag cacccagtcc    660
ttcaatgact tcaccagagt tgtgggagga gaggatgcca agcctggcca gttcccctgg    720
caggtggtgc tgaatggcaa agtggatgcc ttctgtggag gcagcattgt gaatgagaag    780
tggattgtga cagctgccca ctgtgtggag acaggagtga gatcacagt ggtggctgga    840 gaacacaata ttgaggagac agagcacaca gagcagaaga ggaatgtcat caggattatc    900
ccccaccaca actacaatgc tgccatcaac aagtacaacc atgacattgc cctgctggag    960
ctggatgagc tctggtgct gaatagctat gtgaccccca tctgcattgc tgacaaggag   1020
tacaccaaca tcttcctgaa gtttggctca ggctatgtgt caggctgggg cagagtgttc   1080
cacaagggca gatcagccct ggtgctgcag tacctgagag tgccctggt ggacagagcc   1140 acctgcctgt tgagcaccaa gttcaccatc tacaacaaca tgttctgtgc tggcttccat   1200
gagggaggca gagacagctg ccagggagac tcaggaggac ccatgtgac agaagtggag   1260 ggcaccagct tcctgacagg catcatcagc tggggagagg agtgtgccat gaagggcaag   1320
tatggcatct acaccaaagt gagcagatat gtgaactgga tcaaggagaa aaccaagctg   1380
acctg                                                               1385

<210> SEQ ID NO 6
<211> LENGTH: 1386
<212> TYPE: DNA
<213> ORGANISM: Artificial Sequence
<220> FEATURE:
<223> OTHER INFORMATION: CS03-FL-NA
```

<400> SEQUENCE: 6

```
atgcagaggg tgaacatgat catggctgag agccctggcc tgatcaccat ctgcctgctg      60
ggctacctgc tgtctgctga gtgcactgtg ttcctggacc atgagaatgc caacaagatc     120
ctgaacaggc ccaagagata caactctggc aagctggagt agtttgtgca gggcaacctg     180
gagagggagt gcatggagga aagtgcagc tttgaggagg ccagggaagt gtttgagaac      240
actgagagga ccactgagtt ctggaagcag tatgtggatg ggaccagtg tgagagcaac      300
ccttgcctga atggggcag ctgcaaggat gacatcaaca gctatgagtg ctggtgccct      360
tttggctttg agggcaagaa ctgtgagctg atgtgacct gcaacatcaa gaatggcagg      420
tgtgagcagt tctgcaagaa ctctgctgac aacaaagtgg tgtgtagctg cactgagggc      480
tacagactgg ctgagaacca gaagagctgt gagcctgctg tgcccttccc ctgtggcaga      540
gtgtctgtgt cccagaccag caagctgacc agagctgaga ctgtgttccc tgatgtggac      600
tatgtgaata gcactgaggc tgagaccatc ctggacaaca tcacccagag cacccagtcc      660
ttcaatgact tcaccagagt ggtgggggg gaggatgcca agcctggcca gttcccctgg      720
caggtggtgc tgaatggcaa agtggatgcc ttctgtgggg gcagcattgt gaatgagaag      780
tggattgtga ctgctgccca ctgtgtggag actggggtga agatcactgt ggtggctggg      840
gaacacaata ttgaggagac tgagcacact gagcagaaga ggaatgtcat caggattatc      900
ccccaccaca actacaatgc tgccatcaac aagtacaacc atgacattgc cctgctggag      960
ctggatgagc ctctggtgct gaatagctat gtgacccca tctgcattgc tgacaaggag     1020
tacaccaaca tcttcctgaa gtttggctct ggctatgtgt ctggctgggg cagagtgttc     1080
cacaagggca gtgctgccct ggtgctgcag tacctgagag tgcccctggt ggacagagcc     1140
acctgcctgc tgagcaccaa gttcaccatc tacaacaaca tgttctgtgc tggcttccat     1200
gagggggca gagacagctg ccaggggac tctggggggcc ccatgtgac tgaagtggag     1260
ggcaccagct tcctgactgg catcatcagc tggggggagg agtgtgccat gaagggcaag     1320
tatggcatct acaccaaagt gagcaggtat gtgaactgga tcaaggagaa aaccaagctg     1380
acctga                                                              1386
```

<210> SEQ ID NO 7
<211> LENGTH: 1386
<212> TYPE: DNA
<213> ORGANISM: Artificial Sequence
<220> FEATURE:
<223> OTHER INFORMATION: CS04-FL-NA

<400> SEQUENCE: 7

```
atgcagaggg tgaacatgat tatggctgag agccctggcc tgatcaccat ctgcctgctg      60
ggctacctgc tgtctgctga gtgcacagtg ttcctggacc atgagaatgc caacaagatc     120
ctgaacaggc ccaagagata caactctggc aagctggagt agtttgtgca gggcaacctg     180
gagagggagt gcatggagga aagtgcagc tttgaggagg ccagggaggt gtttgagaac      240
acagagagga ccacagagtt ctggaagcag tatgtggatg gtgaccagtg tgagagcaac      300
ccttgcctga atggaggcag ctgcaaggat gacatcaaca gctatgagtg ctggtgccct      360
tttggctttg agggcaagaa ctgtgagctg atgtgacct gcaacatcaa gaatggcagg      420
tgtgagcagt tctgcaagaa ctctgctgac aacaaggtgg tgtgtagctg cacagagggc      480
tacagactgg ctgagaacca gaagagctgt gagcctgctg tgcccttccc ctgtggcaga      540
```

| | |
|---|---|
| gtgtctgtgt cccagaccag caagctgacc agagctgaga cagtgttccc tgatgtggac | 600 |
| tatgtgaaca gcacagaggc tgagaccatc ctggacaaca tcacccagag cacccagtcc | 660 |
| ttcaatgact tcaccagagt ggtgggagga gaggatgcca agcctggcca gttcccctgg | 720 |
| caggtggtgc tgaatggcaa ggtggatgcc ttctgtggag cagcattgt gaatgagaag | 780 |
| tggattgtga cagctgccca ctgtgtggag acaggagtga agatcacagt ggtggctgga | 840 |
| gagcacaaca ttgaggagac agagcacaca gagcagaaga ggaatgtgat caggatcatc | 900 |
| cctcaccaca actacaatgc tgccatcaac aagtacaacc atgacattgc cctgctggag | 960 |
| ctggatgagc tctggtgct gaacagctat gtgaccccta tctgcattgc tgacaaggag | 1020 |
| tacaccaaca tcttcctgaa gtttggctct ggctatgtgt ctggctgggg cagagtgttc | 1080 |
| cacaagggca ggtctgccct ggtgctgcag tacctgagag tgcccctggt ggacagagcc | 1140 |
| acctgcctgt tgagcaccaa gttcaccatc tacaacaaca tgttctgtgc tggcttccat | 1200 |
| gagggaggca gagacagctg ccaggtgac tctggaggac ccatgtgac agaggtggag | 1260 |
| ggcaccagct tcctgacagg catcatcagc tggggagagg agtgtgccat gaagggcaag | 1320 |
| tatggcatct acaccaaagt gagcagatat gtgaactgga tcaaggagaa gaccaagctg | 1380 |
| acctga | 1386 |

<210> SEQ ID NO 8
<211> LENGTH: 1386
<212> TYPE: DNA
<213> ORGANISM: Artificial Sequence
<220> FEATURE:
<223> OTHER INFORMATION: CS05-FL-NA

<400> SEQUENCE: 8

| | |
|---|---|
| atgcagaggg tgaacatgat tatggctgag agccctggcc tgatcaccat ctgcctgctg | 60 |
| ggctacctgc tgtctgctga gtgcactgtg ttcctggacc atgagaatgc caacaagatc | 120 |
| ctgaaccgcc ccaagcgcta caactctggc aagctggagg agtttgtgca gggcaacctg | 180 |
| gagagggagt gcatggagga gaagtgcagc tttgaggagg ccagggaggt gtttgagaac | 240 |
| actgagcgca ccactgagtt ctggaagcag tatgtggatg gggaccagtg tgagagcaac | 300 |
| ccctgcctga atgggggag ctgcaaggat gacatcaaca gctatgagtg ctggtgcccc | 360 |
| tttggctttg agggcaagaa ctgtgagctg gatgtgacct gcaacatcaa gaatggccgc | 420 |
| tgtgagcagt tctgcaagaa ctctgctgac aacaaggtgg tgtgctcttg cactgagggc | 480 |
| taccgcctgg ctgagaacca gaagagctgt gagcctgctg tgccttccc ctgtggcagg | 540 |
| gtgtctgtga gccagaccag caagctgacc agggctgaga ctgtgttccc tgacgtggac | 600 |
| tatgtgaaca gcactgaggc tgagaccatc ctggacaaca tcacccagag cacccagagc | 660 |
| ttcaatgact tcaccagggt ggtgggagga gaggatgcca agcctggcca gttccctgg | 720 |
| caggtggtgc tgaatggcaa ggtggatgcc ttctgtggag cagcattgt gaatgagaag | 780 |
| tggattgtga ccgctgccca ctgtgtggag actggagtga agatcactgt ggtggctggg | 840 |
| gagcacaaca ttgaggagac agagcacaca gagcagaagc gcaatgtgat caggatcatc | 900 |
| ccccaccaca actacaatgc tgccatcaac aagtacaacc atgacattgc cctgctggag | 960 |
| ctggatgagc cctggtgct gaacagctac gtgaccccca tctgcattgc agacaaggag | 1020 |
| tacaccaaca tcttcctgaa gtttggctct ggctatgtgt ctggctgggg cagggtgttc | 1080 |
| cacaagggca ggtctgccct ggtgctgcag tacctgaggg tgcccctggt ggacagggcc | 1140 |
| acctgcctgc tgagcaccaa gttcaccatc tacaacaaca tgttctgcgc tggcttccat | 1200 |

```
gagggaggaa gggacagctg ccagggagac tctggaggcc cccatgtgac agaggtggag    1260
ggcaccagct tcctgacagg catcatcagc tgggggagg agtgtgccat gaagggcaag    1320
tatggcatct acaccaaagt gtcccgctat gtgaactgga tcaaggagaa gaccaagctg   1380
acctga                                                              1386
```

<210> SEQ ID NO 9
<211> LENGTH: 1386
<212> TYPE: DNA
<213> ORGANISM: Artificial Sequence
<220> FEATURE:
<223> OTHER INFORMATION: CS06-FL-NA

<400> SEQUENCE: 9

```
atgcagaggg tcaacatgat catggctgag tcccctggcc tcatcaccat ctgcctgctg     60
ggctacctgc tgtctgctga gtgcactgtc ttcctggacc atgagaatgc caacaagatc    120
ctcaacaggc ccaagagata caactctggc aaactggagg agtttgtcca gggcaacctg    180
gagagggagt gcatggagga gaagtgctcc tttgaggagg ccagggaggt ctttgagaac    240
actgagcgca ccactgagtt ctggaaacag tatgtggatg gggaccagtg tgagtccaac    300
ccctgcctga atggggcag ctgcaaggat gacatcaaca gctatgagtg ctggtgcccc    360
tttggctttg agggcaagaa ctgtgagctg gatgtgacct gcaacatcaa gaatggcaga    420
tgtgagcagt tctgcaagaa ctctgctgac aacaaggtgg tgtgctcctg cactgagggc    480
taccgcctgg ctgagaacca gaagagctgt gagcctgctg tgccattccc atgtggcaga    540
gtctctgtga gccagaccag caagctcacc agggctgaga ctgtgttccc tgatgtggac    600
tatgtgaaca gcactgaggc tgaaaccatc ctggacaaca tcacccagag cacccagagc    660
ttcaatgact tcaccagagt ggtgggagga gaggatgcca agcctggcca gttcccctgg    720
caagtggtgc tcaatggcaa ggtggatgcc ttctgtgggg ctccattgt gaatgagaag    780 tggattgtca ctgctgccca ctgtgtggag actggggtca agatcactgt ggtggctggg    840
gagcacaaca ttgaggagac tgagcacact gagcagaagc gcaatgtgat caggatcatc    900
ccccaccaca actacaatgc tgccatcaac aagtacaacc atgacattgc cctgctggag    960
ctggatgagc ccctggtcct caacagctat gtgaccccca tctgcattgc tgacaaggag   1020
tacaccaaca tcttcctcaa gtttggctct ggctatgtct ctggctgggg cagagtgttc   1080
cacaaaggca gtctgccct ggtgctccag tacctgagag tgccctggt ggacagggcc   1140 acctgcctct tgagcaccaa gttcaccatc tacaacaaca tgttctgtgc tggcttccat   1200
gagggaggaa gagacagctg ccaggggac tctggaggac cccatgtcac tgaggtggag   1260
ggcacctcct tcctcactgg catcatctcc tgggagagg agtgtgccat gaaaggcaaa   1320
tatggcatct acaccaaagt ctccagatat gtcaactgga tcaaggagaa gaccaagctg   1380
acctga                                                              1386
```

<210> SEQ ID NO 10
<211> LENGTH: 415
<212> TYPE: PRT
<213> ORGANISM: Artificial Sequence
<220> FEATURE:
<223> OTHER INFORMATION: FIX-MP-AA

<400> SEQUENCE: 10

```
Tyr Asn Ser Gly Lys Leu Glu Glu Phe Val Gln Gly Asn Leu Glu Arg
1               5                   10                  15
```

Glu Cys Met Glu Glu Lys Cys Ser Phe Glu Ala Arg Glu Val Phe
               20                  25                  30

Glu Asn Thr Glu Arg Thr Thr Glu Phe Trp Lys Gln Tyr Val Asp Gly
         35                  40                  45

Asp Gln Cys Glu Ser Asn Pro Cys Leu Asn Gly Gly Ser Cys Lys Asp
 50                  55                  60

Asp Ile Asn Ser Tyr Glu Cys Trp Cys Pro Phe Gly Phe Glu Gly Lys
 65                  70                  75                  80

Asn Cys Glu Leu Asp Val Thr Cys Asn Ile Lys Asn Gly Arg Cys Glu
             85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
            115                 120                 125

Pro Phe Pro Cys Gly Arg Val Ser Val Ser Gln Thr Ser Lys Leu Thr
     130                 135                 140

Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
     195                 200                 205

Ser Ile Val Asn Glu Lys Trp Ile Val Thr Ala Ala His Cys Val Glu
            210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270

Leu Glu Leu Asp Glu Pro Leu Val Leu Asn Ser Tyr Val Thr Pro Ile
     275                 280                 285

Cys Ile Ala Asp Lys Glu Tyr Thr Asn Ile Phe Leu Lys Phe Gly Ser
290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Arg Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
     355                 360                 365

His Val Thr Glu Val Glu Gly Thr Ser Phe Leu Thr Gly Ile Ile Ser
     370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr
                405                 410                 415

<210> SEQ ID NO 11
<211> LENGTH: 377

```
<212> TYPE: PRT
<213> ORGANISM: Artificial Sequence
<220> FEATURE:
<223> OTHER INFORMATION: FIX2-MP-AA

<400> SEQUENCE: 11

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Val
        35                  40                  45

Thr Cys Asn Ile Lys Asn Gly Arg Cys Glu Gln Phe Cys Lys Asn Ser
    50                  55                  60

Ala Asp Asn Lys Val Val Cys Ser Cys Thr Glu Gly Tyr Arg Leu Ala
65                  70                  75                  80

Glu Asn Gln Lys Ser Cys Glu Pro Ala Val Pro Phe Pro Cys Gly Arg
            85                  90                  95

Val Ser Val Ser Gln Thr Ser Lys Leu Thr Arg Ala Glu Thr Val Phe
            100                 105                 110

Pro Asp Val Asp Tyr Val Asn Ser Thr Glu Ala Glu Thr Ile Leu Asp
            115                 120                 125

Asn Ile Thr Gln Ser Thr Gln Ser Phe Asn Asp Phe Thr Arg Val Val
130                 135                 140

Gly Gly Glu Asp Ala Lys Pro Gly Gln Phe Pro Trp Gln Val Val Leu
145                 150                 155                 160

Asn Gly Lys Val Asp Ala Phe Cys Gly Gly Ser Ile Val Asn Glu Lys
                165                 170                 175

Trp Ile Val Thr Ala Ala His Cys Val Glu Thr Gly Val Lys Ile Thr
            180                 185                 190

Val Val Ala Gly Glu His Asn Ile Glu Glu Thr Glu His Thr Glu Gln
            195                 200                 205

Lys Arg Asn Val Ile Arg Ile Ile Pro His His Asn Tyr Asn Ala Ala
210                 215                 220

Ile Asn Lys Tyr Asn His Asp Ile Ala Leu Leu Glu Leu Asp Glu Pro
225                 230                 235                 240

Leu Val Leu Asn Ser Tyr Val Thr Pro Ile Cys Ile Ala Asp Lys Glu
                245                 250                 255

Tyr Thr Asn Ile Phe Leu Lys Phe Gly Ser Gly Tyr Val Ser Gly Trp
            260                 265                 270

Gly Arg Val Phe His Lys Gly Arg Ser Ala Leu Val Leu Gln Tyr Leu
            275                 280                 285

Arg Val Pro Leu Val Asp Arg Ala Thr Cys Leu Arg Ser Thr Lys Phe
290                 295                 300

Thr Ile Tyr Asn Asn Met Phe Cys Ala Gly Phe His Glu Gly Gly Arg
305                 310                 315                 320

Asp Ser Cys Gln Gly Asp Ser Gly Gly Pro His Val Thr Glu Val Glu
                325                 330                 335

Gly Thr Ser Phe Leu Thr Gly Ile Ile Ser Trp Gly Glu Glu Cys Ala
            340                 345                 350

Met Lys Gly Lys Tyr Gly Ile Tyr Thr Lys Val Ser Arg Tyr Val Asn
            355                 360                 365

Trp Ile Lys Glu Lys Thr Lys Leu Thr
    370                 375
```

<210> SEQ ID NO 12
<211> LENGTH: 415
<212> TYPE: PRT
<213> ORGANISM: Artificial Sequence
<220> FEATURE:
<223> OTHER INFORMATION: FIXp-MP-AA

<400> SEQUENCE: 12

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270

Leu Glu Leu Asp Glu Pro Leu Val Leu Asn Ser Tyr Val Thr Pro Ile
        275                 280                 285

Cys Ile Ala Asp Lys Glu Tyr Thr Asn Ile Phe Leu Lys Phe Gly Ser
    290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Leu Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
        355                 360                 365

His Val Thr Glu Val Glu Gly Thr Ser Phe Leu Thr Gly Ile Ile Ser
    370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr
                405                 410                 415

<210> SEQ ID NO 13
<211> LENGTH: 1248
<212> TYPE: DNA
<213> ORGANISM: Artificial Sequence
<220> FEATURE:
<223> OTHER INFORMATION: CS02-MP-NA

<400> SEQUENCE: 13

```
tacaactcag gcaagctgga ggagtttgtg cagggcaacc tggagaggga gtgcatggag      60
gagaagtgca gctttgagga ggccagagag gtgtttgaga acacagagag gaccacagag     120
ttctggaagc agtatgtgga tggagaccag tgtgagagca acccttgcct gaatggaggc     180
agctgcaagg atgacatcaa cagctatgag tgctggtgcc ttttggctt tgagggcaag      240
aactgtgagc tggatgtgac ctgcaacatc aagaatggca gtgtgagca gttctgcaag      300
aactcagctg acaacaaagt ggtgtgtagc tgcacagagg ctacagact ggctgagaac      360
cagaagagct gtgagcctgc tgtgccctc ccctgtggca gagtgtcagt gtcccagacc      420
agcaagctga ccagagctga cagtgttc cctgatgtgg actatgtgaa tagcacagag      480
gctgagacca tcctggacaa catcacccag agcacccagt ccttcaatga cttcaccaga     540
gttgtgggag gagaggatgc caagcctggc cagttcccct ggcaggtggt gctgaatggc     600
aaagtggatg ccttctgtgg aggcagcatt gtgaatgaga gtggattgt gacagctgcc      660
cactgtgtgg agacaggagt gaagatcaca gtggtggctg agaacacaa tattgaggag      720
acagagcaca cagagcagaa gaggaatgtc atcaggatta ccccccacca caactacaat      780
gctgccatca acaagtacaa ccatgacatt gccctgctgg agctggatga gcctctggtg      840
ctgaatagct atgtgacccc catctgcatt gctgacaagg agtacaccaa catcttcctg      900
aagtttggct caggctatgt gtcaggctgg ggcagagtgt ccacaaggg cagatcagcc      960
ctggtgctgc agtacctgag agtgcccctg gtgacagag ccacctgcct gttgagcacc     1020
aagttccacca tctacaacaa catgttctgt gctggcttcc atgagggagg cagagacagc     1080
tgccagggag actcaggagg accccatgtg acagaagtgg agggcaccag cttcctgaca     1140
ggcatcatca gctggggaga ggagtgtgcc atgaagggca gtatggcat ctacaccaaa     1200
gtgagcagat atgtgaactg gatcaaggag aaaaccaagc tgacctga                1248
```

<210> SEQ ID NO 14
<211> LENGTH: 1248
<212> TYPE: DNA
<213> ORGANISM: Artificial Sequence
<220> FEATURE:
<223> OTHER INFORMATION: CS03-MP-NA

<400> SEQUENCE: 14

```
tacaactctg gcaagctgga ggagtttgtg cagggcaacc tggagaggga gtgcatggag      60
gagaagtgca gctttgagga ggccagggaa gtgtttgaga cactgagag gaccactgag      120
ttctggaagc agtatgtgga tggggaccag tgtgagagca acccttgcct gaatgggggc     180
agctgcaagg atgacatcaa cagctatgag tgctggtgcc ttttggctt tgagggcaag      240
```

```
aactgtgagc tggatgtgac ctgcaacatc aagaatggca ggtgtgagca gttctgcaag    300
aactctgctg acaacaaagt ggtgtgtagc tgcactgagg gctacagact ggctgagaac    360
cagaagagct gtgagcctgc tgtgcccttc cctgtggca gagtgtctgt gtcccagacc     420
agcaagctga ccagagctga gactgtgttc cctgatgtgg actatgtgaa tagcactgag    480
gctgagacca tcctggacaa catcacccag agcacccagt ccttcaatga cttcaccaga    540
gtggtggggg gggaggatgc caagcctggc cagttcccct ggcaggtggt gctgaatggc    600
aaagtggatg ccttctgtgg gggcagcatt gtgaatgaga agtggattgt gactgctgcc    660
cactgtgtgg agactggggt gaagatcact gtggtggctg ggaacacaa tattgaggag     720 actgagcaca ctgagcagaa gaggaatgtc atcaggatta ccccccacca caactacaat    780
gctgccatca acaagtacaa ccatgacatt gccctgctgg agctggatga gcctctggtg    840
ctgaatagct atgtgacccc catctgcatt gctgacaagg agtacaccaa catcttcctg    900
aagtttggct ctggctatgt gtctggctgg ggcagagtgt tccacaaggg caggtctgcc    960
ctggtgctgc agtacctgag agtgcccctg gtggacagag ccacctgcct gctgagcacc    1020
aagttcacca tctacaacaa catgttctgt gctggcttcc atgagggggg cagagacagc    1080
tgccaggggg actctggggg cccccatgtg actgaagtgg agggcaccag cttcctgact    1140
ggcatcatca gctgggggga ggagtgtgcc atgaagggca gtatggcat ctacaccaaa     1200 gtgagcaggt atgtgaactg gatcaaggag aaaaccaagc tgacctga                 1248

```

<210> SEQ ID NO 15
<211> LENGTH: 1250
<212> TYPE: DNA
<213> ORGANISM: Artificial Sequence
<220> FEATURE:
<223> OTHER INFORMATION: CS04-MP-NA
<400> SEQUENCE: 15

```
cstacaactc tggcaagctg gaggagtttg tgcagggcaa cctggagagg gagtgcatgg     60
aggagaagtg cagctttgag gaggccaggg aggtgtttga aacacagag aggaccacag      120 agttctggaa gcagtatgtg gatggtgacc agtgtgagag caacccttgc ctgaatggag     180
gcagctgcaa ggatgacatc aacagctatg agtgctggtg cccttttggc tttgagggca    240
agaactgtga gctggatgtg acctgcaaca tcaagaatgg caggtgtgag cagttctgca    300
agaactctgc tgacaacaag gtggtgtgta gctgcacaga gggctacaga ctggctgaga    360
accagaagag ctgtgagcct gctgtgccct tccctgtgg cagagtgtct gtgtcccaga     420
ccagcaagct gaccagagct gagacagtgt tccctgatgt ggactatgtg aacagcacag    480
aggctgagac catcctggac aacatcaccc agagcaccca gtccttcaat gacttcacca    540
gagtggtggg aggagaggat gccaagcctg gccagttccc ctggcaggtg gtgctgaatg    600
gcaaggtgga tgccttctgt ggaggcagca ttgtgaatga agtggatt gtgacagctg       660 cccactgtgt ggagacagga gtgaagatca cagtggtggc tggagagcac aacattgagg    720
agacagagca cacagagcag aagaggaatg tgatcaggat catccctcac acaactaca     780 atgctgccat caacaagtac aaccatgaca ttgccctgct ggagctggat gagcctctgg    840
tgctgaacag ctatgtgacc cctatctgca ttgctgacaa ggagtacacc aacatcttcc    900
tgaagtttgg ctctggctat gtgtctggct ggggcagagt gttccacaag gcaggtctg    960 ccctggtgct gcagtacctg agagtgcccc tggtggacag agccacctgc ctgttgagca    1020
ccaagttcac catctacaac aacatgttct gtgctggctt ccatgaggga ggcagagaca    1080
```

```
gctgccaggg tgactctgga ggaccccatg tgacagaggt ggagggcacc agcttcctga    1140
caggcatcat cagctgggga gaggagtgtg ccatgaaggg caagtatggc atctacacca    1200
aagtgagcag atatgtgaac tggatcaagg agaagaccaa gctgacctga              1250
```

<210> SEQ ID NO 16
<211> LENGTH: 1248
<212> TYPE: DNA
<213> ORGANISM: Artificial Sequence
<220> FEATURE:
<223> OTHER INFORMATION: CS05-MP-NA

<400> SEQUENCE: 16

```
tacaactctg gcaagctgga ggagtttgtg cagggcaacc tggagaggga gtgcatggag     60
gagaagtgca gctttgagga ggccagggag gtgtttgaga acactgagcg caccactgag    120
ttctggaagc agtatgtgga tggggaccag tgtgagagca ccccctgcct gaatgggggg    180
agctgcaagg atgacatcaa cagctatgag tgctggtgcc cctttggctt tgagggcaag    240
aactgtgagc tggatgtgac ctgcaacatc aagaatggcc gctgtgagca gttctgcaag    300
aactctgctg acaacaaggt ggtgtgctct tgcactgagg gctaccgcct ggctgagaac    360
cagaagagct gtgagcctgc tgtgcccttc ccctgtggca gggtgtctgt gagccagacc    420
agcaagctga ccagggctga gactgtgttc cctgacgtgg actatgtgaa cagcactgag    480
gctgagacca tcctggacaa catcacccag agcacccaga gcttcaatga cttcaccagg    540
gtggtgggag gagaggatgc caagcctggc cagttcccct ggcaggtggt gctgaatggc    600
aaggtggatg ccttctgtgg aggcagcatt gtgaatgaga gtggattgt gaccgctgcc    660 cactgtgtgg agactggagt gaagatcact gtggtggctg gggagcacaa cattgaggag    720
acagagcaca cagagcagaa gcgcaatgtg atcaggatca tcccccacca caactacaat    780
gctgccatca caagtacaa ccatgacatt gccctgctgg agctggatga gccctggtg    840 ctgaacagct acgtgacccc catctgcatt gcagacaagg agtacaccaa catcttcctg    900
aagtttggct ctggctatgt gtctggctgg ggcagggtgt tccacaaggg caggtctgcc    960
ctggtgctgc agtacctgag ggtgcccctg gtggacaggg ccacctgcct gctgagcacc    1020
aagttcacca tctacaacaa catgttctgc gctggcttcc atgagggag aagggacagc    1080 tgccagggag actctggagg cccccatgtg acagaggtga gggcaccag cttcctgaca    1140 ggcatcatca gctgggggga ggagtgtgcc atgaagggca agtatggcat ctacaccaaa    1200
gtgtcccgct atgtgaactg gatcaaggag aagaccaagc tgacctga                1248
```

<210> SEQ ID NO 17
<211> LENGTH: 1248
<212> TYPE: DNA
<213> ORGANISM: Artificial Sequence
<220> FEATURE:
<223> OTHER INFORMATION: CS06-MP-NA

<400> SEQUENCE: 17

```
tacaactctg gcaaactgga ggagtttgtc cagggcaacc tggagaggga gtgcatggag     60
gagaagtgct cctttgagga ggccagggag gtctttgaga acactgagcg caccactgag    120
ttctggaaac agtatgtgga tggggaccag tgtgagtcca ccccctgcct gaatgggggc    180
agctgcaagg atgacatcaa cagctatgag tgctggtgcc cctttggctt tgagggcaag    240
aactgtgagc tggatgtgac ctgcaacatc aagaatggcc gatgtgagca gttctgcaag    300
```

```
aactctgctg acaacaaggt ggtgtgctcc tgcactgagg gctaccgcct ggctgagaac      360
cagaagagct gtgagcctgc tgtgccattc ccatgtggca gagtctctgt gagccagacc      420
agcaagctca ccagggctga gactgtgttc cctgatgtgg actatgtgaa cagcactgag      480
gctgaaacca tcctggacaa catcacccag agcacccaga gcttcaatga cttcaccaga      540
gtggtgggag gagaggatgc caagcctggc cagttcccct ggcaagtggt gctcaatggc      600
aaggtggatg ccttctgtgg gggctccatt gtgaatgaga agtggattgt cactgctgcc      660
cactgtgtgg agactggggt caagatcact gtggtggctg gggagcacaa cattgaggag      720
actgagcaca ctgagcagaa gcgcaatgtg atcaggatca tcccccacca caactacaat      780
gctgccatca acaagtacaa ccatgacatt gccctgctgg agctggatga gcccctggtc      840
ctcaacagct atgtgacccc catctgcatt gctgacaagg agtacaccaa catcttcctc      900
aagtttggct ctggctatgt ctctggctgg ggcagagtgt ccacaaagg caggtctgcc       960 ctggtgctcc agtacctgag agtgcccctg gtggacaggg ccacctgcct cttgagcacc     1020
aagttcacca tctacaacaa catgttctgt gctggcttcc atgagggagg aagagacagc     1080
tgccaggggg actctggagg accccatgtc actgaggtgg agggcaccctc cttcctcact    1140 ggcatcatct cctggggaga ggagtgtgcc atgaaaggca aatatggcat ctacaccaaa     1200
gtctccagat atgtcaactg gatcaaggag aagaccaagc tgacctga                 1248

<210> SEQ ID NO 18
<211> LENGTH: 138
<212> TYPE: DNA
<213> ORGANISM: Artificial Sequence
<220> FEATURE:
<223> OTHER INFORMATION: FIX-PPP-NA

<400> SEQUENCE: 18
atgcagcgcg tgaacatgat catggcagaa tcaccaggcc tcatcaccat ctgcctttta       60
ggatatctac tcagtgctga atgtacagtt tttcttgatc atgaaaacgc caacaaaatt      120
ctgaatcggc caaagagg                                                    138

<210> SEQ ID NO 19
<211> LENGTH: 138
<212> TYPE: DNA
<213> ORGANISM: Artificial Sequence
<220> FEATURE:
<223> OTHER INFORMATION: CS02-PPP-NA

<400> SEQUENCE: 19
atgcagaggg tgaacatgat catggctgag agccctggcc tgatcaccat ctgcctgctg       60
ggctacctgc tgtcagcaga gtgcacagtg ttcctggacc atgagaatgc caacaagatc      120
ctgaacaggc ccaagaga                                                    138

<210> SEQ ID NO 20
<211> LENGTH: 138
<212> TYPE: DNA
<213> ORGANISM: Artificial Sequence
<220> FEATURE:
<223> OTHER INFORMATION: CS03-PPP-NA

<400> SEQUENCE: 20
atgcagaggg tgaacatgat catggctgag agccctggcc tgatcaccat ctgcctgctg       60
ggctacctgc tgtctgctga gtgcactgtg ttcctggacc atgagaatgc caacaagatc      120
ctgaacaggc ccaagaga                                                    138
```

```
<210> SEQ ID NO 21
<211> LENGTH: 138
<212> TYPE: DNA
<213> ORGANISM: Artificial Sequence
<220> FEATURE:
<223> OTHER INFORMATION: CS04-PPP-NA

<400> SEQUENCE: 21
atgcagaggg tgaacatgat tatggctgag agccctggcc tgatcaccat ctgcctgctg      60
ggctacctgc tgtctgctga gtgcacagtg ttcctggacc atgagaatgc caacaagatc     120
ctgaacaggc ccaagaga                                                   138

<210> SEQ ID NO 22
<211> LENGTH: 138
<212> TYPE: DNA
<213> ORGANISM: Artificial Sequence
<220> FEATURE:
<223> OTHER INFORMATION: CS05-PPP-NA

<400> SEQUENCE: 22
atgcagaggg tgaacatgat tatggctgag agccctggcc tgatcaccat ctgcctgctg      60
ggctacctgc tgtctgctga gtgcactgtg ttcctggacc atgagaatgc caacaagatc     120
ctgaaccgcc ccaagcgc                                                   138

<210> SEQ ID NO 23
<211> LENGTH: 138
<212> TYPE: DNA
<213> ORGANISM: Artificial Sequence
<220> FEATURE:
<223> OTHER INFORMATION: CS06-PPP-NA

<400> SEQUENCE: 23
atgcagaggg tcaacatgat catggctgag tccctggcc tcatcaccat ctgcctgctg       60
ggctacctgc tgtctgctga gtgcactgtc ttcctggacc atgagaatgc caacaagatc     120
ctcaacaggc ccaagaga                                                   138

<210> SEQ ID NO 24
<211> LENGTH: 84
<212> TYPE: DNA
<213> ORGANISM: Artificial Sequence
<220> FEATURE:
<223> OTHER INFORMATION: FIX-SP-NA

<400> SEQUENCE: 24
atgcagcgcg tgaacatgat catggcagaa tcaccaggcc tcatcaccat ctgcctttta      60
ggatatctac tcagtgctga atgt                                             84

<210> SEQ ID NO 25
<211> LENGTH: 84
<212> TYPE: DNA
<213> ORGANISM: Artificial Sequence
<220> FEATURE:
<223> OTHER INFORMATION: CS02-SP-NA

<400> SEQUENCE: 25
atgcagaggg tgaacatgat catggctgag agccctggcc tgatcaccat ctgcctgctg      60
ggctacctgc tgtcagcaga gtgc                                             84

<210> SEQ ID NO 26
```

```
<211> LENGTH: 84
<212> TYPE: DNA
<213> ORGANISM: Artificial Sequence
<220> FEATURE:
<223> OTHER INFORMATION: CS03-SP-NA

<400> SEQUENCE: 26
atgcagaggg tgaacatgat catggctgag agccctggcc tgatcaccat ctgcctgctg      60
ggctacctgc tgtctgctga gtgc                                             84

<210> SEQ ID NO 27
<211> LENGTH: 84
<212> TYPE: DNA
<213> ORGANISM: Artificial Sequence
<220> FEATURE:
<223> OTHER INFORMATION: CS04-SP-NA

<400> SEQUENCE: 27
atgcagaggg tgaacatgat tatggctgag agccctggcc tgatcaccat ctgcctgctg      60
ggctacctgc tgtctgctga gtgc                                             84

<210> SEQ ID NO 28
<211> LENGTH: 84
<212> TYPE: DNA
<213> ORGANISM: Artificial Sequence
<220> FEATURE:
<223> OTHER INFORMATION: CS05-SP-NA

<400> SEQUENCE: 28
atgcagaggg tgaacatgat tatggctgag agccctggcc tgatcaccat ctgcctgctg      60
ggctacctgc tgtctgctga gtgc                                             84

<210> SEQ ID NO 29
<211> LENGTH: 84
<212> TYPE: DNA
<213> ORGANISM: Artificial Sequence
<220> FEATURE:
<223> OTHER INFORMATION: CS06--SP-NA

<400> SEQUENCE: 29
atgcagaggg tcaacatgat catggctgag tccctggcc tcatcaccat ctgcctgctg       60
ggctacctgc tgtctgctga gtgc                                             84

<210> SEQ ID NO 30
<211> LENGTH: 54
<212> TYPE: DNA
<213> ORGANISM: Artificial Sequence
<220> FEATURE:
<223> OTHER INFORMATION: FIX-PP-NA

<400> SEQUENCE: 30 acagttttc ttgatcatga aaacgccaac aaaattctga atcggccaaa gagg             54

<210> SEQ ID NO 31
<211> LENGTH: 54
<212> TYPE: DNA
<213> ORGANISM: Artificial Sequence
<220> FEATURE:
<223> OTHER INFORMATION: CS02-PP-NA

<400> SEQUENCE: 31
acagtgttcc tggaccatga gaatgccaac aagatcctga acaggcccaa gaga            54
```

```
<210> SEQ ID NO 32
<211> LENGTH: 54
<212> TYPE: DNA
<213> ORGANISM: Artificial Sequence
<220> FEATURE:
<223> OTHER INFORMATION: CS03-PP-NA

<400> SEQUENCE: 32
actgtgttcc tggaccatga gaatgccaac aagatcctga acaggcccaa gaga      54

<210> SEQ ID NO 33
<211> LENGTH: 54
<212> TYPE: DNA
<213> ORGANISM: Artificial Sequence
<220> FEATURE:
<223> OTHER INFORMATION: CS04-PP-NA

<400> SEQUENCE: 33
acagtgttcc tggaccatga gaatgccaac aagatcctga acaggcccaa gaga      54

<210> SEQ ID NO 34
<211> LENGTH: 54
<212> TYPE: DNA
<213> ORGANISM: Artificial Sequence
<220> FEATURE:
<223> OTHER INFORMATION: CS05-PP-NA

<400> SEQUENCE: 34
actgtgttcc tggaccatga gaatgccaac aagatcctga accgcccaa gcgc       54

<210> SEQ ID NO 35
<211> LENGTH: 54
<212> TYPE: DNA
<213> ORGANISM: Artificial Sequence
<220> FEATURE:
<223> OTHER INFORMATION: CS06-PP-NA

<400> SEQUENCE: 35
actgtcttcc tggaccatga gaatgccaac aagatcctca acaggcccaa gaga      54

<210> SEQ ID NO 36
<211> LENGTH: 46
<212> TYPE: PRT
<213> ORGANISM: Artificial Sequence
<220> FEATURE:
<223> OTHER INFORMATION: FIX-PPP-AA

<400> SEQUENCE: 36

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg
        35                  40                  45

<210> SEQ ID NO 37
<211> LENGTH: 28
<212> TYPE: PRT
<213> ORGANISM: Artificial Sequence
<220> FEATURE:
<223> OTHER INFORMATION: FIX-SP-AA

<400> SEQUENCE: 37

Met Gln Arg Val Asn Met Ile Met Ala Glu Ser Pro Gly Leu Ile Thr
1               5                   10                  15
```

Ile Cys Leu Leu Gly Tyr Leu Leu Ser Ala Glu Cys
            20                  25

<210> SEQ ID NO 38
<211> LENGTH: 18
<212> TYPE: PRT
<213> ORGANISM: Artificial Sequence
<220> FEATURE:
<223> OTHER INFORMATION: FIX-PP-AA

<400> SEQUENCE: 38

Thr Val Phe Leu Asp His Glu Asn Ala Asn Lys Ile Leu Asn Arg Pro
1               5                   10                  15

Lys Arg

<210> SEQ ID NO 39
<211> LENGTH: 72
<212> TYPE: DNA
<213> ORGANISM: Artificial Sequence
<220> FEATURE:
<223> OTHER INFORMATION: CRM8

<400> SEQUENCE: 39
gggggaggct gctggtgaat attaaccaag gtcaccccag ttatcggagg agcaaacagg    60
ggctaagtcc ac                                                       72

<210> SEQ ID NO 40
<211> LENGTH: 5276
<212> TYPE: DNA
<213> ORGANISM: Artificial Sequence
<220> FEATURE:
<223> OTHER INFORMATION: CS06-CRM8.3-ssV

<400> SEQUENCE: 40
ttggccactc cctctctgcg cgctcgctcg ctcactgagg ccgggcgacc aaaggtcgcc    60
cgacgcccgg gctttgcccg gcggcctca gtgagcgagc gagcgcgcag agagggagtg    120
gccaactcca tcactagggg ttcctgagtt taaacttcgt cgacggggga ggctgctggt    180
gaatattaac caaggtcacc ccagttatcg gaggagcaaa caggggctaa gtccaccggg    240
ggaggctgct ggtgaatatt aaccaaggtc accccagtta tcggaggagc aaacaggggc    300
taagtccacc gggggaggct gctggtgaat attaaccaag gtcaccccag ttatcggagg    360
agcaaacagg ggctaagtcc accgagggca ctggaggat gttgagtaag atggaaaact    420
actgatgacc cttgcagaga cagagtatta ggacatgttt gaacaggggc cgggcgatca    480
gcaggtagct ctagaggatc cccgtctgtc tgcacatttc gtagagcgag tgttccgata    540
ctctaatctc cctaggcaag gttcatattt gtgtaggtta cttattctcc ttttgttgac    600
taagtcaata atcagaatca gcaggtttgg agtcagcttg gcagggatca gcagcctggg    660
ttggaaggag ggggtataaa agccccttca ccaggagaag ccgtcacaca gactaggcgc    720
gccctaaggt aagttggcgc cgtttaaggg atggttggtt ggtggggtat taatgtttaa    780 ttacctttt tacaggcctg aagatctgcc accatgcaga gggtcaacat gatcatggct    840
gagtcccctg gcctcatcac catctgcctg ctgggctacc tgctgtctgc tgagtgcact    900
gtcttcctgg accatgagaa tgccaacaag atcctcaaca gcccaagag atacaactct    960 ggcaaactgg aggagtttgt ccagggcaac ctgagagggg agtgcatgga ggagaagtgc    1020 tccttgagg aggccaggga ggtctttgag aacactgagc gcaccactga gttctggaaa    1080
cagtatgtgg atggggacca gtgtgagtcc aaccctgcc tgaatggggg cagctgcaag    1140

```
gatgacatca acagctatga gtgctggtgc cccttttggct ttgagggcaa gaactgtgag    1200
ctggatgtga cctgcaacat caagaatggc agatgtgagc agttctgcaa gaactctgct    1260
gacaacaagg tggtgtgctc ctgcactgag ggctaccgcc tggctgagaa ccagaagagc    1320
tgtgagcctg ctgtgccatt cccatgtggc agagtctctg tgagccagac cagcaagctc    1380
accagggctg agactgtgtt ccctgatgtg gactatgtga acagcactga ggctgaaacc    1440
atcctggaca catcacccca gagcacccag agcttcaatg acttcaccag agtggtggga    1500
ggagaggatg ccaagcctgg ccagttcccc tggcaagtgg tgctcaatgg caaggtggat    1560
gccttctgtg ggggctccat tgtgaatgag aagtggattg tcactgctgc ccactgtgtg    1620
gagactgggg tcaagatcac tgtggtggct ggggagcaca acattgagga gactgagcac    1680
actgagcaga agcgcaatgt gatcaggatc atcccccacc acaactacaa tgctgccatc    1740
aacaagtaca accatgacat tgccctgctg agctggatg agccctggt cctcaacagc      1800 tatgtgaccc ccatctgcat tgctgacaag gagtacacca acatcttcct caagtttggc    1860
tctggctatg tctctggctg gggcagagtg ttccacaaag gcaggtctgc cctggtgctc    1920
cagtacctga gagtgcccct ggtggacagg gccacctgcc tcttgagcac caagttcacc    1980
atctacaaca acatgttctg tgctggcttc catgagggag gaagagacag ctgccagggg    2040
gactctggag acccccatgt cactgaggtg gagggcacct ccttcctcac tggcatcatc    2100
tcctggggag aggagtgtgc catgaaaggc aaatatggca tctacaccaa agtctccaga    2160
tatgtcaact ggatcaagga gaagaccaag ctgacctgat gagcatgcct agagctcgct    2220
gatcagcctc gactgtgcct tctagttgcc agccatctgt tgtttgcccc tcccccgtgc    2280
cttccttgac cctggaaggt gccactccca ctgtcctttc ctaataaaat gaggaaattg    2340
catcgcattg tctgagtagg tgtcattcta ttctgggggg tggggtgggg caggacagca    2400
agggggagga ttgggaagac aatagcaggc atgctgggga attaattaag ctcgcgaagg    2460
aacccctagt gatggagttg ccactccct ctctgcgcgc tcgctcgctc actgaggccg      2520
ggcgaccaaa ggtcgcccga cgcccgggct ttgcccgggc ggcctcagtg agcgagcgag    2580
cgcgcagaga gggagtggcc aagacgattt aaatgacaag cttggcgtaa tcatggtcat    2640 agctgttttcc tgtgtgaaat tgttatccgc tcacaattcc acacaacata cgagccggaa    2700
gcataaagtg taaagcctgg ggtgcctaat gagtgagcta actcacatta attgcgttgc    2760
gctcactgcc cgctttccag tcgggaaacc tgtcgtgcca gctgcattaa tgaatcggcc    2820
aacgcgcggg gagaggcggt ttgcgtattg ggcgctcttc cgcttcctcg ctcactgact    2880
cgctgcgctc ggtcgttcgg ctgcggcgag cggtatcagc tcactcaaag gcggtaatac    2940
ggttatccac agaatcaggg gataacgcag gaaagaacat gtgagcaaaa ggccagcaaa    3000
aggccaggaa ccgtaaaaag gccgcgttgc tggcgttttt ccataggctc cgcccccctg    3060
acgagcatca caaaaatcga cgctcaagtc agaggtggcg aaacccgaca ggactataaa    3120
gataccaggc gtttccccct ggaagctccc tcgtgcgctc tcctgttccg accctgccgc    3180
ttaccggata cctgtccgcc tttctcccct tcgggaagcgt ggcgctttct catagctcac    3240
gctgtaggta tctcagttcg gtgtaggtcg ttcgctccaa gctgggctgt gtgcacgaac    3300
cccccgttca gcccgaccgc tgcgccttat ccggtaacta tcgtcttgag tccaacccgg    3360
taagacacga cttatcgcca ctggcagcag ccactggtaa caggattagc agagcgaggt    3420
atgtaggcgg tgctacagag ttcttgaagt ggtggcctaa ctacggctac actagaagaa    3480
```

| | |
|---|---|
| cagtatttgg tatctgcgct ctgctgaagc cagttacctt cggaaaaaga gttggtagct | 3540 |
| cttgatccgg caaacaaacc accgctggta gcggtggttt ttttgtttgc aagcagcaga | 3600 |
| ttacgcgcag aaaaaaagga tctcaagaag atcctttgat cttttctacg gggtctgacg | 3660 |
| ctcagtggaa cgaaaactca cgttaaggga ttttggtcat gagattatca aaaggatct | 3720 |
| tcacctagat ccttttaaat taaaaatgaa gttttaaatc aatctaaagt atatatgagt | 3780 |
| aaacttggtc tgacagttac caatgcttaa tcagtgaggc acctatctca gcgatctgtc | 3840 |
| tatttcgttc atccatagtt gcctgactcc ccgtcgtgta gataactacg atacgggagg | 3900 |
| gcttaccatc tggccccagt gctgcaatga taccgcgaga cccacgctca ccggctccag | 3960 |
| atttatcagc aataaaccag ccagccggaa gggccgagcg cagaagtggt cctgcaactt | 4020 |
| tatccgcctc catccagtct attaattgtt gccgggaagc tagagtaagt agttcgccag | 4080 |
| ttaatagttt gcgcaacgtt gttgccattg ctacaggcat cgtggtgtca cgctcgtcgt | 4140 |
| ttggtatggc ttcattcagc tccggttccc aacgatcaag gcgagttaca tgatccccca | 4200 |
| tgttgtgcaa aaaagcggtt agctccttcg gtcctccgat cgttgtcaga agtaagttgg | 4260 |
| ccgcagtgtt atcactcatg gttatggcag cactgcataa ttctcttact gtcatgccat | 4320 |
| ccgtaagatg cttttctgtg actggtgagt actcaaccaa gtcattctga atagtgta | 4380 |
| tgcggcgacc gagttgctct tgcccggcgt caatacggga taataccgcg ccacatagca | 4440 |
| gaactttaaa agtgctcatc attggaaaac gttcttcggg gcgaaaactc tcaaggatct | 4500 |
| taccgctgtt gagatccagt tcgatgtaac ccactcgtgc acccaactga tcttcagcat | 4560 |
| cttttacttt caccagcgtt tctgggtgag caaaaacagg aaggcaaaat gccgcaaaaa | 4620 |
| agggaataag ggcgacacgg aaatgttgaa tactcatact cttcctttt caatattatt | 4680 |
| gaagcattta tcagggttat tgtctcatga gcggatacat atttgaatgt atttagaaaa | 4740 |
| ataaacaaat aggggttccg cgcacatttc cccgaaaagt gccacctgac gtctaagaaa | 4800 |
| ccattattat catgacatta acctataaaa ataggcgtat cacgaggccc tttcgtctcg | 4860 |
| cgcgtttcgg tgatgacggt gaaaacctct gacacatgca gctcccggag acggtcacag | 4920 |
| cttgtctgta agcggatgcc gggagcagac aagcccgtca gggcgcgtca gcgggtgttg | 4980 |
| gcgggtgtcg gggctggctt aactatgcgg catcagagca gattgtactg agagtgcacc | 5040 |
| atatgcggtg tgaaataccg cacagatgcg taaggagaaa ataccgcatc aggcgccatt | 5100 |
| cgccattcag gctgcgcaac tgttgggaag ggcgatcggt gcgggcctct tcgctattac | 5160 |
| gccagctggc gaaagggga tgtgctgcaa ggcgattaag ttgggtaacg ccagggtttt | 5220 |
| cccagtcacg acgttgtaaa acgacggcca gtgaattcct cgagatttaa atgacg | 5276 |

<210> SEQ ID NO 41
<211> LENGTH: 702
<212> TYPE: DNA
<213> ORGANISM: Artificial Sequence
<220> FEATURE:
<223> OTHER INFORMATION: CS02-HC-NA

<400> SEQUENCE: 41

| | |
|---|---|
| gttgtgggag gagaggatgc caagcctggc cagttcccct ggcaggtggt gctgaatggc | 60 |
| aaagtggatg ccttctgtgg aggcagcatt gtgaatgaga agtggattgt gacagctgcc | 120 |
| cactgtgtgg agacaggagt gaagatcaca gtggtggctg agaacacaa tattgaggag | 180 |
| acagagcaca cagagcagaa gaggaatgtc atcaggatta tccccccacca caactacaat | 240 |
| gctgccatca acaagtacaa ccatgacatt gccctgctgg agctggatga gcctctggtg | 300 |

```
ctgaatagct atgtgacccc catctgcatt gctgacaagg agtacaccaa catcttcctg    360
aagtttggct caggctatgt gtcaggctgg ggcagagtgt tccacaaggg cagatcagcc    420
ctggtgctgc agtacctgag agtgcccctg gtggacagag ccacctgcct gttgagcacc    480
aagttcacca tctacaacaa catgttctgt gctggcttcc atgagggagg cagagacagc    540
tgccagggag actcaggagg accccatgtg acagaagtgg agggaccag cttcctgaca     600 ggcatcatca gctggggaga ggagtgtgcc atgaagggca gtatggcat ctacaccaaa     660 gtgagcagat atgtgaactg gatcaaggag aaaaccaagc tg                       702
```

<210> SEQ ID NO 42
<211> LENGTH: 435
<212> TYPE: DNA
<213> ORGANISM: Artificial Sequence
<220> FEATURE:
<223> OTHER INFORMATION: CS02-LC-NA

<400> SEQUENCE: 42

```
tacaactcag gcaagctgga ggagtttgtg cagggcaacc tggagaggga gtgcatggag    60
gagaagtgca gctttgagga ggccagagag gtgtttgaga acacagagag gaccacagag   120
ttctggaagc agtatgtgga tggagaccag tgtgagagca accccttgcct gaatggaggc   180 agctgcaagg atgacatcaa cagctatgag tgctggtgcc cttttggctt tgagggcaag   240
aactgtgagc tggatgtgac ctgcaacatc aagaatggca ggtgtgagca gttctgcaag   300
aactcagctg acaacaaagt ggtgtgtagc tgcacagagg gctacagact ggctgagaac   360
cagaagagct gtgagcctgc tgtgcccttc ccctgtggca gagtgtcagt gtcccagacc   420
agcaagctga ccaga                                                     435
```

<210> SEQ ID NO 43
<211> LENGTH: 705
<212> TYPE: DNA
<213> ORGANISM: Artificial Sequence
<220> FEATURE:
<223> OTHER INFORMATION: CS03-HC-NA

<400> SEQUENCE: 43

```
gtggtggggg gggaggatgc caagcctggc cagttccct ggcaggtggt gctgaatggc     60
aaagtggatg ccttctgtgg gggcagcatt gtgaatgaga gtggattgt gactgctgcc   120 cactgtgtgg agactggggt gaagatcact gtggtggctg ggaacacaa tattgaggag   180 actgagcaca ctgagcagaa gaggaatgtc atcaggatta tccccaccac caactacaat   240
gctgccatca acaagtacaa ccatgacatt gccctgctgg agctggatga gcctctggtg   300
ctgaatagct atgtgacccc catctgcatt gctgacaagg agtacaccaa catcttcctg    360
aagtttggct ctggctatgt gtctggctgg ggcagagtgt tccacaaggg caggtctgcc    420
ctggtgctgc agtacctgag agtgcccctg gtggacagag ccacctgcct gctgagcacc   480
aagttcacca tctacaacaa catgttctgt gctggcttcc atgagggggg cagagacagc   540
tgccaggggg actctggggg cccccatgtg actgaagtgg agggaccag cttcctgact    600 ggcatcatca gctgggggga ggagtgtgcc atgaagggca gtatggcat ctacaccaaa    660 gtgagcaggt atgtgaactg gatcaaggag aaaaccaagc tgacc                   705
```

<210> SEQ ID NO 44
<211> LENGTH: 435
<212> TYPE: DNA

<213> ORGANISM: Artificial Sequence
<220> FEATURE:
<223> OTHER INFORMATION: CS03-LC-NA

<400> SEQUENCE: 44

```
tacaactctg gcaagctgga ggagtttgtg cagggcaacc tggagaggga gtgcatggag      60
gagaagtgca gctttgagga ggccagggaa gtgtttgaga acactgagag gaccactgag     120
ttctggaagc agtatgtgga tggggaccag tgtgagagca acccttgcct gaatgggggc     180
agctgcaagg atgacatcaa cagctatgag tgctggtgcc cttttggctt tgagggcaag     240
aactgtgagc tggatgtgac ctgcaacatc aagaatggca ggtgtgagca gttctgcaag     300
aactctgctg acaacaaagt ggtgtgtagc tgcactgagg gctacagact ggctgagaac     360
cagaagagct gtgagcctgc tgtgcccttc ccctgtggca gagtgtctgt gtcccagacc     420
agcaagctga ccaga                                                      435
```

<210> SEQ ID NO 45
<211> LENGTH: 705
<212> TYPE: DNA
<213> ORGANISM: Artificial Sequence
<220> FEATURE:
<223> OTHER INFORMATION: CS04-HC-NA

<400> SEQUENCE: 45

```
gtggtgggag gagaggatgc caagcctggc cagttcccct ggcaggtggt gctgaatggc      60
aaggtggatg ccttctgtgg aggcagcatt gtgaatgaga gtggattgt gacagctgcc     120 cactgtgtgg agacaggagt gaagatcaca gtggtggctg agagcacaa cattgaggag     180 acagagcaca cagagcagaa gaggaatgtg atcaggatca tccctcacca caactacaat     240
gctgccatca acaagtacaa ccatgacatt gccctgctgg agctggatga gcctctggtg     300
ctgaacagct atgtgacccc tatctgcatt gctgacaagg agtacaccaa catcttcctg     360
aagtttggct ctggctatgt gtctggctgg ggcagagtgt tccacaaggg caggtctgcc     420
ctggtgctgc agtacctgag agtgcccctg gtggacagag ccacctgcct gttgagcacc     480
aagttccacc tctacaacaa catgttctgt gctggcttcc atgagggagg cagagacagc     540
tgccagggtg actctggagg accccatgtg acagaggtgg agggcaccag cttcctgaca     600
ggcatcatca gctgggggag gggtgtgcc atgaagggca gtatggcat ctacaccaaa     660 gtgagcagat atgtgaactg gatcaaggag aagaccaagc tgacc                     705
```

<210> SEQ ID NO 46
<211> LENGTH: 435
<212> TYPE: DNA
<213> ORGANISM: Artificial Sequence
<220> FEATURE:
<223> OTHER INFORMATION: CS04-LC-NA

<400> SEQUENCE: 46

```
tacaactctg gcaagctgga ggagtttgtg cagggcaacc tggagaggga gtgcatggag      60
gagaagtgca gctttgagga ggccagggag gtgtttgaga acacagagag gaccacagag     120
ttctggaagc agtatgtgga tggtgaccag tgtgagagca acccttgcct gaatggaggc     180
agctgcaagg atgacatcaa cagctatgag tgctggtgcc cttttggctt tgagggcaag     240
aactgtgagc tggatgtgac ctgcaacatc aagaatggca ggtgtgagca gttctgcaag     300
aactctgctg acaacaaggt ggtgtgtagc tgcacagagg gctacagact ggctgagaac     360
cagaagagct gtgagcctgc tgtgcccttc ccctgtggca gagtgtctgt gtcccagacc     420
```

```
agcaagctga ccaga                                                      435

<210> SEQ ID NO 47
<211> LENGTH: 705
<212> TYPE: DNA
<213> ORGANISM: Artificial Sequence
<220> FEATURE:
<223> OTHER INFORMATION: CS05-HC-NA

<400> SEQUENCE: 47
gtggtgggag gagaggatgc caagcctggc cagttcccct ggcaggtggt gctgaatggc     60
aaggtggatg ccttctgtgg aggcagcatt gtgaatgaga gtggattgt gaccgctgcc     120
cactgtgtgg agactggagt gaagatcact gtggtggctg gggagcacaa cattgaggag    180
acagagcaca cagagcagaa gcgcaatgtg atcaggatca tcccccacca caactacaat    240
gctgccatca caagtacaa ccatgacatt gccctgctgg agctggatga gccctggtg      300
ctgaacagct acgtgacccc catctgcatt gcagacaagg agtacaccaa catcttcctg    360
aagtttggct ctggctatgt gtctggctgg ggcaggtgt tccacaaggg caggtctgcc     420
ctggtgctgc agtacctgag ggtgcccctg gtggacaggg ccacctgcct gctgagcacc    480
aagttcacca tctacaacaa catgttctgc gctggcttcc atgagggagg aagggacagc    540
tgccagggag actctggagg ccccatgtg acagaggtgg agggcaccag cttcctgaca    600
ggcatcatca gctgggggga ggagtgtgcc atgaagggca agtatggcat ctacaccaaa    660
gtgtcccgct atgtgaactg gatcaaggag aagaccaagc tgacc                   705

<210> SEQ ID NO 48
<211> LENGTH: 435
<212> TYPE: DNA
<213> ORGANISM: Artificial Sequence
<220> FEATURE:
<223> OTHER INFORMATION: CS05-LC-NA

<400> SEQUENCE: 48
tacaactctg gcaagctgga ggagtttgtg cagggcaacc tggagaggga gtgcatggag     60
gagaagtgca gctttgagga ggccaggag gtgtttgaga cactgagcg caccactgag     120
ttctggaagc agtatgtgga tggggaccag tgtgagagca cccctgcct gaatgggggg    180
agctgcaagg atgacatcaa cagctatgag tgctggtgcc ctttggctt tgagggcaag    240
aactgtgagc tggatgtgac ctgcaacatc aagaatggcc gctgtgagca gttctgcaag    300
aactctgctg acaacaaggt ggtgtgctct tgcactgagg gctaccgcct ggctgagaac    360
cagaagagct gtgagcctgc tgtgcccttc ccctgtggca gggtgtctgt gagccagacc    420
agcaagctga ccagg                                                      435

<210> SEQ ID NO 49
<211> LENGTH: 705
<212> TYPE: DNA
<213> ORGANISM: Artificial Sequence
<220> FEATURE:
<223> OTHER INFORMATION: CS06-HC-NA

<400> SEQUENCE: 49
gtggtgggag gagaggatgc caagcctggc cagttcccct ggcaagtggt gctcaatggc     60
aaggtggatg ccttctgtgg gggctccatt gtgaatgaga gtggattgt cactgctgcc     120
cactgtgtgg agactgggt caagatcact gtggtggctg gggagcacaa cattgaggag    180
```

```
actgagcaca ctgagcagaa gcgcaatgtg atcaggatca tcccccacca caactacaat    240
gctgccatca acaagtacaa ccatgacatt gccctgctgg agctggatga gcccctggtc    300
ctcaacagct atgtgacccc catctgcatt gctgacaagg agtacaccaa catcttcctc    360
aagtttggct ctggctatgt ctctggctgg ggcagagtgt tccacaaagg caggtctgcc    420
ctggtgctcc agtacctgag agtgcccctg gtggacaggg ccacctgcct cttgagcacc    480
aagttcacca tctacaacaa catgttctgt gctggcttcc atgagggagg aagagacagc    540
tgccaggggg actctggagg accccatgtc actgaggtgg agggcacctc cttcctcact    600
ggcatcatct cctggggaga ggagtgtgcc atgaaaggca aatatggcat ctacaccaaa    660
gtctccagat atgtcaactg gatcaaggag aagaccaagc tgacc                    705

<210> SEQ ID NO 50
<211> LENGTH: 435
<212> TYPE: DNA
<213> ORGANISM: Artificial Sequence
<220> FEATURE:
<223> OTHER INFORMATION: CS06-LC-NA

<400> SEQUENCE: 50
tacaactctg gcaaactgga ggagtttgtc cagggcaacc tggagaggga gtgcatggag     60
gagaagtgct cctttgagga ggccagggag gtctttgaga acactgagcg caccactgag    120
ttctggaaac agtatgtgga tggggaccag tgtgagtcca accctgcct gaatgggggc     180 agctgcaagg atgacatcaa cagctatgag tgctggtgcc cctttggctt tgagggcaag    240
aactgtgagc tggatgtgac ctgcaacatc aagaatggca gatgtgagca gttctgcaag    300
aactctgctg acaacaaggt ggtgtgctcc tgcactgagg gctaccgcct ggctgagaac    360
cagaagagct gtgagcctgc tgtgccattc ccatgtggca gagtctctgt gagccagacc    420
agcaagctca ccagg                                                      435

<210> SEQ ID NO 51
<211> LENGTH: 145
<212> TYPE: DNA
<213> ORGANISM: Artificial Sequence
<220> FEATURE:
<223> OTHER INFORMATION: AAV2_5'-ITR

<400> SEQUENCE: 51
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcct                                           145

<210> SEQ ID NO 52
<211> LENGTH: 330
<212> TYPE: DNA
<213> ORGANISM: Artificial Sequence
<220> FEATURE:
<223> OTHER INFORMATION: truncated_TTR_enhancer/promoter

<400> SEQUENCE: 52
cgagggcact gggaggatgt tgagtaagat ggaaaactac tgatgaccct tgcagagaca     60
gagtattagg acatgtttga acaggggccg ggcgatcagc aggtagctct agaggatccc    120
cgtctgtctg cacatttcgt agagcgagtg ttccgatact ctaatctccc taggcaaggt    180
tcatatttgt gtaggttact tattctcctt ttgttgacta agtcaataat cagaatcagc    240
aggtttggag tcagcttggc aggatcagc agcctgggtt ggaaggaggg ggtataaaag    300
```

```
ccccttcacc aggagaagcc gtcacacaga                                    330
```

<210> SEQ ID NO 53
<211> LENGTH: 77
<212> TYPE: DNA
<213> ORGANISM: Artificial Sequence
<220> FEATURE:
<223> OTHER INFORMATION: MVM_intron

<400> SEQUENCE: 53

```
ctaaggtaag ttggcgccgt ttaagggatg gttggttggt ggggtattaa tgtttaatta    60 cctttttttac aggcctg                                                  77
```

<210> SEQ ID NO 54
<211> LENGTH: 234
<212> TYPE: DNA
<213> ORGANISM: Artificial Sequence
<220> FEATURE:
<223> OTHER INFORMATION: BGH_poly-adenylation_signal

<400> SEQUENCE: 54

```
cctagagctc gctgatcagc ctcgactgtg ccttctagtt gccagccatc tgttgtttgc    60
ccctcccccg tgccttcctt gaccctggaa ggtgccactc ccactgtcct ttcctaataa   120
aatgaggaaa ttgcatcgca ttgtctgagt aggtgtcatt ctattctggg gggtggggtg   180
gggcaggaca gcaagggga ggattgggaa gacaatagca ggcatgctgg ggaa          234
```

<210> SEQ ID NO 55
<211> LENGTH: 145
<212> TYPE: DNA
<213> ORGANISM: Artificial Sequence
<220> FEATURE:
<223> OTHER INFORMATION: AAV2 3'-ITR

<400> SEQUENCE: 55

```
aggaacccct agtgatggag ttggccactc cctctctgcg cgctcgctcg ctcactgagg    60
ccgggcgacc aaaggtcgcc cgacgcccgg gctttgcccg ggcggcctca gtgagcgagc   120
gagcgcgcag agagggagtg gccaa                                         145
```

<210> SEQ ID NO 56
<211> LENGTH: 35
<212> TYPE: PRT
<213> ORGANISM: Artificial Sequence
<220> FEATURE:
<223> OTHER INFORMATION: FIX-AP-AA

<400> SEQUENCE: 56

Ala Glu Thr Val Phe Pro Asp Val Asp Tyr Val Asn Ser Thr Glu Ala
1               5                   10                  15

Glu Thr Ile Leu Asp Asn Ile Thr Gln Ser Thr Gln Ser Phe Asn Asp
            20                  25                  30

Phe Thr Arg
        35

<210> SEQ ID NO 57
<211> LENGTH: 105
<212> TYPE: DNA
<213> ORGANISM: Artificial Sequence
<220> FEATURE:
<223> OTHER INFORMATION: CS02-AP-NA

<400> SEQUENCE: 57

```
gctgagacag tgttccctga tgtggactat gtgaatagca cagaggctga gaccatcctg      60
gacaacatca cccagagcac ccagtccttc aatgacttca ccaga                     105

<210> SEQ ID NO 58
<211> LENGTH: 105
<212> TYPE: DNA
<213> ORGANISM: Artificial Sequence
<220> FEATURE:
<223> OTHER INFORMATION: CS03-AP-NA

<400> SEQUENCE: 58
gctgagactg tgttccctga tgtggactat gtgaatagca ctgaggctga gaccatcctg      60
gacaacatca cccagagcac ccagtccttc aatgacttca ccaga                     105

<210> SEQ ID NO 59
<211> LENGTH: 105
<212> TYPE: DNA
<213> ORGANISM: Artificial Sequence
<220> FEATURE:
<223> OTHER INFORMATION: CS04-AP-NA

<400> SEQUENCE: 59
gctgagacag tgttccctga tgtggactat gtgaacagca cagaggctga gaccatcctg      60
gacaacatca cccagagcac ccagtccttc aatgacttca ccaga                     105

<210> SEQ ID NO 60
<211> LENGTH: 105
<212> TYPE: DNA
<213> ORGANISM: Artificial Sequence
<220> FEATURE:
<223> OTHER INFORMATION: CS05-AP-NA

<400> SEQUENCE: 60
gctgagactg tgttccctga cgtggactat gtgaacagca ctgaggctga gaccatcctg      60
gacaacatca cccagagcac ccagagcttc aatgacttca ccagg                     105

<210> SEQ ID NO 61
<211> LENGTH: 105
<212> TYPE: DNA
<213> ORGANISM: Artificial Sequence
<220> FEATURE:
<223> OTHER INFORMATION: CS06-AP-NA

<400> SEQUENCE: 61
gctgagactg tgttccctga tgtggactat gtgaacagca ctgaggctga aaccatcctg      60
gacaacatca cccagagcac ccagagcttc aatgacttca ccaga                     105

<210> SEQ ID NO 62
<211> LENGTH: 145
<212> TYPE: PRT
<213> ORGANISM: Artificial Sequence
<220> FEATURE:
<223> OTHER INFORMATION: FIX-LC-AA

<400> SEQUENCE: 62

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45
```

```
Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg
145

<210> SEQ ID NO 63
<211> LENGTH: 235
<212> TYPE: PRT
<213> ORGANISM: Artificial Sequence
<220> FEATURE:
<223> OTHER INFORMATION: FIX-HC-AA

<400> SEQUENCE: 63

Val Val Gly Gly Glu Asp Ala Lys Pro Gly Gln Phe Pro Trp Gln Val
1               5                   10                  15

Val Leu Asn Gly Lys Val Asp Ala Phe Cys Gly Gly Ser Ile Val Asn
            20                  25                  30

Glu Lys Trp Ile Val Thr Ala Ala His Cys Val Glu Thr Gly Val Lys
        35                  40                  45

Ile Thr Val Val Ala Gly Glu His Asn Ile Glu Thr Glu His Thr
    50                  55                  60

Glu Gln Lys Arg Asn Val Ile Arg Ile Pro His His Asn Tyr Asn
65                  70                  75                  80

Ala Ala Ile Asn Lys Tyr Asn His Asp Ile Ala Leu Leu Glu Leu Asp
                85                  90                  95

Glu Pro Leu Val Leu Asn Ser Tyr Val Thr Pro Ile Cys Ile Ala Asp
            100                 105                 110

Lys Glu Tyr Thr Asn Ile Phe Leu Lys Phe Gly Ser Gly Tyr Val Ser
        115                 120                 125

Gly Trp Gly Arg Val Phe His Lys Gly Arg Ser Ala Leu Val Leu Gln
    130                 135                 140

Tyr Leu Arg Val Pro Leu Val Asp Arg Ala Thr Cys Leu Arg Ser Thr
145                 150                 155                 160

Lys Phe Thr Ile Tyr Asn Asn Met Phe Cys Ala Gly Phe His Glu Gly
                165                 170                 175

Gly Arg Asp Ser Cys Gln Gly Asp Ser Gly Gly Pro His Val Thr Glu
            180                 185                 190

Val Glu Gly Thr Ser Phe Leu Thr Gly Ile Ile Ser Trp Gly Glu Glu
        195                 200                 205

Cys Ala Met Lys Gly Lys Tyr Gly Ile Tyr Thr Lys Val Ser Arg Tyr
    210                 215                 220

Val Asn Trp Ile Lys Glu Lys Thr Lys Leu Thr
225                 230                 235
```

```
<210> SEQ ID NO 64
<211> LENGTH: 235
<212> TYPE: PRT
<213> ORGANISM: Artificial Sequence
<220> FEATURE:
<223> OTHER INFORMATION: FIXp-HC-AA

<400> SEQUENCE: 64

Val Val Gly Gly Glu Asp Ala Lys Pro Gly Gln Phe Pro Trp Gln Val
1               5                   10                  15

Val Leu Asn Gly Lys Val Asp Ala Phe Cys Gly Gly Ser Ile Val Asn
            20                  25                  30

Glu Lys Trp Ile Val Thr Ala Ala His Cys Val Glu Thr Gly Val Lys
        35                  40                  45

Ile Thr Val Val Ala Gly Glu His Asn Ile Glu Glu Thr Glu His Thr
    50                  55                  60

Glu Gln Lys Arg Asn Val Ile Arg Ile Ile Pro His His Asn Tyr Asn
65                  70                  75                  80

Ala Ala Ile Asn Lys Tyr Asn His Asp Ile Ala Leu Leu Glu Leu Asp
                85                  90                  95

Glu Pro Leu Val Leu Asn Ser Tyr Val Thr Pro Ile Cys Ile Ala Asp
            100                 105                 110

Lys Glu Tyr Thr Asn Ile Phe Leu Lys Phe Gly Ser Gly Tyr Val Ser
        115                 120                 125

Gly Trp Gly Arg Val Phe His Lys Gly Arg Ser Ala Leu Val Leu Gln
    130                 135                 140

Tyr Leu Arg Val Pro Leu Val Asp Arg Ala Thr Cys Leu Leu Ser Thr
145                 150                 155                 160

Lys Phe Thr Ile Tyr Asn Asn Met Phe Cys Ala Gly Phe His Glu Gly
                165                 170                 175

Gly Arg Asp Ser Cys Gln Gly Asp Ser Gly Gly Pro His Val Thr Glu
            180                 185                 190

Val Glu Gly Thr Ser Phe Leu Thr Gly Ile Ile Ser Trp Gly Glu Glu
        195                 200                 205

Cys Ala Met Lys Gly Lys Tyr Gly Ile Tyr Thr Lys Val Ser Arg Tyr
    210                 215                 220

Val Asn Trp Ile Lys Glu Lys Thr Lys Leu Thr
225                 230                 235
```

VIRAL VECTORS ENCODING RECOMBINANT FIX WITH INCREASED EXPRESSION FOR GENE THERAPY OF HEMOPHILIA B

CROSS-REFERENCE TO RELATED APPLICATIONS

This application claims the benefit of U.S. Provisional Application No. 62/509,616, filed on May 22, 2017, which is herein expressly incorporated by reference in its entirety for all purposes.

REFERENCE TO A "SEQUENCE LISTING," A TABLE, OR A COMPUTER PROGRAM, LISTING APPENDIX SUBMITTED ON A COMPACT DISK

This disclosure incorporates by reference the Sequence Listing text copy submitted herewith, which was created on May 21, 2018, entitled 008073_5117_US_Sequence_Listing.txt which is 73 kilobytes in size.

BACKGROUND OF THE DISCLOSURE

Blood coagulation proceeds through a complex and dynamic biological pathway of interdependent biochemical reactions, referred to as the coagulation cascade. Coagulation Factor VIII (FVIII) and Factor IX (FIX) are key components in the cascade. Factor VIII is recruited to bleeding sites, and forms a Xase complex with activated Factor IX and Factor X (FX). The Xase complex activates FX, which in turn activates prothrombin to thrombin, which then activates other components in the coagulation cascade to generate a stable clot (reviewed in Saenko et al., *Trends Cardiovasc. Med.*, 9:185-192 (1999); Lenting et al., *Blood*, 92:3983-3996 (1998)).

Hemophilia B is a congenital X-linked bleeding disorder characterized by a deficiency in Factor IX activity. Generally, diminished Factor VIII/Factor IX activity inhibits a positive feedback loop in the coagulation cascade. This causes incomplete coagulation, which manifests as bleeding episodes with increased duration, extensive bruising, spontaneous oral and nasal bleeding, joint stiffness and chronic pain, and possibly internal bleeding and anemia in severe cases. (Zhang et al., *Clinic. Rev. Allerg. Immunol.*, 37:114-124 (2009)).

Conventionally, hemophilia B is treated by Factor IX replacement therapy, which consists of administering Factor IX protein (e.g., plasma-derived or recombinantly-produced Factor IX) to an individual with hemophilia B. Factor IX is administered prophylactically to prevent or reduce frequency of bleeding episodes, in response to an acute bleeding episode, and/or perioperatively to manage bleeding during surgery. However, there are several undesirable features of Factor IX replacement therapy.

First, Factor IX replacement therapy is used to treat or manage hemophilia B, but does not cure the underlying Factor IX deficiency. Because of this, individuals with hemophilia B require Factor IX replacement therapy for the duration of their lives. Continuous treatment is expensive and requires the individual to maintain strict compliance, as missing only a few prophylactic doses can have serious consequences for individuals with severe hemophilia B.

Second, because conventional Factor IX products have a relatively short half-life in vivo, about 24 hours, prophylactic Factor IX replacement therapy requires administration two or three times weekly. This places a burden on the individual to maintain compliance throughout their life. While third generation "long-acting" Factor IX drugs may reduce the frequency of administration, prophylactic Factor FIX replacement therapy with these drugs still requires monthly, weekly, or more frequent administration in perpetuity. For example, prophylactic treatment with Nonacog beta pegol [pegylated recombinant Factor IX] (Novo Nordisk, U.S. and EP regulatory approval pending) still requires weekly administration (Collins P. W., et al., *Blood*, 124(26): 3880-86 (2014)). Moreover, the long-term effects of chemically modified biologics (e.g., pegylated polypeptides) are not yet fully understood.

Third, up to 5% of severe hemophilia B patients Factor IX replacement therapy form anti-Factor IX inhibitor antibodies, rendering the therapy inefficient (Osooli and Berntorp, *J. Intern. Med.*, 277(1):1-15 (2015)). Unlike Factor VIII bypass therapies that may be used to treat hemophilia A patients who have developed anti-Factor VIII inhibitory antibodies, no Factor IX bypass therapy exists for the treatment of hemophilia B.

Fourth, Factor IX replacement therapy is expensive, ranging from about $1,000 to about $3,000 per dose, depending on the weight of the patient (Hemophilia Federation of America online materials). Thus, with twice weekly dosing, Factor IX replacement therapy may cost up to $300,000 annually.

Gene therapy holds great promise for the treatment of hemophilia B because it would remedy the underlying under-expression of functional Factor IX activity (e.g., due to missense or nonsense mutations), rather than provide a one-time dose of Factor IX activity to the individual. Because of the difference in the mechanism for providing Factor IX, as compared to Factor IX replacement therapy, a single administration of a Factor IX gene therapy vector may provide an individual with sufficient levels of Factor IX for several years, if not longer. This reduces the cost of treatment and eliminates the need for continued patient compliance.

Proof of concept for Factor IX gene therapy treatment of hemophilia B has been shown. See, e.g., Manno C. S., et al., Nat Med., 12(3):342-47 (2006). However, questions remain as to whether therapeutically effective amounts of Factor IX can be expressed for sufficient periods of time. See, e.g., Giangrande, Semin Thromb Hemost. 42(5):513-17 (2016).

Several attempts have been made to construct codon-optimized Factor IX. For example, WO 2006/036502 discloses a codon-optimized Factor IX AAV gene therapy vector with an ApoE HCR-1 enhancer and an alpha-1 antitrypsin (AAT) promoter. Similarly, WO 2014/064277 and WO 2016/146757 disclose codon-optimized Factor VIII and Factor IX AAV gene therapy vectors that include one or more copies of a liver-specific SERPIN regulatory element. Finally, WO 2016/210170 discloses codon-optimized Factor IX AAV gene therapy vectors with an ApoE HCR-1 enhancer and an alpha-1 antitrypsin (AAT) promoter.

BRIEF SUMMARY OF DISCLOSURE

Accordingly, there is a need for improved Factor IX gene therapy constructs. For example, there is a need for synthetic, codon-altered nucleic acids encoding Factor IX that are more efficiently packaged into, and delivered via, gene therapy vectors. There is also a need for synthetic, codon-altered nucleic acids that express Factor IX more efficiently. There is also a need for codon-altered nucleic acids encoding Factor IX polypeptides with improved folding properties, improved secretion from expressing cells, and/or increased activity, as compared to wild-type Factor IX. Such Factor IX encoding, codon-altered nucleic acids allow for improved treatment of Factor IX deficiencies (e.g., hemophilia B). The above deficiencies and other problems associated with the treatment of Factor IX deficiencies (e.g., hemophilia B) are reduced or eliminated by the disclosed codon-altered nucleic acids encoding Factor IX proteins.

In one aspect, nucleic acid compositions (e.g., codon-altered polynucleotides) encoding Factor IX and Factor IX variants are described. The nucleic acid compositions include polynucleotides with high sequence identity to the CS02, CS03, CS04, CS05, and CS06 sequences encoding Factor IX, as described herein. The nucleic acid compositions described herein provide increased Factor IX expression relative to wild-type Factor IX coding sequences. The nucleic acid compositions also allow for increased production of AAV-based gene therapy virions. In some embodiments, the nucleic acid compositions described herein have decreased GC content and or include fewer CpG dinucleotides, as compared to wild-type sequences encoding Factor IX.

In some embodiments, a nucleic acid composition includes a polynucleotide encoding Factor IX that has a nucleotide sequence with at least 95% sequence identity (e.g., at least 95%, 96%, 97%, 98%, 99%, or 100% sequence identity) to a disclosed sequence selected from CS02-FL-NA (SEQ ID NO:5), CS02-MP-NA (SEQ ID NO:13), CS03-FL-NA (SEQ ID NO:6), CS03-MP-NA (SEQ ID NO: 14), CS04-FL-NA (SEQ ID NO:7), CS04-MP-NA (SEQ ID NO: 15), CS05-FL-NA (SEQ ID NO:8), CS05-MP-NA (SEQ ID NO:16), CS06-FL-NA (SEQ ID NO:9), and CS06-MP-NA (SEQ ID NO: 17).

In some embodiments, a nucleic acid composition includes a polynucleotide encoding Factor IX that has a nucleotide sequence with at least 95% sequence identity (e.g., at least 95%, 96%, 97%, 98%, 99%, or 100% sequence identity) to a disclosed sequence encoding a Factor IX light chain (e.g., CS02-LC-NA (SEQ ID NO:42), CS03-LC-NA (SEQ ID NO:44), CS04-LC-NA (SEQ ID NO:46), CS05-LC-NA (SEQ ID NO:48), or CS06-LC-NA (SEQ ID NO:50)) and a disclosed sequence encoding a Factor IX heavy chain (e.g., CS02-HC-NA (SEQ ID NO:41), CS03-HC-NA (SEQ ID NO:43), CS04-HC-NA (SEQ ID NO:45), CS05-HC-NA (SEQ ID NO:47), or CS06-HC-NA (SEQ ID NO:49)).

In some embodiments, a nucleic acid composition includes a polynucleotide that encodes a Factor IX polypeptide having a light chain, a heavy chain, and a polypeptide linker joining the C-terminus of the light chain to the N-terminus of the heavy chain (e.g., an activation peptide). The light chain of the Factor IX polypeptide is encoded by a first nucleotide sequence with high sequence identity to one of CS02-LC-NA (SEQ ID NO:42), CS03-LC-NA (SEQ ID NO:44), CS04-LC-NA (SEQ ID NO:46), CS05-LC-NA (SEQ ID NO:48), and CS06-LC-NA (SEQ ID NO:50). The heavy chain of the Factor IX polypeptide is encoded by a second nucleotide sequence with high sequence identity to one of CS02-HC-NA (SEQ ID NO:41), CS03-HC-NA (SEQ ID NO:43), CS04-HC-NA (SEQ ID NO:45), CS05-HC-NA (SEQ ID NO:47), and CS06-HC-NA (SEQ ID NO:49). The polypeptide linker comprises a protease cleavage site (e.g., two Factor XIa cleavage sites).

In some embodiments of the polynucleotides described above, the polypeptide linker has an amino acid sequence with high sequence identity to the wild-type Factor IX activation peptide FIX-AP-AA (SEQ ID NO:56; amino acids 192-226 of FIX-FL-AA (SEQ ID NO:2)). In some embodiments, the polypeptide linker is encoded by a third nucleic acid sequence having high sequence identity to one of CS02-AP-NA (SEQ ID NO:57), CS03-AP-NA (SEQ ID NO:58), CS04-AP-NA (SEQ ID NO:59), CS05-AP-NA (SEQ ID NO:60), and CS06-AP-NA (SEQ ID NO:61).

In some embodiments, the codon-altered polynucleotides described herein encode a pre-pro-Factor IX polypeptide, e.g., where the encoded Factor IX protein includes a signal peptide and a pro-peptide. In some embodiments, the signal peptide, the pro-peptide, or both the signal peptide and the pro-peptide are encoded by a codon-altered sequence. In some embodiments, the signal peptide, the pro-peptide, or both the signal peptide and the pro-peptide are encoded by a wild-type sequence, while the portion of the nucleic acid encoding the mature Factor IX single-chain polypeptide (e.g., FIX-MP-AA (SEQ ID NO:10); amino acids 47-461 of FIX-FL-AA (SEQ ID NO:2)) is codon altered.

In some embodiment, the codon-altered polynucleotides described herein encode a Factor IX variant polypeptide, e.g., having one or more amino acid substitution with respect to the wild-type Factor IX amino acid sequence (e.g., FIX-FL-AA (SEQ ID NO:2) or FIX-MP-AA (SEQ ID NO: 10)). In some embodiments, the Factor IX variant is a hyperactive Factor IX variant with increased Factor IX activity, as compared to wild-type Factor IX. In a particular embodiment, the encoded Factor IX polypeptide has a 'Padua' R384L amino acid substitution (relative to the Factor IX pre-pro-polypeptide sequence FIX-FL-AA (SEQ ID NO:2), R338L amino acid substitution relative to the mature Factor IX single-chain sequence FIX-MP-AA (SEQ ID NO: 10)).

In one aspect, methods for treating hemophilia B are described. The methods include administering to a patient in need thereof a nucleic acid composition (e.g., a codon-altered Factor IX polynucleotide construct) described herein (e.g., a polynucleotide having high sequence identity to a CS02, CS03, CS04, CS05, or CS06 Factor IX coding sequence). In some embodiments, the Factor IX polynucleotide construct is a mammalian gene therapy vector, as described herein. In a particular embodiment, the Factor IX polynucleotide construct is an adeno-associated virus (AAV) vector. In some embodiments, the gene therapy vector includes one or more copies of a liver-specific regulatory control element (e.g., 1 to 3 copies of a CRM8 regulatory control element).

In one aspect, methods for producing an adeno-associated virus (AAV) particle are described. The method includes introducing a nucleic acid composition (e.g., a codon-altered Factor IX polynucleotide construct) described herein (e.g., a polynucleotide having high sequence identity to a CS02, CS03, CS04, CS05, or CS06 Factor IX coding sequence) into a mammalian host cell, wherein the polynucleotide is competent for replication in the mammalian host cell.

BRIEF DESCRIPTION OF DRAWINGS

FIG. 2 shows the wild-type Factor IX coding sequence (SEQ ID NO: 1) for accession number CCDS14666.1 ("FIX-FL-NA").

FIG. 3A and FIG. 3B shows the amino acid sequences of two wild-type Factor IX pre-pro-polypeptide isoforms expressed in humans. FIG. 3A shows the wild-type amino acid sequence for the first, longer Factor IX pre-pro-polypeptide isoform (SEQ ID NO:2) corresponding to UniProt accession number P00740 and NCBI accession number NP_000124.1 ("FIX-FL-AA").

FIG. 3B shows the wild-type amino acid sequence for the second, shorter Factor IX pre-pro-polypeptide isoform (SEQ ID NO:3) corresponding to NCBI accession number NP_001300842.1 ("FIX2-FL-AA").

FIG. 4 shows the Padua (R384L) Factor IX amino acid sequence (SEQ ID NO:4; "FIXp-FL-AA").

FIG. 5 shows the CS02 codon-altered nucleotide sequence (SEQ ID NO:5) encoding a Factor IX variant with an R384L amino acid substitution (CS02-FL-NA), in accordance with some implementations.

FIG. 6 shows the CS03 codon-altered nucleotide sequence (SEQ ID NO:6) encoding a Factor IX variant with an R384L amino acid substitution (CS03-FL-NA), in accordance with some implementations.

FIG. 7 shows the CS04 codon-altered nucleotide sequence (SEQ ID NO:7) encoding a Factor IX variant with an R384L amino acid substitution (CS04-FL-NA), in accordance with some implementations.

FIG. 8 shows the CS05 codon-altered nucleotide sequence (SEQ ID NO:8) encoding a Factor IX variant with an R384L amino acid substitution (CS05-FL-NA), in accordance with some implementations.

FIG. 9 shows the CS06 codon-altered nucleotide sequence (SEQ ID NO:9) encoding a Factor IX variant with an R384L amino acid substitution (CS06-FL-NA), in accordance with some implementations.

FIG. 11A and FIG. 11B show the amino acid sequences of two single-chain, wild-type Factor IX protein isoforms (e.g., lacking signal and propeptides) expressed in humans. FIG. 11A shows the wild-type amino acid sequence for the first, longer Factor IX pre-pro-polypeptide isoform (SEQ ID NO: 10) corresponding to UniProt accession number P00740 and NCBI accession number NP_000124.1 ("FIX-MA-AA"). FIG. 11B shows the wild-type amino acid sequence for the second, shorter Factor IX pre-pro-polypeptide isoform (SEQ ID NO:11) corresponding to NCBI accession number NP_001300842.1 ("FIX2-MA-AA").

FIG. 12 shows the single-chain Factor IX(R338L) "Padua" amino acid sequence (SEQ ID NO: 12; "FIXp-MP-AA").

FIG. 13 shows the CS02 codon-altered nucleotide sequence (SEQ ID NO:13) encoding a single-chain Factor IX variant with an R338L amino acid substitution (CS02-MP-NA), in accordance with some implementations.

FIG. 14 shows the CS03 codon-altered nucleotide sequence (SEQ ID NO:14) encoding a single-chain Factor IX variant with an R338L amino acid substitution (CS03-MP-NA), in accordance with some implementations.

FIG. 15 shows the CS04 codon-altered nucleotide sequence (SEQ ID NO:15) encoding a single-chain Factor IX variant with an R338L amino acid substitution (CS04-MP-NA), in accordance with some implementations.

FIG. 16 shows the CS05 codon-altered nucleotide sequence (SEQ ID NO:16) encoding a single-chain Factor IX variant with an R338L amino acid substitution (CS05-MP-NA), in accordance with some implementations.

FIG. 17 shows the CS06 codon-altered nucleotide sequence (SEQ ID NO:17) encoding a single-chain Factor IX variant with an R338L amino acid substitution (CS06-MP-NA), in accordance with some implementations.

FIG. 18 shows nucleic acid sequences (NA) encoding the pre-pro-peptide (PPP) of a number of constructs described herein, in accordance with some implementations.

FIG. 19 shows nucleic acid sequences (NA) encoding the signal peptide (SP) for a number of constructs described herein, in accordance with some implementations.

FIG. 20 shows nucleic acid sequences (NA) encoding the pro-peptide (PP) for a number of constructs described herein, in accordance with some implementations.

FIG. 21 shows the amino acid sequence (AA) of the FIX pre-pro-peptide (PPP).

FIG. 22 shows the amino acid sequence (AA) of the FIX signal peptide (SP).

FIG. 23 shows the amino acid sequence (AA) of the FIX pro-peptide (PP).

FIG. 24 shows the nucleic acid sequence of the CRM8 sequence (SEQ ID NO:39).

FIGS. 25A and B shows the nucleic acid sequence of the CS06-CRM8.3-ssV construct (SEQ ID NO:40).

DETAILED DESCRIPTION OF DISCLOSURE

I. Introduction

Figure 1:
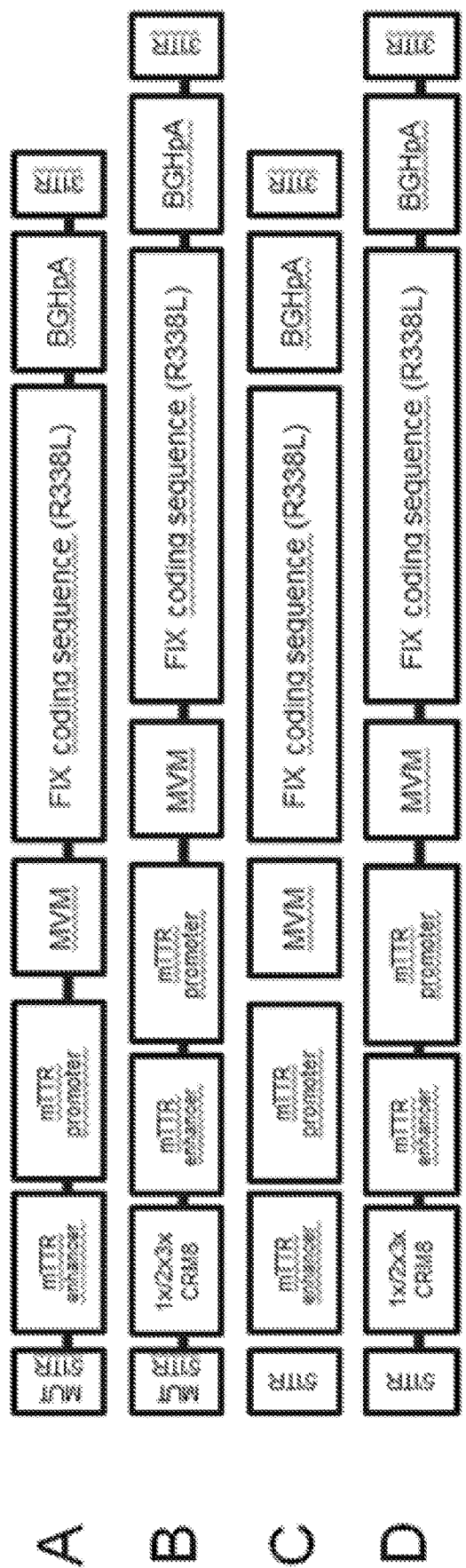
FIG. 1 illustrates exemplary Factor IX gene therapy constructs, in accordance with some implementations. The sequence elements for self-complementary (A, B) and single-stranded (C, D) vectors are shown without (A, C) and with (B, D) liver-specific cis-regulatory modules (CRM8).
Figure 10:
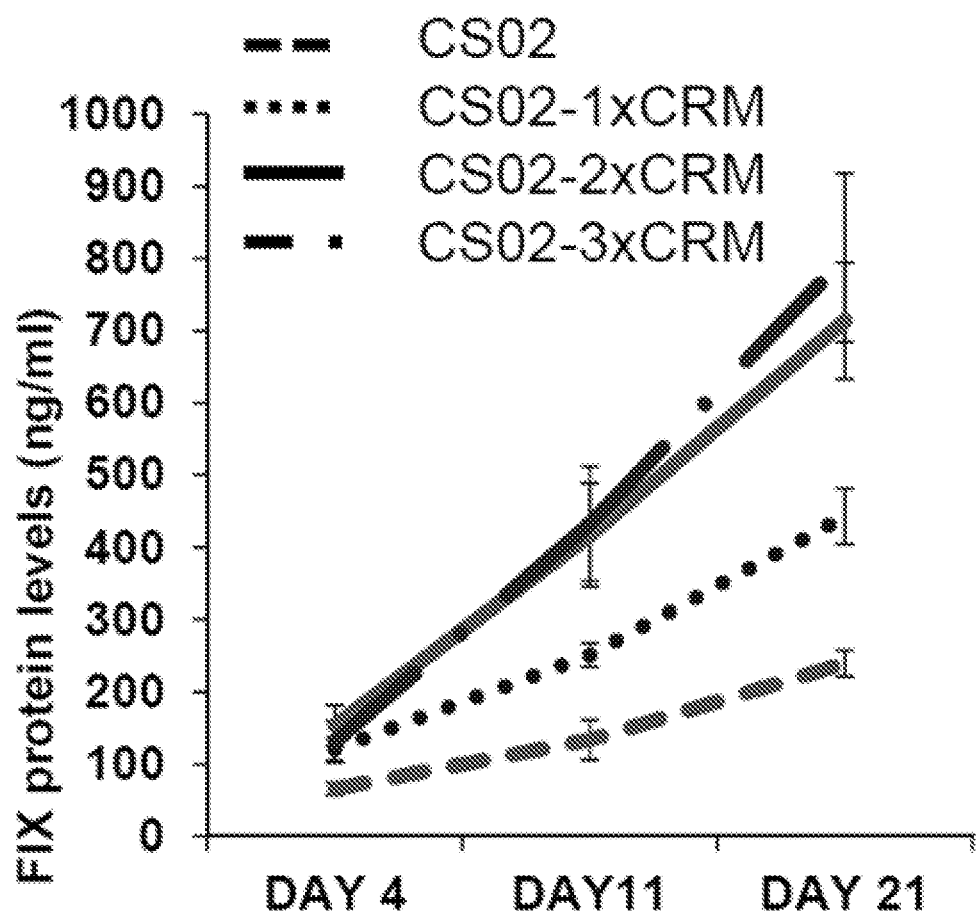
FIG. 10 illustrates FIX antigen levels in wild-type mice injected with a CS02 gene therapy construct having 0, 1, 2, or 3 copies of a CRM8 liver-specific cis-regulatory control element, at a dose of 2×10E11 vg/kg body weight.

AAV-based gene therapy holds great promise for the treatment of hemophilia. For hemophilia B, first clinical data are encouraging in that FIX levels of about 10% can be maintained in at least some patients for more than 1 year. For example, in initial human trials demonstrated that hepatic artery catherization of AVV-FIX constructs resulted in transient expression of Factor IX in vivo. Kay M. et al., Nat Genet. 24(3):257-61 (2000). However, the transduction resulted in modest activation of the immune system against AAV-derived capsid antigens. Manno C. S. et al., Nat Med. 12(3):342-47 (2006) and Mingozzi F. et al., Nat Med. 13(4):419-22 (2007).

Non-viral vectors may be less immunogenic because they are based on delivery of naked DNA or DNA associated with non-antigenic carriers (e.g., inert polymers, lipids, or nanoparticles). However, cellular transfection rates of non-viral vectors are lower than those for viral delivery vectors. Additionally, long-term expression from non-viral vectors is hampered by the presence of bacterial sequences used for large-scale production of the constructs.

These challenges, however, cannot be addressed by simply administering higher doses of the gene therapy construct. According to current knowledge, the vector dose of an AAV-based gene therapy vector should not be increased above $2\times10^{12}$ vg/kg bodyweight. This is because at such high doses a T cell immune response is triggered, which destroys transduced cells and, as a consequence, transgene expression is reduced or even eliminated. Therefore, strategies to improve the expression of FIX are needed to make FIX gene therapy a viable therapeutic option for hemophilia B patients.

Thus, improved Factor IX polypeptide constructs that support improved Factor IX expression and activity would improve both therapeutic approaches. For example, viral delivery methods would be improved by reducing the initial dose of the construct, thereby reducing stimulation of the subject's immune system. Methods relying on administration of naked DNA would be improved by supporting greater Factor IX activity with fewer copies of the therapeutic polynucleotide.

The present disclosure relates to the discovery of codon-altered Factor IX variant coding sequences that solve these and other problems associated with Factor IX gene therapy. For example, the polynucleotides disclosed herein provide markedly improved Factor IX expression and activity in a mammalian host. In some implementations, these advantages are realized by using Factor IX-encoding polynucleotides with high sequence identity to the codon-altered CS02, CS03, CS04, CS05, and CS06 constructs. In some embodiments, these sequences include significantly fewer CpG dinucleotides, as compared to wild type constructs, as is more fully described below.

Advantageously, the CS02, CS03, CS04, CS05, and CS06 codon-altered Factor IX sequences described herein provide superior Factor IX expression in vivo, as compared to equivalent wild-type sequences. For example, Example 1 shows that self-complementary AAV vectors carrying a CS02, CS03, CS04, CS05, or CS06 codon-altered Factor IX(R384L) coding sequence provide 20-fold to 40-fold increases in Factor IX activity in vivo, relative to a self-complementary AAV vector carrying a wild-type Factor IX coding sequence. Similarly, 2-fold to 4-fold increases are seen in Factor IX expression relative to a self-complementary AAV vector carrying a wild-type Factor IX(R384L) coding sequence (Table 2).

Advantageously, the improved Factor IX activity generated from the CS02, CS03, CS04, CS05, and CS06 codon altered sequences can be further enhanced by introducing one or more copies of a liver-specific regulatory element upstream of the Factor IX coding sequence. For example, as demonstrated in Examples 2 and 3, inclusion of one or more liver-specific CRM8 regulatory control elements in the self-complementary AAV Factor IX vector further increased Factor IX expression 2-fold to 3-fold in a mouse model and 2-fold to 13-fold in human hepatocytes (Tables 3 and 4, respectively). Likewise, inclusion of one or more copies of a liver-specific CRM8 regulatory control element in a single-stranded AAV Factor IX vector increased Factor IX activity 2-fold in vivo (mouse model; Table 5) and up to 26-fold in human hepatocytes (Table 6).

Surprisingly, while self-complementary AAV vectors encoding a codon-altered Factor IX polypeptide lacking liver-specific CRM8 regulatory control elements provided greater increases in Factor IX expression than similar single-stranded AAV vectors (compare the 6.2-fold increase in FIX activity provided by CS06-CRM.0-scV with the 3.9-fold increase in Factor IX activity provided by CS06-CRM.0-ssV (SEQ ID NO:40) in Table 6), single-stranded AAV Factor IX vectors containing multiple copies of the liver-specific CRM8 regulatory control elements significantly outperformed similar self-complementary AAV vectors (compare the 12.8-fold increase in Factor IX activity provided by CS02-CRM8.3-scV, relative to CS02-CRM8.0-scV, in Table 4 to the 16.8-fold increase in Factor IX activity provided by CS06-CRM8.3-ssV (SEQ ID NO:40), relative to CS06-CRM8.0-scV, in Table 6).

II. Definitions

As used herein, the following terms have the meanings ascribed to them unless specified otherwise.

As used herein, the terms "Factor IX" and "FIX" (with the "IX" referring to the Roman numerals to mean "nine") are used interchangeably, and refer to any protein with Factor IX activity (e.g., active FIX, often referred to as "FIXa") or a protein precursor (e.g., a pro-protein or a pre-pro-protein, often referred to as pFIX and ppFIX) of a protein with Factor IX activity, particularly Factor X cleavage activity in the presence of Factor VIII, e.g., as measured using the one stage Factor IX clotting assay described in Chapter 2.7.11 of the European Pharmacopoeia 9.0, the content of which is hereby incorporated by reference.

Factor IX is translated as an inactive, single-chain polypeptide that includes a signal peptide, a propeptide, a light chain, an activation peptide, and a heavy chain, often referred to as a Factor IX pre-pro-polypeptide. The Factor IX pre-pro-peptide undergoes post-translational processing to form an active Factor IX protein (e.g., FIXa). This processing includes removal (e.g., by cleavage) of the signal peptide, followed by removal (e.g., by cleavage) of the propeptide, to form a single-chain mature Factor IX polypeptide, containing the Factor IX light chain and Factor IX heavy chain, which is still inactive. The mature Factor IX polypeptide is further cleaved to excise the activation peptide between the Factor IX light chain and Factor IX heavy chain, forming an active Factor IX protein (e.g., FIXa). The Factor IX light chain and Factor IX light chain remain associated through a disulfide bond.

For example, the wild type human Factor IX pre-pro-protein is first cleaved to release the encoded signal peptide (amino acids 1-28 of FIX-FL-AA (SEQ ID NO:2)), forming a first single-chain pro-protein. This single-chain pro-peptide is then cleaved to release the propeptide (amino acids 29-46 of FIX-FL-AA (SEQ ID NO:2)) to form a second single-chain pro-protein (e.g., FIX-MP-AA (SEQ ID NO: 10), with the "MP" designation standing for "mature protein"). The second single-chain pro-protein is then cleaved twice between the FIX light chain and FIX heavy chain, by Factor XIa, to release an activation peptide (amino acids 192-226 of FIX-FL-AA (SEQ ID NO:2)). This forms the active Factor IXa protein consisting of separate light and heavy chains associated through a disulfide bond. For additional information on the structure, function, and activation of Factor IX see, e.g., Brandstetter H. et al. P.N.A.S. USA, 92(21):9796-800 (1995), Hopfner K P et al., Structure, 7(8):989-96 (1999), and Gailani D. et al., Thromb Res., 133 Suppl 1:S48-51 (2014), the contents of which are incorporated herein by reference, in their entireties, for all purposes.

As described herein, this active Factor IXa protein can include one or more variants, with the R338L variant finding particular use in some embodiments. This is referred to as "FIXp-MP-AA" (SEQ ID NO: 12) with the nucleic acid sequence being referred to herein as "FIXp-MP-NA"; the "FIXp" stands for the inclusion of the Padua R338L variant in the final protein. It should be noted that codon-optimized sequences CS02-CS06, exemplified herein, encode the FIXp protein, including the R338L variant. Thus, specifically included in the definition of FIX is FIXp.

As used herein, the terms "Factor IX polypeptide" and "FIX polypeptide" refer to a polypeptide having Factor IX serine protease activity under particular conditions, e.g., as measured using the one stage Factor IX clotting assay described in Chapter 2.7.11 of the European Pharmacopoeia 9.0. Factor IX polypeptides include single-chain precursor polypeptides (including Factor IX pre-pro-polypeptides, Factor IX pro-peptides, and mature, single-chain Factor IX polypeptides) which, when activated by the post-translational processing described above, become active Factor IX protein with Factor IX serine protease activity, as well as the active Factor IX proteins, themselves. Specifically included in the definition of Factor IX polypeptides are Factor IX polypeptides including the R338L variant. In an exemplary embodiment, a human Factor IX polypeptide refers to a polypeptide that includes an amino acid sequence with high sequence identity (e.g., at least 85%, 90%, 95%, 99%, or more) to the portion of the wild type human Factor IX polypeptide that includes the light and heavy chains, FIX-MP-AA (SEQ ID NO:10, shown in FIG. 11A) or to the portion of the padua human Factor IX polypeptide that includes the light and heavy chains, FIXp-MP-AA (SEQ ID NO: 12, shown in FIG. 12).

As used herein, the terms "Factor IX light chain," or simply "light chain," refer to the polypeptide in an activated Factor IXa protein derived from the N-terminal portion of the Factor IX single-chain polypeptide, containing the Gla module, EGF-like 1, and EGF-like 2 domains of Factor IX. In an exemplary embodiment, amino acids 47-191 of the human pre-pro-Factor IX polypeptide (FIX-FL-AA (SEQ ID NO:2)) constitute a Factor IX light chain. As used herein, the amino acid sequence of the wild-type Factor IX light chain is referred to as FIX-LC-AA (SEQ ID NO:62).

As used herein, the term "Factor IX heavy chain," or simply "heavy chain," refers to the polypeptide in an activated Factor IXa protein derived from the C-terminal portion of the Factor IX single-chain polypeptide, containing the peptidase S1 domain of Factor IX. In an exemplary embodiment, amino acids 227-461 of the human pre-pro-Factor IX polypeptide (FIX-FL-AA (SEQ ID NO:2)) constitute a Factor IX heavy chain. As used herein, the amino acid sequence of the wild-type Factor IX heavy chain is referred to as FIX-HC-AA (SEQ ID NO:63) and FIXp-HC-AA (SEQ ID NO:64) when the R338L variant is included.

Generally, Factor IX light and heavy chains are expressed as a single polypeptide chain, e.g., along with an activation peptide. However, in some embodiments, a Factor IX light chain and Factor VIII heavy chain are expressed as separate polypeptide chains (e.g., co-expressed), and reconstituted to form a Factor IX protein (e.g., in vivo or in vitro). In general, for the purposes of the present invention, even if two chains are expressed separately, they are generally on the same expression vector (e.g. the viral genome), rather than on different expression vectors.

As used herein, the term "Factor IX activation peptide," or simply "activation peptide," refers to the peptide excised from a Factor IX single-chain polypeptide upon activation of the Factor IXa protein. In an exemplary embodiment, amino acids 192-226 of the human pre-pro-Factor IX polypeptide (FIX-FL-AA (SEQ ID NO:2)) constitute a Factor IX activation peptide. As used herein, the amino acid sequence of the wild-type Factor IX activation peptide is referred to as FIX-AP-AA (SEQ ID NO:56).

As used herein, the term "Factor IX signal peptide," or simply "signal peptide," refers to the peptide excised from the N-terminus of a Factor IX pre-pro-polypeptide by a signal peptidase. The signal peptide directs newly translated Factor IX pre-pro-protein to the endoplasmic reticulum. In an exemplary embodiment, amino acids 1-28 of the human pre-pro-Factor IX polypeptide (FIX-FL-AA (SEQ ID NO:2)) constitute a Factor IX signal peptide. As used herein, the amino acid sequence of the wild-type Factor IX signal peptide is referred to as FIX-SP-AA (SEQ ID NO:37). A number of signal peptides of the invention are shown in FIGS. 19 and 22.

As used herein, the term "Factor IX pro-peptide," or simply "pro-peptide," refers to the peptide excised from the N-terminus of a Factor IX pro-polypeptide (e.g., after cleavage of the signal peptide) by Furin. The pro-peptide includes a γ-carboxylation recognition site that recruits carboxylase to the adjacent Gla module, thereby promoting carboxylation of glutamine residues. In an exemplary embodiment, amino acids 29-46 of the human pre-pro-Factor IX polypeptide (FIX-FL-AA (SEQ ID NO:2)) constitute a Factor IX pro-peptide. As used herein, the amino acid sequence of the wild-type Factor IX pro-peptide is referred to as FIX-PP-AA (SEQ ID NO:38).

As used herein, the term "Factor IX pre-pro-peptide," or simply "pre-pro-peptide," refers to the aggregate of the Factor IX signal peptide and pro-polypeptide. In an exemplary embodiment, amino acids 1-46 of the human pre-pro-Factor IX polypeptide (FIX-FL-AA (SEQ ID NO:2)) constitute a Factor IX pre-pro-peptide. As used herein, the amino acid sequence of the wild-type Factor IX pre-pro-peptide is referred to as FIX-PPP-AA (SEQ ID NO:36) with the nucleic acid sequence, shown in FIG. 18, referred to as FIX-PPP-NA (SEQ ID NO: 18) (with the corresponding FIXp-PPP-AA and FIXp-PPP-NA when the R338L variant is used).

Unless otherwise specified herein, the numbering of Factor IX amino acids refers to the corresponding amino acid in the full-length, wild-type human Factor IX pre-pro-polypeptide sequence (FIX-FL-AA), presented as SEQ ID NO:2 in FIG. 3A. As such, when referring to an amino acid substitution in a Factor IX polypeptide disclosed herein, the recited amino acid number refers to the analogous (e.g., structurally or functionally equivalent) and/or homologous (e.g., evolutionarily conserved in the primary amino acid sequence) amino acid in the full-length, wild-type Factor IX pre-pro-polypeptide sequence. For example, an R384L amino acid substitution refers to an R to L substitution at position 384 of the full-length, wild-type human Factor IX pre-pro-peptide sequence (FIX-FL-AA (SEQ ID NO:2)), an R to L substitution at position 338 of the mature, wild-type Factor IX single-chain polypeptide (FIX-MP-AA (SEQ ID NO:10), an R to L substitution at position 346 of the full-length, wild-type human Factor IX pre-pro-peptide isoform 2 sequence (FIX2-FL-AA (SEQ ID NO:3)), an R to L substitution at position 300 of the mature, wild-type human Factor IX pre-pro-peptide isoform 2 sequence (FIX2-FL-AA (SEQ ID NO:3)), and an R to L substitution at position 158 of the wild-type human Factor IX heavy chain sequence (FIX-HC-AA (SEQ ID NO:63)). Thus, all of these nomenclatures describe the same "Padua" amino acid substitution, in different Factor IX constructs.

As described herein, the Factor IX amino acid numbering system is dependent on whether the Factor IX pre-pro-peptide (e.g., amino acids 1-46 of the full-length, wild-type human Factor IX sequence, inclusive of the signal peptide and pro-peptide) is included. Where the pre-pro-peptide is included, the numbering is referred to as "pre-pro-peptide inclusive" or "PPI". Where the pre-pro-peptide is not included, the numbering is referred to as "pre-pro-peptide exclusive" or "PPE." For example, R384L is PPI numbering for the same amino acid substitution as R338L, in PPE numbering. Similarly, the Factor IX amino acid numbering is also dependent upon the Factor IX isoform. For example, R384L is isoform 1 numbering for the same amino acid substitution as R346L, in isoform 2 numbering. Unless otherwise indicated, all amino acid numbering refers to the corresponding amino acid in the full-length, wild-type human Factor IX isoform 1 sequence (FIX-FL-AA), presented as SEQ ID NO:2 in FIG. 3A. This numbering is identical for the FIXp-FL-AA (SEQ ID NO:4), which has the same amino acid sequence, aside from the R384L "Padua" mutation.

Non-limiting examples of wild type Factor IX polypeptides include human pre-pro-Factor IX (e.g., GenBank accession nos. NP_000124.1 (FIX-FL-AA (SEQ ID NO:2)) and NP_001300842.1 (FIX2-FL-AA (SEQ ID NO:3)), corresponding single chain Factor IX lacking the signal peptide (amino acids 1-28 of the pre-pro-protein) and/or propeptide (amino acids 29-46 of the pre-pro-protein), and natural variants thereof; porcine pre-pro-Factor IX (e.g., UniProt accession no. P00741), corresponding single chain Factor IX lacking the signal peptide, and natural variants thereof; murine pre-pro-Factor IX (e.g., UniProt accession no. P16294), corresponding single chain Factor IX lacking the signal peptide, and natural variants thereof; rat pre-pro-Factor IX (e.g., UniProt accession no. P16296), corresponding single chain Factor IX lacking the signal peptide, and natural variants thereof; and other mammalian Factor VIII homologues (e.g., chimpanzee, ape, hamster, guinea pig, etc.).

As used herein, a Factor IX polypeptide includes natural variants and artificial constructs with Factor X cleavage activity in the presence of Factor VIII. As used in the present disclosure, Factor IX encompasses any natural variants, alternative sequences, isoforms, or mutant proteins that retain some basal Factor IX cleavage activity (e.g., at least 5%, 10%, 25%, 50%, 75%, or more of the corresponding wild type activity as assayed in a one stage clotting assay according to Chapter 2.7.11 of the European Pharmacopoeia 9.0, which is specifically incorporated herein by reference for its teachings of the Assay of Human Coagulation Factor IX in chapter 2.7.11. Examples of Factor IX amino acid variations (relative to FIX-FL-AA (SEQ ID NO:2)) found in the human population include, without limitation, I17N, L20S, C28R, C28Y, V30I, R43L, R43Q, R43W, K45N, R46S, R46T, N48I, S49P, L52S, E53A, E54D, E54G, F55C, G58A, G58E, G58R, E66V, E67K, F71S, E73K, E73V, R75Q, E79D, T84R, Y91C, D93G, Q96P, C97S, P101R, C102R, C102R, G106D, G106S, C108S, D110N, I112S, N113K, Y115C, C119F, C119R, E124K, G125E, G125R, G125V, C134Y, I136T, N138H, G139D, G139S, C155F, G160E, Q167H, S169C, C170F, C178R, C178W, R191C, R191H, R226G, R226Q, R226W, V227D, V227F, V228F, V228L, Q241H, Q241K, C252S, C252Y, G253E, G253R, A265T, C268W, A279T, N283D, E291V, R294G, R294Q, V296M, H302R, N306S, I316F, L318R, L321Q, N328K, N328Y, P333H, P333T, T342K, T342M, I344L, G351D, W356C, G357E, G357R, K362E, G363W, A366D, R379G, R379Q, C382Y, L392F, L383I, R384L, K387E, I390F, M394K, F395I, F395L, C396F, C396S, A397P, R404T, C407R, C407S, D410H, S411G, S411I, G412E, G413R, P414T, V419E, F424V, T426P, S430T, W431G, W431R, G432S, E433A, G433K, C435Y, A436V, G442E, G442R, I443T, R449Q, R449W, Y450C, W453R, and I454T. As discussed more fully below, this numbering is relative to the wild type human FIX. Other amino acid variations identified in the human population are known and can be found, for example, using the National Center for Biotechnology Information's ("NCBI") variation viewer, accession number GCF_000001405.25. Factor VIII proteins also include polypeptides containing post-translational modifications.

Of particular use in the present disclosure is a FIX protein that includes the so called "Padua" mutation, an arginine to leucine change at position 338 of the mature single-strand Factor IX protein (R338L), position 384 of the Factor IX pre-pro-polypeptide (R384L). This mutation confers hyperfunctional activity to the FIX protein. For example, it was shown that "Padua" protein (e.g., Factor IX containing the R338L mutation) is 5-fold to 10-fold more active than wild-type Factor IX in vivo. U.S. Pat. No. 6,531,298; Simioni P. et al., N Engl J Med. 361(17): 1671-75 (2009), hereby incorporated by reference in its entirety. Accordingly, the disclosure provides amino acid and nucleic acid constructs that encode a Padua-FIX protein, sometimes referred to herein as "FIXp" or "pFIX".

As used herein, the terms "Factor IX polynucleotide" and "FIX polynucleotide" refer to a polynucleotide encoding a Factor IX polypeptide having Factor IX serine protease activity under particular conditions, e.g., as measured using the one stage Factor IX clotting assay described in Chapter 2.7.11 of the European Pharmacopoeia 9.0. Factor IX polynucleotides include polynucleotides encoding Factor IX single-chain precursor polypeptides, including Factor IX pre-pro-polypeptides, Factor IX pro-peptides, and mature, single-chain Factor IX polypeptides, which, when activated by the post-translational processing described above, become active Factor IX protein with Factor IX serine protease activity. Specifically included in the definition of Factor IX polynucleotides are polynucleotides encoding a Factor IX polypeptide that includes the R338L variant. In an exemplary embodiment, a human Factor IX polynucleotide refers to a polynucleotide that encodes a polypeptide that includes an amino acid sequence with high sequence identity (e.g., at least 85%, 90%, 95%, 99%, or more) to the portion of the wild type human Factor IX polypeptide that includes the light and heavy chains, FIX-MP-AA (SEQ ID NO: 10, shown in FIG. 11A) or to the portion of the padua human Factor IX polypeptide that includes the light and heavy chains, FIXp-MP-AA (SEQ ID NO: 12, shown in FIG. 12).

As described herein, Factor IX polynucleotides can include regulatory elements, such as promoters, enhancers, terminators, polyadenylation sequences, and introns, as well as viral packaging elements, such as inverted terminal repeats ("ITRs"), and/or other elements that support replication of the polynucleotide in a non-viral host cell, e.g., a replicon supporting propagation of the polynucleotide, e.g., in a bacterial, yeast, or mammalian host cell.

Of particular use in the present disclosure are codon-altered Factor IX polynucleotides. As described herein, the codon-altered FIX polynucleotides provide increased expression of transgenic Factor IX in vivo, as compared to the level of Factor IX expression provided by a natively-coded Factor IX construct (e.g., a polynucleotide encoding the same Factor IX amino acid sequence using the wild-type human codons). As used herein, the term "increased expression" refers to an increased level of transgenic Factor IX protein in the blood of an animal administered the codon-altered polynucleotide encoding Factor IX, as compared to the level of transgenic Factor IX protein in the blood of an animal administered a natively-coded Factor IX construct. Increased expression of the protein leads to an increase in Factor IX activity; thus, increased expression leads to increased activity.

In some embodiments, increased expression refers to at least 25% greater transgenic Factor IX polypeptide in the blood of an animal administered the codon-altered Factor IX polynucleotide, as compared to the level of transgenic Factor IX polypeptide in the blood of an animal administered a natively-coded Factor IX polynucleotide. For the purpose of the present disclosure, increased expression refers to an effect generated by the alteration of the codon sequence, rather than hyperactivity caused by an underlying amino acid substitution, e.g., a "Padua" mutation. That is, the expression level obtained from a codon-optimized sequence encoding a "Padua" Factor IX polynucleotide is compared relative to the expression level obtained from a natively-coded "Padua" protein. In some embodiments, increased expression refers to at least 50% greater, at least 75% greater, at least 100% greater, at least 3-fold greater, at least 4-fold greater, at least 5-fold greater, at least 6-fold greater, at least 7-fold greater, at least 8-fold greater, at least 9-fold greater, at least 10-fold greater, at least 15-fold greater, at least 20-fold greater, at least 25-fold greater, at least 30-fold greater, at least 40-fold greater, at least 50-fold greater, at least 60-fold greater, at least 70-fold greater, at least 80-fold greater, at least 90-fold greater, at least 100-fold greater, at least 125-fold greater, at least 150-fold greater, at least 175-fold greater, at least 200-fold greater, at least 225-fold greater, or at least 250-fold greater transgenic Factor IX polypeptide in the blood of an animal administered the codon-altered Factor IX polynucleotide, as compared to the level of transgenic Factor IX polypeptide in the blood of an animal administered a natively coded Factor IX polynucleotide. Factor IX polypeptide levels in the blood of an animal can be measured, for example, using an ELISA assay specific for Factor IX polypeptide.

By "Factor IX activity" or "Factor IX serine protease activity" herein is meant the ability to cleave a Factor X polypeptide in the presence of a Factor VIIIa co-factor, e.g., via hydrolysis of the Arg194-Ile195 peptide bond in wild-type Factor IX, thus activating Factor X to Factor Xa. The activity levels can be measured using any Factor IX activity known in the art; suitable assays are outlined herein; an exemplary assay for determining Factor IX activity is the one stage Factor IX clotting assay described in Chapter 2.7.11 of the European Pharmacopoeia 9.0, used in the examples provided herein. In some embodiments, human plasma deficient of FIX activity is used as a control in the one stage clotting assay to determine the Factor IX specificity.

Because certain Factor IX variants have enhanced specific activities as compared to wild type Factor IX in vivo, e.g., the human 'Padua' variant has 5-fold to 10-fold greater Factor IX serine protease activity than does natively-coded type human Factor IX, in some embodiments, the therapeutic potential of a Factor IX polynucleotide composition is evaluated by the increase in Factor IX activity in the blood of an animal administered a Factor IX polynucleotide, e.g., instead of or in addition to increased Factor IX expression. In some embodiments, as used herein, increased Factor IX activity refers to a greater increase in Factor IX activity in the blood of an animal administered a codon-altered Factor IX polynucleotide, relative to a baseline Factor IX activity in the blood of the animal prior to administration of the codon-altered Factor IX polynucleotide, as compared to the increase in Factor IX activity in the blood of an animal administered a natively-coded Factor IX polynucleotide, relative to a baseline Factor IX activity in the blood of the animal prior to administration of the natively-coded Factor IX polynucleotide. In some embodiments, increased Factor IX activity refers to at least a 25% greater increase in Factor IX activity in the blood of an animal administered the codon-altered Factor IX polynucleotide, relative to a baseline level of Factor IX activity in the blood of the animal prior to administration of the codon-altered Factor IX polynucleotide, as compared to the increase in the level Factor IX activity in the blood of an animal administered a natively-coded Factor IX polynucleotide, relative to the baseline level of Factor IX activity in the animal prior to administration of the natively-coded Factor IX polynucleotide. In some embodiments, increased Factor IX activity refers to at least 50% greater, at least 75% greater, at least 100% greater, at least 3-fold greater, at least 4-fold greater, at least 5-fold greater, at least 6-fold greater, at least 7-fold greater, at least 8-fold greater, at least 9-fold greater, at least 10-fold greater, at least 15-fold greater, at least 20-fold greater, at least 25-fold greater, at least 30-fold greater, at least 40-fold greater, at least 50-fold greater, at least 60-fold greater, at least 70-fold greater, at least 80-fold greater, at least 90-fold greater, at least 100-fold greater, at least 125-fold greater, at least 150-fold greater, at least 175-fold greater, at least 200-fold greater, at least 225-fold greater, or at least 250-fold greater increase in Factor IX activity in the blood of an animal administered the codon-altered Factor IX polynucleotide, relative to a baseline level of Factor IX activity in the blood of the animal prior to administration of the codon-altered Factor IX polynucleotide, as compared to the increase in the level Factor IX activity in the blood of an animal administered a natively-coded Factor IX polynucleotide, relative to the baseline level of Factor IX activity in the animal prior to administration of the natively-coded Factor IX polynucleotide. Activity is measured using the one stage Factor IX clotting assay described in Chapter 2.7.11 of the European Pharmacopoeia 9.0, as described herein.

As used herein, the term "hemophilia" refers to a group of disease states broadly characterized by reduced blood clotting or coagulation. Hemophilia may refer to Type A, Type B, or Type C hemophilia, or to the composite of all three diseases types. Type A hemophilia (hemophilia A) is caused by a reduction or loss of factor VIII (FVIII) activity and is the most prominent of the hemophilia subtypes. Type B hemophilia (hemophilia B) results from the loss or reduction of factor IX (FIX) clotting function. Type C hemophilia (hemophilia C) is a consequence of the loss or reduction in factor XI (FXI) clotting activity. Hemophilia A and B are X-linked diseases, while hemophilia C is autosomal. Conventional treatments for hemophilia include both prophylactic and on-demand administration of clotting factors, such as FVIII, FIX, including Bebulin®-VH, and FXI, as well as FEIBA-VH, desmopressin, and plasma infusions.

As used herein, the term "Factor IX gene therapy," or "FIX gene therapy," includes any therapeutic approach of providing a nucleic acid encoding Factor IX to a patient to relieve, diminish, or prevent the reoccurrence of one or more symptoms (e.g., clinical factors) associated with a Factor IX deficiency (e.g., hemophilia B). The term encompasses administering any compound, drug, procedure, or regimen comprising a nucleic acid encoding a Factor IX molecule, including any modified form of Factor IX (e.g., a Factor VIII R384L variant), for maintaining or improving the health of an individual with a Factor IX deficiency (e.g., hemophilia B). One skilled in the art will appreciate that either the course of FIX gene therapy or the dose of a FIX gene therapy therapeutic agent can be changed, e.g., based upon the results obtained in accordance with the present disclosure.

The terms "therapeutically effective amount or dose" or "therapeutically sufficient amount or dose" or "effective or sufficient amount or dose" refer to a dose that produces therapeutic effects for which it is administered. For example, a therapeutically effective amount of a drug useful for treating hemophilia can be the amount that is capable of preventing or relieving one or more symptoms associated with hemophilia.

In some embodiments, a therapeutically effective treatment results in a decrease in the frequency and/or severity of bleeding incidents in a subject.

As used herein, the term "gene" refers to the segment of a DNA molecule that codes for a polypeptide chain (e.g., the coding region). In some embodiments, a gene is positioned by regions immediately preceding, following, and/or intervening the coding region that are involved in producing the polypeptide chain (e.g., regulatory elements such as a promoter, enhancer, polyadenylation sequence, 5'-untranslated region, 3'-untranslated region, or intron).

As used herein, the term "regulatory elements" refers to nucleotide sequences, such as promoters, enhancers, terminators, polyadenylation sequences, introns, etc., that provide for the expression of a coding sequence in a cell.

As used herein, the term "promoter element" refers to a nucleotide sequence that assists with controlling expression of a coding sequence. Generally, promoter elements are located 5' of the translation start site of a gene. However, in certain embodiments, a promoter element may be located within an intron sequence, or 3' of the coding sequence. In some embodiments, a promoter useful for a gene therapy vector is derived from the native gene of the target protein (e.g., a Factor VIII promoter). In some embodiments, a promoter useful for a gene therapy vector is specific for expression in a particular cell or tissue of the target organism (e.g., a liver-specific promoter). In yet other embodiments, one of a plurality of well characterized promoter elements is used in a gene therapy vector described herein. Non-limiting examples of well-characterized promoter elements include the CMV early promoter, the β-actin promoter, and the methyl CpG binding protein 2 (MeCP2) promoter. In some embodiments, the promoter is a constitutive promoter, which drives substantially constant expression of the target protein. In other embodiments, the promoter is an inducible promoter, which drives expression of the target protein in response to a particular stimulus (e.g., exposure to a particular treatment or agent). For a review of designing promoters for AAV-mediated gene therapy, see Gray et al. (Human Gene Therapy 22:1143-53 (2011)), the contents of which are expressly incorporated by reference in their entirety for all purposes.

As used herein, a "CRM8" element refers to cis-acting regulatory module derived from the SERPINA1 gene (NCBI accession number NM_000295.4) that enhances expression of an operatively linked gene, e.g., a sequence encoding a Factor IX polypeptide, in a liver-specific fashion having high sequence identity to SEQ ID NO:39. As used herein, a CRM8 element refers to a single copy of the regulatory element which, in some embodiments, is included in one or more copies within a Factor IX polynucleotide, e.g., 1, 2, 3, or more copies. For further information on CRM elements, such as CRM8, see Chuah M K et al., Mol Ther., 22(9): 1605-13 (2014), which is hereby incorporated by reference.

As used herein an "MVM intron" refers to an intron sequence derived from minute virus of mice having high sequence identity to SEQ ID NO:53. For further information on the MVM intron itself, see Haut and Pintel, J Virol. 72(3):1834-43 (1998), and use of the MVM intron in AAV gene therapy vectors, see Wu Z et al., Mol Ther., 16(2):280-9 (2008), both of which are hereby incorporated by reference.

As used herein, the term "operably linked" refers to the relationship between a first reference nucleotide sequence (e.g., a gene) and a second nucleotide sequence (e.g., a regulatory control element) that allows the second nucleotide sequence to affect one or more properties associated with the first reference nucleotide sequence (e.g., a transcription rate). In the context of the present disclosure, a regulatory control element is operably linked to a Factor IX transgene when the regulatory element is positioned within a gene therapy vector such that it exerts an affect (e.g., a promotive or tissue selective affect) on transcription of the Factor IX transgene.

As used herein, the term "vector" refers to any nucleic acid construct used to transfer a Factor IX nucleic acid into a host cell. In some embodiments, a vector includes a replicon, which functions to replicate the nucleic acid construct. Non-limiting examples of vectors useful for gene therapy include plasmids, phages, cosmids, artificial chromosomes, and viruses, which function as autonomous units of replication in vivo. In some embodiments, a vector is a viral vector for introducing a Factor IX nucleic acid into the host cell. Many modified eukaryotic viruses useful for gene therapy are known in the art. For example, adeno-associated viruses (AAVs) are particularly well suited for use in human gene therapy because humans are a natural host for the virus, the native viruses are not known to contribute to any diseases, and the viruses illicit a mild immune response.

As used herein, the term "Factor IX viral vector" refers to a recombinant virus comprising a Factor IX polynucleotide, encoding a Factor IX polypeptide, which is sufficient for expression of the Factor IX polypeptide when introduced into a suitable animal host (e.g., a human). Specifically included within the definition of Factor IX viral vector are recombinant viruses in which a codon-altered Factor IX polynucleotide, which encodes a Factor IX polypeptide, has been inserted into the genome of the virus. Also specifically included within the definition of Factor IX viral vectors are recombinant viruses in which the native genome of the virus has been replaced with a Factor IX polynucleotide, which encodes a Factor IX polypeptide. Included within the definition of Factor IX viral vectors are recombinant viruses comprising a Factor IX polynucleotide, which encodes a "Padua" variant of Factor IX.

As used herein, the term "Factor IX viral particle" refers to a viral particle encapsulating a Factor IX polynucleotide, encoding a Factor IX polypeptide, which is specific for expression of the Factor IX polypeptide when introduced into a suitable animal host (e.g., a human). Specifically included within the definition of Factor IX viral particles are recombinant viral particles encapsulating a genome in which a codon-altered Factor IX polynucleotide, which encodes a Factor IX polypeptide, has been inserted. Also specifically included within the definition of Factor IX viral particles are recombinant viral particles encapsulating a Factor IX polynucleotide, which encodes a Factor IX polypeptide, which replaces the natice genome of the virus. Included within the definition of Factor IX viral particles are recombinant viral particles encapsulating a Factor IX polynucleotide, which encodes a "Padua" variant of Factor IX.

By "AAV" or "adeno-associated virus" herein is meant a Dependoparvovirus within the Parvoviridae genus of viruses. As used herein, AAV can refer to a virus derived from a naturally occurring "wild-type" AAV genome into which a Factor IX polynucleotide has been inserted, a recombinant virus derived from a recombinant Factor IX polynucleotide packaged into a capsid using capsid proteins encoded by a naturally occurring AAV cap gene, or a recombinant virus derived from a recombinant Factor IX polynucleotide packaged into a capsid using capsid proteins encoded by a non-natural capsid cap gene. Included within the definition of AAV are AAV type 1 (AAV1), AAV type 2 (AAV2), AAV type 3 (AAV3), AAV type 4 (AAV4), AAV type 5 (AAV5), AAV type 6 (AAV6), AAV type 7 (AAV7), AAV type 8 (AAV8), and AAV type 9 (AAV9) viruses encapsulating a Factor IX polynucleotide and viruses formed by one or more variant AAV capsid proteins encapsulating a Factor IX polynucleotide.

By "AAV8," "AAV-8," or "AAV serotype 8" herein is meant a virus formed by an AAV8 capsid viral protein that encapsulates a Factor IX polynucleotide.

As used herein, the term "CpG" refers to a cytosine-guanine dinucleotide along a single strand of DNA, with the "p" representing the phosphate linkage between the two.

As used herein, the term "CpG island" refers to a region within a polynucleotide having a statistically elevated density of CpG dinucleotides. As used herein, a region of a polynucleotide (e.g., a polynucleotide encoding a codon-altered Factor IX protein) is a CpG island if, over a 200-base pair window: (i) the region has GC content of greater than 50%, and (ii) the ratio of observed CpG dinucleotides per expected CpG dinucleotides is at least 0.6, as defined by the relationship:

$$\frac{N[CpG] * N[\text{length of window}]}{N[C] * N[G]} \geq 0.6.$$

For additional information on methods for identifying CpG islands, see Gardiner-Garden M. et al., J Mol Biol., 196(2): 261-82 (1987), the content of which is expressly incorporated herein by reference, in its entirety, for all purposes.

As used herein, the term "nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs). However, particularly useful embodiments herein, for use in gene therapy in patients, use phosphodiester bonds.

By "nucleic acid compositions" herein is meant any molecule or formulation of a molecule that includes a Factor IX polynucleotide, encoding a Factor IX polynucleotide. Included within the definition of nucleic acid compositions are Factor IX polynucleotides, aqueous solutions of Factor IX polynucleotides, viral particles encapsulating a Factor IX polynucleotide, and aqueous formulations of viral particles encapsulating a Factor IX polynucleotide. A nucleic acid composition, as disclosed herein, includes a codon-altered FIX gene, that encodes a FIX polypeptide.

The term "amino acid" refers to naturally occurring and non-natural amino acids, including amino acid analogs and amino acid mimetics that function in a manner similar to the naturally occurring amino acids. Naturally occurring amino acids include those encoded by the genetic code, as well as those amino acids that are later modified, e.g., hydroxyproline, y-carboxyglutamate, and O-phosphoserine. Naturally occurring amino acids can include, e.g., D- and L-amino acids. As to amino acid sequences, one of ordinary skill in the art will recognize that individual substitutions, deletions or additions to a nucleic acid or peptide sequence that alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

Conservative amino acid substitutions providing functionally similar amino acids are well known in the art. Dependent on the functionality of the particular amino acid, e.g., catalytic, structural, or sterically important amino acids, different groupings of amino acid may be considered conservative substitutions for each other. Table 1 provides groupings of amino acids that are considered conservative substitutions based on the charge and polarity of the amino acid, the hydrophobicity of the amino acid, the surface exposure/structural nature of the amino acid, and the secondary structure propensity of the amino acid.

TABLE 1

Groupings of conservative amino acid substitutions based on the functionality of the residue in the protein.

| Important Feature | Conservative Groupings |
|---|---|
| Charge/Polarity | 1. H, R, and K |
| | 2. D and E |
| | 3. C, T, S, G, N, Q, and Y |
| | 4. A, P, M, L, I, V, F, and W |
| Hydrophobicity | 1. D, E, N, Q, R, and K |
| | 2. C, S, T, P, G, H, and Y |
| | 3. A, M, I, L, V, F, and W |
| Structural/Surface Exposure | 1. D, E, N, Q, H, R, and K |
| | 2. C, S, T, P, A, G, W, and Y |
| | 3. M, I, L, V, and F |
| Secondary Structure Propensity | 1. A, E, Q, H, K, M, L, and R |
| | 2. C, T, I, V, F, Y, and W |
| | 3. S, G, P, D, and N |
| Evolutionary Conservation | 1. D and E |
| | 2. H, K, and R |
| | 3. N and Q |
| | 4. S and T |
| | 5. L, I, and V |
| | 6. F, Y, and W |
| | 7. A and G |
| | 8. M and C |

The terms "identical" or percent "identity," in the context of two or more nucleic acids or peptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection.

As is known in the art, a number of different programs may be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman, Adv. Appl. Math., 2:482 (1981), by the sequence identity alignment algorithm of Needleman & Wunsch, J. Mol. Biol., 48:443 (1970), by the search for similarity method of Pearson & Lipman, Proc. Natl. Acad. Sci. U.S.A., 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res., 12:387-395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis,"

Macromolecule Sequencing and Synthesis, Selected Methods and Applications, pp 127-149 (1988), Alan R. Liss, Inc, all of which are incorporated by reference.

An example of a useful algorithm is PILEUP. PILEUP creates a multiple sequence alignment from a group of related sequences using progressive, pair wise alignments. It may also plot a tree showing the clustering relationships used to create the alignment. PILEUP uses a simplification of the progressive alignment method of Feng & Doolittle, J. Mol. Evol. 35:351-360 (1987); the method is similar to that described by Higgins & Sharp CABIOS 5:151-153 (1989), both incorporated by reference. Useful PILEUP parameters including a default gap weight of 3.00, a default gap length weight of 0.10, and weighted end gaps.

Another example of a useful algorithm is the BLAST algorithm, described in: Altschul et al., J. Mol. Biol. 215, 403-410, (1990); Altschul et al., Nucleic Acids Res. 25:3389-3402 (1997); and Karlin et al., Proc. Natl. Acad. Sci. U.S.A. 90:5873-5787 (1993), both incorporated by reference. A particularly useful BLAST program is the WU-BLAST-2 program which was obtained from Altschul et al., Methods in Enzymology, 266:460-480 (1996); http://blast.wustl/edu/blast/README.html]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST, as reported by Altschul et al., Nucl. Acids Res., 25:3389-3402, incorporated by reference. Gapped BLAST uses BLOSUM-62 substitution scores; threshold T parameter set to 9; the two-hit method to trigger ungapped extensions; charges gap lengths of k a cost of 10+k; Xu set to 16, and Xg set to 40 for database search stage and to 67 for the output stage of the algorithms. Gapped alignments are triggered by a score corresponding to ~22 bits.

A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored). In a similar manner, "percent (%) nucleic acid sequence identity" with respect to the coding sequence of the polypeptides identified is defined as the percentage of nucleotide residues in a candidate sequence that are identical with the nucleotide residues in the coding sequence of the cell cycle protein. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer amino acids than the protein encoded by the wild-type Factor IX sequence of FIG. 3A (SEQ ID NO:2), it is understood that in one embodiment, the percentage of sequence identity will be determined based on the number of identical amino acids or nucleotides in relation to the total number of amino acids or nucleotides. Thus, for example, sequence identity of sequences shorter than that shown in FIG. 3A (SEQ ID NO:2), as discussed below, will be determined using the number of nucleotides in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "O", which obviates the need for a weighted scale or parameters as described below for sequence similarity calculations. Percent sequence identity may be calculated, for example, by dividing the number of matching identical residues by the total number of residues of the "shorter" sequence in the aligned region and multiplying by 100. The "longer" sequence is the one having the most actual residues in the aligned region.

The term "allelic variants" refers to polymorphic forms of a gene at a particular genetic locus, as well as cDNAs derived from mRNA transcripts of the genes, and the polypeptides encoded by them. The term "preferred mammalian codon" refers a subset of codons from among the set of codons encoding an amino acid that are most frequently used in proteins expressed in mammalian cells as chosen from the following list: Gly (GGC, GGG); Glu (GAG); Asp (GAC); Val (GTG, GTC); Ala (GCC, GCT); Ser (AGC, TCC); Lys (AAG); Asn (AAC); Met (ATG); Ile (ATC); Thr (ACC); Trp (TGG); Cys (TGC); Tyr (TAT, TAC); Leu (CTG); Phe (TTC); Arg (CGC, AGG, AGA); Gln (CAG); His (CAC); and Pro (CCC).

As used herein, the term codon-altered refers to a polynucleotide sequence encoding a polypeptide (e.g., a Factor IX protein), where at least one codon of the native polynucleotide encoding the polypeptide has been changed to improve a property of the polynucleotide sequence. In some embodiments, the improved property promotes increased transcription of mRNA coding for the polypeptide, increased stability of the mRNA (e.g., improved mRNA half-life), increased translation of the polypeptide, and/or increased packaging of the polynucleotide within the vector. Non-limiting examples of alterations that can be used to achieve the improved properties include changing the usage and/or distribution of codons for particular amino acids, adjusting global and/or local GC content, removing AT-rich sequences, removing repeated sequence elements, adjusting global and/or local CpG dinucleotide content, removing cryptic regulatory elements (e.g., TATA box and CCAAT box elements), removing of intron/exon splice sites, improving regulatory sequences (e.g., introduction of a Kozak consensus sequence), and removing sequence elements capable of forming secondary structure (e.g., stem-loops) in the transcribed mRNA.

As discussed herein, there are various nomenclatures to refer to components of the disclosure herein. "CS-number" (e.g. "CS02," "CS03," "CS04," "CS05," "CS06," etc.) refer to codon altered polynucleotides encoding FIX polypeptides and/or the encoded polypeptides, including variants. For example, CS02-FL refers to the Full Length codon altered CS02 polynucleotide sequence or amino acid sequence (sometimes referred to herein as "CS02-FL-AA" for the Amino Acid sequence and "CS02-FL-NA" (SEQ ID NO:5) for the Nucleic Acid sequence) encoded by the CS02 polynucleotide sequence. Similarly, "CS02-LC" refers to either the codon altered nucleic acid sequence ("CS02-LC-NA" (SEQ ID NO:42)) encoding the light chain of a FIX polypeptide or the amino acid sequence (also sometimes referred to herein as "CS02-LC-AA") of the FIX light chain encoded by the CS02 polynucleotide sequence. Likewise, CS02-HC, CS02-HC-AA, and CS02-HC-NA (SEQ ID NO:41) are the same for the FIX heavy chain. As will be appreciated by those in the art, for constructs such as CS02, CS03, CS04, CS05, CS06, etc., that are only codon-altered (e.g. they do not contain additional amino acid substitutions as compared to the Padua Factor IX variant), the amino acid sequences will be identical, as the amino acid sequences are not altered by the codon optimization. Thus, sequence constructs of the disclosure include, but are not limited to, CS02-FL-NA (SEQ ID NO:5), CS02-FL-AA, CS02-LC-NA (SEQ ID NO:42), CS02-LC-AA, CS02-HC-AA, CS02-HC-NA (SEQ ID NO:41), CS03-FL-NA (SEQ ID NO:6), CS03-FL-AA, CS03-LC-NA (SEQ ID NO:44), CS03-LC-AA, CS03-HC-AA, CS03-HC-NA (SEQ ID NO:43), CS04-FL-NA (SEQ ID NO:7), CS04-FL-AA, CS04-LC-NA (SEQ ID NO:46), CS04-LC-AA, CS04-HC-AA, CS04-HC-NA, CS05-FL-NA (SEQ ID NO:8), CS05-FL-AA, CS05-LC-NA (SEQ ID NO:48), CS05-LC-AA, CS05-HC-AA, CS05-HC-NA (SEQ ID NO:47), CS06-FL-NA (SEQ ID NO:9), CS06-FL-AA, CS06-LC-NA (SEQ ID NO:50), CS06-LC-AA, CS06-HC-AA, and CS06-HC-NA (SEQ ID NO:49). It should be noted that all "CS" constructs herein encode or contain the FIXp amino acid sequence, although included within the definition of CS constructs are those that encode or contain the human wild type FIX amino acid sequence.

As used herein, the term "liver-specific expression" refers to the preferential or predominant in vivo expression of a particular gene (e.g., a codon-altered, transgenic Factor IX gene) in hepatic tissue, as compared to in other tissues. In some embodiments, liver-specific expression means that at least 50% of all expression of the particular gene occurs within hepatic tissues of a subject. In other embodiments, liver-specific expression means that at least 55%, 60%, 65%, 70%, 75%, 80%, 85%, 90%, 95%, 99%, or 100% of all expression of the particular gene occurs within hepatic tissues of a subject. Accordingly, a liver-specific regulatory element is a regulatory element that drives liver-specific expression of a gene in hepatic tissue.

As used herein, the terms "less than" X and "less than" X % refer to a range of from 0 to X, exclusive of the value X, e.g., from 0% to X %, exclusive of X %. As used herein, the terms are used interchangeably with a range starting at 0 or 0% through, but not including, X or X %.

As used herein, the terms "no more than" X or "no more than" X % refer to a range of from 0 to X, inclusive of the value X, e.g., from 0% to X %, inclusive of X %. As used herein, the terms are used interchangeably with a range starting at 0 or 0% through, and including, X or X %.

As used herein, the terms "greater than" X or "greater than" X % refer to a range of from X to an upper limit, exclusive of the value X, e.g., from X % to 100%, exclusive of X %. As used herein, the terms are used interchangeably with a range starting at, but not including, X or X % through an upper limit which is 100% in the context of a percentage.

As used herein, the terms "at least" X or "at least" X % refer to a range of from X to an upper limit, inclusive of the value X, e.g., from X % to 100%, inclusive of X %. As used herein, the terms are used interchangeably with a range starting at, and including, X or X % through an upper limit which is 100% in the context of a percentage.

As used herein, the terms "between 'X' and 'Y'," "between 'X'% and 'Y'%," "from 'X' to 'Y'," and "from 'X'% to 'Y'%" refer to a range of from X to Y, inclusive of the values X and Y, e.g., from X % to Y %, inclusive of X % and Y %. As used herein, the terms are used interchangeably with a range starting at X or X % through, and including, Y or Y %.

III. Codon-Altered Factor IX Polynucleotides

In some embodiments, the present disclosure provides codon altered nucleic acid compositions encoding Factor IX or a Factor IX variant (with FIXp finding use in particular embodiments). These codon-altered polynucleotides provide markedly improved expression of Factor IX when administered in an AAV-based gene therapy construct. The codon-altered polynucleotides also demonstrate improved AAV-virion packaging, as compared to conventionally codon-optimized constructs. As demonstrated in Example 1, Applicants have achieve these advantages through the discovery of several codon-altered polynucleotides (e.g., CS02-FL-NA, CS03-FL-NA, CS04-FL-NA, CS05-FL-NA, and CS06-FL-NA (SEQ ID NOS:5-9 respectively)) encoding a Factor IXp polypeptides with a hyperactive R338L amino acid substitution (based on the mature, single-chain Factor IX polypeptide sequence; R384L based on the Factor IX pre-pro-protein sequence). As demonstrated in Examples 2 and 3, incorporation of one or more liver-specific regulatory control element (e.g., CRM8) into gene therapy vectors encoding the Factor IX molecule further increased in vivo and in vitro expression of Factor IX and Factor IX activity.

Wild-type Factor IX is encoded with a 28 amino acid signal peptide (FIX-SP-AA (SEQ ID NO:37)) and an 18 amino acid pro-peptide (FIX-PP-AA (SEQ ID NO:38)), which are cleaved from the encoded polypeptide prior to activation of Factor IXa. As appreciated by those in the art, signal peptides and/or pro-peptides may be mutated, replaced by signal peptides and/or pro-peptides from other genes or other organisms, or completely removed, without affecting the sequence of the mature polypeptide left after the signal and pro-peptide are removed by cellular processing.

Accordingly, in some embodiments, a codon-altered polynucleotide (e.g., a nucleic acid composition) provided herein has a nucleotide sequence with high sequence identity to CS02-FL-NA, CS03-FL-NA, CS04-FL-NA, CS05-FL-NA, or CS06-FL-NA (SEQ ID NOS:5-9, respectively) encoding the mature Factor IX single-chain polypeptide, that is, the Factor IX light chain, activation peptide, and heavy chain (e.g., amino acids 47-461 of the full-length polypeptide encoded by the wild-type Factor IX gene; FIX-FL-AA (SEQ ID NO:2)).

Additionally, as known in the art, human wild type Factor IX has a 34 amino acid activation peptide positioned between the Factor IX light chain and heavy chain that is excised from the single-chain Factor IX polypeptide upon activation of the protein. Because the activation peptide is removed from the active Factor IX polypeptide, the peptide itself is dispensable for ultimate Factor IX activity. Accordingly, it is not required that the Factor IX polypeptides encoded by the codon-altered polynucleotides disclosed herein have high sequence identity to the human wild type activation peptide sequence (FIX-AP-AA (SEQ ID NO:56)). However, the encoded activation peptide should be excisable upon activation of the Factor IX polypeptide. For example, in some embodiments, the encoded activation peptide should include Factor XI cleavage sites at its N- and C-termini, that are recognizable and cleavable by human Factor IX in-vivo.

Accordingly, in some embodiments, a codon-altered polynucleotide (e.g., a nucleic acid composition) provided herein encodes for a single-chain Factor IX polypeptide with high sequence identity to the human wild type FIX light chain sequence (FIX-LC-AA (SEQ ID NO:62)) and human wild type FIX heavy chain sequence (FIX-HC-AA (SEQ ID NO:63)), and additionally encode for a polypeptide linker joining the C-terminus of the light chain to the N-terminus of the heavy chain (e.g., an activation peptide) with two Factor XI cleavage sites.

In some embodiments, the Factor IX light and heavy chains encoded by the codon-altered polynucleotide are human Factor IX light and heavy chains, respectively, including the FIXp heavy chain. In other embodiments, the Factor IX light and heavy chains encoded by the codon-altered polynucleotide are heavy and light chain sequences from another mammal (e.g., porcine Factor IX). In yet other embodiments, the Factor IX light and heavy chains are chimeric light and heavy chains (e.g., a combination of human and a second mammalian sequence). In yet other embodiments, the Factor IX light and heavy chains are humanized version of the light and heavy chains from another mammal, e.g., light and heavy chain sequences from another mammal in which human residues are substituted at select positions to reduce the immunogenicity of the resulting peptide when administered to a human.

The GC content of human genes varies widely, from less than 25% to greater than 90%. However, in general, human genes with higher GC contents are expressed at higher levels. For example, Kudla et al. (PLoS Biol., 4(6):80 (2006)) demonstrate that increasing a gene's GC content increases expression of the encoded polypeptide, primarily by increasing transcription and effecting a higher steady state level of the mRNA transcript. Generally, the desired GC content of a codon-optimized gene construct is thought to be equal or greater than 60%. For example, the Factor IX gene in the scAAV8.FIXR338L gene therapy vector was specifically codon altered, using the GeneOptimizer software (Geneart), to increase the GC content of the wild type coding sequence from 41% GC to 61% GC. See, Wu Z. et al., Mol Ther 16:280-89 (2008) and Monahan P E et al., Hum Gene Ther., 26(2):69-81 (2015). However, native AAV genomes have GC contents of around 56%.

Accordingly, in some embodiments, the codon-altered polynucleotides (e.g., nucleic acid compositions) provided herein have a CG content that more closely matches the GC content of native AAV virions (e.g., around 56% GC), which is lower than the preferred CG contents of polynucleotides that are conventionally codon-optimized for expression in mammalian cells (e.g., at or above 60% GC). For example, CS02-FL-NA (SEQ ID NO:5) has a GC content of about 54%, CS03-FL-NA (SEQ ID NO:6) has a GC content of about 55%, CS04-FL-NA (SEQ ID NO:7) has a GC content of about 54.5%, CS05-FL-NA (SEQ ID NO:8) has a GC content of about 56.6%, and CS06-FL-NA (SEQ ID NO:9) has a GC content of about 55%. These constructs should provide has improved virion packaging as compared to similarly codon-altered sequences with higher GC content.

Thus, in some embodiments, the overall GC content of a codon-altered polynucleotide encoding a Factor IX polypeptide (e.g., a polynucleotide having high sequence identity to one of the CS02-CS06 Factor IX coding sequences) is less than 60%. In some embodiments, the overall GC content of a codon-altered polynucleotide encoding a Factor IX polypeptide is less than 59%. In some embodiments, the overall GC content of a codon-altered polynucleotide encoding a Factor IX polypeptide is less than 58%. In some embodiments, the overall GC content of a codon-altered polynucleotide encoding a Factor IX polypeptide is less than 57%. In some embodiments, the overall GC content of a codon-altered polynucleotide encoding a Factor IX polypeptide is no more than 56%. In some embodiments, the overall GC content of a codon-altered polynucleotide encoding a Factor IX polypeptide is no more than 55%. In some embodiments, the overall GC content of a codon-altered polynucleotide encoding a Factor IX polypeptide is no more than 54%.

In some embodiments, the overall GC content of a codon-altered polynucleotide encoding a Factor IX polypeptide is from 53% to 59%. In some embodiments, the overall GC content of a codon-altered polynucleotide encoding a Factor IX polypeptide is from 54% to 59%. In some embodiments, the overall GC content of a codon-altered polynucleotide encoding a Factor IX polypeptide is from 55% to 59%. In some embodiments, the overall GC content of a codon-altered polynucleotide encoding a Factor IX polypeptide is from 56% to 59%. In some embodiments, the overall GC content of a codon-altered polynucleotide encoding a Factor IX polypeptide is from 53% to 58%. In some embodiments, the overall GC content of a codon-altered polynucleotide encoding a Factor IX polypeptide is from 54% to 58%. In some embodiments, the overall GC content of a codon-altered polynucleotide encoding a Factor IX polypeptide is from 55% to 58%. In some embodiments, the overall GC content of a codon-altered polynucleotide encoding a Factor IX polypeptide is from 56% to 58%. In some embodiments, the overall GC content of a codon-altered polynucleotide encoding a Factor IX polypeptide is from 53% to 57%. In some embodiments, the overall GC content of a codon-altered polynucleotide encoding a Factor IX polypeptide is from 54% to 57%. In some embodiments, the overall GC content of a codon-altered polynucleotide encoding a Factor IX polypeptide is from 55% to 57%. In some embodiments, the overall GC content of a codon-altered polynucleotide encoding a Factor IX polypeptide is from 56% to 57%. In some embodiments, the overall GC content of a codon-altered polynucleotide encoding a Factor IX polypeptide is from 53% to 56%. In some embodiments, the overall GC content of a codon-altered polynucleotide encoding a Factor IX polypeptide is from 54% to 56%. In some embodiments, the overall GC content of a codon-altered polynucleotide encoding a Factor IX polypeptide is from 55% to 56%. In some embodiments, the overall GC content of a codon-altered polynucleotide encoding a Factor IX polypeptide is from 53% to 55%. In some embodiments, the overall GC content of a codon-altered polynucleotide encoding a Factor IX polypeptide is from 54% to 55%.

In some embodiments, the overall GC content of a codon-altered polynucleotide encoding a Factor IX polypeptide is 54±0.5%. In some embodiments, the overall GC content of a codon-altered polynucleotide encoding a Factor IX polypeptide is 54±0.4%. In some embodiments, the overall GC content of a codon-altered polynucleotide encoding a Factor IX polypeptide is 54±0.3%. In some embodiments, the overall GC content of a codon-altered polynucleotide encoding a Factor IX polypeptide is 54±0.2%. In some embodiments, the overall GC content of a codon-altered polynucleotide encoding a Factor IX polypeptide is 54±0.1%. In some embodiments, the overall GC content of a codon-altered polynucleotide encoding a Factor IX polypeptide is 54%.

In some embodiments, the overall GC content of a codon-altered polynucleotide encoding a Factor IX polypeptide is 55±0.5%. In some embodiments, the overall GC content of a codon-altered polynucleotide encoding a Factor IX polypeptide is 55±0.4%. In some embodiments, the overall GC content of a codon-altered polynucleotide encoding a Factor IX polypeptide is 55±0.3%. In some embodiments, the overall GC content of a codon-altered polynucleotide encoding a Factor IX polypeptide is 55±0.2%. In some embodiments, the overall GC content of a codon-altered polynucleotide encoding a Factor IX polypeptide is 55±0.1%. In some embodiments, the overall GC content of a codon-altered polynucleotide encoding a Factor IX polypeptide is 55%.

In some embodiments, the overall GC content of a codon-altered polynucleotide encoding a Factor IX polypeptide is 56±0.5%. In some embodiments, the overall GC content of a codon-altered polynucleotide encoding a Factor IX polypeptide is 56±0.4%. In some embodiments, the overall GC content of a codon-altered polynucleotide encoding a Factor IX polypeptide is 56±0.3%. In some embodiments, the overall GC content of a codon-altered polynucleotide encoding a Factor IX polypeptide is 56±0.2%. In some embodiments, the overall GC content of a codon-altered polynucleotide encoding a Factor IX polypeptide is 56±0.1%. In some embodiments, the overall GC content of a codon-altered polynucleotide encoding a Factor IX polypeptide is 56%.

It has been theorized that these CpG dinucleotides (i.e., a cytosine nucleotide followed by a guanine nucleotide) induce immune responses via toll-like receptors, in vivo. Some evidence suggests that CpG-depleted AAV vectors evade immune detection in mice, under certain circumstances (Faust et al., J. Clin. Invest. 2013; 123, 2994-3001). The wild type Factor IX coding sequence (FIX-FL-NA (SEQ ID NO:1)) contains 20 CpG dinucleotides.

Accordingly, in some embodiments, the nucleic acid compositions (e.g., codon-altered polynucleotides) provided herein are codon-altered to reduce the number of CpG dinucleotides in the Factor IX coding sequence. For example, CS02-FL-NA (SEQ ID NO:5) has no CpG dinucleotides, CS03-FL-NA (SEQ ID NO:6) has no CpG dinucleotides, CS04-FL-NA (SEQ ID NO:7) has no CpG dinucleotides, CS05-FL-NA (SEQ ID NO:8) has 11 CpG dinucleotides, and CS06-FL-NA (SEQ ID NO:9) has 3 CpG dinucleotides. These constructs should illicit lower immunogenic responses than the wild type Factor IX coding sequence and similarly codon-altered sequences with higher numbers of CpG dinucleotides.

Thus, in some embodiments, a sequence of a codon-altered polynucleotide encoding a Factor IX polypeptide (e.g., a polynucleotide having high sequence identity to one of the CS02-CS06 Factor IX coding sequences) has less than 20 CpG dinucleotides. In some embodiments, a sequence of a codon-altered polynucleotide encoding a Factor IX polypeptide has less than 15 CpG dinucleotides. In some embodiments, a sequence of a codon-altered polynucleotide encoding a Factor IX polypeptide has less than 12 CpG dinucleotides. In some embodiments, a sequence of a codon-altered polynucleotide encoding a Factor IX polypeptide has less than 10 CpG dinucleotides. In some embodiments, a sequence of a codon-altered polynucleotide encoding a Factor IX polypeptide has less than 5 CpG dinucleotides. In some embodiments, a sequence of a codon-altered polynucleotide encoding a Factor IX polypeptide has less than 3 CpG dinucleotides. In some embodiments, a sequence of a codon-altered polynucleotide encoding a Factor IX polypeptide has no CpG dinucleotides.

In some embodiments, a sequence of a codon-altered polynucleotide encoding a Factor IX polypeptide has more than 15 CpG dinucleotides. In some embodiments, a sequence of a codon-altered polynucleotide encoding a Factor IX polypeptide has no more than 12 CpG dinucleotides. In some embodiments, a sequence of a codon-altered polynucleotide encoding a Factor IX polypeptide has no more than 10 CpG dinucleotides. In some embodiments, a sequence of a codon-altered polynucleotide encoding a Factor IX polypeptide has no more than 5 CpG dinucleotides. In some embodiments, a sequence of a codon-altered polynucleotide encoding a Factor IX polypeptide has no more than 3 CpG dinucleotides. In some embodiments, a sequence of a codon-altered polynucleotide encoding a Factor IX polypeptide has no CpG dinucleotides. In some embodiments, sequence of a codon-altered polynucleotide encoding a Factor IX polypeptide has no more than 18, 17, 16, 15, 14, 13, 12, 11, 10, 9, 8, 7, 6, 5, 4, 3, 2, 1, or no CpG dinucleotides.

A. Factor IX Amino Acid Substitutions

To further increase the efficiency of AAV-vector based expression of the Factor IX constructs described herein, amino acid substitutions know to improve secretion, increase specific activity, and/or enhanced the stability of Factor IX are further incorporated, in accordance with some implementations. A number of potential Factor IX variants are known in the art to increase the plasma levels of FIX activity. These variants include amino acid substitutions that increase Factor IX catalytic activity (e.g., hyperactive mutants), increase resistance to antithrombin III and/or heparin, increase serum half-life, and result in altered patterns of post-translational modification.

For example, mutation of residue R338 (PPE) can increase the clotting activity of Factor IX. For review, see U.S. Pat. No. 6,531,298, the contents of which are hereby incorporated by reference in its entirety for all purposes. As disclosed in U.S. Pat. No. 6,531,298, an arginine to leucine amino acid substitution at this position increases the activity of Factor IX. This was later confirmed in vivo, where the R338L (PPE) mutation increases Factor IX activity 5-fold to 10-fold in vivo. For review, see Simioni P. et al., N Engl J Med. 361(17):1671-75 (2009), hereby incorporated by reference in its entirety. Accordingly, in some embodiments, the codon-altered polynucleotides described herein encode a Factor IX polypeptide with an amino acid substitution at arginine 384 (PPI; residue 338 (PPE). In a specific embodiment, the amino acid substitution is R384L (PPI). In other embodiments, the amino acid substitution at residue 384 (PPI)/338 (PPE) to a residue other than leucine. For example, it was reported that an R384A (PPI) amino acid substitution provided 2- for to 6-fold higher activity in mice. Schuettrumpf J et al., Blood, 105(6):2316-23 (2005), the content of which is expressly incorporated herein by reference, in its entirety, for all purposes.

Similarly, mutation of residues Y305, K311, S365, and Y391 leads to increased Factor IX activity on a synthetic substrate. In particular, K311M and K311T single mutations resulted in 2.8-fold and 6.7-fold increased activity on a synthetic cleavage substrate. Sichler K. et al., J Biol Chem. 278(6):4121-26 (2003) (using different residue numbering). Further, a Y305F/K311T/Y391T triple mutant resulted in 7000-fold increased activity on the synthetic substrate. Id. Accordingly, in some embodiments, the codon-altered polynucleotides described herein encode a Factor IX polypeptide with an amino acid substitution at one or more of tyrosine 305 (PPI), lysine 311 (PPI), and tyrosine 391 (PPI). In a specific embodiment, the amino acid substitution is K311M (PPI). In a specific embodiment, the amino acid substitution is K311T (PPI). In another specific embodiment, the amino acid substitution is Y305F/K311T/Y391T (PPI).

Other amino acid substitutions that provide improved properties are known in the art and may be incorporated into the described codon-altered Factor IX polynucleotides. For example, see, U.S. Pat. No. 8,778,870, the content of which is expressly incorporated herein by reference, in its entirety, for all purposes.

B. Codon-altered Polynucleotides Encoding a Factor IX Protein

CS02 Codon Altered Polynucleotides

In one embodiment, a nucleic acid composition provided herein includes a Factor IX polynucleotide (e.g., a codon-optimized polynucleotide) encoding a single-chain Factor IX polypeptide, where the Factor IX polynucleotide includes a nucleotide sequence having high sequence identity to CS02-FL-NA (SEQ ID NO:5). In some embodiments, the nucleotide sequence of the Factor IX polynucleotide having high sequence identity to CS02-FL-NA (SEQ ID NO:5) has a reduced GC content, as compared to the wild-type Factor IX coding sequence (FIX-FL-NA (SEQ ID NO:1)). In some embodiments, the nucleotide sequence of the Factor IX polynucleotide having high sequence identity to CS02-FL-NA (SEQ ID NO:5) has a reduced number of CpG dinucleotides, as compared to the wild-type Factor IX coding sequence (FIX-FL-NA (SEQ ID NO: 1)).

In a specific embodiment, the sequence of the codon-altered polynucleotide has at least 95% identity to CS02-FL-NA (SEQ ID NO:5). In a specific embodiment, the sequence of the codon-altered polynucleotide has at least 96% identity to CS02-FL-NA (SEQ ID NO:5). In a specific embodiment, the sequence of the codon-altered polynucleotide has at least 97% identity to CS02-FL-NA (SEQ ID NO:5). In a specific embodiment, the sequence of the codon-altered polynucleotide has at least 98% identity to CS02-FL-NA (SEQ ID NO:5). In a specific embodiment, the sequence of the codon-altered polynucleotide has at least 99% identity to CS02-FL-NA (SEQ ID NO:5). In a specific embodiment, the sequence of the codon-altered polynucleotide has at least 99.5% identity to CS02-FL-NA (SEQ ID NO:5). In a specific embodiment, the sequence of the codon-altered polynucleotide has at least 99.9% identity to CS02-FL-NA (SEQ ID NO:5). In another specific embodiment, the sequence of the codon-altered polynucleotide is CS02-FL-NA (SEQ ID NO:5).

In some embodiments, the sequence of the codon-altered polynucleotide having high sequence identity to CS02-FL-NA (SEQ ID NO:5) has a GC content of less than 60%. In some embodiments, the sequence of the codon-altered polynucleotide having high sequence identity to CS02-FL-NA (SEQ ID NO:5) has a GC content of less than 59%. In some embodiments, the sequence of the codon-altered polynucleotide having high sequence identity to CS02-FL-NA (SEQ ID NO:5) has a GC content of less than 58%. In some embodiments, the sequence of the codon-altered polynucleotide having high sequence identity to CS02-FL-NA (SEQ ID NO:5) has a GC content of less than 57%. In some embodiments, the sequence of the codon-altered polynucleotide having high sequence identity to CS02-FL-NA (SEQ ID NO:5) has a GC content of less than 56%. In some embodiments, the sequence of the codon-altered polynucleotide having high sequence identity to CS02-FL-NA (SEQ ID NO:5) has a GC content of less than 55%. In some embodiments, the sequence of the codon-altered polynucleotide having high sequence identity to CS02-FL-NA (SEQ ID NO:5) has a GC content of less than 54%.

In some embodiments, the sequence of the codon-altered polynucleotide having high sequence identity to CS02-FL-NA (SEQ ID NO:5) has a GC content of from 50% to 60%. In some embodiments, the sequence of the codon-altered polynucleotide having high sequence identity to CS02-FL-NA (SEQ ID NO:5) has a GC content of from 50% to 59%. In some embodiments, the sequence of the codon-altered polynucleotide having high sequence identity to CS02-FL-NA (SEQ ID NO:5) has a GC content of from 50% to 58%. In some embodiments, the sequence of the codon-altered polynucleotide having high sequence identity to CS02-FL-NA (SEQ ID NO:5) has a GC content of from 50% to 57%. In some embodiments, the sequence of the codon-altered polynucleotide having high sequence identity to CS02-FL-NA (SEQ ID NO:5) has a GC content of from 50% to 56%. In some embodiments, the sequence of the codon-altered polynucleotide having high sequence identity to CS02-FL-NA (SEQ ID NO:5) has a GC content of from 50% to 55%. In some embodiments, the sequence of the codon-altered polynucleotide having high sequence identity to CS02-FL-NA (SEQ ID NO:5) has a GC content of from 50% to 54%.

In some embodiments, the sequence of the codon-altered polynucleotide having high sequence identity to CS02-FL-NA (SEQ ID NO:5) has a GC content of 53.8%±1.0. In some embodiments, the sequence of the codon-altered polynucleotide having high sequence identity to CS02-FL-NA (SEQ ID NO:5) has a GC content of 53.8%±0.8. In some embodiments, the sequence of the codon-altered polynucleotide having high sequence identity to CS02-FL-NA (SEQ ID NO:5) has a GC content of 53.8%±0.6. In some embodiments, the sequence of the codon-altered polynucleotide having high sequence identity to CS02-FL-NA (SEQ ID NO:5) has a GC content of 53.8%±0.5. In some embodiments, the sequence of the codon-altered polynucleotide having high sequence identity to CS02-FL-NA (SEQ ID NO:5) has a GC content of 53.8%±0.4. In some embodiments, the sequence of the codon-altered polynucleotide having high sequence identity to CS02-FL-NA (SEQ ID NO:5) has a GC content of 53.8%±0.3. In some embodiments, the sequence of the codon-altered polynucleotide having high sequence identity to CS02-FL-NA (SEQ ID NO:5) has a GC content of 53.8%±0.2. In some embodiments, the sequence of the codon-altered polynucleotide having high sequence identity to CS02-FL-NA (SEQ ID NO:5) has a GC content of 53.8%±0.1. In some embodiments, the sequence of the codon-altered polynucleotide having high sequence identity to CS02-FL-NA (SEQ ID NO:5) has a GC content of 53.8%.

In some embodiments, the sequence of the codon-altered polynucleotide having high sequence identity to CS02-FL-NA (SEQ ID NO:5) has no more than 15 CpG dinucleotides. In some embodiments, the sequence of the codon-altered polynucleotide having high sequence identity to CS02-FL-NA (SEQ ID NO:5) has no more than 12 CpG dinucleotides. In some embodiments, the sequence of the codon-altered polynucleotide having high sequence identity to CS02-FL-NA (SEQ ID NO:5) has no more than 10 CpG dinucleotides. In some embodiments, the sequence of the codon-altered polynucleotide having high sequence identity to CS02-FL-NA (SEQ ID NO:5) has no more than 9 CpG dinucleotides. In some embodiments, the sequence of the codon-altered polynucleotide having high sequence identity to CS02-FL-NA (SEQ ID NO:5) has no more than 8 CpG dinucleotides. In some embodiments, the sequence of the codon-altered polynucleotide having high sequence identity to CS02-FL-NA (SEQ ID NO:5) has no more than 7 CpG dinucleotides. In some embodiments, the sequence of the codon-altered polynucleotide having high sequence identity to CS02-FL-NA (SEQ ID NO:5) has no more than 6 CpG dinucleotides. In some embodiments, the sequence of the codon-altered polynucleotide having high sequence identity to CS02-FL-NA (SEQ ID NO:5) has no more than 5 CpG dinucleotides. In some embodiments, the sequence of the codon-altered polynucleotide having high sequence identity to CS02-FL-NA (SEQ ID NO:5) has no more than 4 CpG dinucleotides. In some embodiments, the sequence of the codon-altered polynucleotide having high sequence identity to CS02-FL-NA (SEQ ID NO:5) has no more than 3 CpG dinucleotides. In some embodiments, the sequence of the codon-altered polynucleotide having high sequence identity to CS02-FL-NA (SEQ ID NO:5) has no more than 2 CpG dinucleotides.

In some embodiments, the sequence of the codon-altered polynucleotide having high sequence identity to CS02-FL-NA (SEQ ID NO:5) has no more than 1 CpG dinucleotide. In some embodiments, the sequence of the codon-altered polynucleotide having high sequence identity to CS02-FL-NA (SEQ ID NO:5) has no CpG dinucleotides.

In some embodiments, the encoded Factor IX polypeptide, e.g., the polypeptide encoded by the polynucleotide having high sequence homology to CS02-FL-NA (SEQ ID NO:5), has high sequence identity to the wild type Factor IX pre-pro-protein sequence FIX-FL-AA (SEQ ID NO:2) and/or the Padua (hFIX(R384L)) pre-pro-protein sequence FIXp-FL-AA (SEQ ID NO:4). The encoded Factor IX polypeptide should retain the ability to become activated into a function Factor IXa protein (e.g., by removal of the signal peptide and the pro-peptide, and by excision of the activation polypeptide).

In one embodiment, the sequence of the encoded Factor IX polypeptide has at least 85% identity to FIX-FL-AA (SEQ ID NO:2). In one embodiment, the sequence of the encoded Factor IX polypeptide has at least 90% identity to FIX-FL-AA (SEQ ID NO:2). In one embodiment, the sequence of the encoded Factor IX polypeptide has at least 95% identity to FIX-FL-AA (SEQ ID NO:2). In one embodiment, the sequence of the encoded Factor IX polypeptide has at least 96% identity to FIX-FL-AA (SEQ ID NO:2). In one embodiment, the sequence of the encoded Factor IX polypeptide has at least 97% identity to FIX-FL-AA (SEQ ID NO:2). In one embodiment, the sequence of the encoded Factor IX polypeptide has at least 98% identity to FIX-FL-AA (SEQ ID NO:2). In one embodiment, the sequence of the encoded Factor IX polypeptide has at least 99% identity to FIX-FL-AA (SEQ ID NO:2). In one embodiment, the sequence of the encoded Factor IX polypeptide has at least 99.5% identity to FIX-FL-AA (SEQ ID NO:2). In one embodiment, the sequence of the encoded Factor IX polypeptide has at least 99.9% identity to FIX-FL-AA (SEQ ID NO:2). In one embodiment, the sequence of the encoded Factor IX polypeptide is FIX-FL-AA (SEQ ID NO:2).

In one embodiment, the sequence of the encoded Factor IX polypeptide has at least 85% identity to FIXp-FL-AA (SEQ ID NO:4) and includes a leucine at position 384 of the pre-pro-polypeptide (e.g., position 338 of the mature Factor IX single-chain polypeptide FIXp-MP-AA (SEQ ID NO: 12)). In one embodiment, the sequence of the encoded Factor IX polypeptide has at least 90% identity to FIXp-FL-AA (SEQ ID NO:4) and includes a leucine at position 384 of the pre-pro-polypeptide. In one embodiment, the sequence of the encoded Factor IX polypeptide has at least 95% identity to FIXp-FL-AA (SEQ ID NO:4) and includes a leucine at position 384 of the pre-pro-polypeptide. In one embodiment, the sequence of the encoded Factor IX polypeptide has at least 96% identity to FIXp-FL-AA (SEQ ID NO:4) and includes a leucine at position 384 of the pre-pro-polypeptide. In one embodiment, the sequence of the encoded Factor IX polypeptide has at least 97% identity FIXp-FL-AA (SEQ ID NO:4) and includes a leucine at position 384 of the pre-pro-polypeptide. In one embodiment, the sequence of the encoded Factor IX polypeptide has at least 98% identity to FIXp-FL-AA (SEQ ID NO:4) and includes a leucine at position 384 of the pre-pro-polypeptide. In one embodiment, the sequence of the encoded Factor IX polypeptide has at least 99% identity to FIXp-FL-AA (SEQ ID NO:4) and includes a leucine at position 384 of the pre-pro-polypeptide. In one embodiment, the sequence of the encoded Factor IX polypeptide has at least 99.5% identity to FIXp-FL-AA (SEQ ID NO:4) and includes a leucine at position 384 of the pre-pro-polypeptide. In one embodiment, the sequence of the encoded Factor IX polypeptide has at least 99.9% identity to FIXp-FL-AA (SEQ ID NO:4) and includes a leucine at position 384 of the pre-pro-polypeptide. In one embodiment, the sequence of the encoded Factor IX polypeptide is FIXp-FL-AA (SEQ ID NO:4).

In one embodiment, a nucleic acid composition provided herein includes a Factor IX polynucleotide (e.g., a codon-altered polynucleotide) encoding a single-chain Factor IX polypeptide (e.g., having serine protease activity), where the Factor IX polynucleotide includes a nucleotide sequence having high sequence identity to CS02-MP-NA (SEQ ID NO: 13). In some embodiments, the nucleotide sequence of the Factor IX polynucleotide having high sequence identity to CS02-MP-NA (SEQ ID NO:13) has a reduced GC content, as compared to the wild-type Factor IX coding sequence (FIX-FL-NA (SEQ ID NO:1)). In some embodiments, the nucleotide sequence of the Factor IX polynucleotide having high sequence identity to CS02-MP-NA (SEQ ID NO: 13) has a reduced number of CpG dinucleotides, as compared to the wild-type Factor IX coding sequence (FIX-FL-NA (SEQ ID NO: 1)).

In a specific embodiment, the sequence of the codon-altered polynucleotide has at least 95% identity to CS02-MP-NA (SEQ ID NO:13). In a specific embodiment, the sequence of the codon-altered polynucleotide has at least 96% identity to CS02-MP-NA (SEQ ID NO:13). In a specific embodiment, the sequence of the codon-altered polynucleotide has at least 97% identity to CS02-MP-NA (SEQ ID NO: 13). In a specific embodiment, the sequence of the codon-altered polynucleotide has at least 98% identity to CS02-MP-NA (SEQ ID NO:13). In a specific embodiment, the sequence of the codon-altered polynucleotide has at least 99% identity to CS02-MP-NA (SEQ ID NO:13). In a specific embodiment, the sequence of the codon-altered polynucleotide has at least 99.5% identity to CS02-MP-NA (SEQ ID NO:13). In a specific embodiment, the sequence of the codon-altered polynucleotide has at least 99.9% identity to CS02-MP-NA (SEQ ID NO:13). In another specific embodiment, the sequence of the codon-altered polynucleotide is CS02-MP-NA (SEQ ID NO:13).

In some embodiments, the sequence of the codon-altered polynucleotide having high sequence identity to CS02-MP-NA (SEQ ID NO:13) has a GC content of less than 60%. In some embodiments, the sequence of the codon-altered polynucleotide having high sequence identity to CS02-MP-NA (SEQ ID NO:13) has a GC content of less than 59%. In some embodiments, the sequence of the codon-altered polynucleotide having high sequence identity to CS02-MP-NA (SEQ ID NO:13) has a GC content of less than 58%. In some embodiments, the sequence of the codon-altered polynucleotide having high sequence identity to CS02-MP-NA (SEQ ID NO: 13) has a GC content of less than 57%. In some embodiments, the sequence of the codon-altered polynucleotide having high sequence identity to CS02-MP-NA (SEQ ID NO: 13) has a GC content of less than 56%. In some embodiments, the sequence of the codon-altered polynucleotide having high sequence identity to CS02-MP-NA (SEQ ID NO:13) has a GC content of less than 55%. In some embodiments, the sequence of the codon-altered polynucleotide having high sequence identity to CS02-MP-NA (SEQ ID NO:13) has a GC content of less than 54%.

In some embodiments, the sequence of the codon-altered polynucleotide having high sequence identity to CS02-MP-NA (SEQ ID NO: 13) has a GC content of from 50% to 60%. In some embodiments, the sequence of the codon-altered polynucleotide having high sequence identity to CS02-MP-NA (SEQ ID NO:13) has a GC content of from 50% to 59%. In some embodiments, the sequence of the codon-altered polynucleotide having high sequence identity to CS02-MP-NA (SEQ ID NO: 13) has a GC content of from 50% to 58%. In some embodiments, the sequence of the codon-altered polynucleotide having high sequence identity to CS02-MP-NA (SEQ ID NO:13) has a GC content of from 50% to 57%. In some embodiments, the sequence of the codon-altered polynucleotide having high sequence identity to CS02-MP-NA (SEQ ID NO: 13) has a GC content of from 50% to 56%. In some embodiments, the sequence of the codon-altered polynucleotide having high sequence identity to CS02-MP-NA (SEQ ID NO: 13) has a GC content of from 50% to 55%. In some embodiments, the sequence of the codon-altered polynucleotide having high sequence identity to CS02-MP-NA (SEQ ID NO: 13) has a GC content of from 50% to 54%.

In some embodiments, the sequence of the codon-altered polynucleotide having high sequence identity to CS02-MP-NA (SEQ ID NO:13) has a GC content of 53.8%±1.0. In some embodiments, the sequence of the codon-altered polynucleotide having high sequence identity to CS02-MP-NA (SEQ ID NO:13) has a GC content of 53.8%±0.8. In some embodiments, the sequence of the codon-altered polynucleotide having high sequence identity to CS02-MP-NA (SEQ ID NO:13) has a GC content of 53.8%±0.6. In some embodiments, the sequence of the codon-altered polynucleotide having high sequence identity to CS02-MP-NA (SEQ ID NO: 13) has a GC content of 53.8%±0.5. In some embodiments, the sequence of the codon-altered polynucleotide having high sequence identity to CS02-MP-NA (SEQ ID NO: 13) has a GC content of 53.8%±0.4. In some embodiments, the sequence of the codon-altered polynucleotide having high sequence identity to CS02-MP-NA (SEQ ID NO:13) has a GC content of 53.8%±0.3. In some embodiments, the sequence of the codon-altered polynucleotide having high sequence identity to CS02-MP-NA (SEQ ID NO: 13) has a GC content of 53.8%±0.2. In some embodiments, the sequence of the codon-altered polynucleotide having high sequence identity to CS02-MP-NA (SEQ ID NO:13) has a GC content of 53.8%±0.1. In some embodiments, the sequence of the codon-altered polynucleotide having high sequence identity to CS02-MP-NA (SEQ ID NO: 13) has a GC content of 53.8%.

In some embodiments, the sequence of the codon-altered polynucleotide having high sequence identity to CS02-MP-NA (SEQ ID NO:13) has no more than 15 CpG dinucleotides. In some embodiments, the sequence of the codon-altered polynucleotide having high sequence identity to CS02-MP-NA (SEQ ID NO:13) has no more than 12 CpG dinucleotides. In some embodiments, the sequence of the codon-altered polynucleotide having high sequence identity to CS02-MP-NA (SEQ ID NO:13) has no more than 10 CpG dinucleotides. In some embodiments, the sequence of the codon-altered polynucleotide having high sequence identity to CS02-MP-NA (SEQ ID NO:13) has no more than 9 CpG dinucleotides. In some embodiments, the sequence of the codon-altered polynucleotide having high sequence identity to CS02-MP-NA (SEQ ID NO: 13) has no more than 8 CpG dinucleotides. In some embodiments, the sequence of the codon-altered polynucleotide having high sequence identity to CS02-MP-NA (SEQ ID NO: 13) has no more than 7 CpG dinucleotides. In some embodiments, the sequence of the codon-altered polynucleotide having high sequence identity to CS02-MP-NA (SEQ ID NO:13) has no more than 6 CpG dinucleotides. In some embodiments, the sequence of the codon-altered polynucleotide having high sequence identity to CS02-MP-NA (SEQ ID NO: 13) has no more than 5 CpG dinucleotides. In some embodiments, the sequence of the codon-altered polynucleotide having high sequence identity to CS02-MP-NA (SEQ ID NO:13) has no more than 4 CpG dinucleotides. In some embodiments, the sequence of the codon-altered polynucleotide having high sequence identity to CS02-MP-NA (SEQ ID NO:13) has no more than 3 CpG dinucleotides. In some embodiments, the sequence of the codon-altered polynucleotide having high sequence identity to CS02-MP-NA (SEQ ID NO:13) has no more than 2 CpG dinucleotides. In some embodiments, the sequence of the codon-altered polynucleotide having high sequence identity to CS02-MP-NA (SEQ ID NO: 13) has no more than 1 CpG dinucleotide. In some embodiments, the sequence of the codon-altered polynucleotide having high sequence identity to CS02-MP-NA (SEQ ID NO:13) has no CpG dinucleotides.

In some embodiments, the Factor IX polynucleotide high sequence identity to CS02-MP-NA (SEQ ID NO:13) further includes a Factor IX signal polynucleotide encoding a Factor IX signal peptide having the amino acid sequence of FIX-SP-AA (SEQ ID NO:37). In some embodiments, the Factor IX signal polynucleotide has a nucleic acid sequence that is at least 90%, 95%, 96%, 97%, 98%, 99%, or 100% identical to CS02-SP-NA (SEQ ID NO:25). In some embodiments, the Factor IX signal polynucleotide has a nucleic acid sequence that is at least 90%, 95%, 96%, 97%, 98%, 99%, or 100% identical to CS03-SP-NA (SEQ ID NO:26). In some embodiments, the Factor IX signal polynucleotide has a nucleic acid sequence that is at least 90%, 95%, 96%, 97%, 98%, 99%, or 100% identical to CS04-SP-NA (SEQ ID NO:27). In some embodiments, the Factor IX signal polynucleotide has a nucleic acid sequence that is at least 90%, 95%, 96%, 97%, 98%, 99%, or 100% identical to CS05-SP-NA (SEQ ID NO:28). In some embodiments, the Factor IX signal polynucleotide has a nucleic acid sequence that is at least 90%, 95%, 96%, 97%, 98%, 99%, or 100% identical to CS06-SP-NA (SEQ ID NO:29).

In some embodiments, the Factor IX polynucleotide high sequence identity to CS02-MP-NA (SEQ ID NO:13) further includes a Factor IX pro-peptide polynucleotide encoding a Factor IX pro-peptide having the amino acid sequence of FIX-PP-AA (SEQ ID NO:38). In some embodiments, the Factor IX pro-peptide polynucleotide has a nucleic acid sequence that is at least 90%, 95%, 96%, 97%, 98%, 99%, or 100% identical to CS02-PP-NA (SEQ ID NO:31). In some embodiments, the Factor IX pro-peptide polynucleotide has a nucleic acid sequence that is at least 90%, 95%, 96%, 97%, 98%, 99%, or 100% identical to CS03-PP-NA (SEQ ID NO:32). In some embodiments, the Factor IX pro-peptide polynucleotide has a nucleic acid sequence that is at least 90%, 95%, 96%, 97%, 98%, 99%, or 100% identical to CS04-PP-NA (SEQ ID NO:33). In some embodiments, the Factor IX pro-peptide polynucleotide has a nucleic acid sequence that is at least 90%, 95%, 96%, 97%, 98%, 99%, or 100% identical to CS05-PP-NA (SEQ ID NO:34). In some embodiments, the Factor IX pro-peptide polynucleotide has a nucleic acid sequence that is at least 90%, 95%, 96%, 97%, 98%, 99%, or 100% identical to CS06-PP-NA (SEQ ID NO:35).

In some embodiments, the Factor IX polynucleotide high sequence identity to CS02-MP-NA (SEQ ID NO: 13) further includes a Factor IX pre-pro-peptide polynucleotide encoding a Factor IX pre-pro-peptide having the amino acid sequence of FIX-PPP-AA (SEQ ID NO:36). In some embodiments, the Factor IX pre-pro-peptide polynucleotide has a nucleic acid sequence that is at least 90%, 95%, 96%, 97%, 98%, 99%, or 100% identical to CS02-PPP-NA (SEQ ID NO:19). In some embodiments, the Factor IX pre-pro-peptide polynucleotide has a nucleic acid sequence that is at least 90%, 95%, 96%, 97%, 98%, 99%, or 100% identical to CS03-PPP-NA (SEQ ID NO:20). In some embodiments, the Factor IX pre-pro-peptide polynucleotide has a nucleic acid sequence that is at least 90%, 95%, 96%, 97%, 98%, 99%, or 100% identical to CS04-PPP-NA (SEQ ID NO:21). In some embodiments, the Factor IX pre-pro-peptide polynucleotide has a nucleic acid sequence that is at least 90%, 95%, 96%, 97%, 98%, 99%, or 100% identical to CS05-PPP-NA (SEQ ID NO:22). In some embodiments, the Factor IX pre-pro-peptide polynucleotide has a nucleic acid sequence that is at least 90%, 95%, 96%, 97%, 98%, 99%, or 100% identical to CS06-PPP-NA (SEQ ID NO:23).

In some embodiments, the encoded Factor IX polypeptide, e.g., the polypeptide encoded by the polynucleotide having high sequence homology to CS02-FL-NA (SEQ ID NO:5), has high sequence identity to the wild type, mature Factor IX single-chain polypeptide sequence FIX-MP-AA (SEQ ID NO: 10) and/or the mature Padua (hFIX(R384L)) single-chain sequence FIXp-MP-AA (SEQ ID NO: 12). The encoded Factor IX polypeptide should retain the ability to become activated into a function Factor IXa protein (e.g., by removal of any signal peptide and the pro-peptide, and by excision of the activation polypeptide).

In one embodiment, the sequence of the encoded Factor IX polypeptide has at least 85% identity to FIX-MP-AA (SEQ ID NO: 10). In one embodiment, the sequence of the encoded Factor IX polypeptide has at least 90% identity to FIX-MP-AA (SEQ ID NO:10). In one embodiment, the sequence of the encoded Factor IX polypeptide has at least 95% identity to FIX-MP-AA (SEQ ID NO: 10). In one embodiment, the sequence of the encoded Factor IX polypeptide has at least 96% identity to FIX-MP-AA (SEQ ID NO: 10). In one embodiment, the sequence of the encoded Factor IX polypeptide has at least 97% identity to FIX-MP-AA (SEQ ID NO: 10). In one embodiment, the sequence of the encoded Factor IX polypeptide has at least 98% identity to FIX-MP-AA (SEQ ID NO:10). In one embodiment, the sequence of the encoded Factor IX polypeptide has at least 99% identity to FIX-MP-AA (SEQ ID NO:10). In one embodiment, the sequence of the encoded Factor IX polypeptide has at least 99.5% identity to FIX-MP-AA (SEQ ID NO: 10). In one embodiment, the sequence of the encoded Factor IX polypeptide has at least 99.9% identity to FIX-MP-AA (SEQ ID NO: 10). In one embodiment, the sequence of the encoded Factor IX polypeptide is FIX-MP-AA (SEQ ID NO: 10).

In one embodiment, the sequence of the encoded Factor IX polypeptide has at least 85% identity to FIXp-MP-AA (SEQ ID NO:12) and includes a leucine at position 384 of the pre-pro-polypeptide (e.g., position 338 of the mature Factor IX single-chain polypeptide FIXp-MP-AA (SEQ ID NO: 12)). In one embodiment, the sequence of the encoded Factor IX polypeptide has at least 90% identity to FIXp-MP-AA (SEQ ID NO: 12) and includes a leucine at position 384 of the pre-pro-polypeptide. In one embodiment, the sequence of the encoded Factor IX polypeptide has at least 95% identity to FIXp-MP-AA (SEQ ID NO: 12) and includes a leucine at position 384 of the pre-pro-polypeptide. In one embodiment, the sequence of the encoded Factor IX polypeptide has at least 96% identity to FIXp-MP-AA (SEQ ID NO: 12) and includes a leucine at position 384 of the pre-pro-polypeptide. In one embodiment, the sequence of the encoded Factor IX polypeptide has at least 97% identity FIXp-MP-AA (SEQ ID NO: 12) and includes a leucine at position 384 of the pre-pro-polypeptide. In one embodiment, the sequence of the encoded Factor IX polypeptide has at least 98% identity to FIXp-MP-AA (SEQ ID NO:12) and includes a leucine at position 384 of the pre-pro-polypeptide. In one embodiment, the sequence of the encoded Factor IX polypeptide has at least 99% identity to FIXp-MP-AA (SEQ ID NO: 12) and includes a leucine at position 384 of the pre-pro-polypeptide. In one embodiment, the sequence of the encoded Factor IX polypeptide has at least 99.5% identity to FIXp-MP-AA (SEQ ID NO: 12) and includes a leucine at position 384 of the pre-pro-polypeptide. In one embodiment, the sequence of the encoded Factor IX polypeptide has at least 99.9% identity to FIXp-MP-AA (SEQ ID NO: 12) and includes a leucine at position 384 of the pre-pro-polypeptide. In one embodiment, the sequence of the encoded Factor IX polypeptide is FIXp-MP-AA (SEQ ID NO: 12).

In one embodiment, a codon-altered polynucleotides provided herein encodes for a single-chain Factor IX polypeptide including a light chain, a heavy chain, and a polypeptide linker joining the C-terminus of the light chain to the N-terminus of the heavy chain. The light chain of the Factor IX polypeptide is encoded by a first nucleotide sequence having high sequence identity to CS02-LC-NA (SEQ ID NO:42), which is the portion of CS02-FL-NA (SEQ ID NO:5) encoding the Factor IX light chain. The heavy chain of the Factor IX polypeptide is encoded by a second nucleotide sequence having high sequence identity to CS02-HC-NA (SEQ ID NO:41), which is the portion of CS02-FL-NA (SEQ ID NO:5) encoding the Factor IX heavy chain. The polypeptide linker includes Factor XI cleavage sites, which allow for maturation in vivo (e.g., after expression of the precursor single-chain Factor IX polypeptide.

In some embodiments, the first and second nucleotide sequences have at least 95% sequence identity to CS02-LC-NA and CS02-HC-NA (SEQ ID NOS:42 and 41), respectively. In some embodiments, the first and second nucleotide sequences have at least 96% sequence identity to CS02-LC-NA and CS02-HC-NA (SEQ ID NOS:42 and 41), respectively. In some embodiments, the first and second nucleotide sequences have at least 97% sequence identity to CS02-LC-NA and CS02-HC-NA (SEQ ID NOS:42 and 41), respectively. In some embodiments, the first and second nucleotide sequences have at least 98% sequence identity to CS02-LC-NA and CS02-HC-NA (SEQ ID NOS:42 and 41), respectively. In some embodiments, the first and second nucleotide sequences have at least 99% sequence identity to CS02-LC-NA and CS02-HC-NA (SEQ ID NOS:42 and 41), respectively, respectively. In some embodiments, the first and second nucleotide sequences have at least 99.5% sequence identity to CS02-LC-NA and CS02-HC-NA (SEQ ID NOS: 42 and 41), respectively. In some embodiments, the first and second nucleotide sequences have at least 99.9% sequence identity to CS02-LC-NA and CS02-HC-NA (SEQ ID NOS: 42 and 41), respectively. In some embodiments, the first and second nucleotide sequences are CS02-LC-NA and CS02-HC-NA (SEQ ID NOS:42 and 41), respectively.

In some embodiments, the polypeptide linker of the Factor IX construct is encoded by a third nucleotide sequence having high sequence identity to CS02-AP-NA (SEQ ID NO:57), which is a codon-altered sequence encoding the wild type Factor IX activation polypeptide, e.g., amino acids 192-226 of FIX-FL-AA (SEQ ID NO:2). In some embodiments, the third nucleotide sequence has at least 80% identity to CS02-AP-NA (SEQ ID NO:57). In some embodiments, the third nucleotide sequence has at least 90% identity to CS02-AP-NA (SEQ ID NO:57). In some embodiments, the third nucleotide sequence has at least 95% identity to CS02-AP-NA (SEQ ID NO:57). In some embodiments, the third nucleotide sequence has at least 96% identity to CS02-AP-NA (SEQ ID NO:57). In some embodiments, the third nucleotide sequence has at least 97% identity to CS02-AP-NA (SEQ ID NO:57). In some embodiments, the third nucleotide sequence has at least 98% identity to CS02-AP-NA (SEQ ID NO:57). In some embodiments, the third nucleotide sequence has at least 99% identity to CS02-AP-NA (SEQ ID NO:57). In some embodiments, the third nucleotide sequence is CS02-AP-NA (SEQ ID NO:57).

In some embodiments, the encoded Factor IX polypeptide also includes a signal peptide (e.g., a Factor IX signal peptide) and/or a pro-peptide (e.g., a Factor IX pro-peptide). In some embodiments, the signal peptide is the wild-type Factor IX signal peptide (FIX-SP-AA (SEQ ID NO:37)). In some embodiments, the signal peptide is encoded by a codon-altered polynucleotide sequence having high sequence identity (e.g., at least 95%, 96%, 97%, 98%, or 99%) to CS02-SP-NA (SEQ ID NO:25). In some embodiments, the pro-peptide is the wild-type Factor IX pro-peptide (FIX-PP-AA (SEQ ID NO:38)). In some embodiments, the pro-peptide peptide is encoded by a codon-altered polynucleotide sequence having high sequence identity (e.g., at least 95%, 96%, 97%, 98%, or 99%) to CS02-PP-NA (SEQ ID NO:31).

In some embodiments, the encoded Factor IX polypeptide, e.g., the polypeptide encoded by the polynucleotide having high sequence homology to CS02-LC-NA (SEQ ID NO:42) and CS02-HC-NA (SEQ ID NO:41), has high sequence identity to the wild type, mature Factor IX single-chain polypeptide sequence FIX-MP-AA (SEQ ID NO:10) and/or the mature Padua (hFIX(R384L)) single-chain sequence FIXp-MP-AA (SEQ ID NO: 12). The encoded Factor IX polypeptide should retain the ability to become activated into a function Factor IXa protein (e.g., by removal of any signal peptide and the pro-peptide, and by excision of the activation polypeptide).

In one embodiment, the sequence of the encoded Factor IX polypeptide has at least 85% identity to FIX-MP-AA (SEQ ID NO: 10). In one embodiment, the sequence of the encoded Factor IX polypeptide has at least 90% identity to FIX-MP-AA (SEQ ID NO:10). In one embodiment, the sequence of the encoded Factor IX polypeptide has at least 95% identity to FIX-MP-AA (SEQ ID NO: 10). In one embodiment, the sequence of the encoded Factor IX polypeptide has at least 96% identity to FIX-MP-AA (SEQ ID NO: 10). In one embodiment, the sequence of the encoded Factor IX polypeptide has at least 97% identity to FIX-MP-AA (SEQ ID NO: 10). In one embodiment, the sequence of the encoded Factor IX polypeptide has at least 98% identity to FIX-MP-AA (SEQ ID NO:10). In one embodiment, the sequence of the encoded Factor IX polypeptide has at least 99% identity to FIX-MP-AA (SEQ ID NO:10). In one embodiment, the sequence of the encoded Factor IX polypeptide has at least 99.5% identity to FIX-MP-AA (SEQ ID NO: 10). In one embodiment, the sequence of the encoded Factor IX polypeptide has at least 99.9% identity to FIX-MP-AA (SEQ ID NO: 10). In one embodiment, the sequence of the encoded Factor IX polypeptide is FIX-MP-AA (SEQ ID NO: 10).

In one embodiment, the sequence of the encoded Factor IX polypeptide has at least 85% identity to FIXp-MP-AA (SEQ ID NO:12) and includes a leucine at position 384 of the pre-pro-polypeptide (e.g., position 338 of the mature Factor IX single-chain polypeptide FIXp-MP-AA (SEQ ID NO: 12)). In one embodiment, the sequence of the encoded Factor IX polypeptide has at least 90% identity to FIXp-MP-AA (SEQ ID NO: 12) and includes a leucine at position 384 of the pre-pro-polypeptide. In one embodiment, the sequence of the encoded Factor IX polypeptide has at least 95% identity to FIXp-MP-AA (SEQ ID NO: 12) and includes a leucine at position 384 of the pre-pro-polypeptide. In one embodiment, the sequence of the encoded Factor IX polypeptide has at least 96% identity to FIXp-MP-AA (SEQ ID NO: 12) and includes a leucine at position 384 of the pre-pro-polypeptide. In one embodiment, the sequence of the encoded Factor IX polypeptide has at least 97% identity FIXp-MP-AA (SEQ ID NO: 12) and includes a leucine at position 384 of the pre-pro-polypeptide. In one embodiment, the sequence of the encoded Factor IX polypeptide has at least 98% identity to FIXp-MP-AA (SEQ ID NO:12) and includes a leucine at position 384 of the pre-pro-polypeptide. In one embodiment, the sequence of the encoded Factor IX polypeptide has at least 99% identity to FIXp-MP-AA (SEQ ID NO: 12) and includes a leucine at position 384 of the pre-pro-polypeptide. In one embodiment, the sequence of the encoded Factor IX polypeptide has at least 99.5% identity to FIXp-MP-AA (SEQ ID NO: 12) and includes a leucine at position 384 of the pre-pro-polypeptide. In one embodiment, the sequence of the encoded Factor IX polypeptide has at least 99.9% identity to FIXp-MP-AA (SEQ ID NO: 12) and includes a leucine at position 384 of the pre-pro-polypeptide. In one embodiment, the sequence of the encoded Factor IX polypeptide is FIXp-MP-AA (SEQ ID NO: 12).

In some embodiments, with reference to FIG. 1, a nucleic acid composition is provided that includes a self-complementary polynucleotide of structure A, where the FIX coding sequence portion of the polynucleotide includes a nucleic acid sequence, encoding a mature Factor IX polypeptide, that has at least 95%, 96%, 97%, 98%, 99%, 99.5%, 99.9%, or 100% identity to CS02-MP-NA (SEQ ID NO: 13). In some embodiments, the FIX coding sequence portion of the polynucleotide also includes a nucleic acid sequence, encoding a Factor IX signal peptide, that has at least 90%, 95%, 96%, 97%, 98%, 99%, or 100% identity to one of FIX-SP-NA (SEQ ID NO:24), CS02-SP-NA (SEQ ID NO:25), CS03-SP-NA (SEQ ID NO:26), CS04-SP-NA (SEQ ID NO:27), CS05-SP-NA (SEQ ID NO:28), and CS06-SP-NA (SEQ ID NO:29). In some embodiments, the FIX coding sequence portion of the polynucleotide also includes a nucleic acid sequence, encoding a Factor IX pro-peptide (optionally in combination with a nucleic acid sequence for a Factor IX signal peptide, as described above), that has at least 90%, 95%, 96%, 97%, 98%, 99%, or 100% identity to one of FIX-PP-NA (SEQ ID NO:30), CS02-PP-NA (SEQ ID NO:31), CS03-PP-NA (SEQ ID NO:32), CS04-PP-NA (SEQ ID NO:33), CS05-PP-NA (SEQ ID NO:34), and CS06-PP-NA (SEQ ID NO:35). In some embodiments, the FIX coding sequence portion of the polynucleotide includes a nucleic acid sequence, encoding a pre-pro-Factor IX polypeptide, that has at least 95%, 96%, 97%, 98%, 99%, 99.5%, 99.9%, or 100% identity to CS02-FL-NA (SEQ ID NO:5).

In some embodiments, with reference to FIG. 1, a nucleic acid composition is provided that includes a self-complementary polynucleotide of structure B, where the FIX coding sequence portion of the polynucleotide includes a nucleic acid sequence, encoding a mature Factor IX polypeptide, that has at least 95%, 96%, 97%, 98%, 99%, 99.5%, 99.9%, or 100% identity to CS02-MP-NA (SEQ ID NO: 13). In some embodiments, the FIX coding sequence portion of the polynucleotide also includes a nucleic acid sequence, encoding a Factor IX signal peptide, that has at least 90%, 95%, 96%, 97%, 98%, 99%, or 100% identity to one of FIX-SP-NA (SEQ ID NO:24), CS02-SP-NA (SEQ ID NO:25), CS03-SP-NA (SEQ ID NO:26), CS04-SP-NA (SEQ ID NO:27), CS05-SP-NA (SEQ ID NO:28), and CS06-SP-NA (SEQ ID NO:29). In some embodiments, the FIX coding sequence portion of the polynucleotide also includes a nucleic acid sequence, encoding a Factor IX pro-peptide (optionally in combination with a nucleic acid sequence for a Factor IX signal peptide, as described above), that has at least 90%, 95%, 96%, 97%, 98%, 99%, or 100% identity to one of FIX-PP-NA (SEQ ID NO:30), CS02-PP-NA (SEQ ID NO:31), CS03-PP-NA (SEQ ID NO:32), CS04-PP-NA (SEQ ID NO:33), CS05-PP-NA (SEQ ID NO:34), and CS06-PP-NA (SEQ ID NO:35). In some embodiments, the FIX coding sequence portion of the polynucleotide includes a nucleic acid sequence, encoding a pre-pro-Factor IX polypeptide, that has at least 95%, 96%, 97%, 98%, 99%, 99.5%, 99.9%, or 100% identity to CS02-FL-NA (SEQ ID NO:5).

In some embodiments, with reference to FIG. 1, a nucleic acid composition is provided that includes a polynucleotide of structure C (e.g., a single-stranded polynucleotide), where the FIX coding sequence portion of the polynucleotide includes a nucleic acid sequence, encoding a mature Factor IX polypeptide, that has at least 95%, 96%, 97%, 98%, 99%, 99.5%, 99.9%, or 100% identity to CS02-MP-NA (SEQ ID NO:13). In some embodiments, the FIX coding sequence portion of the polynucleotide also includes a nucleic acid sequence, encoding a Factor IX signal peptide, that has at least 90%, 95%, 96%, 97%, 98%, 99%, or 100% identity to one of FIX-SP-NA (SEQ ID NO:24), CS02-SP-NA (SEQ ID NO:25), CS03-SP-NA (SEQ ID NO:26), CS04-SP-NA (SEQ ID NO:27), CS05-SP-NA (SEQ ID NO:28), and CS06-SP-NA (SEQ ID NO:29). In some embodiments, the FIX coding sequence portion of the polynucleotide also includes a nucleic acid sequence, encoding a Factor IX pro-peptide (optionally in combination with a nucleic acid sequence for a Factor IX signal peptide, as described above), that has at least 90%, 95%, 96%, 97%, 98%, 99%, or 100% identity to one of FIX-PP-NA (SEQ ID NO:30), CS02-PP-NA (SEQ ID NO:31), CS03-PP-NA (SEQ ID NO:32), CS04-PP-NA (SEQ ID NO:33), CS05-PP-NA (SEQ ID NO:34), and CS06-PP-NA (SEQ ID NO:35). In some embodiments, the FIX coding sequence portion of the polynucleotide includes a nucleic acid sequence, encoding a pre-pro-Factor IX polypeptide, that has at least 95%, 96%, 97%, 98%, 99%, 99.5%, 99.9%, or 100% identity to CS02-FL-NA (SEQ ID NO:5).

In some embodiments, with reference to FIG. 1, a nucleic acid composition is provided that includes a polynucleotide of structure D (e.g., a single-stranded polynucleotide), where the FIX coding sequence portion of the polynucleotide includes a nucleic acid sequence, encoding a mature Factor IX polypeptide, that has at least 95%, 96%, 97%, 98%, 99%, 99.5%, 99.9%, or 100% identity to CS02-MP-NA (SEQ ID NO:13). In some embodiments, the FIX coding sequence portion of the polynucleotide also includes a nucleic acid sequence, encoding a Factor IX signal peptide, that has at least 90%, 95%, 96%, 97%, 98%, 99%, or 100% identity to one of FIX-SP-NA (SEQ ID NO:24), CS02-SP-NA (SEQ ID NO:25), CS03-SP-NA (SEQ ID NO:26), CS04-SP-NA (SEQ ID NO:27), CS05-SP-NA (SEQ ID NO:28), and CS06-SP-NA (SEQ ID NO:29). In some embodiments, the FIX coding sequence portion of the polynucleotide also includes a nucleic acid sequence, encoding a Factor IX pro-peptide (optionally in combination with a nucleic acid sequence for a Factor IX signal peptide, as described above), that has at least 90%, 95%, 96%, 97%, 98%, 99%, or 100% identity to one of FIX-PP-NA (SEQ ID NO:30), CS02-PP-NA (SEQ ID NO:31), CS03-PP-NA (SEQ ID NO:32), CS04-PP-NA (SEQ ID NO:33), CS05-PP-NA (SEQ ID NO:34), and CS06-PP-NA (SEQ ID NO:35). In some embodiments, the FIX coding sequence portion of the polynucleotide includes a nucleic acid sequence, encoding a pre-pro-Factor IX polypeptide, that has at least 95%, 96%, 97%, 98%, 99%, 99.5%, 99.9%, or 100% identity to CS02-FL-NA (SEQ ID NO:5).

CS03 Codon Altered Polynucleotides

In one embodiment, a nucleic acid composition provided herein includes a Factor IX polynucleotide (e.g., a codon-altered polynucleotide) encoding a single-chain Factor IX polypeptide, where the Factor IX polynucleotide includes a nucleotide sequence having high sequence identity to CS03-FL-NA (SEQ ID NO:6). In some embodiments, the nucleotide sequence of the Factor IX polynucleotide having high sequence identity to CS03-FL-NA (SEQ ID NO:6) has a reduced GC content, as compared to the wild-type Factor IX coding sequence (FIX-FL-NA (SEQ ID NO:1)). In some embodiments, the nucleotide sequence of the Factor IX polynucleotide having high sequence identity to CS03-FL-NA (SEQ ID NO:6) has a reduced number of CpG dinucleotides, as compared to the wild-type Factor IX coding sequence (FIX-FL-NA (SEQ ID NO: 1)).

In a specific embodiment, the sequence of the codon-altered polynucleotide has at least 95% identity to CS03-FL-NA (SEQ ID NO:6). In a specific embodiment, the sequence of the codon-altered polynucleotide has at least 96% identity to CS03-FL-NA (SEQ ID NO:6). In a specific embodiment, the sequence of the codon-altered polynucleotide has at least 97% identity to CS03-FL-NA (SEQ ID NO:6). In a specific embodiment, the sequence of the codon-altered polynucleotide has at least 98% identity to CS03-FL-NA (SEQ ID NO:6). In a specific embodiment, the sequence of the codon-altered polynucleotide has at least 99% identity to CS03-FL-NA (SEQ ID NO:6). In a specific embodiment, the sequence of the codon-altered polynucleotide has at least 99.5% identity to CS03-FL-NA (SEQ ID NO:6). In a specific embodiment, the sequence of the codon-altered polynucleotide has at least 99.9% identity to CS03-FL-NA (SEQ ID NO:6). In another specific embodiment, the sequence of the codon-altered polynucleotide is CS03-FL-NA (SEQ ID NO:6).

In some embodiments, the sequence of the codon-altered polynucleotide having high sequence identity to CS03-FL-NA (SEQ ID NO:6) has a GC content of less than 60%. In some embodiments, the sequence of the codon-altered polynucleotide having high sequence identity to CS03-FL-NA (SEQ ID NO:6) has a GC content of less than 59%. In some embodiments, the sequence of the codon-altered polynucleotide having high sequence identity to CS03-FL-NA (SEQ ID NO:6) has a GC content of less than 58%. In some embodiments, the sequence of the codon-altered polynucleotide having high sequence identity to CS03-FL-NA (SEQ ID NO:6) has a GC content of less than 57%. In some embodiments, the sequence of the codon-altered polynucleotide having high sequence identity to CS03-FL-NA (SEQ ID NO:6) has a GC content of less than 56%. In some embodiments, the sequence of the codon-altered polynucleotide having high sequence identity to CS03-FL-NA (SEQ ID NO:6) has a GC content of less than 55%. In some embodiments, the sequence of the codon-altered polynucleotide having high sequence identity to CS03-FL-NA (SEQ ID NO:6) has a GC content of less than 54%.

In some embodiments, the sequence of the codon-altered polynucleotide having high sequence identity to CS03-FL-NA (SEQ ID NO:6) has a GC content of from 50% to 60%. In some embodiments, the sequence of the codon-altered polynucleotide having high sequence identity to CS03-FL-NA (SEQ ID NO:6) has a GC content of from 50% to 59%. In some embodiments, the sequence of the codon-altered polynucleotide having high sequence identity to CS03-FL-NA (SEQ ID NO:6) has a GC content of from 50% to 58%. In some embodiments, the sequence of the codon-altered polynucleotide having high sequence identity to CS03-FL-NA (SEQ ID NO:6) has a GC content of from 50% to 57%. In some embodiments, the sequence of the codon-altered polynucleotide having high sequence identity to CS03-FL-NA (SEQ ID NO:6) has a GC content of from 50% to 56%. In some embodiments, the sequence of the codon-altered polynucleotide having high sequence identity to CS03-FL-NA (SEQ ID NO:6) has a GC content of from 50% to 55%. In some embodiments, the sequence of the codon-altered polynucleotide having high sequence identity to CS03-FL-NA (SEQ ID NO:6) has a GC content of from 50% to 54%.

In some embodiments, the sequence of the codon-altered polynucleotide having high sequence identity to CS03-FL-NA (SEQ ID NO:6) has a GC content of 53.8%±1.0. In some embodiments, the sequence of the codon-altered polynucleotide having high sequence identity to CS03-FL-NA (SEQ ID NO:6) has a GC content of 53.8%±0.8. In some embodiments, the sequence of the codon-altered polynucleotide having high sequence identity to CS03-FL-NA (SEQ ID NO:6) has a GC content of 53.8%±0.6. In some embodiments, the sequence of the codon-altered polynucleotide having high sequence identity to CS03-FL-NA (SEQ ID NO:6) has a GC content of 53.8%±0.5. In some embodiments, the sequence of the codon-altered polynucleotide having high sequence identity to CS03-FL-NA (SEQ ID NO:6) has a GC content of 53.8%±0.4. In some embodiments, the sequence of the codon-altered polynucleotide having high sequence identity to CS03-FL-NA (SEQ ID NO:6) has a GC content of 53.8%±0.3. In some embodiments, the sequence of the codon-altered polynucleotide having high sequence identity to CS03-FL-NA (SEQ ID NO:6) has a GC content of 53.8%±0.2. In some embodiments, the sequence of the codon-altered polynucleotide having high sequence identity to CS03-FL-NA (SEQ ID NO:6) has a GC content of 53.8%±0.1. In some embodiments, the sequence of the codon-altered polynucleotide having high sequence identity to CS03-FL-NA (SEQ ID NO:6) has a GC content of 53.8%.

In some embodiments, the sequence of the codon-altered polynucleotide having high sequence identity to CS03-FL-NA (SEQ ID NO:6) has no more than 15 CpG dinucleotides. In some embodiments, the sequence of the codon-altered polynucleotide having high sequence identity to CS03-FL-NA (SEQ ID NO:6) has no more than 12 CpG dinucleotides. In some embodiments, the sequence of the codon-altered polynucleotide having high sequence identity to CS03-FL-NA (SEQ ID NO:6) has no more than 10 CpG dinucleotides. In some embodiments, the sequence of the codon-altered polynucleotide having high sequence identity to CS03-FL-NA (SEQ ID NO:6) has no more than 9 CpG dinucleotides. In some embodiments, the sequence of the codon-altered polynucleotide having high sequence identity to CS03-FL-NA (SEQ ID NO:6) has no more than 8 CpG dinucleotides. In some embodiments, the sequence of the codon-altered polynucleotide having high sequence identity to CS03-FL-NA (SEQ ID NO:6) has no more than 7 CpG dinucleotides. In some embodiments, the sequence of the codon-altered polynucleotide having high sequence identity to CS03-FL-NA (SEQ ID NO:6) has no more than 6 CpG dinucleotides. In some embodiments, the sequence of the codon-altered polynucleotide having high sequence identity to CS03-FL-NA (SEQ ID NO:6) has no more than 5 CpG dinucleotides. In some embodiments, the sequence of the codon-altered polynucleotide having high sequence identity to CS03-FL-NA (SEQ ID NO:6) has no more than 4 CpG dinucleotides. In some embodiments, the sequence of the codon-altered polynucleotide having high sequence identity to CS03-FL-NA (SEQ ID NO:6) has no more than 3 CpG dinucleotides. In some embodiments, the sequence of the codon-altered polynucleotide having high sequence identity to CS03-FL-NA (SEQ ID NO:6) has no more than 2 CpG dinucleotides. In some embodiments, the sequence of the codon-altered polynucleotide having high sequence identity to CS03-FL-NA (SEQ ID NO:6) has no more than 1 CpG dinucleotide. In some embodiments, the sequence of the codon-altered polynucleotide having high sequence identity to CS03-FL-NA (SEQ ID NO:6) has no CpG dinucleotides.

In some embodiments, the encoded Factor IX polypeptide, e.g., the polypeptide encoded by the polynucleotide having high sequence homology to CS03-FL-NA (SEQ ID NO:6), has high sequence identity to the wild type Factor IX pre-pro-protein sequence FIX-FL-AA (SEQ ID NO:2) and/or the Padua (hFIX(R384L)) pre-pro-protein sequence FIXp-FL-AA (SEQ ID NO:4). The encoded Factor IX polypeptide should retain the ability to become activated into a function Factor IXa protein (e.g., by removal of the signal peptide and the pro-peptide, and by excision of the activation polypeptide).

In one embodiment, the sequence of the encoded Factor IX polypeptide has at least 85% identity to FIX-FL-AA (SEQ ID NO:2). In one embodiment, the sequence of the encoded Factor IX polypeptide has at least 90% identity to FIX-FL-AA (SEQ ID NO:2). In one embodiment, the sequence of the encoded Factor IX polypeptide has at least 95% identity to FIX-FL-AA (SEQ ID NO:2). In one embodiment, the sequence of the encoded Factor IX polypeptide has at least 96% identity to FIX-FL-AA (SEQ ID NO:2). In one embodiment, the sequence of the encoded Factor IX polypeptide has at least 97% identity to FIX-FL-AA (SEQ ID NO:2). In one embodiment, the sequence of the encoded Factor IX polypeptide has at least 98% identity to FIX-FL-AA (SEQ ID NO:2). In one embodiment, the sequence of the encoded Factor IX polypeptide has at least 99% identity to FIX-FL-AA (SEQ ID NO:2). In one embodiment, the sequence of the encoded Factor IX polypeptide has at least 99.5% identity to FIX-FL-AA (SEQ ID NO:2). In one embodiment, the sequence of the encoded Factor IX polypeptide has at least 99.9% identity to FIX-FL-AA (SEQ ID NO:2). In one embodiment, the sequence of the encoded Factor IX polypeptide is FIX-FL-AA (SEQ ID NO:2).

In one embodiment, the sequence of the encoded Factor IX polypeptide has at least 85% identity to FIXp-FL-AA (SEQ ID NO:4) and includes a leucine at position 384 of the pre-pro-polypeptide (e.g., position 338 of the mature Factor IX single-chain polypeptide FIXp-MP-AA (SEQ ID NO: 12)). In one embodiment, the sequence of the encoded Factor IX polypeptide has at least 90% identity to FIXp-FL-AA (SEQ ID NO:4) and includes a leucine at position 384 of the pre-pro-polypeptide. In one embodiment, the sequence of the encoded Factor IX polypeptide has at least 95% identity to FIXp-FL-AA (SEQ ID NO:4) and includes a leucine at position 384 of the pre-pro-polypeptide. In one embodiment, the sequence of the encoded Factor IX polypeptide has at least 96% identity to FIXp-FL-AA (SEQ ID NO:4) and includes a leucine at position 384 of the pre-pro-polypeptide. In one embodiment, the sequence of the encoded Factor IX polypeptide has at least 97% identity FIXp-FL-AA (SEQ ID NO:4) and includes a leucine at position 384 of the pre-pro-polypeptide. In one embodiment, the sequence of the encoded Factor IX polypeptide has at least 98% identity to FIXp-FL-AA (SEQ ID NO:4) and includes a leucine at position 384 of the pre-pro-polypeptide. In one embodiment, the sequence of the encoded Factor IX polypeptide has at least 99% identity to FIXp-FL-AA (SEQ ID NO:4) and includes a leucine at position 384 of the pre-pro-polypeptide. In one embodiment, the sequence of the encoded Factor IX polypeptide has at least 99.5% identity to FIXp-FL-AA (SEQ ID NO:4) and includes a leucine at position 384 of the pre-pro-polypeptide. In one embodiment, the sequence of the encoded Factor IX polypeptide has at least 99.9% identity to FIXp-FL-AA (SEQ ID NO:4) and includes a leucine at position 384 of the pre-pro-polypeptide. In one embodiment, the sequence of the encoded Factor IX polypeptide is FIXp-FL-AA (SEQ ID NO:4).

In one embodiment, a nucleic acid composition provided herein includes a Factor IX polynucleotide (e.g., a codon-altered polynucleotide) encoding a single-chain Factor IX polypeptide (e.g., having serine protease activity), where the Factor IX polynucleotide includes a nucleotide sequence having high sequence identity to CS03-MP-NA (SEQ ID NO: 14). In some embodiments, the nucleotide sequence of the Factor IX polynucleotide having high sequence identity to CS03-MP-NA (SEQ ID NO: 14) has a reduced GC content, as compared to the wild-type Factor IX coding sequence (FIX-FL-NA (SEQ ID NO:1)). In some embodiments, the nucleotide sequence of the Factor IX polynucleotide having high sequence identity to CS03-MP-NA (SEQ ID NO: 14) has a reduced number of CpG dinucleotides, as compared to the wild-type Factor IX coding sequence (FIX-FL-NA (SEQ ID NO: 1)).

In a specific embodiment, the sequence of the codon-altered polynucleotide has at least 95% identity to CS03-MP-NA (SEQ ID NO: 14). In a specific embodiment, the sequence of the codon-altered polynucleotide has at least 96% identity to CS03-MP-NA (SEQ ID NO:14). In a specific embodiment, the sequence of the codon-altered polynucleotide has at least 97% identity to CS03-MP-NA (SEQ ID NO: 14). In a specific embodiment, the sequence of the codon-altered polynucleotide has at least 98% identity to CS03-MP-NA (SEQ ID NO:14). In a specific embodiment, the sequence of the codon-altered polynucleotide has at least 99% identity to CS03-MP-NA (SEQ ID NO:14). In a specific embodiment, the sequence of the codon-altered polynucleotide has at least 99.5% identity to CS03-MP-NA (SEQ ID NO:14). In a specific embodiment, the sequence of the codon-altered polynucleotide has at least 99.9% identity to CS03-MP-NA (SEQ ID NO: 14). In another specific embodiment, the sequence of the codon-altered polynucleotide is CS03-MP-NA (SEQ ID NO: 14).

In some embodiments, the sequence of the codon-altered polynucleotide having high sequence identity to CS03-MP-NA (SEQ ID NO:14) has a GC content of less than 60%. In some embodiments, the sequence of the codon-altered polynucleotide having high sequence identity to CS03-MP-NA (SEQ ID NO: 14) has a GC content of less than 59%. In some embodiments, the sequence of the codon-altered polynucleotide having high sequence identity to CS03-MP-NA (SEQ ID NO:14) has a GC content of less than 58%. In some embodiments, the sequence of the codon-altered polynucleotide having high sequence identity to CS03-MP-NA (SEQ ID NO: 14) has a GC content of less than 57%. In some embodiments, the sequence of the codon-altered polynucleotide having high sequence identity to CS03-MP-NA (SEQ ID NO: 14) has a GC content of less than 56%. In some embodiments, the sequence of the codon-altered polynucleotide having high sequence identity to CS03-MP-NA (SEQ ID NO:14) has a GC content of less than 55%. In some embodiments, the sequence of the codon-altered polynucleotide having high sequence identity to CS03-MP-NA (SEQ ID NO:14) has a GC content of less than 54%.

In some embodiments, the sequence of the codon-altered polynucleotide having high sequence identity to CS03-MP-NA (SEQ ID NO: 14) has a GC content of from 50% to 60%. In some embodiments, the sequence of the codon-altered polynucleotide having high sequence identity to CS03-MP-NA (SEQ ID NO:14) has a GC content of from 50% to 59%. In some embodiments, the sequence of the codon-altered polynucleotide having high sequence identity to CS03-MP-NA (SEQ ID NO:14) has a GC content of from 50% to 58%. In some embodiments, the sequence of the codon-altered polynucleotide having high sequence identity to CS03-MP-NA (SEQ ID NO: 14) has a GC content of from 50% to 57%. In some embodiments, the sequence of the codon-altered polynucleotide having high sequence identity to CS03-MP-NA (SEQ ID NO: 14) has a GC content of from 50% to 56%. In some embodiments, the sequence of the codon-altered polynucleotide having high sequence identity to CS03-MP-NA (SEQ ID NO: 14) has a GC content of from 50% to 55%. In some embodiments, the sequence of the codon-altered polynucleotide having high sequence identity to CS03-MP-NA (SEQ ID NO: 14) has a GC content of from 50% to 54%.

In some embodiments, the sequence of the codon-altered polynucleotide having high sequence identity to CS03-MP-NA (SEQ ID NO:14) has a GC content of 53.8%±1.0. In some embodiments, the sequence of the codon-altered polynucleotide having high sequence identity to CS03-MP-NA (SEQ ID NO:14) has a GC content of 53.8%±0.8. In some embodiments, the sequence of the codon-altered polynucleotide having high sequence identity to CS03-MP-NA (SEQ ID NO:14) has a GC content of 53.8%±0.6. In some embodiments, the sequence of the codon-altered polynucleotide having high sequence identity to CS03-MP-NA (SEQ ID NO: 14) has a GC content of 53.8%±0.5. In some embodiments, the sequence of the codon-altered polynucleotide having high sequence identity to CS03-MP-NA (SEQ ID NO: 14) has a GC content of 53.8%±0.4. In some embodiments, the sequence of the codon-altered polynucleotide having high sequence identity to CS03-MP-NA (SEQ ID NO:14) has a GC content of 53.8%±0.3. In some embodiments, the sequence of the codon-altered polynucleotide having high sequence identity to CS03-MP-NA (SEQ ID NO: 14) has a GC content of 53.8%±0.2. In some embodiments, the sequence of the codon-altered polynucleotide having high sequence identity to CS03-MP-NA (SEQ ID NO:14) has a GC content of 53.8%±0.1. In some embodiments, the sequence of the codon-altered polynucleotide having high sequence identity to CS03-MP-NA (SEQ ID NO: 14) has a GC content of 53.8%.

In some embodiments, the sequence of the codon-altered polynucleotide having high sequence identity to CS03-MP-NA (SEQ ID NO:14) has no more than 15 CpG dinucleotides. In some embodiments, the sequence of the codon-altered polynucleotide having high sequence identity to CS03-MP-NA (SEQ ID NO:14) has no more than 12 CpG dinucleotides. In some embodiments, the sequence of the codon-altered polynucleotide having high sequence identity to CS03-MP-NA (SEQ ID NO:14) has no more than 10 CpG dinucleotides. In some embodiments, the sequence of the codon-altered polynucleotide having high sequence identity to CS03-MP-NA (SEQ ID NO: 14) has no more than 9 CpG dinucleotides. In some embodiments, the sequence of the codon-altered polynucleotide having high sequence identity to CS03-MP-NA (SEQ ID NO: 14) has no more than 8 CpG dinucleotides. In some embodiments, the sequence of the codon-altered polynucleotide having high sequence identity to CS03-MP-NA (SEQ ID NO: 14) has no more than 7 CpG dinucleotides. In some embodiments, the sequence of the codon-altered polynucleotide having high sequence identity to CS03-MP-NA (SEQ ID NO:14) has no more than 6 CpG dinucleotides. In some embodiments, the sequence of the codon-altered polynucleotide having high sequence identity to CS03-MP-NA (SEQ ID NO: 14) has no more than 5 CpG dinucleotides. In some embodiments, the sequence of the codon-altered polynucleotide having high sequence identity to CS03-MP-NA (SEQ ID NO:14) has no more than 4 CpG dinucleotides. In some embodiments, the sequence of the codon-altered polynucleotide having high sequence identity to CS03-MP-NA (SEQ ID NO: 14) has no more than 3 CpG dinucleotides. In some embodiments, the sequence of the codon-altered polynucleotide having high sequence identity to CS03-MP-NA (SEQ ID NO: 14) has no more than 2 CpG dinucleotides. In some embodiments, the sequence of the codon-altered polynucleotide having high sequence identity to CS03-MP-NA (SEQ ID NO: 14) has no more than 1 CpG dinucleotide. In some embodiments, the sequence of the codon-altered polynucleotide having high sequence identity to CS03-MP-NA (SEQ ID NO:14) has no CpG dinucleotides.

In some embodiments, the Factor IX polynucleotide high sequence identity to CS03-MP-NA (SEQ ID NO:14) further includes a Factor IX signal polynucleotide encoding a Factor IX signal peptide having the amino acid sequence of FIX-SP-AA (SEQ ID NO:37). In some embodiments, the Factor IX signal polynucleotide has a nucleic acid sequence that is at least 90%, 95%, 96%, 97%, 98%, 99%, or 100% identical to CS02-SP-NA (SEQ ID NO:25). In some embodiments, the Factor IX signal polynucleotide has a nucleic acid sequence that is at least 90%, 95%, 96%, 97%, 98%, 99%, or 100% identical to CS03-SP-NA (SEQ ID NO:26). In some embodiments, the Factor IX signal polynucleotide has a nucleic acid sequence that is at least 90%, 95%, 96%, 97%, 98%, 99%, or 100% identical to CS04-SP-NA (SEQ ID NO:27). In some embodiments, the Factor IX signal polynucleotide has a nucleic acid sequence that is at least 90%, 95%, 96%, 97%, 98%, 99%, or 100% identical to CS05-SP-NA (SEQ ID NO:28). In some embodiments, the Factor IX signal polynucleotide has a nucleic acid sequence that is at least 90%, 95%, 96%, 97%, 98%, 99%, or 100% identical to CS06-SP-NA (SEQ ID NO:29).

In some embodiments, the Factor IX polynucleotide high sequence identity to CS03-MP-NA (SEQ ID NO:14) further includes a Factor IX pro-peptide polynucleotide encoding a Factor IX pro-peptide having the amino acid sequence of FIX-PP-AA (SEQ ID NO:38). In some embodiments, the Factor IX pro-peptide polynucleotide has a nucleic acid sequence that is at least 90%, 95%, 96%, 97%, 98%, 99%, or 100% identical to CS02-PP-NA (SEQ ID NO:31). In some embodiments, the Factor IX pro-peptide polynucleotide has a nucleic acid sequence that is at least 90%, 95%, 96%, 97%, 98%, 99%, or 100% identical to CS03-PP-NA (SEQ ID NO:32). In some embodiments, the Factor IX pro-peptide polynucleotide has a nucleic acid sequence that is at least 90%, 95%, 96%, 97%, 98%, 99%, or 100% identical to CS04-PP-NA (SEQ ID NO:33). In some embodiments, the Factor IX pro-peptide polynucleotide has a nucleic acid sequence that is at least 90%, 95%, 96%, 97%, 98%, 99%, or 100% identical to CS05-PP-NA (SEQ ID NO:34). In some embodiments, the Factor IX pro-peptide polynucleotide has a nucleic acid sequence that is at least 90%, 95%, 96%, 97%, 98%, 99%, or 100% identical to CS06-PP-NA (SEQ ID NO:35).

In some embodiments, the Factor IX polynucleotide high sequence identity to CS03-MP-NA (SEQ ID NO: 14) further includes a Factor IX pre-pro-peptide polynucleotide encoding a Factor IX pre-pro-peptide having the amino acid sequence of FIX-PPP-AA (SEQ ID NO:36). In some embodiments, the Factor IX pre-pro-peptide polynucleotide has a nucleic acid sequence that is at least 90%, 95%, 96%, 97%, 98%, 99%, or 100% identical to CS02-PPP-NA (SEQ ID NO:19). In some embodiments, the Factor IX pre-pro-peptide polynucleotide has a nucleic acid sequence that is at least 90%, 95%, 96%, 97%, 98%, 99%, or 100% identical to CS03-PPP-NA (SEQ ID NO:20). In some embodiments, the Factor IX pre-pro-peptide polynucleotide has a nucleic acid sequence that is at least 90%, 95%, 96%, 97%, 98%, 99%, or 100% identical to CS04-PPP-NA (SEQ ID NO:21). In some embodiments, the Factor IX pre-pro-peptide polynucleotide has a nucleic acid sequence that is at least 90%, 95%, 96%, 97%, 98%, 99%, or 100% identical to CS05-PPP-NA (SEQ ID NO:22). In some embodiments, the Factor IX pre-pro-peptide polynucleotide has a nucleic acid sequence that is at least 90%, 95%, 96%, 97%, 98%, 99%, or 100% identical to CS06-PPP-NA (SEQ ID NO:23).

In some embodiments, the encoded Factor IX polypeptide, e.g., the polypeptide encoded by the polynucleotide having high sequence homology to CS03-FL-NA (SEQ ID NO:6), has high sequence identity to the wild type, mature Factor IX single-chain polypeptide sequence FIX-MP-AA (SEQ ID NO: 10) and/or the mature Padua (hFIX(R384L)) single-chain sequence FIXp-MP-AA (SEQ ID NO: 12). The encoded Factor IX polypeptide should retain the ability to become activated into a function Factor IXa protein (e.g., by removal of any signal peptide and the pro-peptide, and by excision of the activation polypeptide).

In one embodiment, the sequence of the encoded Factor IX polypeptide has at least 85% identity to FIX-MP-AA (SEQ ID NO: 10). In one embodiment, the sequence of the encoded Factor IX polypeptide has at least 90% identity to FIX-MP-AA (SEQ ID NO:10). In one embodiment, the sequence of the encoded Factor IX polypeptide has at least 95% identity to FIX-MP-AA (SEQ ID NO: 10). In one embodiment, the sequence of the encoded Factor IX polypeptide has at least 96% identity to FIX-MP-AA (SEQ ID NO: 10). In one embodiment, the sequence of the encoded Factor IX polypeptide has at least 97% identity to FIX-MP-AA (SEQ ID NO: 10). In one embodiment, the sequence of the encoded Factor IX polypeptide has at least 98% identity to FIX-MP-AA (SEQ ID NO:10). In one embodiment, the sequence of the encoded Factor IX polypeptide has at least 99% identity to FIX-MP-AA (SEQ ID NO:10). In one embodiment, the sequence of the encoded Factor IX polypeptide has at least 99.5% identity to FIX-MP-AA (SEQ ID NO: 10). In one embodiment, the sequence of the encoded Factor IX polypeptide has at least 99.9% identity to FIX-MP-AA (SEQ ID NO: 10). In one embodiment, the sequence of the encoded Factor IX polypeptide is FIX-MP-AA (SEQ ID NO: 10).

In one embodiment, the sequence of the encoded Factor IX polypeptide has at least 85% identity to FIXp-MP-AA (SEQ ID NO:12) and includes a leucine at position 384 of the pre-pro-polypeptide (e.g., position 338 of the mature Factor IX single-chain polypeptide FIXp-MP-AA (SEQ ID NO: 12)). In one embodiment, the sequence of the encoded Factor IX polypeptide has at least 90% identity to FIXp-MP-AA (SEQ ID NO: 12) and includes a leucine at position 384 of the pre-pro-polypeptide. In one embodiment, the sequence of the encoded Factor IX polypeptide has at least 95% identity to FIXp-MP-AA (SEQ ID NO: 12) and includes a leucine at position 384 of the pre-pro-polypeptide. In one embodiment, the sequence of the encoded Factor IX polypeptide has at least 96% identity to FIXp-MP-AA (SEQ ID NO: 12) and includes a leucine at position 384 of the pre-pro-polypeptide. In one embodiment, the sequence of the encoded Factor IX polypeptide has at least 97% identity FIXp-MP-AA (SEQ ID NO: 12) and includes a leucine at position 384 of the pre-pro-polypeptide. In one embodiment, the sequence of the encoded Factor IX polypeptide has at least 98% identity to FIXp-MP-AA (SEQ ID NO:12) and includes a leucine at position 384 of the pre-pro-polypeptide. In one embodiment, the sequence of the encoded Factor IX polypeptide has at least 99% identity to FIXp-MP-AA (SEQ ID NO: 12) and includes a leucine at position 384 of the pre-pro-polypeptide. In one embodiment, the sequence of the encoded Factor IX polypeptide has at least 99.5% identity to FIXp-MP-AA (SEQ ID NO: 12) and includes a leucine at position 384 of the pre-pro-polypeptide. In one embodiment, the sequence of the encoded Factor IX polypeptide has at least 99.9% identity to FIXp-MP-AA (SEQ ID NO: 12) and includes a leucine at position 384 of the pre-pro-polypeptide. In one embodiment, the sequence of the encoded Factor IX polypeptide is FIXp-MP-AA (SEQ ID NO: 12).

In one embodiment, a codon-altered polynucleotides provided herein encodes for a single-chain Factor IX polypeptide including a light chain, a heavy chain, and a polypeptide linker joining the C-terminus of the light chain to the N-terminus of the heavy chain. The light chain of the Factor IX polypeptide is encoded by a first nucleotide sequence having high sequence identity to CS03-LC-NA (SEQ ID NO:44), which is the portion of CS03-FL-NA (SEQ ID NO:6) encoding the Factor IX light chain. The heavy chain of the Factor IX polypeptide is encoded by a second nucleotide sequence having high sequence identity to CS03-HC-NA (SEQ ID NO:43), which is the portion of CS03-FL-NA (SEQ ID NO:6) encoding the Factor IX heavy chain. The polypeptide linker includes Factor XI cleavage sites, which allow for maturation in vivo (e.g., after expression of the precursor single-chain Factor IX polypeptide.

In some embodiments, the first and second nucleotide sequences have at least 95% sequence identity to CS03-LC-NA (SEQ ID NO:44) and CS03-HC-NA (SEQ ID NO:43), respectively. In some embodiments, the first and second nucleotide sequences have at least 96% sequence identity to CS03-LC-NA (SEQ ID NO:44) and CS03-HC-NA (SEQ ID NO:43), respectively. In some embodiments, the first and second nucleotide sequences have at least 97% sequence identity to CS03-LC-NA (SEQ ID NO:44) and CS03-HC-NA (SEQ ID NO:43), respectively. In some embodiments, the first and second nucleotide sequences have at least 98% sequence identity to CS03-LC-NA (SEQ ID NO:44) and CS03-HC-NA (SEQ ID NO:43), respectively. In some embodiments, the first and second nucleotide sequences have at least 99% sequence identity to CS03-LC-NA (SEQ ID NO:44) and CS03-HC-NA (SEQ ID NO:43), respectively. In some embodiments, the first and second nucleotide sequences have at least 99.5% sequence identity to CS03-LC-NA (SEQ ID NO:44) and CS03-HC-NA (SEQ ID NO:43), respectively. In some embodiments, the first and second nucleotide sequences have at least 99.9% sequence identity to CS03-LC-NA (SEQ ID NO:44) and CS03-HC-NA (SEQ ID NO:43), respectively. In some embodiments, the first and second nucleotide sequences are CS03-LC-NA (SEQ ID NO:44) and CS03-HC-NA (SEQ ID NO:43), respectively.

In some embodiments, the polypeptide linker of the Factor IX construct is encoded by a third nucleotide sequence having high sequence identity to CS03-AP-NA (SEQ ID NO:58), which is a codon-altered sequence encoding the wild type Factor IX activation polypeptide, e.g., amino acids 192-226 of FIX-FL-AA (SEQ ID NO:2). In some embodiments, the third nucleotide sequence has at least 80% identity to CS03-AP-NA (SEQ ID NO:58). In some embodiments, the third nucleotide sequence has at least 90% identity to CS03-AP-NA (SEQ ID NO:58). In some embodiments, the third nucleotide sequence has at least 95% identity to CS03-AP-NA (SEQ ID NO:58). In some embodiments, the third nucleotide sequence has at least 96% identity to CS03-AP-NA (SEQ ID NO:58). In some embodiments, the third nucleotide sequence has at least 97% identity to CS03-AP-NA (SEQ ID NO:58). In some embodiments, the third nucleotide sequence has at least 98% identity to CS03-AP-NA (SEQ ID NO:58). In some embodiments, the third nucleotide sequence has at least 99% identity to CS03-AP-NA (SEQ ID NO:58). In some embodiments, the third nucleotide sequence is CS03-AP-NA (SEQ ID NO:58).

In some embodiments, the encoded Factor IX polypeptide also includes a signal peptide (e.g., a Factor IX signal peptide) and/or a pro-peptide (e.g., a Factor IX pro-peptide). In some embodiments, the signal peptide is the wild-type Factor IX signal peptide (FIX-SP-AA (SEQ ID NO:37)). In some embodiments, the signal peptide is encoded by a codon-altered polynucleotide sequence having high sequence identity (e.g., at least 95%, 96%, 97%, 98%, or 99%) to CS03-SP-NA (SEQ ID NO:26). In some embodiments, the pro-peptide is the wild-type Factor IX pro-peptide (FIX-PP-AA (SEQ ID NO:38)). In some embodiments, the pro-peptide peptide is encoded by a codon-altered polynucleotide sequence having high sequence identity (e.g., at least 95%, 96%, 97%, 98%, or 99%) to CS03-PP-NA (SEQ ID NO:32).

In some embodiments, the encoded Factor IX polypeptide, e.g., the polypeptide encoded by the polynucleotide having high sequence homology to CS03-LC-NA (SEQ ID NO:44) and CS03-HC-NA (SEQ ID NO:43), has high sequence identity to the wild type, mature Factor IX single-chain polypeptide sequence FIX-MP-AA (SEQ ID NO:10) and/or the mature Padua (hFIX(R384L)) single-chain sequence FIXp-MP-AA (SEQ ID NO: 12). The encoded Factor IX polypeptide should retain the ability to become activated into a function Factor IXa protein (e.g., by removal of any signal peptide and the pro-peptide, and by excision of the activation polypeptide).

In one embodiment, the sequence of the encoded Factor IX polypeptide has at least 85% identity to FIX-MP-AA (SEQ ID NO: 10). In one embodiment, the sequence of the encoded Factor IX polypeptide has at least 90% identity to FIX-MP-AA (SEQ ID NO:10). In one embodiment, the sequence of the encoded Factor IX polypeptide has at least 95% identity to FIX-MP-AA (SEQ ID NO: 10). In one embodiment, the sequence of the encoded Factor IX polypeptide has at least 96% identity to FIX-MP-AA (SEQ ID NO: 10). In one embodiment, the sequence of the encoded Factor IX polypeptide has at least 97% identity to FIX-MP-AA (SEQ ID NO: 10). In one embodiment, the sequence of the encoded Factor IX polypeptide has at least 98% identity to FIX-MP-AA (SEQ ID NO:10). In one embodiment, the sequence of the encoded Factor IX polypeptide has at least 99% identity to FIX-MP-AA (SEQ ID NO:10). In one embodiment, the sequence of the encoded Factor IX polypeptide has at least 99.5% identity to FIX-MP-AA (SEQ ID NO: 10). In one embodiment, the sequence of the encoded Factor IX polypeptide has at least 99.9% identity to FIX-MP-AA (SEQ ID NO: 10). In one embodiment, the sequence of the encoded Factor IX polypeptide is FIX-MP-AA (SEQ ID NO: 10).

In one embodiment, the sequence of the encoded Factor IX polypeptide has at least 85% identity to FIXp-MP-AA (SEQ ID NO:12) and includes a leucine at position 384 of the pre-pro-polypeptide (e.g., position 338 of the mature Factor IX single-chain polypeptide FIXp-MP-AA (SEQ ID NO: 12)). In one embodiment, the sequence of the encoded Factor IX polypeptide has at least 90% identity to FIXp-MP-AA (SEQ ID NO: 12) and includes a leucine at position 384 of the pre-pro-polypeptide. In one embodiment, the sequence of the encoded Factor IX polypeptide has at least 95% identity to FIXp-MP-AA (SEQ ID NO: 12) and includes a leucine at position 384 of the pre-pro-polypeptide. In one embodiment, the sequence of the encoded Factor IX polypeptide has at least 96% identity to FIXp-MP-AA (SEQ ID NO: 12) and includes a leucine at position 384 of the pre-pro-polypeptide. In one embodiment, the sequence of the encoded Factor IX polypeptide has at least 97% identity FIXp-MP-AA (SEQ ID NO: 12) and includes a leucine at position 384 of the pre-pro-polypeptide. In one embodiment, the sequence of the encoded Factor IX polypeptide has at least 98% identity to FIXp-MP-AA (SEQ ID NO:12) and includes a leucine at position 384 of the pre-pro-polypeptide. In one embodiment, the sequence of the encoded Factor IX polypeptide has at least 99% identity to FIXp-MP-AA (SEQ ID NO: 12) and includes a leucine at position 384 of the pre-pro-polypeptide. In one embodiment, the sequence of the encoded Factor IX polypeptide has at least 99.5% identity to FIXp-MP-AA (SEQ ID NO: 12) and includes a leucine at position 384 of the pre-pro-polypeptide. In one embodiment, the sequence of the encoded Factor IX polypeptide has at least 99.9% identity to FIXp-MP-AA (SEQ ID NO: 12) and includes a leucine at position 384 of the pre-pro-polypeptide. In one embodiment, the sequence of the encoded Factor IX polypeptide is FIXp-MP-AA (SEQ ID NO: 12).

In some embodiments, with reference to FIG. 1, a nucleic acid composition is provided that includes a self-complementary polynucleotide of structure A, where the FIX coding sequence portion of the polynucleotide includes a nucleic acid sequence, encoding a mature Factor IX polypeptide, that has at least 95%, 96%, 97%, 98%, 99%, 99.5%, 99.9%, or 100% identity to CS03-MP-NA (SEQ ID NO: 14). In some embodiments, the FIX coding sequence portion of the polynucleotide also includes a nucleic acid sequence, encoding a Factor IX signal peptide, that has at least 90%, 95%, 96%, 97%, 98%, 99%, or 100% identity to one of FIX-SP-NA (SEQ ID NO:24), CS02-SP-NA (SEQ ID NO:25), CS03-SP-NA (SEQ ID NO:26), CS04-SP-NA (SEQ ID NO:27), CS05-SP-NA (SEQ ID NO:28), and CS06-SP-NA (SEQ ID NO:29). In some embodiments, the FIX coding sequence portion of the polynucleotide also includes a nucleic acid sequence, encoding a Factor IX pro-peptide (optionally in combination with a nucleic acid sequence for a Factor IX signal peptide, as described above), that has at least 90%, 95%, 96%, 97%, 98%, 99%, or 100% identity to one of FIX-PP-NA (SEQ ID NO:30), CS02-PP-NA (SEQ ID NO:31), CS03-PP-NA (SEQ ID NO:32), CS04-PP-NA (SEQ ID NO:33), CS05-PP-NA (SEQ ID NO:34), and CS06-PP-NA (SEQ ID NO:35). In some embodiments, the FIX coding sequence portion of the polynucleotide includes a nucleic acid sequence, encoding a pre-pro-Factor IX polypeptide, that has at least 95%, 96%, 97%, 98%, 99%, 99.5%, 99.9%, or 100% identity to CS03-FL-NA (SEQ ID NO:6).

In some embodiments, with reference to FIG. 1, a nucleic acid composition is provided that includes a self-complementary polynucleotide of structure B, where the FIX coding sequence portion of the polynucleotide includes a nucleic acid sequence, encoding a mature Factor IX polypeptide, that has at least 95%, 96%, 97%, 98%, 99%, 99.5%, 99.9%, or 100% identity to CS03-MP-NA (SEQ ID NO: 14). In some embodiments, the FIX coding sequence portion of the polynucleotide also includes a nucleic acid sequence, encoding a Factor IX signal peptide, that has at least 90%, 95%, 96%, 97%, 98%, 99%, or 100% identity to one of FIX-SP-NA (SEQ ID NO:24), CS02-SP-NA (SEQ ID NO:25), CS03-SP-NA (SEQ ID NO:26), CS04-SP-NA (SEQ ID NO:27), CS05-SP-NA (SEQ ID NO:28), and CS06-SP-NA (SEQ ID NO:29). In some embodiments, the FIX coding sequence portion of the polynucleotide also includes a nucleic acid sequence, encoding a Factor IX pro-peptide (optionally in combination with a nucleic acid sequence for a Factor IX signal peptide, as described above), that has at least 90%, 95%, 96%, 97%, 98%, 99%, or 100% identity to one of FIX-PP-NA (SEQ ID NO:30), CS02-PP-NA (SEQ ID NO:31), CS03-PP-NA (SEQ ID NO:32), CS04-PP-NA (SEQ ID NO:33), CS05-PP-NA (SEQ ID NO:34), and CS06-PP-NA (SEQ ID NO:35). In some embodiments, the FIX coding sequence portion of the polynucleotide includes a nucleic acid sequence, encoding a pre-pro-Factor IX polypeptide, that has at least 95%, 96%, 97%, 98%, 99%, 99.5%, 99.9%, or 100% identity to CS03-FL-NA (SEQ ID NO:6).

In some embodiments, with reference to FIG. 1, a nucleic acid composition is provided that includes a polynucleotide of structure C (e.g., a single-stranded polynucleotide), where the FIX coding sequence portion of the polynucleotide includes a nucleic acid sequence, encoding a mature Factor IX polypeptide, that has at least 95%, 96%, 97%, 98%, 99%, 99.5%, 99.9%, or 100% identity to CS03-MP-NA (SEQ ID NO:14). In some embodiments, the FIX coding sequence portion of the polynucleotide also includes a nucleic acid sequence, encoding a Factor IX signal peptide, that has at least 90%, 95%, 96%, 97%, 98%, 99%, or 100% identity to one of FIX-SP-NA (SEQ ID NO:24), CS02-SP-NA (SEQ ID NO:25), CS03-SP-NA (SEQ ID NO:26), CS04-SP-NA (SEQ ID NO:27), CS05-SP-NA (SEQ ID NO:28), and CS06-SP-NA (SEQ ID NO:29). In some embodiments, the FIX coding sequence portion of the polynucleotide also includes a nucleic acid sequence, encoding a Factor IX pro-peptide (optionally in combination with a nucleic acid sequence for a Factor IX signal peptide, as described above), that has at least 90%, 95%, 96%, 97%, 98%, 99%, or 100% identity to one of FIX-PP-NA (SEQ ID NO:30), CS02-PP-NA (SEQ ID NO:31), CS03-PP-NA (SEQ ID NO:32), CS04-PP-NA (SEQ ID NO:33), CS05-PP-NA (SEQ ID NO:34), and CS06-PP-NA (SEQ ID NO:35). In some embodiments, the FIX coding sequence portion of the polynucleotide includes a nucleic acid sequence, encoding a pre-pro-Factor IX polypeptide, that has at least 95%, 96%, 97%, 98%, 99%, 99.5%, 99.9%, or 100% identity to CS03-FL-NA (SEQ ID NO:6).

In some embodiments, with reference to FIG. 1, a nucleic acid composition is provided that includes a polynucleotide of structure D (e.g., a single-stranded polynucleotide), where the FIX coding sequence portion of the polynucleotide includes a nucleic acid sequence, encoding a mature Factor IX polypeptide, that has at least 95%, 96%, 97%, 98%, 99%, 99.5%, 99.9%, or 100% identity to CS03-MP-NA (SEQ ID NO:14). In some embodiments, the FIX coding sequence portion of the polynucleotide also includes a nucleic acid sequence, encoding a Factor IX signal peptide, that has at least 90%, 95%, 96%, 97%, 98%, 99%, or 100% identity to one of FIX-SP-NA (SEQ ID NO:24), CS02-SP-NA (SEQ ID NO:25), CS03-SP-NA (SEQ ID NO:26), CS04-SP-NA (SEQ ID NO:27), CS05-SP-NA (SEQ ID NO:28), and CS06-SP-NA (SEQ ID NO:29). In some embodiments, the FIX coding sequence portion of the polynucleotide also includes a nucleic acid sequence, encoding a Factor IX pro-peptide (optionally in combination with a nucleic acid sequence for a Factor IX signal peptide, as described above), that has at least 90%, 95%, 96%, 97%, 98%, 99%, or 100% identity to one of FIX-PP-NA (SEQ ID NO:30), CS02-PP-NA (SEQ ID NO:31), CS03-PP-NA (SEQ ID NO:32), CS04-PP-NA (SEQ ID NO:33), CS05-PP-NA (SEQ ID NO:34), and CS06-PP-NA (SEQ ID NO:35). In some embodiments, the FIX coding sequence portion of the polynucleotide includes a nucleic acid sequence, encoding a pre-pro-Factor IX polypeptide, that has at least 95%, 96%, 97%, 98%, 99%, 99.5%, 99.9%, or 100% identity to CS03-FL-NA (SEQ ID NO:6).

CS04 Codon Altered Polynucleotides

In one embodiment, a nucleic acid composition provided herein includes a Factor IX polynucleotide (e.g., a codon-altered polynucleotide) encoding a single-chain Factor IX polypeptide, where the Factor IX polynucleotide includes a nucleotide sequence having high sequence identity to CS04-FL-NA (SEQ ID NO:7). In some embodiments, the nucleotide sequence of the Factor IX polynucleotide having high sequence identity to CS04-FL-NA (SEQ ID NO:7) has a reduced GC content, as compared to the wild-type Factor IX coding sequence (FIX-FL-NA (SEQ ID NO:1)). In some embodiments, the nucleotide sequence of the Factor IX polynucleotide having high sequence identity to CS04-FL-NA (SEQ ID NO:7) has a reduced number of CpG dinucleotides, as compared to the wild-type Factor IX coding sequence (FIX-FL-NA (SEQ ID NO: 1)).

In a specific embodiment, the sequence of the codon-altered polynucleotide has at least 95% identity to CS04-FL-NA (SEQ ID NO:7). In a specific embodiment, the sequence of the codon-altered polynucleotide has at least 96% identity to CS04-FL-NA (SEQ ID NO:7). In a specific embodiment, the sequence of the codon-altered polynucleotide has at least 97% identity to CS04-FL-NA (SEQ ID NO:7). In a specific embodiment, the sequence of the codon-altered polynucleotide has at least 98% identity to CS04-FL-NA (SEQ ID NO:7). In a specific embodiment, the sequence of the codon-altered polynucleotide has at least 99% identity to CS04-FL-NA (SEQ ID NO:7). In a specific embodiment, the sequence of the codon-altered polynucleotide has at least 99.5% identity to CS04-FL-NA (SEQ ID NO:7). In a specific embodiment, the sequence of the codon-altered polynucleotide has at least 99.9% identity to CS04-FL-NA (SEQ ID NO:7). In another specific embodiment, the sequence of the codon-altered polynucleotide is CS04-FL-NA (SEQ ID NO:7).

In some embodiments, the sequence of the codon-altered polynucleotide having high sequence identity to CS04-FL-NA (SEQ ID NO:7) has a GC content of less than 60%. In some embodiments, the sequence of the codon-altered polynucleotide having high sequence identity to CS04-FL-NA (SEQ ID NO:7) has a GC content of less than 59%. In some embodiments, the sequence of the codon-altered polynucleotide having high sequence identity to CS04-FL-NA (SEQ ID NO:7) has a GC content of less than 58%. In some embodiments, the sequence of the codon-altered polynucleotide having high sequence identity to CS04-FL-NA (SEQ ID NO:7) has a GC content of less than 57%. In some embodiments, the sequence of the codon-altered polynucleotide having high sequence identity to CS04-FL-NA (SEQ ID NO:7) has a GC content of less than 56%. In some embodiments, the sequence of the codon-altered polynucleotide having high sequence identity to CS04-FL-NA (SEQ ID NO:7) has a GC content of less than 55%. In some embodiments, the sequence of the codon-altered polynucleotide having high sequence identity to CS04-FL-NA (SEQ ID NO:7) has a GC content of less than 54%.

In some embodiments, the sequence of the codon-altered polynucleotide having high sequence identity to CS04-FL-NA (SEQ ID NO:7) has a GC content of from 50% to 60%. In some embodiments, the sequence of the codon-altered polynucleotide having high sequence identity to CS04-FL-NA (SEQ ID NO:7) has a GC content of from 50% to 59%. In some embodiments, the sequence of the codon-altered polynucleotide having high sequence identity to CS04-FL-NA (SEQ ID NO:7) has a GC content of from 50% to 58%. In some embodiments, the sequence of the codon-altered polynucleotide having high sequence identity to CS04-FL-NA (SEQ ID NO:7) has a GC content of from 50% to 57%. In some embodiments, the sequence of the codon-altered polynucleotide having high sequence identity to CS04-FL-NA (SEQ ID NO:7) has a GC content of from 50% to 56%. In some embodiments, the sequence of the codon-altered polynucleotide having high sequence identity to CS04-FL-NA (SEQ ID NO:7) has a GC content of from 50% to 55%. In some embodiments, the sequence of the codon-altered polynucleotide having high sequence identity to CS04-FL-NA (SEQ ID NO:7) has a GC content of from 50% to 54%.

In some embodiments, the sequence of the codon-altered polynucleotide having high sequence identity to CS04-FL-NA (SEQ ID NO:7) has a GC content of 53.8%±1.0. In some embodiments, the sequence of the codon-altered polynucleotide having high sequence identity to CS04-FL-NA (SEQ ID NO:7) has a GC content of 53.8%±0.8. In some embodiments, the sequence of the codon-altered polynucleotide having high sequence identity to CS04-FL-NA (SEQ ID NO:7) has a GC content of 53.8%±0.6. In some embodiments, the sequence of the codon-altered polynucleotide having high sequence identity to CS04-FL-NA (SEQ ID NO:7) has a GC content of 53.8%±0.5. In some embodiments, the sequence of the codon-altered polynucleotide having high sequence identity to CS04-FL-NA (SEQ ID NO:7) has a GC content of 53.8%±0.4. In some embodiments, the sequence of the codon-altered polynucleotide having high sequence identity to CS04-FL-NA (SEQ ID NO:7) has a GC content of 53.8%±0.3. In some embodiments, the sequence of the codon-altered polynucleotide having high sequence identity to CS04-FL-NA (SEQ ID NO:7) has a GC content of 53.8%±0.2. In some embodiments, the sequence of the codon-altered polynucleotide having high sequence identity to CS04-FL-NA (SEQ ID NO:7) has a GC content of 53.8%±0.1. In some embodiments, the sequence of the codon-altered polynucleotide having high sequence identity to CS04-FL-NA (SEQ ID NO:7) has a GC content of 53.8%.

In some embodiments, the sequence of the codon-altered polynucleotide having high sequence identity to CS04-FL-NA (SEQ ID NO:7) has no more than 15 CpG dinucleotides. In some embodiments, the sequence of the codon-altered polynucleotide having high sequence identity to CS04-FL-NA (SEQ ID NO:7) has no more than 12 CpG dinucleotides. In some embodiments, the sequence of the codon-altered polynucleotide having high sequence identity to CS04-FL-NA (SEQ ID NO:7) has no more than 10 CpG dinucleotides. In some embodiments, the sequence of the codon-altered polynucleotide having high sequence identity to CS04-FL-NA (SEQ ID NO:7) has no more than 9 CpG dinucleotides. In some embodiments, the sequence of the codon-altered polynucleotide having high sequence identity to CS04-FL-NA (SEQ ID NO:7) has no more than 8 CpG dinucleotides. In some embodiments, the sequence of the codon-altered polynucleotide having high sequence identity to CS04-FL-NA (SEQ ID NO:7) has no more than 7 CpG dinucleotides. In some embodiments, the sequence of the codon-altered polynucleotide having high sequence identity to CS04-FL-NA (SEQ ID NO:7) has no more than 6 CpG dinucleotides. In some embodiments, the sequence of the codon-altered polynucleotide having high sequence identity to CS04-FL-NA (SEQ ID NO:7) has no more than 5 CpG dinucleotides. In some embodiments, the sequence of the codon-altered polynucleotide having high sequence identity to CS04-FL-NA (SEQ ID NO:7) has no more than 4 CpG dinucleotides. In some embodiments, the sequence of the codon-altered polynucleotide having high sequence identity to CS04-FL-NA (SEQ ID NO:7) has no more than 3 CpG dinucleotides. In some embodiments, the sequence of the codon-altered polynucleotide having high sequence identity to CS04-FL-NA (SEQ ID NO:7) has no more than 2 CpG dinucleotides. In some embodiments, the sequence of the codon-altered polynucleotide having high sequence identity to CS04-FL-NA (SEQ ID NO:7) has no more than 1 CpG dinucleotide. In some embodiments, the sequence of the codon-altered polynucleotide having high sequence identity to CS04-FL-NA (SEQ ID NO:7) has no CpG dinucleotides.

In some embodiments, the encoded Factor IX polypeptide, e.g., the polypeptide encoded by the polynucleotide having high sequence homology to CS04-FL-NA (SEQ ID NO:7), has high sequence identity to the wild type Factor IX pre-pro-protein sequence FIX-FL-AA (SEQ ID NO:2) and/or the Padua (hFIX(R384L)) pre-pro-protein sequence FIXp-FL-AA (SEQ ID NO:4). The encoded Factor IX polypeptide should retain the ability to become activated into a function Factor IXa protein (e.g., by removal of the signal peptide and the pro-peptide, and by excision of the activation polypeptide).

In one embodiment, the sequence of the encoded Factor IX polypeptide has at least 85% identity to FIX-FL-AA (SEQ ID NO:2). In one embodiment, the sequence of the encoded Factor IX polypeptide has at least 90% identity to FIX-FL-AA (SEQ ID NO:2). In one embodiment, the sequence of the encoded Factor IX polypeptide has at least 95% identity to FIX-FL-AA (SEQ ID NO:2). In one embodiment, the sequence of the encoded Factor IX polypeptide has at least 96% identity to FIX-FL-AA (SEQ ID NO:2). In one embodiment, the sequence of the encoded Factor IX polypeptide has at least 97% identity to FIX-FL-AA (SEQ ID NO:2). In one embodiment, the sequence of the encoded Factor IX polypeptide has at least 98% identity to FIX-FL-AA (SEQ ID NO:2). In one embodiment, the sequence of the encoded Factor IX polypeptide has at least 99% identity to FIX-FL-AA (SEQ ID NO:2). In one embodiment, the sequence of the encoded Factor IX polypeptide has at least 99.5% identity to FIX-FL-AA (SEQ ID NO:2). In one embodiment, the sequence of the encoded Factor IX polypeptide has at least 99.9% identity to FIX-FL-AA (SEQ ID NO:2). In one embodiment, the sequence of the encoded Factor IX polypeptide is FIX-FL-AA (SEQ ID NO:2).

In one embodiment, the sequence of the encoded Factor IX polypeptide has at least 85% identity to FIXp-FL-AA (SEQ ID NO:4) and includes a leucine at position 384 of the pre-pro-polypeptide (e.g., position 338 of the mature Factor IX single-chain polypeptide FIXp-MP-AA (SEQ ID NO: 12)). In one embodiment, the sequence of the encoded Factor IX polypeptide has at least 90% identity to FIXp-FL-AA (SEQ ID NO:4) and includes a leucine at position 384 of the pre-pro-polypeptide. In one embodiment, the sequence of the encoded Factor IX polypeptide has at least 95% identity to FIXp-FL-AA (SEQ ID NO:4) and includes a leucine at position 384 of the pre-pro-polypeptide. In one embodiment, the sequence of the encoded Factor IX polypeptide has at least 96% identity to FIXp-FL-AA (SEQ ID NO:4) and includes a leucine at position 384 of the pre-pro-polypeptide. In one embodiment, the sequence of the encoded Factor IX polypeptide has at least 97% identity FIXp-FL-AA (SEQ ID NO:4) and includes a leucine at position 384 of the pre-pro-polypeptide. In one embodiment, the sequence of the encoded Factor IX polypeptide has at least 98% identity to FIXp-FL-AA (SEQ ID NO:4) and includes a leucine at position 384 of the pre-pro-polypeptide. In one embodiment, the sequence of the encoded Factor IX polypeptide has at least 99% identity to FIXp-FL-AA (SEQ ID NO:4) and includes a leucine at position 384 of the pre-pro-polypeptide. In one embodiment, the sequence of the encoded Factor IX polypeptide has at least 99.5% identity to FIXp-FL-AA (SEQ ID NO:4) and includes a leucine at position 384 of the pre-pro-polypeptide. In one embodiment, the sequence of the encoded Factor IX polypeptide has at least 99.9% identity to FIXp-FL-AA (SEQ ID NO:4) and includes a leucine at position 384 of the pre-pro-polypeptide. In one embodiment, the sequence of the encoded Factor IX polypeptide is FIXp-FL-AA (SEQ ID NO:4).

In one embodiment, a nucleic acid composition provided herein includes a Factor IX polynucleotide (e.g., a codon-altered polynucleotide) encoding a single-chain Factor IX polypeptide (e.g., having serine protease activity), where the Factor IX polynucleotide includes a nucleotide sequence having high sequence identity to CS04-MP-NA (SEQ ID NO:15). In some embodiments, the nucleotide sequence of the Factor IX polynucleotide having high sequence identity to CS04-MP-NA (SEQ ID NO:15) has a reduced GC content, as compared to the wild-type Factor IX coding sequence (FIX-FL-NA (SEQ ID NO:1)). In some embodiments, the nucleotide sequence of the Factor IX polynucleotide having high sequence identity to CS04-MP-NA (SEQ ID NO:15) has a reduced number of CpG dinucleotides, as compared to the wild-type Factor IX coding sequence (FIX-FL-NA (SEQ ID NO: 1)).

In a specific embodiment, the sequence of the codon-altered polynucleotide has at least 95% identity to CS04-MP-NA (SEQ ID NO:15). In a specific embodiment, the sequence of the codon-altered polynucleotide has at least 96% identity to CS04-MP-NA (SEQ ID NO:15). In a specific embodiment, the sequence of the codon-altered polynucleotide has at least 97% identity to CS04-MP-NA (SEQ ID NO: 15). In a specific embodiment, the sequence of the codon-altered polynucleotide has at least 98% identity to CS04-MP-NA (SEQ ID NO:15). In a specific embodiment, the sequence of the codon-altered polynucleotide has at least 99% identity to CS04-MP-NA (SEQ ID NO:15). In a specific embodiment, the sequence of the codon-altered polynucleotide has at least 99.5% identity to CS04-MP-NA (SEQ ID NO:15). In a specific embodiment, the sequence of the codon-altered polynucleotide has at least 99.9% identity to CS04-MP-NA (SEQ ID NO:15). In another specific embodiment, the sequence of the codon-altered polynucleotide is CS04-MP-NA (SEQ ID NO:15).

In some embodiments, the sequence of the codon-altered polynucleotide having high sequence identity to CS04-MP-NA (SEQ ID NO:15) has a GC content of less than 60%. In some embodiments, the sequence of the codon-altered polynucleotide having high sequence identity to CS04-MP-NA (SEQ ID NO:15) has a GC content of less than 59%. In some embodiments, the sequence of the codon-altered polynucleotide having high sequence identity to CS04-MP-NA (SEQ ID NO:15) has a GC content of less than 58%. In some embodiments, the sequence of the codon-altered polynucleotide having high sequence identity to CS04-MP-NA (SEQ ID NO:15) has a GC content of less than 57%. In some embodiments, the sequence of the codon-altered polynucleotide having high sequence identity to CS04-MP-NA (SEQ ID NO: 15) has a GC content of less than 56%. In some embodiments, the sequence of the codon-altered polynucleotide having high sequence identity to CS04-MP-NA (SEQ ID NO:15) has a GC content of less than 55%. In some embodiments, the sequence of the codon-altered polynucleotide having high sequence identity to CS04-MP-NA (SEQ ID NO:15) has a GC content of less than 54%.

In some embodiments, the sequence of the codon-altered polynucleotide having high sequence identity to CS04-MP-NA (SEQ ID NO:15) has a GC content of from 50% to 60%. In some embodiments, the sequence of the codon-altered polynucleotide having high sequence identity to CS04-MP-NA (SEQ ID NO:15) has a GC content of from 50% to 59%. In some embodiments, the sequence of the codon-altered polynucleotide having high sequence identity to CS04-MP-NA (SEQ ID NO:15) has a GC content of from 50% to 58%. In some embodiments, the sequence of the codon-altered polynucleotide having high sequence identity to CS04-MP-NA (SEQ ID NO:15) has a GC content of from 50% to 57%. In some embodiments, the sequence of the codon-altered polynucleotide having high sequence identity to CS04-MP-NA (SEQ ID NO: 15) has a GC content of from 50% to 56%. In some embodiments, the sequence of the codon-altered polynucleotide having high sequence identity to CS04-MP-NA (SEQ ID NO: 15) has a GC content of from 50% to 55%. In some embodiments, the sequence of the codon-altered polynucleotide having high sequence identity to CS04-MP-NA (SEQ ID NO: 15) has a GC content of from 50% to 54%.

In some embodiments, the sequence of the codon-altered polynucleotide having high sequence identity to CS04-MP-NA (SEQ ID NO:15) has a GC content of 53.8%±1.0. In some embodiments, the sequence of the codon-altered polynucleotide having high sequence identity to CS04-MP-NA (SEQ ID NO:15) has a GC content of 53.8%±0.8. In some embodiments, the sequence of the codon-altered polynucleotide having high sequence identity to CS04-MP-NA (SEQ ID NO:15) has a GC content of 53.8%±0.6. In some embodiments, the sequence of the codon-altered polynucleotide having high sequence identity to CS04-MP-NA (SEQ ID NO:15) has a GC content of 53.8%±0.5. In some embodiments, the sequence of the codon-altered polynucleotide having high sequence identity to CS04-MP-NA (SEQ ID NO: 15) has a GC content of 53.8%±0.4. In some embodiments, the sequence of the codon-altered polynucleotide having high sequence identity to CS04-MP-NA (SEQ ID NO:15) has a GC content of 53.8%±0.3. In some embodiments, the sequence of the codon-altered polynucleotide having high sequence identity to CS04-MP-NA (SEQ ID NO: 15) has a GC content of 53.8%±0.2. In some embodiments, the sequence of the codon-altered polynucleotide having high sequence identity to CS04-MP-NA (SEQ ID NO:15) has a GC content of 53.8%±0.1. In some embodiments, the sequence of the codon-altered polynucleotide having high sequence identity to CS04-MP-NA (SEQ ID NO:15) has a GC content of 53.8%.

In some embodiments, the sequence of the codon-altered polynucleotide having high sequence identity to CS04-MP-NA (SEQ ID NO:15) has no more than 15 CpG dinucleotides. In some embodiments, the sequence of the codon-altered polynucleotide having high sequence identity to CS04-MP-NA (SEQ ID NO:15) has no more than 12 CpG dinucleotides. In some embodiments, the sequence of the codon-altered polynucleotide having high sequence identity to CS04-MP-NA (SEQ ID NO:15) has no more than 10 CpG dinucleotides. In some embodiments, the sequence of the codon-altered polynucleotide having high sequence identity to CS04-MP-NA (SEQ ID NO:15) has no more than 9 CpG dinucleotides. In some embodiments, the sequence of the codon-altered polynucleotide having high sequence identity to CS04-MP-NA (SEQ ID NO: 15) has no more than 8 CpG dinucleotides. In some embodiments, the sequence of the codon-altered polynucleotide having high sequence identity to CS04-MP-NA (SEQ ID NO: 15) has no more than 7 CpG dinucleotides. In some embodiments, the sequence of the codon-altered polynucleotide having high sequence identity to CS04-MP-NA (SEQ ID NO:15) has no more than 6 CpG dinucleotides. In some embodiments, the sequence of the codon-altered polynucleotide having high sequence identity to CS04-MP-NA (SEQ ID NO:15) has no more than 5 CpG dinucleotides. In some embodiments, the sequence of the codon-altered polynucleotide having high sequence identity to CS04-MP-NA (SEQ ID NO:15) has no more than 4 CpG dinucleotides. In some embodiments, the sequence of the codon-altered polynucleotide having high sequence identity to CS04-MP-NA (SEQ ID NO:15) has no more than 3 CpG dinucleotides. In some embodiments, the sequence of the codon-altered polynucleotide having high sequence identity to CS04-MP-NA (SEQ ID NO:15) has no more than 2 CpG dinucleotides. In some embodiments, the sequence of the codon-altered polynucleotide having high sequence identity to CS04-MP-NA (SEQ ID NO: 15) has no more than 1 CpG dinucleotide. In some embodiments, the sequence of the codon-altered polynucleotide having high sequence identity to CS04-MP-NA (SEQ ID NO:15) has no CpG dinucleotides.

In some embodiments, the Factor IX polynucleotide high sequence identity to CS04-MP-NA (SEQ ID NO:15) further includes a Factor IX signal polynucleotide encoding a Factor IX signal peptide having the amino acid sequence of FIX-SP-AA (SEQ ID NO:37). In some embodiments, the Factor IX signal polynucleotide has a nucleic acid sequence that is at least 90%, 95%, 96%, 97%, 98%, 99%, or 100% identical to CS02-SP-NA (SEQ ID NO:25). In some embodiments, the Factor IX signal polynucleotide has a nucleic acid sequence that is at least 90%, 95%, 96%, 97%, 98%, 99%, or 100% identical to CS03-SP-NA (SEQ ID NO:26). In some embodiments, the Factor IX signal polynucleotide has a nucleic acid sequence that is at least 90%, 95%, 96%, 97%, 98%, 99%, or 100% identical to CS04-SP-NA (SEQ ID NO:27). In some embodiments, the Factor IX signal polynucleotide has a nucleic acid sequence that is at least 90%, 95%, 96%, 97%, 98%, 99%, or 100% identical to CS05-SP-NA (SEQ ID NO:28). In some embodiments, the Factor IX signal polynucleotide has a nucleic acid sequence that is at least 90%, 95%, 96%, 97%, 98%, 99%, or 100% identical to CS06-SP-NA (SEQ ID NO:29).

In some embodiments, the Factor IX polynucleotide high sequence identity to CS04-MP-NA (SEQ ID NO:15) further includes a Factor IX pro-peptide polynucleotide encoding a Factor IX pro-peptide having the amino acid sequence of FIX-PP-AA (SEQ ID NO:38). In some embodiments, the Factor IX pro-peptide polynucleotide has a nucleic acid sequence that is at least 90%, 95%, 96%, 97%, 98%, 99%, or 100% identical to CS02-PP-NA (SEQ ID NO:31). In some embodiments, the Factor IX pro-peptide polynucleotide has a nucleic acid sequence that is at least 90%, 95%, 96%, 97%, 98%, 99%, or 100% identical to CS03-PP-NA (SEQ ID NO:32). In some embodiments, the Factor IX pro-peptide polynucleotide has a nucleic acid sequence that is at least 90%, 95%, 96%, 97%, 98%, 99%, or 100% identical to CS04-PP-NA (SEQ ID NO:33). In some embodiments, the Factor IX pro-peptide polynucleotide has a nucleic acid sequence that is at least 90%, 95%, 96%, 97%, 98%, 99%, or 100% identical to CS05-PP-NA (SEQ ID NO:34). In some embodiments, the Factor IX pro-peptide polynucleotide has a nucleic acid sequence that is at least 90%, 95%, 96%, 97%, 98%, 99%, or 100% identical to CS06-PP-NA (SEQ ID NO:35).

In some embodiments, the Factor IX polynucleotide high sequence identity to CS04-MP-NA (SEQ ID NO: 15) further includes a Factor IX pre-pro-peptide polynucleotide encoding a Factor IX pre-pro-peptide having the amino acid sequence of FIX-PPP-AA (SEQ ID NO:36). In some embodiments, the Factor IX pre-pro-peptide polynucleotide has a nucleic acid sequence that is at least 90%, 95%, 96%, 97%, 98%, 99%, or 100% identical to CS02-PPP-NA (SEQ ID NO:19). In some embodiments, the Factor IX pre-pro-peptide polynucleotide has a nucleic acid sequence that is at least 90%, 95%, 96%, 97%, 98%, 99%, or 100% identical to CS03-PPP-NA (SEQ ID NO:20). In some embodiments, the Factor IX pre-pro-peptide polynucleotide has a nucleic acid sequence that is at least 90%, 95%, 96%, 97%, 98%, 99%, or 100% identical to CS04-PPP-NA (SEQ ID NO:21). In some embodiments, the Factor IX pre-pro-peptide polynucleotide has a nucleic acid sequence that is at least 90%, 95%, 96%, 97%, 98%, 99%, or 100% identical to CS05-PPP-NA (SEQ ID NO:22). In some embodiments, the Factor IX pre-pro-peptide polynucleotide has a nucleic acid sequence that is at least 90%, 95%, 96%, 97%, 98%, 99%, or 100% identical to CS06-PPP-NA (SEQ ID NO:23).

In some embodiments, the encoded Factor IX polypeptide, e.g., the polypeptide encoded by the polynucleotide having high sequence homology to CS04-FL-NA (SEQ ID NO:7), has high sequence identity to the wild type, mature Factor IX single-chain polypeptide sequence FIX-MP-AA (SEQ ID NO: 10) and/or the mature Padua (hFIX(R384L)) single-chain sequence FIXp-MP-AA (SEQ ID NO: 12). The encoded Factor IX polypeptide should retain the ability to become activated into a function Factor IXa protein (e.g., by removal of any signal peptide and the pro-peptide, and by excision of the activation polypeptide).

In one embodiment, the sequence of the encoded Factor IX polypeptide has at least 85% identity to FIX-MP-AA (SEQ ID NO: 10). In one embodiment, the sequence of the encoded Factor IX polypeptide has at least 90% identity to FIX-MP-AA (SEQ ID NO:10). In one embodiment, the sequence of the encoded Factor IX polypeptide has at least 95% identity to FIX-MP-AA (SEQ ID NO: 10). In one embodiment, the sequence of the encoded Factor IX polypeptide has at least 96% identity to FIX-MP-AA (SEQ ID NO: 10). In one embodiment, the sequence of the encoded Factor IX polypeptide has at least 97% identity to FIX-MP-AA (SEQ ID NO: 10). In one embodiment, the sequence of the encoded Factor IX polypeptide has at least 98% identity to FIX-MP-AA (SEQ ID NO:10). In one embodiment, the sequence of the encoded Factor IX polypeptide has at least 99% identity to FIX-MP-AA (SEQ ID NO:10). In one embodiment, the sequence of the encoded Factor IX polypeptide has at least 99.5% identity to FIX-MP-AA (SEQ ID NO: 10). In one embodiment, the sequence of the encoded Factor IX polypeptide has at least 99.9% identity to FIX-MP-AA (SEQ ID NO: 10). In one embodiment, the sequence of the encoded Factor IX polypeptide is FIX-MP-AA (SEQ ID NO: 10).

In one embodiment, the sequence of the encoded Factor IX polypeptide has at least 85% identity to FIXp-MP-AA (SEQ ID NO:12) and includes a leucine at position 384 of the pre-pro-polypeptide (e.g., position 338 of the mature Factor IX single-chain polypeptide FIXp-MP-AA (SEQ ID NO: 12)). In one embodiment, the sequence of the encoded Factor IX polypeptide has at least 90% identity to FIXp-MP-AA (SEQ ID NO: 12) and includes a leucine at position 384 of the pre-pro-polypeptide. In one embodiment, the sequence of the encoded Factor IX polypeptide has at least 95% identity to FIXp-MP-AA (SEQ ID NO: 12) and includes a leucine at position 384 of the pre-pro-polypeptide. In one embodiment, the sequence of the encoded Factor IX polypeptide has at least 96% identity to FIXp-MP-AA (SEQ ID NO: 12) and includes a leucine at position 384 of the pre-pro-polypeptide. In one embodiment, the sequence of the encoded Factor IX polypeptide has at least 97% identity FIXp-MP-AA (SEQ ID NO: 12) and includes a leucine at position 384 of the pre-pro-polypeptide. In one embodiment, the sequence of the encoded Factor IX polypeptide has at least 98% identity to FIXp-MP-AA (SEQ ID NO:12) and includes a leucine at position 384 of the pre-pro-polypeptide. In one embodiment, the sequence of the encoded Factor IX polypeptide has at least 99% identity to FIXp-MP-AA (SEQ ID NO: 12) and includes a leucine at position 384 of the pre-pro-polypeptide. In one embodiment, the sequence of the encoded Factor IX polypeptide has at least 99.5% identity to FIXp-MP-AA (SEQ ID NO: 12) and includes a leucine at position 384 of the pre-pro-polypeptide. In one embodiment, the sequence of the encoded Factor IX polypeptide has at least 99.9% identity to FIXp-MP-AA (SEQ ID NO: 12) and includes a leucine at position 384 of the pre-pro-polypeptide. In one embodiment, the sequence of the encoded Factor IX polypeptide is FIXp-MP-AA (SEQ ID NO: 12).

In one embodiment, a codon-altered polynucleotides provided herein encodes for a single-chain Factor IX polypeptide including a light chain, a heavy chain, and a polypeptide linker joining the C-terminus of the light chain to the N-terminus of the heavy chain. The light chain of the Factor IX polypeptide is encoded by a first nucleotide sequence having high sequence identity to CS04-LC-NA (SEQ ID NO:46), which is the portion of CS04-FL-NA (SEQ ID NO:7) encoding the Factor IX light chain. The heavy chain of the Factor IX polypeptide is encoded by a second nucleotide sequence having high sequence identity to CS04-HC-NA (SEQ ID NO:45), which is the portion of CS04-FL-NA (SEQ ID NO:7) encoding the Factor IX heavy chain. The polypeptide linker includes Factor XI cleavage sites, which allow for maturation in vivo (e.g., after expression of the precursor single-chain Factor IX polypeptide.

In some embodiments, the first and second nucleotide sequences have at least 95% sequence identity to CS04-LC-NA and CS04-HC-NA (SEQ ID NOS:46 and 45), respectively. In some embodiments, the first and second nucleotide sequences have at least 96% sequence identity to CS04-LC-NA and CS04-HC-NA (SEQ ID NOS:46 and 45), respectively. In some embodiments, the first and second nucleotide sequences have at least 97% sequence identity to CS04-LC-NA and CS04-HC-NA (SEQ ID NOS:46 and 45), respectively. In some embodiments, the first and second nucleotide sequences have at least 98% sequence identity to CS04-LC-NA and CS04-HC-NA (SEQ ID NOS:46 and 45), respectively. In some embodiments, the first and second nucleotide sequences have at least 99% sequence identity to CS04-LC-NA and CS04-HC-NA (SEQ ID NOS:46 and 45), respectively, respectively. In some embodiments, the first and second nucleotide sequences have at least 99.5% sequence identity to CS04-LC-NA and CS04-HC-NA (SEQ ID NOS: 46 and 45), respectively. In some embodiments, the first and second nucleotide sequences have at least 99.9% sequence identity to CS04-LC-NA and CS04-HC-NA (SEQ ID NOS: 46 and 45), respectively. In some embodiments, the first and second nucleotide sequences are CS04-LC-NA and CS04-HC-NA (SEQ ID NOS:46 and 45), respectively.

In some embodiments, the polypeptide linker of the Factor IX construct is encoded by a third nucleotide sequence having high sequence identity to CS04-AP-NA (SEQ ID NO:59), which is a codon-altered sequence encoding the wild type Factor IX activation polypeptide, e.g., amino acids 192-226 of FIX-FL-AA (SEQ ID NO:2). In some embodiments, the third nucleotide sequence has at least 80% identity to CS04-AP-NA (SEQ ID NO:59). In some embodiments, the third nucleotide sequence has at least 90% identity to CS04-AP-NA (SEQ ID NO:59). In some embodiments, the third nucleotide sequence has at least 95% identity to CS04-AP-NA (SEQ ID NO:59). In some embodiments, the third nucleotide sequence has at least 96% identity to CS04-AP-NA (SEQ ID NO:59). In some embodiments, the third nucleotide sequence has at least 97% identity to CS04-AP-NA (SEQ ID NO:59). In some embodiments, the third nucleotide sequence has at least 98% identity to CS04-AP-NA (SEQ ID NO:59). In some embodiments, the third nucleotide sequence has at least 99% identity to CS04-AP-NA (SEQ ID NO:59). In some embodiments, the third nucleotide sequence is CS04-AP-NA (SEQ ID NO:59).

In some embodiments, the encoded Factor IX polypeptide also includes a signal peptide (e.g., a Factor IX signal peptide) and/or a pro-peptide (e.g., a Factor IX pro-peptide). In some embodiments, the signal peptide is the wild-type Factor IX signal peptide (FIX-SP-AA (SEQ ID NO:37)). In some embodiments, the signal peptide is encoded by a codon-altered polynucleotide sequence having high sequence identity (e.g., at least 95%, 96%, 97%, 98%, or 99%) to CS04-SP-NA (SEQ ID NO:27). In some embodiments, the pro-peptide is the wild-type Factor IX pro-peptide (FIX-PP-AA (SEQ ID NO:38)). In some embodiments, the pro-peptide peptide is encoded by a codon-altered polynucleotide sequence having high sequence identity (e.g., at least 95%, 96%, 97%, 98%, or 99%) to CS04-PP-NA (SEQ ID NO:33).

In some embodiments, the encoded Factor IX polypeptide, e.g., the polypeptide encoded by the polynucleotide having high sequence homology to CS04-LC-NA (SEQ ID NO:46) and CS04-HC-NA (SEQ ID NO:45), has high sequence identity to the wild type, mature Factor IX single-chain polypeptide sequence FIX-MP-AA (SEQ ID NO:10) and/or the mature Padua (hFIX(R384L)) single-chain sequence FIXp-MP-AA (SEQ ID NO: 12). The encoded Factor IX polypeptide should retain the ability to become activated into a function Factor IXa protein (e.g., by removal of any signal peptide and the pro-peptide, and by excision of the activation polypeptide).

In one embodiment, the sequence of the encoded Factor IX polypeptide has at least 85% identity to FIX-MP-AA (SEQ ID NO: 10). In one embodiment, the sequence of the encoded Factor IX polypeptide has at least 90% identity to FIX-MP-AA (SEQ ID NO:10). In one embodiment, the sequence of the encoded Factor IX polypeptide has at least 95% identity to FIX-MP-AA (SEQ ID NO: 10). In one embodiment, the sequence of the encoded Factor IX polypeptide has at least 96% identity to FIX-MP-AA (SEQ ID NO: 10). In one embodiment, the sequence of the encoded Factor IX polypeptide has at least 97% identity to FIX-MP-AA (SEQ ID NO: 10). In one embodiment, the sequence of the encoded Factor IX polypeptide has at least 98% identity to FIX-MP-AA (SEQ ID NO:10). In one embodiment, the sequence of the encoded Factor IX polypeptide has at least 99% identity to FIX-MP-AA (SEQ ID NO:10). In one embodiment, the sequence of the encoded Factor IX polypeptide has at least 99.5% identity to FIX-MP-AA (SEQ ID NO: 10). In one embodiment, the sequence of the encoded Factor IX polypeptide has at least 99.9% identity to FIX-MP-AA (SEQ ID NO: 10). In one embodiment, the sequence of the encoded Factor IX polypeptide is FIX-MP-AA (SEQ ID NO: 10).

In one embodiment, the sequence of the encoded Factor IX polypeptide has at least 85% identity to FIXp-MP-AA (SEQ ID NO:12) and includes a leucine at position 384 of the pre-pro-polypeptide (e.g., position 338 of the mature Factor IX single-chain polypeptide FIXp-MP-AA (SEQ ID NO: 12)). In one embodiment, the sequence of the encoded Factor IX polypeptide has at least 90% identity to FIXp-MP-AA (SEQ ID NO: 12) and includes a leucine at position 384 of the pre-pro-polypeptide. In one embodiment, the sequence of the encoded Factor IX polypeptide has at least 95% identity to FIXp-MP-AA (SEQ ID NO: 12) and includes a leucine at position 384 of the pre-pro-polypeptide. In one embodiment, the sequence of the encoded Factor IX polypeptide has at least 96% identity to FIXp-MP-AA (SEQ ID NO: 12) and includes a leucine at position 384 of the pre-pro-polypeptide. In one embodiment, the sequence of the encoded Factor IX polypeptide has at least 97% identity FIXp-MP-AA (SEQ ID NO: 12) and includes a leucine at position 384 of the pre-pro-polypeptide. In one embodiment, the sequence of the encoded Factor IX polypeptide has at least 98% identity to FIXp-MP-AA (SEQ ID NO:12) and includes a leucine at position 384 of the pre-pro-polypeptide. In one embodiment, the sequence of the encoded Factor IX polypeptide has at least 99% identity to FIXp-MP-AA (SEQ ID NO: 12) and includes a leucine at position 384 of the pre-pro-polypeptide. In one embodiment, the sequence of the encoded Factor IX polypeptide has at least 99.5% identity to FIXp-MP-AA (SEQ ID NO: 12) and includes a leucine at position 384 of the pre-pro-polypeptide. In one embodiment, the sequence of the encoded Factor IX polypeptide has at least 99.9% identity to FIXp-MP-AA (SEQ ID NO: 12) and includes a leucine at position 384 of the pre-pro-polypeptide. In one embodiment, the sequence of the encoded Factor IX polypeptide is FIXp-MP-AA (SEQ ID NO: 12).

In some embodiments, with reference to FIG. 1, a nucleic acid composition is provided that includes a self-complementary polynucleotide of structure A, where the FIX coding sequence portion of the polynucleotide includes a nucleic acid sequence, encoding a mature Factor IX polypeptide, that has at least 95%, 96%, 97%, 98%, 99%, 99.5%, 99.9%, or 100% identity to CS04-MP-NA (SEQ ID NO: 15). In some embodiments, the FIX coding sequence portion of the polynucleotide also includes a nucleic acid sequence, encoding a Factor IX signal peptide, that has at least 90%, 95%, 96%, 97%, 98%, 99%, or 100% identity to one of FIX-SP-NA (SEQ ID NO:24), CS02-SP-NA (SEQ ID NO:25), CS03-SP-NA (SEQ ID NO:26), CS04-SP-NA (SEQ ID NO:27), CS05-SP-NA (SEQ ID NO:28), and CS06-SP-NA (SEQ ID NO:29). In some embodiments, the FIX coding sequence portion of the polynucleotide also includes a nucleic acid sequence, encoding a Factor IX pro-peptide (optionally in combination with a nucleic acid sequence for a Factor IX signal peptide, as described above), that has at least 90%, 95%, 96%, 97%, 98%, 99%, or 100% identity to one of FIX-PP-NA (SEQ ID NO:30), CS02-PP-NA (SEQ ID NO:31), CS03-PP-NA (SEQ ID NO:32), CS04-PP-NA (SEQ ID NO:33), CS05-PP-NA (SEQ ID NO:34), and CS06-PP-NA (SEQ ID NO:35). In some embodiments, the FIX coding sequence portion of the polynucleotide includes a nucleic acid sequence, encoding a pre-pro-Factor IX polypeptide, that has at least 95%, 96%, 97%, 98%, 99%, 99.5%, 99.9%, or 100% identity to CS04-FL-NA (SEQ ID NO:7).

In some embodiments, with reference to FIG. 1, a nucleic acid composition is provided that includes a self-complementary polynucleotide of structure B, where the FIX coding sequence portion of the polynucleotide includes a nucleic acid sequence, encoding a mature Factor IX polypeptide, that has at least 95%, 96%, 97%, 98%, 99%, 99.5%, 99.9%, or 100% identity to CS04-MP-NA (SEQ ID NO: 15). In some embodiments, the FIX coding sequence portion of the polynucleotide also includes a nucleic acid sequence, encoding a Factor IX signal peptide, that has at least 90%, 95%, 96%, 97%, 98%, 99%, or 100% identity to one of FIX-SP-NA (SEQ ID NO:24), CS02-SP-NA (SEQ ID NO:25), CS03-SP-NA (SEQ ID NO:26), CS04-SP-NA (SEQ ID NO:27), CS05-SP-NA (SEQ ID NO:28), and CS06-SP-NA (SEQ ID NO:29). In some embodiments, the FIX coding sequence portion of the polynucleotide also includes a nucleic acid sequence, encoding a Factor IX pro-peptide (optionally in combination with a nucleic acid sequence for a Factor IX signal peptide, as described above), that has at least 90%, 95%, 96%, 97%, 98%, 99%, or 100% identity to one of FIX-PP-NA (SEQ ID NO:30), CS02-PP-NA (SEQ ID NO:31), CS03-PP-NA (SEQ ID NO:32), CS04-PP-NA (SEQ ID NO:33), CS05-PP-NA (SEQ ID NO:34), and CS06-PP-NA (SEQ ID NO:35). In some embodiments, the FIX coding sequence portion of the polynucleotide includes a nucleic acid sequence, encoding a pre-pro-Factor IX polypeptide, that has at least 95%, 96%, 97%, 98%, 99%, 99.5%, 99.9%, or 100% identity to CS04-FL-NA (SEQ ID NO:7).

In some embodiments, with reference to FIG. 1, a nucleic acid composition is provided that includes a polynucleotide of structure C (e.g., a single-stranded polynucleotide), where the FIX coding sequence portion of the polynucleotide includes a nucleic acid sequence, encoding a mature Factor IX polypeptide, that has at least 95%, 96%, 97%, 98%, 99%, 99.5%, 99.9%, or 100% identity to CS04-MP-NA (SEQ ID NO:15). In some embodiments, the FIX coding sequence portion of the polynucleotide also includes a nucleic acid sequence, encoding a Factor IX signal peptide, that has at least 90%, 95%, 96%, 97%, 98%, 99%, or 100% identity to one of FIX-SP-NA (SEQ ID NO:24), CS02-SP-NA (SEQ ID NO:25), CS03-SP-NA (SEQ ID NO:26), CS04-SP-NA (SEQ ID NO:27), CS05-SP-NA (SEQ ID NO:28), and CS06-SP-NA (SEQ ID NO:29). In some embodiments, the FIX coding sequence portion of the polynucleotide also includes a nucleic acid sequence, encoding a Factor IX pro-peptide (optionally in combination with a nucleic acid sequence for a Factor IX signal peptide, as described above), that has at least 90%, 95%, 96%, 97%, 98%, 99%, or 100% identity to one of FIX-PP-NA (SEQ ID NO:30), CS02-PP-NA (SEQ ID NO:31), CS03-PP-NA (SEQ ID NO:32), CS04-PP-NA (SEQ ID NO:33), CS05-PP-NA (SEQ ID NO:34), and CS06-PP-NA (SEQ ID NO:35). In some embodiments, the FIX coding sequence portion of the polynucleotide includes a nucleic acid sequence, encoding a pre-pro-Factor IX polypeptide, that has at least 95%, 96%, 97%, 98%, 99%, 99.5%, 99.9%, or 100% identity to CS04-FL-NA (SEQ ID NO:7).

In some embodiments, with reference to FIG. 1, a nucleic acid composition is provided that includes a polynucleotide of structure D (e.g., a single-stranded polynucleotide), where the FIX coding sequence portion of the polynucleotide includes a nucleic acid sequence, encoding a mature Factor IX polypeptide, that has at least 95%, 96%, 97%, 98%, 99%, 99.5%, 99.9%, or 100% identity to CS04-MP-NA (SEQ ID NO:15). In some embodiments, the FIX coding sequence portion of the polynucleotide also includes a nucleic acid sequence, encoding a Factor IX signal peptide, that has at least 90%, 95%, 96%, 97%, 98%, 99%, or 100% identity to one of FIX-SP-NA (SEQ ID NO:24), CS02-SP-NA (SEQ ID NO:25), CS03-SP-NA (SEQ ID NO:26), CS04-SP-NA (SEQ ID NO:27), CS05-SP-NA (SEQ ID NO:28), and CS06-SP-NA (SEQ ID NO:29). In some embodiments, the FIX coding sequence portion of the polynucleotide also includes a nucleic acid sequence, encoding a Factor IX pro-peptide (optionally in combination with a nucleic acid sequence for a Factor IX signal peptide, as described above), that has at least 90%, 95%, 96%, 97%, 98%, 99%, or 100% identity to one of FIX-PP-NA (SEQ ID NO:30), CS02-PP-NA (SEQ ID NO:31), CS03-PP-NA (SEQ ID NO:32), CS04-PP-NA (SEQ ID NO:33), CS05-PP-NA (SEQ ID NO:34), and CS06-PP-NA (SEQ ID NO:35). In some embodiments, the FIX coding sequence portion of the polynucleotide includes a nucleic acid sequence, encoding a pre-pro-Factor IX polypeptide, that has at least 95%, 96%, 97%, 98%, 99%, 99.5%, 99.9%, or 100% identity to CS04-FL-NA (SEQ ID NO:7).

CS05 Codon Altered Polynucleotides

In one embodiment, a nucleic acid composition provided herein includes a Factor IX polynucleotide (e.g., a codon-altered polynucleotide) encoding a single-chain Factor IX polypeptide, where the Factor IX polynucleotide includes a nucleotide sequence having high sequence identity to CS05-FL-NA (SEQ ID NO:8). In some embodiments, the nucleotide sequence of the Factor IX polynucleotide having high sequence identity to CS05-FL-NA (SEQ ID NO:8) has a reduced GC content, as compared to the wild-type Factor IX coding sequence (FIX-FL-NA (SEQ ID NO:1)). In some embodiments, the nucleotide sequence of the Factor IX polynucleotide having high sequence identity to CS05-FL-NA (SEQ ID NO:8) has a reduced number of CpG dinucleotides, as compared to the wild-type Factor IX coding sequence (FIX-FL-NA (SEQ ID NO: 1)).

In a specific embodiment, the sequence of the codon-altered polynucleotide has at least 95% identity to CS05-

FL-NA (SEQ ID NO:8). In a specific embodiment, the sequence of the codon-altered polynucleotide has at least 96% identity to CS05-FL-NA (SEQ ID NO:8). In a specific embodiment, the sequence of the codon-altered polynucleotide has at least 97% identity to CS05-FL-NA (SEQ ID NO:8). In a specific embodiment, the sequence of the codon-altered polynucleotide has at least 98% identity to CS05-FL-NA (SEQ ID NO:8). In a specific embodiment, the sequence of the codon-altered polynucleotide has at least 99% identity to CS05-FL-NA (SEQ ID NO:8). In a specific embodiment, the sequence of the codon-altered polynucleotide has at least 99.5% identity to CS05-FL-NA (SEQ ID NO:8). In a specific embodiment, the sequence of the codon-altered polynucleotide has at least 99.9% identity to CS05-FL-NA (SEQ ID NO:8). In another specific embodiment, the sequence of the codon-altered polynucleotide is CS05-FL-NA (SEQ ID NO:8).

In some embodiments, the sequence of the codon-altered polynucleotide having high sequence identity to CS05-FL-NA (SEQ ID NO:8) has a GC content of less than 60%. In some embodiments, the sequence of the codon-altered polynucleotide having high sequence identity to CS05-FL-NA (SEQ ID NO:8) has a GC content of less than 59%. In some embodiments, the sequence of the codon-altered polynucleotide having high sequence identity to CS05-FL-NA (SEQ ID NO:8) has a GC content of less than 58%. In some embodiments, the sequence of the codon-altered polynucleotide having high sequence identity to CS05-FL-NA (SEQ ID NO:8) has a GC content of less than 57%. In some embodiments, the sequence of the codon-altered polynucleotide having high sequence identity to CS05-FL-NA (SEQ ID NO:8) has a GC content of less than 56%. In some embodiments, the sequence of the codon-altered polynucleotide having high sequence identity to CS05-FL-NA (SEQ ID NO:8) has a GC content of less than 55%. In some embodiments, the sequence of the codon-altered polynucleotide having high sequence identity to CS05-FL-NA (SEQ ID NO:8) has a GC content of less than 54%.

In some embodiments, the sequence of the codon-altered polynucleotide having high sequence identity to CS05-FL-NA (SEQ ID NO:8) has a GC content of from 50% to 60%. In some embodiments, the sequence of the codon-altered polynucleotide having high sequence identity to CS05-FL-NA (SEQ ID NO:8) has a GC content of from 50% to 59%. In some embodiments, the sequence of the codon-altered polynucleotide having high sequence identity to CS05-FL-NA (SEQ ID NO:8) has a GC content of from 50% to 58%. In some embodiments, the sequence of the codon-altered polynucleotide having high sequence identity to CS05-FL-NA (SEQ ID NO:8) has a GC content of from 50% to 57%. In some embodiments, the sequence of the codon-altered polynucleotide having high sequence identity to CS05-FL-NA (SEQ ID NO:8) has a GC content of from 50% to 56%. In some embodiments, the sequence of the codon-altered polynucleotide having high sequence identity to CS05-FL-NA (SEQ ID NO:8) has a GC content of from 50% to 55%. In some embodiments, the sequence of the codon-altered polynucleotide having high sequence identity to CS05-FL-NA (SEQ ID NO:8) has a GC content of from 50% to 54%.

In some embodiments, the sequence of the codon-altered polynucleotide having high sequence identity to CS05-FL-NA (SEQ ID NO:8) has a GC content of 53.8%±1.0. In some embodiments, the sequence of the codon-altered polynucleotide having high sequence identity to CS05-FL-NA (SEQ ID NO:8) has a GC content of 53.8%±0.8. In some embodiments, the sequence of the codon-altered polynucleotide having high sequence identity to CS05-FL-NA (SEQ ID NO:8) has a GC content of 53.8%±0.6. In some embodiments, the sequence of the codon-altered polynucleotide having high sequence identity to CS05-FL-NA (SEQ ID NO:8) has a GC content of 53.8%±0.5. In some embodiments, the sequence of the codon-altered polynucleotide having high sequence identity to CS05-FL-NA (SEQ ID NO:8) has a GC content of 53.8%±0.4. In some embodiments, the sequence of the codon-altered polynucleotide having high sequence identity to CS05-FL-NA (SEQ ID NO:8) has a GC content of 53.8%±0.3. In some embodiments, the sequence of the codon-altered polynucleotide having high sequence identity to CS05-FL-NA (SEQ ID NO:8) has a GC content of 53.8%±0.2. In some embodiments, the sequence of the codon-altered polynucleotide having high sequence identity to CS05-FL-NA (SEQ ID NO:8) has a GC content of 53.8%±0.1. In some embodiments, the sequence of the codon-altered polynucleotide having high sequence identity to CS05-FL-NA (SEQ ID NO:8) has a GC content of 53.8%.

In some embodiments, the sequence of the codon-altered polynucleotide having high sequence identity to CS05-FL-NA (SEQ ID NO:8) has no more than 15 CpG dinucleotides. In some embodiments, the sequence of the codon-altered polynucleotide having high sequence identity to CS05-FL-NA (SEQ ID NO:8) has no more than 12 CpG dinucleotides. In some embodiments, the sequence of the codon-altered polynucleotide having high sequence identity to CS05-FL-NA (SEQ ID NO:8) has no more than 10 CpG dinucleotides. In some embodiments, the sequence of the codon-altered polynucleotide having high sequence identity to CS05-FL-NA (SEQ ID NO:8) has no more than 9 CpG dinucleotides. In some embodiments, the sequence of the codon-altered polynucleotide having high sequence identity to CS05-FL-NA (SEQ ID NO:8) has no more than 8 CpG dinucleotides. In some embodiments, the sequence of the codon-altered polynucleotide having high sequence identity to CS05-FL-NA (SEQ ID NO:8) has no more than 7 CpG dinucleotides. In some embodiments, the sequence of the codon-altered polynucleotide having high sequence identity to CS05-FL-NA (SEQ ID NO:8) has no more than 6 CpG dinucleotides. In some embodiments, the sequence of the codon-altered polynucleotide having high sequence identity to CS05-FL-NA (SEQ ID NO:8) has no more than 5 CpG dinucleotides. In some embodiments, the sequence of the codon-altered polynucleotide having high sequence identity to CS05-FL-NA (SEQ ID NO:8) has no more than 4 CpG dinucleotides. In some embodiments, the sequence of the codon-altered polynucleotide having high sequence identity to CS05-FL-NA (SEQ ID NO:8) has no more than 3 CpG dinucleotides. In some embodiments, the sequence of the codon-altered polynucleotide having high sequence identity to CS05-FL-NA (SEQ ID NO:8) has no more than 2 CpG dinucleotides. In some embodiments, the sequence of the codon-altered polynucleotide having high sequence identity to CS05-FL-NA (SEQ ID NO:8) has no more than 1 CpG dinucleotide. In some embodiments, the sequence of the codon-altered polynucleotide having high sequence identity to CS05-FL-NA (SEQ ID NO:8) has no CpG dinucleotides.

In some embodiments, the encoded Factor IX polypeptide, e.g., the polypeptide encoded by the polynucleotide having high sequence homology to CS05-FL-NA (SEQ ID NO:8), has high sequence identity to the wild type Factor IX pre-pro-protein sequence FIX-FL-AA (SEQ ID NO:2) and/or the Padua (hFIX(R384L)) pre-pro-protein sequence FIXp-FL-AA (SEQ ID NO:4). The encoded Factor IX polypeptide should retain the ability to become activated into a function Factor IXa protein (e.g., by removal of the signal peptide and the pro-peptide, and by excision of the activation polypeptide).

In one embodiment, the sequence of the encoded Factor IX polypeptide has at least 85% identity to FIX-FL-AA (SEQ ID NO:2). In one embodiment, the sequence of the encoded Factor IX polypeptide has at least 90% identity to FIX-FL-AA (SEQ ID NO:2). In one embodiment, the sequence of the encoded Factor IX polypeptide has at least 95% identity to FIX-FL-AA (SEQ ID NO:2). In one embodiment, the sequence of the encoded Factor IX polypeptide has at least 96% identity to FIX-FL-AA (SEQ ID NO:2). In one embodiment, the sequence of the encoded Factor IX polypeptide has at least 97% identity to FIX-FL-AA (SEQ ID NO:2). In one embodiment, the sequence of the encoded Factor IX polypeptide has at least 98% identity to FIX-FL-AA (SEQ ID NO:2). In one embodiment, the sequence of the encoded Factor IX polypeptide has at least 99% identity to FIX-FL-AA (SEQ ID NO:2). In one embodiment, the sequence of the encoded Factor IX polypeptide has at least 99.5% identity to FIX-FL-AA (SEQ ID NO:2). In one embodiment, the sequence of the encoded Factor IX polypeptide has at least 99.9% identity to FIX-FL-AA (SEQ ID NO:2). In one embodiment, the sequence of the encoded Factor IX polypeptide is FIX-FL-AA (SEQ ID NO:2).

In one embodiment, the sequence of the encoded Factor IX polypeptide has at least 85% identity to FIXp-FL-AA (SEQ ID NO:4) and includes a leucine at position 384 of the pre-pro-polypeptide (e.g., position 338 of the mature Factor IX single-chain polypeptide FIXp-MP-AA (SEQ ID NO: 12)). In one embodiment, the sequence of the encoded Factor IX polypeptide has at least 90% identity to FIXp-FL-AA (SEQ ID NO:4) and includes a leucine at position 384 of the pre-pro-polypeptide. In one embodiment, the sequence of the encoded Factor IX polypeptide has at least 95% identity to FIXp-FL-AA (SEQ ID NO:4) and includes a leucine at position 384 of the pre-pro-polypeptide. In one embodiment, the sequence of the encoded Factor IX polypeptide has at least 96% identity to FIXp-FL-AA (SEQ ID NO:4) and includes a leucine at position 384 of the pre-pro-polypeptide. In one embodiment, the sequence of the encoded Factor IX polypeptide has at least 97% identity FIXp-FL-AA (SEQ ID NO:4) and includes a leucine at position 384 of the pre-pro-polypeptide. In one embodiment, the sequence of the encoded Factor IX polypeptide has at least 98% identity to FIXp-FL-AA (SEQ ID NO:4) and includes a leucine at position 384 of the pre-pro-polypeptide. In one embodiment, the sequence of the encoded Factor IX polypeptide has at least 99% identity to FIXp-FL-AA (SEQ ID NO:4) and includes a leucine at position 384 of the pre-pro-polypeptide. In one embodiment, the sequence of the encoded Factor IX polypeptide has at least 99.5% identity to FIXp-FL-AA (SEQ ID NO:4) and includes a leucine at position 384 of the pre-pro-polypeptide. In one embodiment, the sequence of the encoded Factor IX polypeptide has at least 99.9% identity to FIXp-FL-AA (SEQ ID NO:4) and includes a leucine at position 384 of the pre-pro-polypeptide. In one embodiment, the sequence of the encoded Factor IX polypeptide is FIXp-FL-AA (SEQ ID NO:4).

In one embodiment, a nucleic acid composition provided herein includes a Factor IX polynucleotide (e.g., a codon-altered polynucleotide) encoding a single-chain Factor IX polypeptide (e.g., having serine protease activity), where the Factor IX polynucleotide includes a nucleotide sequence having high sequence identity to CS05-MP-NA (SEQ ID NO: 16). In some embodiments, the nucleotide sequence of the Factor IX polynucleotide having high sequence identity to CS05-MP-NA (SEQ ID NO:16) has a reduced GC content, as compared to the wild-type Factor IX coding sequence (FIX-FL-NA (SEQ ID NO:1)). In some embodiments, the nucleotide sequence of the Factor IX polynucleotide having high sequence identity to CS05-MP-NA (SEQ ID NO: 16) has a reduced number of CpG dinucleotides, as compared to the wild-type Factor IX coding sequence (FIX-FL-NA (SEQ ID NO: 1)).

In a specific embodiment, the sequence of the codon-altered polynucleotide has at least 95% identity to CS05-MP-NA (SEQ ID NO:16). In a specific embodiment, the sequence of the codon-altered polynucleotide has at least 96% identity to CS05-MP-NA (SEQ ID NO:16). In a specific embodiment, the sequence of the codon-altered polynucleotide has at least 97% identity to CS05-MP-NA (SEQ ID NO: 16). In a specific embodiment, the sequence of the codon-altered polynucleotide has at least 98% identity to CS05-MP-NA (SEQ ID NO:16). In a specific embodiment, the sequence of the codon-altered polynucleotide has at least 99% identity to CS05-MP-NA (SEQ ID NO:16). In a specific embodiment, the sequence of the codon-altered polynucleotide has at least 99.5% identity to CS05-MP-NA (SEQ ID NO:16). In a specific embodiment, the sequence of the codon-altered polynucleotide has at least 99.9% identity to CS05-MP-NA (SEQ ID NO:16). In another specific embodiment, the sequence of the codon-altered polynucleotide is CS05-MP-NA (SEQ ID NO:16).

In some embodiments, the sequence of the codon-altered polynucleotide having high sequence identity to CS05-MP-NA (SEQ ID NO:16) has a GC content of less than 60%. In some embodiments, the sequence of the codon-altered polynucleotide having high sequence identity to CS05-MP-NA (SEQ ID NO:16) has a GC content of less than 59%. In some embodiments, the sequence of the codon-altered polynucleotide having high sequence identity to CS05-MP-NA (SEQ ID NO:16) has a GC content of less than 58%. In some embodiments, the sequence of the codon-altered polynucleotide having high sequence identity to CS05-MP-NA (SEQ ID NO: 16) has a GC content of less than 57%. In some embodiments, the sequence of the codon-altered polynucleotide having high sequence identity to CS05-MP-NA (SEQ ID NO: 16) has a GC content of less than 56%. In some embodiments, the sequence of the codon-altered polynucleotide having high sequence identity to CS05-MP-NA (SEQ ID NO:16) has a GC content of less than 55%. In some embodiments, the sequence of the codon-altered polynucleotide having high sequence identity to CS05-MP-NA (SEQ ID NO:16) has a GC content of less than 54%.

In some embodiments, the sequence of the codon-altered polynucleotide having high sequence identity to CS05-MP-NA (SEQ ID NO: 16) has a GC content of from 50% to 60%. In some embodiments, the sequence of the codon-altered polynucleotide having high sequence identity to CS05-MP-NA (SEQ ID NO:16) has a GC content of from 50% to 59%. In some embodiments, the sequence of the codon-altered polynucleotide having high sequence identity to CS05-MP-NA (SEQ ID NO: 16) has a GC content of from 50% to 58%. In some embodiments, the sequence of the codon-altered polynucleotide having high sequence identity to CS05-MP-NA (SEQ ID NO: 16) has a GC content of from 50% to 57%. In some embodiments, the sequence of the codon-altered polynucleotide having high sequence identity to CS05-MP-NA (SEQ ID NO: 16) has a GC content of from 50% to 56%. In some embodiments, the sequence of the codon-altered polynucleotide having high sequence identity to CS05-MP-NA (SEQ ID NO: 16) has a GC content of from 50% to 55%.

In some embodiments, the sequence of the codon-altered polynucleotide having high sequence identity to CS05-MP-NA (SEQ ID NO: 16) has a GC content of from 50% to 54%.

In some embodiments, the sequence of the codon-altered polynucleotide having high sequence identity to CS05-MP-NA (SEQ ID NO:16) has a GC content of 53.8%±1.0. In some embodiments, the sequence of the codon-altered polynucleotide having high sequence identity to CS05-MP-NA (SEQ ID NO:16) has a GC content of 53.8%±0.8. In some embodiments, the sequence of the codon-altered polynucleotide having high sequence identity to CS05-MP-NA (SEQ ID NO:16) has a GC content of 53.8%±0.6. In some embodiments, the sequence of the codon-altered polynucleotide having high sequence identity to CS05-MP-NA (SEQ ID NO: 16) has a GC content of 53.8%±0.5. In some embodiments, the sequence of the codon-altered polynucleotide having high sequence identity to CS05-MP-NA (SEQ ID NO: 16) has a GC content of 53.8%±0.4. In some embodiments, the sequence of the codon-altered polynucleotide having high sequence identity to CS05-MP-NA (SEQ ID NO:16) has a GC content of 53.8%±0.3. In some embodiments, the sequence of the codon-altered polynucleotide having high sequence identity to CS05-MP-NA (SEQ ID NO: 16) has a GC content of 53.8%±0.2. In some embodiments, the sequence of the codon-altered polynucleotide having high sequence identity to CS05-MP-NA (SEQ ID NO:16) has a GC content of 53.8%±0.1. In some embodiments, the sequence of the codon-altered polynucleotide having high sequence identity to CS05-MP-NA (SEQ ID NO: 16) has a GC content of 53.8%.

In some embodiments, the sequence of the codon-altered polynucleotide having high sequence identity to CS05-MP-NA (SEQ ID NO:16) has no more than 15 CpG dinucleotides. In some embodiments, the sequence of the codon-altered polynucleotide having high sequence identity to CS05-MP-NA (SEQ ID NO:16) has no more than 12 CpG dinucleotides. In some embodiments, the sequence of the codon-altered polynucleotide having high sequence identity to CS05-MP-NA (SEQ ID NO:16) has no more than 10 CpG dinucleotides. In some embodiments, the sequence of the codon-altered polynucleotide having high sequence identity to CS05-MP-NA (SEQ ID NO:16) has no more than 9 CpG dinucleotides. In some embodiments, the sequence of the codon-altered polynucleotide having high sequence identity to CS05-MP-NA (SEQ ID NO: 16) has no more than 8 CpG dinucleotides. In some embodiments, the sequence of the codon-altered polynucleotide having high sequence identity to CS05-MP-NA (SEQ ID NO: 16) has no more than 7 CpG dinucleotides. In some embodiments, the sequence of the codon-altered polynucleotide having high sequence identity to CS05-MP-NA (SEQ ID NO:16) has no more than 6 CpG dinucleotides. In some embodiments, the sequence of the codon-altered polynucleotide having high sequence identity to CS05-MP-NA (SEQ ID NO: 16) has no more than 5 CpG dinucleotides. In some embodiments, the sequence of the codon-altered polynucleotide having high sequence identity to CS05-MP-NA (SEQ ID NO:16) has no more than 4 CpG dinucleotides. In some embodiments, the sequence of the codon-altered polynucleotide having high sequence identity to CS05-MP-NA (SEQ ID NO:16) has no more than 3 CpG dinucleotides. In some embodiments, the sequence of the codon-altered polynucleotide having high sequence identity to CS05-MP-NA (SEQ ID NO:16) has no more than 2 CpG dinucleotides. In some embodiments, the sequence of the codon-altered polynucleotide having high sequence identity to CS05-MP-NA (SEQ ID NO: 16) has no more than 1 CpG dinucleotide. In some embodiments, the sequence of the codon-altered polynucleotide having high sequence identity to CS05-MP-NA (SEQ ID NO:16) has no CpG dinucleotides.

In some embodiments, the Factor IX polynucleotide high sequence identity to CS05-MP-NA (SEQ ID NO:16) further includes a Factor IX signal polynucleotide encoding a Factor IX signal peptide having the amino acid sequence of FIX-SP-AA (SEQ ID NO:37). In some embodiments, the Factor IX signal polynucleotide has a nucleic acid sequence that is at least 90%, 95%, 96%, 97%, 98%, 99%, or 100% identical to CS02-SP-NA (SEQ ID NO:25). In some embodiments, the Factor IX signal polynucleotide has a nucleic acid sequence that is at least 90%, 95%, 96%, 97%, 98%, 99%, or 100% identical to CS03-SP-NA (SEQ ID NO:26). In some embodiments, the Factor IX signal polynucleotide has a nucleic acid sequence that is at least 90%, 95%, 96%, 97%, 98%, 99%, or 100% identical to CS04-SP-NA (SEQ ID NO:27). In some embodiments, the Factor IX signal polynucleotide has a nucleic acid sequence that is at least 90%, 95%, 96%, 97%, 98%, 99%, or 100% identical to CS05-SP-NA (SEQ ID NO:28). In some embodiments, the Factor IX signal polynucleotide has a nucleic acid sequence that is at least 90%, 95%, 96%, 97%, 98%, 99%, or 100% identical to CS06-SP-NA (SEQ ID NO:29).

In some embodiments, the Factor IX polynucleotide high sequence identity to CS05-MP-NA (SEQ ID NO:16) further includes a Factor IX pro-peptide polynucleotide encoding a Factor IX pro-peptide having the amino acid sequence of FIX-PP-AA (SEQ ID NO:38). In some embodiments, the Factor IX pro-peptide polynucleotide has a nucleic acid sequence that is at least 90%, 95%, 96%, 97%, 98%, 99%, or 100% identical to CS02-PP-NA (SEQ ID NO:31). In some embodiments, the Factor IX pro-peptide polynucleotide has a nucleic acid sequence that is at least 90%, 95%, 96%, 97%, 98%, 99%, or 100% identical to CS03-PP-NA (SEQ ID NO:32). In some embodiments, the Factor IX pro-peptide polynucleotide has a nucleic acid sequence that is at least 90%, 95%, 96%, 97%, 98%, 99%, or 100% identical to CS04-PP-NA (SEQ ID NO:33). In some embodiments, the Factor IX pro-peptide polynucleotide has a nucleic acid sequence that is at least 90%, 95%, 96%, 97%, 98%, 99%, or 100% identical to CS05-PP-NA (SEQ ID NO:34). In some embodiments, the Factor IX pro-peptide polynucleotide has a nucleic acid sequence that is at least 90%, 95%, 96%, 97%, 98%, 99%, or 100% identical to CS06-PP-NA (SEQ ID NO:35).

In some embodiments, the Factor IX polynucleotide high sequence identity to CS05-MP-NA (SEQ ID NO: 16) further includes a Factor IX pre-pro-peptide polynucleotide encoding a Factor IX pre-pro-peptide having the amino acid sequence of FIX-PPP-AA (SEQ ID NO:36). In some embodiments, the Factor IX pre-pro-peptide polynucleotide has a nucleic acid sequence that is at least 90%, 95%, 96%, 97%, 98%, 99%, or 100% identical to CS02-PPP-NA (SEQ ID NO:19). In some embodiments, the Factor IX pre-pro-peptide polynucleotide has a nucleic acid sequence that is at least 90%, 95%, 96%, 97%, 98%, 99%, or 100% identical to CS03-PPP-NA (SEQ ID NO:20). In some embodiments, the Factor IX pre-pro-peptide polynucleotide has a nucleic acid sequence that is at least 90%, 95%, 96%, 97%, 98%, 99%, or 100% identical to CS04-PPP-NA (SEQ ID NO:21). In some embodiments, the Factor IX pre-pro-peptide polynucleotide has a nucleic acid sequence that is at least 90%, 95%, 96%, 97%, 98%, 99%, or 100% identical to CS05-PPP-NA (SEQ ID NO:22). In some embodiments, the Factor IX pre-pro-peptide polynucleotide has a nucleic acid sequence that is at least 90%, 95%, 96%, 97%, 98%, 99%, or 100% identical to CS06-PPP-NA (SEQ ID NO:23).

In some embodiments, the encoded Factor IX polypeptide, e.g., the polypeptide encoded by the polynucleotide having high sequence homology to CS05-FL-NA (SEQ ID NO:8), has high sequence identity to the wild type, mature Factor IX single-chain polypeptide sequence FIX-MP-AA (SEQ ID NO: 10) and/or the mature Padua (hFIX(R384L)) single-chain sequence FIXp-MP-AA (SEQ ID NO: 12). The encoded Factor IX polypeptide should retain the ability to become activated into a function Factor IXa protein (e.g., by removal of any signal peptide and the pro-peptide, and by excision of the activation polypeptide).

In one embodiment, the sequence of the encoded Factor IX polypeptide has at least 85% identity to FIX-MP-AA (SEQ ID NO: 10). In one embodiment, the sequence of the encoded Factor IX polypeptide has at least 90% identity to FIX-MP-AA (SEQ ID NO:10). In one embodiment, the sequence of the encoded Factor IX polypeptide has at least 95% identity to FIX-MP-AA (SEQ ID NO: 10). In one embodiment, the sequence of the encoded Factor IX polypeptide has at least 96% identity to FIX-MP-AA (SEQ ID NO: 10). In one embodiment, the sequence of the encoded Factor IX polypeptide has at least 97% identity to FIX-MP-AA (SEQ ID NO: 10). In one embodiment, the sequence of the encoded Factor IX polypeptide has at least 98% identity to FIX-MP-AA (SEQ ID NO:10). In one embodiment, the sequence of the encoded Factor IX polypeptide has at least 99% identity to FIX-MP-AA (SEQ ID NO:10). In one embodiment, the sequence of the encoded Factor IX polypeptide has at least 99.5% identity to FIX-MP-AA (SEQ ID NO: 10). In one embodiment, the sequence of the encoded Factor IX polypeptide has at least 99.9% identity to FIX-MP-AA (SEQ ID NO: 10). In one embodiment, the sequence of the encoded Factor IX polypeptide is FIX-MP-AA (SEQ ID NO: 10).

In one embodiment, the sequence of the encoded Factor IX polypeptide has at least 85% identity to FIXp-MP-AA (SEQ ID NO:12) and includes a leucine at position 384 of the pre-pro-polypeptide (e.g., position 338 of the mature Factor IX single-chain polypeptide FIXp-MP-AA (SEQ ID NO: 12)). In one embodiment, the sequence of the encoded Factor IX polypeptide has at least 90% identity to FIXp-MP-AA (SEQ ID NO: 12) and includes a leucine at position 384 of the pre-pro-polypeptide. In one embodiment, the sequence of the encoded Factor IX polypeptide has at least 95% identity to FIXp-MP-AA (SEQ ID NO: 12) and includes a leucine at position 384 of the pre-pro-polypeptide. In one embodiment, the sequence of the encoded Factor IX polypeptide has at least 96% identity to FIXp-MP-AA (SEQ ID NO: 12) and includes a leucine at position 384 of the pre-pro-polypeptide. In one embodiment, the sequence of the encoded Factor IX polypeptide has at least 97% identity FIXp-MP-AA (SEQ ID NO: 12) and includes a leucine at position 384 of the pre-pro-polypeptide. In one embodiment, the sequence of the encoded Factor IX polypeptide has at least 98% identity to FIXp-MP-AA (SEQ ID NO:12) and includes a leucine at position 384 of the pre-pro-polypeptide. In one embodiment, the sequence of the encoded Factor IX polypeptide has at least 99% identity to FIXp-MP-AA (SEQ ID NO: 12) and includes a leucine at position 384 of the pre-pro-polypeptide. In one embodiment, the sequence of the encoded Factor IX polypeptide has at least 99.5% identity to FIXp-MP-AA (SEQ ID NO: 12) and includes a leucine at position 384 of the pre-pro-polypeptide. In one embodiment, the sequence of the encoded Factor IX polypeptide has at least 99.9% identity to FIXp-MP-AA (SEQ ID NO: 12) and includes a leucine at position 384 of the pre-pro-polypeptide. In one embodiment, the sequence of the encoded Factor IX polypeptide is FIXp-MP-AA (SEQ ID NO: 12).

In one embodiment, a codon-altered polynucleotides provided herein encodes for a single-chain Factor IX polypeptide including a light chain, a heavy chain, and a polypeptide linker joining the C-terminus of the light chain to the N-terminus of the heavy chain. The light chain of the Factor IX polypeptide is encoded by a first nucleotide sequence having high sequence identity to CS05-LC-NA (SEQ ID NO:48), which is the portion of CS05-FL-NA (SEQ ID NO:8) encoding the Factor IX light chain. The heavy chain of the Factor IX polypeptide is encoded by a second nucleotide sequence having high sequence identity to CS05-HC-NA (SEQ ID NO:47), which is the portion of CS05-FL-NA (SEQ ID NO:8) encoding the Factor IX heavy chain. The polypeptide linker includes Factor XI cleavage sites, which allow for maturation in vivo (e.g., after expression of the precursor single-chain Factor IX polypeptide.

In some embodiments, the first and second nucleotide sequences have at least 95% sequence identity to CS05-LC-NA and CS05-HC-NA (SEQ ID NOS:48 and 47), respectively. In some embodiments, the first and second nucleotide sequences have at least 96% sequence identity to CS05-LC-NA and CS05-HC-NA (SEQ ID NOS:48 and 47), respectively. In some embodiments, the first and second nucleotide sequences have at least 97% sequence identity to CS05-LC-NA and CS05-HC-NA (SEQ ID NOS:48 and 47), respectively. In some embodiments, the first and second nucleotide sequences have at least 98% sequence identity to CS05-LC-NA and CS05-HC-NA (SEQ ID NOS:48 and 47), respectively. In some embodiments, the first and second nucleotide sequences have at least 99% sequence identity to CS05-LC-NA and CS05-HC-NA (SEQ ID NOS:48 and 47), respectively, respectively. In some embodiments, the first and second nucleotide sequences have at least 99.5% sequence identity to CS05-LC-NA and CS05-HC-NA (SEQ ID NOS: 48 and 47), respectively. In some embodiments, the first and second nucleotide sequences have at least 99.9% sequence identity to CS05-LC-NA and CS05-HC-NA (SEQ ID NOS: 48 and 47), respectively. In some embodiments, the first and second nucleotide sequences are CS05-LC-NA and CS05-HC-NA (SEQ ID NOS:48 and 47), respectively.

In some embodiments, the polypeptide linker of the Factor IX construct is encoded by a third nucleotide sequence having high sequence identity to CS05-AP-NA (SEQ ID NO:60), which is a codon-altered sequence encoding the wild type Factor IX activation polypeptide, e.g., amino acids 192-226 of FIX-FL-AA (SEQ ID NO:2). In some embodiments, the third nucleotide sequence has at least 80% identity to CS05-AP-NA (SEQ ID NO:60). In some embodiments, the third nucleotide sequence has at least 90% identity to CS05-AP-NA (SEQ ID NO:60). In some embodiments, the third nucleotide sequence has at least 95% identity to CS05-AP-NA (SEQ ID NO:60). In some embodiments, the third nucleotide sequence has at least 96% identity to CS05-AP-NA (SEQ ID NO:60). In some embodiments, the third nucleotide sequence has at least 97% identity to CS05-AP-NA (SEQ ID NO:60). In some embodiments, the third nucleotide sequence has at least 98% identity to CS05-AP-NA (SEQ ID NO:60). In some embodiments, the third nucleotide sequence has at least 99% identity to CS05-AP-NA (SEQ ID NO:60). In some embodiments, the third nucleotide sequence is CS05-AP-NA (SEQ ID NO:60).

In some embodiments, the encoded Factor IX polypeptide also includes a signal peptide (e.g., a Factor IX signal peptide) and/or a pro-peptide (e.g., a Factor IX pro-peptide). In some embodiments, the signal peptide is the wild-type Factor IX signal peptide (FIX-SP-AA (SEQ ID NO:37)). In some embodiments, the signal peptide is encoded by a codon-altered polynucleotide sequence having high sequence identity (e.g., at least 95%, 96%, 97%, 98%, or 99%) to CS05-SP-NA (SEQ ID NO:28). In some embodiments, the pro-peptide is the wild-type Factor IX pro-peptide (FIX-PP-AA (SEQ ID NO:38)). In some embodiments, the pro-peptide peptide is encoded by a codon-altered polynucleotide sequence having high sequence identity (e.g., at least 95%, 96%, 97%, 98%, or 99%) to CS05-PP-NA (SEQ ID NO:34).

In some embodiments, the encoded Factor IX polypeptide, e.g., the polypeptide encoded by the polynucleotide having high sequence homology to CS05-LC-NA (SEQ ID NO:48) and CS05-HC-NA (SEQ ID NO:47), has high sequence identity to the wild type, mature Factor IX single-chain polypeptide sequence FIX-MP-AA (SEQ ID NO:10) and/or the mature Padua (hFIX(R384L)) single-chain sequence FIXp-MP-AA (SEQ ID NO: 12). The encoded Factor IX polypeptide should retain the ability to become activated into a function Factor IXa protein (e.g., by removal of any signal peptide and the pro-peptide, and by excision of the activation polypeptide).

In one embodiment, the sequence of the encoded Factor IX polypeptide has at least 85% identity to FIX-MP-AA (SEQ ID NO: 10). In one embodiment, the sequence of the encoded Factor IX polypeptide has at least 90% identity to FIX-MP-AA (SEQ ID NO:10). In one embodiment, the sequence of the encoded Factor IX polypeptide has at least 95% identity to FIX-MP-AA (SEQ ID NO: 10). In one embodiment, the sequence of the encoded Factor IX polypeptide has at least 96% identity to FIX-MP-AA (SEQ ID NO: 10). In one embodiment, the sequence of the encoded Factor IX polypeptide has at least 97% identity to FIX-MP-AA (SEQ ID NO: 10). In one embodiment, the sequence of the encoded Factor IX polypeptide has at least 98% identity to FIX-MP-AA (SEQ ID NO:10). In one embodiment, the sequence of the encoded Factor IX polypeptide has at least 99% identity to FIX-MP-AA (SEQ ID NO:10). In one embodiment, the sequence of the encoded Factor IX polypeptide has at least 99.5% identity to FIX-MP-AA (SEQ ID NO: 10). In one embodiment, the sequence of the encoded Factor IX polypeptide has at least 99.9% identity to FIX-MP-AA (SEQ ID NO: 10). In one embodiment, the sequence of the encoded Factor IX polypeptide is FIX-MP-AA (SEQ ID NO: 10).

In one embodiment, the sequence of the encoded Factor IX polypeptide has at least 85% identity to FIXp-MP-AA (SEQ ID NO:12) and includes a leucine at position 384 of the pre-pro-polypeptide (e.g., position 338 of the mature Factor IX single-chain polypeptide FIXp-MP-AA (SEQ ID NO: 12)). In one embodiment, the sequence of the encoded Factor IX polypeptide has at least 90% identity to FIXp-MP-AA (SEQ ID NO: 12) and includes a leucine at position 384 of the pre-pro-polypeptide. In one embodiment, the sequence of the encoded Factor IX polypeptide has at least 95% identity to FIXp-MP-AA (SEQ ID NO: 12) and includes a leucine at position 384 of the pre-pro-polypeptide. In one embodiment, the sequence of the encoded Factor IX polypeptide has at least 96% identity to FIXp-MP-AA (SEQ ID NO: 12) and includes a leucine at position 384 of the pre-pro-polypeptide. In one embodiment, the sequence of the encoded Factor IX polypeptide has at least 97% identity FIXp-MP-AA (SEQ ID NO: 12) and includes a leucine at position 384 of the pre-pro-polypeptide. In one embodiment, the sequence of the encoded Factor IX polypeptide has at least 98% identity to FIXp-MP-AA (SEQ ID NO:12) and includes a leucine at position 384 of the pre-pro-polypeptide. In one embodiment, the sequence of the encoded Factor IX polypeptide has at least 99% identity to FIXp-MP-AA (SEQ ID NO: 12) and includes a leucine at position 384 of the pre-pro-polypeptide. In one embodiment, the sequence of the encoded Factor IX polypeptide has at least 99.5% identity to FIXp-MP-AA (SEQ ID NO: 12) and includes a leucine at position 384 of the pre-pro-polypeptide. In one embodiment, the sequence of the encoded Factor IX polypeptide has at least 99.9% identity to FIXp-MP-AA (SEQ ID NO: 12) and includes a leucine at position 384 of the pre-pro-polypeptide. In one embodiment, the sequence of the encoded Factor IX polypeptide is FIXp-MP-AA (SEQ ID NO: 12).

In some embodiments, with reference to FIG. 1, a nucleic acid composition is provided that includes a self-complementary polynucleotide of structure A, where the FIX coding sequence portion of the polynucleotide includes a nucleic acid sequence, encoding a mature Factor IX polypeptide, that has at least 95%, 96%, 97%, 98%, 99%, 99.5%, 99.9%, or 100% identity to CS03-MP-NA (SEQ ID NO: 14). In some embodiments, the FIX coding sequence portion of the polynucleotide also includes a nucleic acid sequence, encoding a Factor IX signal peptide, that has at least 90%, 95%, 96%, 97%, 98%, 99%, or 100% identity to one of FIX-SP-NA (SEQ ID NO:24), CS02-SP-NA (SEQ ID NO:25), CS03-SP-NA (SEQ ID NO:26), CS04-SP-NA (SEQ ID NO:27), CS05-SP-NA (SEQ ID NO:28), and CS06-SP-NA (SEQ ID NO:29). In some embodiments, the FIX coding sequence portion of the polynucleotide also includes a nucleic acid sequence, encoding a Factor IX pro-peptide (optionally in combination with a nucleic acid sequence for a Factor IX signal peptide, as described above), that has at least 90%, 95%, 96%, 97%, 98%, 99%, or 100% identity to one of FIX-PP-NA (SEQ ID NO:30), CS02-PP-NA (SEQ ID NO:31), CS03-PP-NA (SEQ ID NO:32), CS04-PP-NA (SEQ ID NO:33), CS05-PP-NA (SEQ ID NO:34), and CS06-PP-NA (SEQ ID NO:35). In some embodiments, the FIX coding sequence portion of the polynucleotide includes a nucleic acid sequence, encoding a pre-pro-Factor IX polypeptide, that has at least 95%, 96%, 97%, 98%, 99%, 99.5%, 99.9%, or 100% identity to CS05-FL-NA (SEQ ID NO:8).

In some embodiments, with reference to FIG. 1, a nucleic acid composition is provided that includes a self-complementary polynucleotide of structure B, where the FIX coding sequence portion of the polynucleotide includes a nucleic acid sequence, encoding a mature Factor IX polypeptide, that has at least 95%, 96%, 97%, 98%, 99%, 99.5%, 99.9%, or 100% identity to CS05-MP-NA (SEQ ID NO: 16). In some embodiments, the FIX coding sequence portion of the polynucleotide also includes a nucleic acid sequence, encoding a Factor IX signal peptide, that has at least 90%, 95%, 96%, 97%, 98%, 99%, or 100% identity to one of FIX-SP-NA (SEQ ID NO:24), CS02-SP-NA (SEQ ID NO:25), CS03-SP-NA (SEQ ID NO:26), CS04-SP-NA (SEQ ID NO:27), CS05-SP-NA (SEQ ID NO:28), and CS06-SP-NA (SEQ ID NO:29). In some embodiments, the FIX coding sequence portion of the polynucleotide also includes a nucleic acid sequence, encoding a Factor IX pro-peptide (optionally in combination with a nucleic acid sequence for a Factor IX signal peptide, as described above), that has at least 90%, 95%, 96%, 97%, 98%, 99%, or 100% identity to one of FIX-PP-NA (SEQ ID NO:30), CS02-PP-NA (SEQ ID NO:31), CS03-PP-NA (SEQ ID NO:32), CS04-PP-NA (SEQ ID NO:33), CS05-PP-NA (SEQ ID NO:34), and CS06-PP-NA (SEQ ID NO:35). In some embodiments, the FIX coding sequence portion of the polynucleotide includes a nucleic acid sequence, encoding a pre-pro-Factor IX polypeptide, that has at least 95%, 96%, 97%, 98%, 99%, 99.5%, 99.9%, or 100% identity to CS05-FL-NA (SEQ ID NO:8).

In some embodiments, with reference to FIG. 1, a nucleic acid composition is provided that includes a polynucleotide of structure C (e.g., a single-stranded polynucleotide), where the FIX coding sequence portion of the polynucleotide includes a nucleic acid sequence, encoding a mature Factor IX polypeptide, that has at least 95%, 96%, 97%, 98%, 99%, 99.5%, 99.9%, or 100% identity to CS05-MP-NA (SEQ ID NO:16). In some embodiments, the FIX coding sequence portion of the polynucleotide also includes a nucleic acid sequence, encoding a Factor IX signal peptide, that has at least 90%, 95%, 96%, 97%, 98%, 99%, or 100% identity to one of FIX-SP-NA (SEQ ID NO:24), CS02-SP-NA (SEQ ID NO:25), CS03-SP-NA (SEQ ID NO:26), CS04-SP-NA (SEQ ID NO:27), CS05-SP-NA (SEQ ID NO:28), and CS06-SP-NA (SEQ ID NO:29). In some embodiments, the FIX coding sequence portion of the polynucleotide also includes a nucleic acid sequence, encoding a Factor IX pro-peptide (optionally in combination with a nucleic acid sequence for a Factor IX signal peptide, as described above), that has at least 90%, 95%, 96%, 97%, 98%, 99%, or 100% identity to one of FIX-PP-NA (SEQ ID NO:30), CS02-PP-NA (SEQ ID NO:31), CS03-PP-NA (SEQ ID NO:32), CS04-PP-NA (SEQ ID NO:33), CS05-PP-NA (SEQ ID NO:34), and CS06-PP-NA (SEQ ID NO:35). In some embodiments, the FIX coding sequence portion of the polynucleotide includes a nucleic acid sequence, encoding a pre-pro-Factor IX polypeptide, that has at least 95%, 96%, 97%, 98%, 99%, 99.5%, 99.9%, or 100% identity to CS05-FL-NA (SEQ ID NO:8).

In some embodiments, with reference to FIG. 1, a nucleic acid composition is provided that includes a polynucleotide of structure D (e.g., a single-stranded polynucleotide), where the FIX coding sequence portion of the polynucleotide includes a nucleic acid sequence, encoding a mature Factor IX polypeptide, that has at least 95%, 96%, 97%, 98%, 99%, 99.5%, 99.9%, or 100% identity to CS05-MP-NA (SEQ ID NO:16). In some embodiments, the FIX coding sequence portion of the polynucleotide also includes a nucleic acid sequence, encoding a Factor IX signal peptide, that has at least 90%, 95%, 96%, 97%, 98%, 99%, or 100% identity to one of FIX-SP-NA (SEQ ID NO:24), CS02-SP-NA (SEQ ID NO:25), CS03-SP-NA (SEQ ID NO:26), CS04-SP-NA (SEQ ID NO:27), CS05-SP-NA (SEQ ID NO:28), and CS06-SP-NA (SEQ ID NO:29). In some embodiments, the FIX coding sequence portion of the polynucleotide also includes a nucleic acid sequence, encoding a Factor IX pro-peptide (optionally in combination with a nucleic acid sequence for a Factor IX signal peptide, as described above), that has at least 90%, 95%, 96%, 97%, 98%, 99%, or 100% identity to one of FIX-PP-NA (SEQ ID NO:30), CS02-PP-NA (SEQ ID NO:31), CS03-PP-NA (SEQ ID NO:32), CS04-PP-NA (SEQ ID NO:33), CS05-PP-NA (SEQ ID NO:34), and CS06-PP-NA (SEQ ID NO:35). In some embodiments, the FIX coding sequence portion of the polynucleotide includes a nucleic acid sequence, encoding a pre-pro-Factor IX polypeptide, that has at least 95%, 96%, 97%, 98%, 99%, 99.5%, 99.9%, or 100% identity to CS05-FL-NA (SEQ ID NO:8).

CS06 Codon Altered Polynucleotides

In one embodiment, a nucleic acid composition provided herein includes a Factor IX polynucleotide (e.g., a codon-altered polynucleotide) encoding a single-chain Factor IX polypeptide, where the Factor IX polynucleotide includes a nucleotide sequence having high sequence identity to CS06-FL-NA (SEQ ID NO:9). In some embodiments, the nucleotide sequence of the Factor IX polynucleotide having high sequence identity to CS06-FL-NA (SEQ ID NO:9) has a reduced GC content, as compared to the wild-type Factor IX coding sequence (FIX-FL-NA (SEQ ID NO:1)). In some embodiments, the nucleotide sequence of the Factor IX polynucleotide having high sequence identity to CS06-FL-NA (SEQ ID NO:9) has a reduced number of CpG dinucleotides, as compared to the wild-type Factor IX coding sequence (FIX-FL-NA (SEQ ID NO: 1)).

In a specific embodiment, the sequence of the codon-altered polynucleotide has at least 95% identity to CS06-FL-NA (SEQ ID NO:9). In a specific embodiment, the sequence of the codon-altered polynucleotide has at least 96% identity to CS06-FL-NA (SEQ ID NO:9). In a specific embodiment, the sequence of the codon-altered polynucleotide has at least 97% identity to CS06-FL-NA (SEQ ID NO:9). In a specific embodiment, the sequence of the codon-altered polynucleotide has at least 98% identity to CS06-FL-NA (SEQ ID NO:9). In a specific embodiment, the sequence of the codon-altered polynucleotide has at least 99% identity to CS06-FL-NA (SEQ ID NO:9). In a specific embodiment, the sequence of the codon-altered polynucleotide has at least 99.5% identity to CS06-FL-NA (SEQ ID NO:9). In a specific embodiment, the sequence of the codon-altered polynucleotide has at least 99.9% identity to CS06-FL-NA (SEQ ID NO:9). In another specific embodiment, the sequence of the codon-altered polynucleotide is CS06-FL-NA (SEQ ID NO:9).

In some embodiments, the sequence of the codon-altered polynucleotide having high sequence identity to CS06-FL-NA (SEQ ID NO:9) has a GC content of less than 60%. In some embodiments, the sequence of the codon-altered polynucleotide having high sequence identity to CS06-FL-NA (SEQ ID NO:9) has a GC content of less than 59%. In some embodiments, the sequence of the codon-altered polynucleotide having high sequence identity to CS06-FL-NA (SEQ ID NO:9) has a GC content of less than 58%. In some embodiments, the sequence of the codon-altered polynucleotide having high sequence identity to CS06-FL-NA (SEQ ID NO:9) has a GC content of less than 57%. In some embodiments, the sequence of the codon-altered polynucleotide having high sequence identity to CS06-FL-NA (SEQ ID NO:9) has a GC content of less than 56%. In some embodiments, the sequence of the codon-altered polynucleotide having high sequence identity to CS06-FL-NA (SEQ ID NO:9) has a GC content of less than 55%. In some embodiments, the sequence of the codon-altered polynucleotide having high sequence identity to CS06-FL-NA (SEQ ID NO:9) has a GC content of less than 54%.

In some embodiments, the sequence of the codon-altered polynucleotide having high sequence identity to CS06-FL-NA (SEQ ID NO:9) has a GC content of from 50% to 60%. In some embodiments, the sequence of the codon-altered polynucleotide having high sequence identity to CS06-FL-NA (SEQ ID NO:9) has a GC content of from 50% to 59%. In some embodiments, the sequence of the codon-altered polynucleotide having high sequence identity to CS06-FL-NA (SEQ ID NO:9) has a GC content of from 50% to 58%. In some embodiments, the sequence of the codon-altered polynucleotide having high sequence identity to CS06-FL- NA (SEQ ID NO:9) has a GC content of from 50% to 57%. In some embodiments, the sequence of the codon-altered polynucleotide having high sequence identity to CS06-FL-NA (SEQ ID NO:9) has a GC content of from 50% to 56%. In some embodiments, the sequence of the codon-altered polynucleotide having high sequence identity to CS06-FL-NA (SEQ ID NO:9) has a GC content of from 50% to 55%. In some embodiments, the sequence of the codon-altered polynucleotide having high sequence identity to CS06-FL-NA (SEQ ID NO:9) has a GC content of from 50% to 54%.

In some embodiments, the sequence of the codon-altered polynucleotide having high sequence identity to CS06-FL-NA (SEQ ID NO:9) has a GC content of 53.8%±1.0. In some embodiments, the sequence of the codon-altered polynucleotide having high sequence identity to CS06-FL-NA (SEQ ID NO:9) has a GC content of 53.8%±0.8. In some embodiments, the sequence of the codon-altered polynucleotide having high sequence identity to CS06-FL-NA (SEQ ID NO:9) has a GC content of 53.8%±0.6. In some embodiments, the sequence of the codon-altered polynucleotide having high sequence identity to CS06-FL-NA (SEQ ID NO:9) has a GC content of 53.8%±0.5. In some embodiments, the sequence of the codon-altered polynucleotide having high sequence identity to CS06-FL-NA (SEQ ID NO:9) has a GC content of 53.8%±0.4. In some embodiments, the sequence of the codon-altered polynucleotide having high sequence identity to CS06-FL-NA (SEQ ID NO:9) has a GC content of 53.8%±0.3. In some embodiments, the sequence of the codon-altered polynucleotide having high sequence identity to CS06-FL-NA (SEQ ID NO:9) has a GC content of 53.8%±0.2. In some embodiments, the sequence of the codon-altered polynucleotide having high sequence identity to CS06-FL-NA (SEQ ID NO:9) has a GC content of 53.8%±0.1. In some embodiments, the sequence of the codon-altered polynucleotide having high sequence identity to CS06-FL-NA (SEQ ID NO:9) has a GC content of 53.8%.

In some embodiments, the sequence of the codon-altered polynucleotide having high sequence identity to CS06-FL-NA (SEQ ID NO:9) has no more than 15 CpG dinucleotides. In some embodiments, the sequence of the codon-altered polynucleotide having high sequence identity to CS06-FL-NA (SEQ ID NO:9) has no more than 12 CpG dinucleotides. In some embodiments, the sequence of the codon-altered polynucleotide having high sequence identity to CS06-FL-NA (SEQ ID NO:9) has no more than 10 CpG dinucleotides. In some embodiments, the sequence of the codon-altered polynucleotide having high sequence identity to CS06-FL-NA (SEQ ID NO:9) has no more than 9 CpG dinucleotides. In some embodiments, the sequence of the codon-altered polynucleotide having high sequence identity to CS06-FL-NA (SEQ ID NO:9) has no more than 8 CpG dinucleotides. In some embodiments, the sequence of the codon-altered polynucleotide having high sequence identity to CS06-FL-NA (SEQ ID NO:9) has no more than 7 CpG dinucleotides. In some embodiments, the sequence of the codon-altered polynucleotide having high sequence identity to CS06-FL-NA (SEQ ID NO:9) has no more than 6 CpG dinucleotides. In some embodiments, the sequence of the codon-altered polynucleotide having high sequence identity to CS06-FL-NA (SEQ ID NO:9) has no more than 5 CpG dinucleotides. In some embodiments, the sequence of the codon-altered polynucleotide having high sequence identity to CS06-FL-NA (SEQ ID NO:9) has no more than 4 CpG dinucleotides. In some embodiments, the sequence of the codon-altered polynucleotide having high sequence identity to CS06-FL-NA (SEQ ID NO:9) has no more than 3 CpG dinucleotides. In some embodiments, the sequence of the codon-altered polynucleotide having high sequence identity to CS06-FL-NA (SEQ ID NO:9) has no more than 2 CpG dinucleotides. In some embodiments, the sequence of the codon-altered polynucleotide having high sequence identity to CS06-FL-NA (SEQ ID NO:9) has no more than 1 CpG dinucleotide. In some embodiments, the sequence of the codon-altered polynucleotide having high sequence identity to CS06-FL-NA (SEQ ID NO:9) has no CpG dinucleotides.

In some embodiments, the encoded Factor IX polypeptide, e.g., the polypeptide encoded by the polynucleotide having high sequence homology to CS06-FL-NA (SEQ ID NO:9), has high sequence identity to the wild type Factor IX pre-pro-protein sequence FIX-FL-AA (SEQ ID NO:2) and/or the Padua (hFIX(R384L)) pre-pro-protein sequence FIXp-FL-AA (SEQ ID NO:4). The encoded Factor IX polypeptide should retain the ability to become activated into a function Factor IXa protein (e.g., by removal of the signal peptide and the pro-peptide, and by excision of the activation polypeptide).

In one embodiment, the sequence of the encoded Factor IX polypeptide has at least 85% identity to FIX-FL-AA (SEQ ID NO:2). In one embodiment, the sequence of the encoded Factor IX polypeptide has at least 90% identity to FIX-FL-AA (SEQ ID NO:2). In one embodiment, the sequence of the encoded Factor IX polypeptide has at least 95% identity to FIX-FL-AA (SEQ ID NO:2). In one embodiment, the sequence of the encoded Factor IX polypeptide has at least 96% identity to FIX-FL-AA (SEQ ID NO:2). In one embodiment, the sequence of the encoded Factor IX polypeptide has at least 97% identity to FIX-FL-AA (SEQ ID NO:2). In one embodiment, the sequence of the encoded Factor IX polypeptide has at least 98% identity to FIX-FL-AA (SEQ ID NO:2). In one embodiment, the sequence of the encoded Factor IX polypeptide has at least 99% identity to FIX-FL-AA (SEQ ID NO:2). In one embodiment, the sequence of the encoded Factor IX polypeptide has at least 99.5% identity to FIX-FL-AA (SEQ ID NO:2). In one embodiment, the sequence of the encoded Factor IX polypeptide has at least 99.9% identity to FIX-FL-AA (SEQ ID NO:2). In one embodiment, the sequence of the encoded Factor IX polypeptide is FIX-FL-AA (SEQ ID NO:2).

In one embodiment, the sequence of the encoded Factor IX polypeptide has at least 85% identity to FIXp-FL-AA (SEQ ID NO:4) and includes a leucine at position 384 of the pre-pro-polypeptide (e.g., position 338 of the mature Factor IX single-chain polypeptide FIXp-MP-AA (SEQ ID NO: 12)). In one embodiment, the sequence of the encoded Factor IX polypeptide has at least 90% identity to FIXp-FL-AA (SEQ ID NO:4) and includes a leucine at position 384 of the pre-pro-polypeptide. In one embodiment, the sequence of the encoded Factor IX polypeptide has at least 95% identity to FIXp-FL-AA (SEQ ID NO:4) and includes a leucine at position 384 of the pre-pro-polypeptide. In one embodiment, the sequence of the encoded Factor IX polypeptide has at least 96% identity to FIXp-FL-AA (SEQ ID NO:4) and includes a leucine at position 384 of the pre-pro-polypeptide. In one embodiment, the sequence of the encoded Factor IX polypeptide has at least 97% identity FIXp-FL-AA (SEQ ID NO:4) and includes a leucine at position 384 of the pre-pro-polypeptide. In one embodiment, the sequence of the encoded Factor IX polypeptide has at least 98% identity to FIXp-FL-AA (SEQ ID NO:4) and includes a leucine at position 384 of the pre-pro-polypeptide. In one embodiment, the sequence of the encoded Factor IX polypeptide has at least 99% identity to FIXp-FL-AA (SEQ ID NO:4) and includes a leucine at position 384 of the pre-pro-polypeptide. In one embodiment, the sequence of the encoded Factor IX polypeptide has at least 99.5% identity to FIXp-FL-AA (SEQ ID NO:4) and includes a leucine at position 384 of the pre-pro-polypeptide. In one embodiment, the sequence of the encoded Factor IX polypeptide has at least 99.9% identity to FIXp-FL-AA (SEQ ID NO:4) and includes a leucine at position 384 of the pre-pro-polypeptide. In one embodiment, the sequence of the encoded Factor IX polypeptide is FIXp-FL-AA (SEQ ID NO:4).

In one embodiment, a nucleic acid composition provided herein includes a Factor IX polynucleotide (e.g., a codon-altered polynucleotide) encoding a single-chain Factor IX polypeptide (e.g., having serine protease activity), where the Factor IX polynucleotide includes a nucleotide sequence having high sequence identity to CS06-MP-NA (SEQ ID NO: 17). In some embodiments, the nucleotide sequence of the Factor IX polynucleotide having high sequence identity to CS06-MP-NA (SEQ ID NO: 17) has a reduced GC content, as compared to the wild-type Factor IX coding sequence (FIX-FL-NA (SEQ ID NO:1)). In some embodiments, the nucleotide sequence of the Factor IX polynucleotide having high sequence identity to CS06-MP-NA (SEQ ID NO: 17) has a reduced number of CpG dinucleotides, as compared to the wild-type Factor IX coding sequence (FIX-FL-NA (SEQ ID NO: 1)).

In a specific embodiment, the sequence of the codon-altered polynucleotide has at least 95% identity to CS06-MP-NA (SEQ ID NO:17). In a specific embodiment, the sequence of the codon-altered polynucleotide has at least 96% identity to CS06-MP-NA (SEQ ID NO:17). In a specific embodiment, the sequence of the codon-altered polynucleotide has at least 97% identity to CS06-MP-NA (SEQ ID NO: 17). In a specific embodiment, the sequence of the codon-altered polynucleotide has at least 98% identity to CS06-MP-NA (SEQ ID NO:17). In a specific embodiment, the sequence of the codon-altered polynucleotide has at least 99% identity to CS06-MP-NA (SEQ ID NO:17). In a specific embodiment, the sequence of the codon-altered polynucleotide has at least 99.5% identity to CS06-MP-NA (SEQ ID NO:17). In a specific embodiment, the sequence of the codon-altered polynucleotide has at least 99.9% identity to CS06-MP-NA (SEQ ID NO:17). In another specific embodiment, the sequence of the codon-altered polynucleotide is CS06-MP-NA (SEQ ID NO:17).

In some embodiments, the sequence of the codon-altered polynucleotide having high sequence identity to CS06-MP-NA (SEQ ID NO:17) has a GC content of less than 60%. In some embodiments, the sequence of the codon-altered polynucleotide having high sequence identity to CS06-MP-NA (SEQ ID NO:17) has a GC content of less than 59%. In some embodiments, the sequence of the codon-altered polynucleotide having high sequence identity to CS06-MP-NA (SEQ ID NO: 17) has a GC content of less than 58%. In some embodiments, the sequence of the codon-altered polynucleotide having high sequence identity to CS06-MP-NA (SEQ ID NO: 17) has a GC content of less than 57%. In some embodiments, the sequence of the codon-altered polynucleotide having high sequence identity to CS06-MP-NA (SEQ ID NO: 17) has a GC content of less than 56%. In some embodiments, the sequence of the codon-altered polynucleotide having high sequence identity to CS06-MP-NA (SEQ ID NO:17) has a GC content of less than 55%. In some embodiments, the sequence of the codon-altered polynucleotide having high sequence identity to CS06-MP-NA (SEQ ID NO:17) has a GC content of less than 54%.

In some embodiments, the sequence of the codon-altered polynucleotide having high sequence identity to CS06-MP-NA (SEQ ID NO: 17) has a GC content of from 50% to 60%. In some embodiments, the sequence of the codon-altered polynucleotide having high sequence identity to CS06-MP-NA (SEQ ID NO:17) has a GC content of from 50% to 59%. In some embodiments, the sequence of the codon-altered polynucleotide having high sequence identity to CS06-MP-NA (SEQ ID NO: 17) has a GC content of from 50% to 58%. In some embodiments, the sequence of the codon-altered polynucleotide having high sequence identity to CS06-MP-NA (SEQ ID NO: 17) has a GC content of from 50% to 57%. In some embodiments, the sequence of the codon-altered polynucleotide having high sequence identity to CS06-MP-NA (SEQ ID NO: 17) has a GC content of from 50% to 56%. In some embodiments, the sequence of the codon-altered polynucleotide having high sequence identity to CS06-MP-NA (SEQ ID NO: 17) has a GC content of from 50% to 55%. In some embodiments, the sequence of the codon-altered polynucleotide having high sequence identity to CS06-MP-NA (SEQ ID NO: 17) has a GC content of from 50% to 54%.

In some embodiments, the sequence of the codon-altered polynucleotide having high sequence identity to CS06-MP-NA (SEQ ID NO:17) has a GC content of 53.8%±1.0. In some embodiments, the sequence of the codon-altered polynucleotide having high sequence identity to CS06-MP-NA (SEQ ID NO:17) has a GC content of 53.8%±0.8. In some embodiments, the sequence of the codon-altered polynucleotide having high sequence identity to CS06-MP-NA (SEQ ID NO:17) has a GC content of 53.8%±0.6. In some embodiments, the sequence of the codon-altered polynucleotide having high sequence identity to CS06-MP-NA (SEQ ID NO: 17) has a GC content of 53.8%±0.5. In some embodiments, the sequence of the codon-altered polynucleotide having high sequence identity to CS06-MP-NA (SEQ ID NO: 17) has a GC content of 53.8%±0.4. In some embodiments, the sequence of the codon-altered polynucleotide having high sequence identity to CS06-MP-NA (SEQ ID NO:17) has a GC content of 53.8%±0.3. In some embodiments, the sequence of the codon-altered polynucleotide having high sequence identity to CS06-MP-NA (SEQ ID NO: 17) has a GC content of 53.8%±0.2. In some embodiments, the sequence of the codon-altered polynucleotide having high sequence identity to CS06-MP-NA (SEQ ID NO:17) has a GC content of 53.8%±0.1. In some embodiments, the sequence of the codon-altered polynucleotide having high sequence identity to CS06-MP-NA (SEQ ID NO: 17) has a GC content of 53.8%.

In some embodiments, the sequence of the codon-altered polynucleotide having high sequence identity to CS06-MP-NA (SEQ ID NO:17) has no more than 15 CpG dinucleotides. In some embodiments, the sequence of the codon-altered polynucleotide having high sequence identity to CS06-MP-NA (SEQ ID NO:17) has no more than 12 CpG dinucleotides. In some embodiments, the sequence of the codon-altered polynucleotide having high sequence identity to CS06-MP-NA (SEQ ID NO:17) has no more than 10 CpG dinucleotides. In some embodiments, the sequence of the codon-altered polynucleotide having high sequence identity to CS06-MP-NA (SEQ ID NO:17) has no more than 9 CpG dinucleotides. In some embodiments, the sequence of the codon-altered polynucleotide having high sequence identity to CS06-MP-NA (SEQ ID NO: 17) has no more than 8 CpG dinucleotides. In some embodiments, the sequence of the codon-altered polynucleotide having high sequence identity to CS06-MP-NA (SEQ ID NO: 17) has no more than 7 CpG dinucleotides. In some embodiments, the sequence of the codon-altered polynucleotide having high sequence identity to CS06-MP-NA (SEQ ID NO:17) has no more than 6 CpG dinucleotides. In some embodiments, the sequence of the codon-altered polynucleotide having high sequence identity to CS06-MP-NA (SEQ ID NO: 17) has no more than 5 CpG dinucleotides. In some embodiments, the sequence of the codon-altered polynucleotide having high sequence identity to CS06-MP-NA (SEQ ID NO:17) has no more than 4 CpG dinucleotides. In some embodiments, the sequence of the codon-altered polynucleotide having high sequence identity to CS06-MP-NA (SEQ ID NO:17) has no more than 3 CpG dinucleotides. In some embodiments, the sequence of the codon-altered polynucleotide having high sequence identity to CS06-MP-NA (SEQ ID NO:17) has no more than 2 CpG dinucleotides. In some embodiments, the sequence of the codon-altered polynucleotide having high sequence identity to CS06-MP-NA (SEQ ID NO: 17) has no more than 1 CpG dinucleotide. In some embodiments, the sequence of the codon-altered polynucleotide having high sequence identity to CS06-MP-NA (SEQ ID NO:17) has no CpG dinucleotides.

In some embodiments, the Factor IX polynucleotide high sequence identity to CS06-MP-NA (SEQ ID NO:17) further includes a Factor IX signal polynucleotide encoding a Factor IX signal peptide having the amino acid sequence of FIX-SP-AA (SEQ ID NO:37). In some embodiments, the Factor IX signal polynucleotide has a nucleic acid sequence that is at least 90%, 95%, 96%, 97%, 98%, 99%, or 100% identical to CS02-SP-NA (SEQ ID NO:25). In some embodiments, the Factor IX signal polynucleotide has a nucleic acid sequence that is at least 90%, 95%, 96%, 97%, 98%, 99%, or 100% identical to CS03-SP-NA (SEQ ID NO:26). In some embodiments, the Factor IX signal polynucleotide has a nucleic acid sequence that is at least 90%, 95%, 96%, 97%, 98%, 99%, or 100% identical to CS04-SP-NA (SEQ ID NO:27). In some embodiments, the Factor IX signal polynucleotide has a nucleic acid sequence that is at least 90%, 95%, 96%, 97%, 98%, 99%, or 100% identical to CS05-SP-NA (SEQ ID NO:28). In some embodiments, the Factor IX signal polynucleotide has a nucleic acid sequence that is at least 90%, 95%, 96%, 97%, 98%, 99%, or 100% identical to CS06-SP-NA (SEQ ID NO:29).

In some embodiments, the Factor IX polynucleotide high sequence identity to CS06-MP-NA (SEQ ID NO:17) further includes a Factor IX pro-peptide polynucleotide encoding a Factor IX pro-peptide having the amino acid sequence of FIX-PP-AA (SEQ ID NO:38). In some embodiments, the Factor IX pro-peptide polynucleotide has a nucleic acid sequence that is at least 90%, 95%, 96%, 97%, 98%, 99%, or 100% identical to CS02-PP-NA (SEQ ID NO:31). In some embodiments, the Factor IX pro-peptide polynucleotide has a nucleic acid sequence that is at least 90%, 95%, 96%, 97%, 98%, 99%, or 100% identical to CS03-PP-NA (SEQ ID NO:32). In some embodiments, the Factor IX pro-peptide polynucleotide has a nucleic acid sequence that is at least 90%, 95%, 96%, 97%, 98%, 99%, or 100% identical to CS04-PP-NA (SEQ ID NO:33). In some embodiments, the Factor IX pro-peptide polynucleotide has a nucleic acid sequence that is at least 90%, 95%, 96%, 97%, 98%, 99%, or 100% identical to CS05-PP-NA (SEQ ID NO:34). In some embodiments, the Factor IX pro-peptide polynucleotide has a nucleic acid sequence that is at least 90%, 95%, 96%, 97%, 98%, 99%, or 100% identical to CS06-PP-NA (SEQ ID NO:35).

In some embodiments, the Factor IX polynucleotide high sequence identity to CS06-MP-NA (SEQ ID NO: 17) further includes a Factor IX pre-pro-peptide polynucleotide encoding a Factor IX pre-pro-peptide having the amino acid sequence of FIX-PPP-AA (SEQ ID NO:36). In some embodiments, the Factor IX pre-pro-peptide polynucleotide has a nucleic acid sequence that is at least 90%, 95%, 96%, 97%, 98%, 99%, or 100% identical to CS02-PPP-NA (SEQ ID NO:19). In some embodiments, the Factor IX pre-pro-peptide polynucleotide has a nucleic acid sequence that is at least 90%, 95%, 96%, 97%, 98%, 99%, or 100% identical to CS03-PPP-NA (SEQ ID NO:20). In some embodiments, the Factor IX pre-pro-peptide polynucleotide has a nucleic acid sequence that is at least 90%, 95%, 96%, 97%, 98%, 99%, or 100% identical to CS04-PPP-NA (SEQ ID NO:21). In some embodiments, the Factor IX pre-pro-peptide polynucleotide has a nucleic acid sequence that is at least 90%, 95%, 96%, 97%, 98%, 99%, or 100% identical to CS05-PPP-NA (SEQ ID NO:22). In some embodiments, the Factor IX pre-pro-peptide polynucleotide has a nucleic acid sequence that is at least 90%, 95%, 96%, 97%, 98%, 99%, or 100% identical to CS06-PPP-NA (SEQ ID NO:23).

In some embodiments, the encoded Factor IX polypeptide, e.g., the polypeptide encoded by the polynucleotide having high sequence homology to CS06-FL-NA (SEQ ID NO:9), has high sequence identity to the wild type, mature Factor IX single-chain polypeptide sequence FIX-MP-AA (SEQ ID NO: 10) and/or the mature Padua (hFIX(R384L)) single-chain sequence FIXp-MP-AA (SEQ ID NO: 12). The encoded Factor IX polypeptide should retain the ability to become activated into a function Factor IXa protein (e.g., by removal of any signal peptide and the pro-peptide, and by excision of the activation polypeptide).

In one embodiment, the sequence of the encoded Factor IX polypeptide has at least 85% identity to FIX-MP-AA (SEQ ID NO: 10). In one embodiment, the sequence of the encoded Factor IX polypeptide has at least 90% identity to FIX-MP-AA (SEQ ID NO:10). In one embodiment, the sequence of the encoded Factor IX polypeptide has at least 95% identity to FIX-MP-AA (SEQ ID NO: 10). In one embodiment, the sequence of the encoded Factor IX polypeptide has at least 96% identity to FIX-MP-AA (SEQ ID NO: 10). In one embodiment, the sequence of the encoded Factor IX polypeptide has at least 97% identity to FIX-MP-AA (SEQ ID NO: 10). In one embodiment, the sequence of the encoded Factor IX polypeptide has at least 98% identity to FIX-MP-AA (SEQ ID NO:10). In one embodiment, the sequence of the encoded Factor IX polypeptide has at least 99% identity to FIX-MP-AA (SEQ ID NO:10). In one embodiment, the sequence of the encoded Factor IX polypeptide has at least 99.5% identity to FIX-MP-AA (SEQ ID NO: 10). In one embodiment, the sequence of the encoded Factor IX polypeptide has at least 99.9% identity to FIX-MP-AA (SEQ ID NO: 10). In one embodiment, the sequence of the encoded Factor IX polypeptide is FIX-MP-AA (SEQ ID NO: 10).

In one embodiment, the sequence of the encoded Factor IX polypeptide has at least 85% identity to FIXp-MP-AA (SEQ ID NO:12) and includes a leucine at position 384 of the pre-pro-polypeptide (e.g., position 338 of the mature Factor IX single-chain polypeptide FIXp-MP-AA (SEQ ID NO: 12)). In one embodiment, the sequence of the encoded Factor IX polypeptide has at least 90% identity to FIXp-MP-AA (SEQ ID NO: 12) and includes a leucine at position 384 of the pre-pro-polypeptide. In one embodiment, the sequence of the encoded Factor IX polypeptide has at least 95% identity to FIXp-MP-AA (SEQ ID NO: 12) and includes a leucine at position 384 of the pre-pro-polypeptide. In one embodiment, the sequence of the encoded Factor IX polypeptide has at least 96% identity to FIXp-MP-AA (SEQ ID NO: 12) and includes a leucine at position 384 of the pre-pro-polypeptide. In one embodiment, the sequence of the encoded Factor IX polypeptide has at least 97% identity FIXp-MP-AA (SEQ ID NO: 12) and includes a leucine at position 384 of the pre-pro-polypeptide. In one embodiment, the sequence of the encoded Factor IX polypeptide has at least 98% identity to FIXp-MP-AA (SEQ ID NO:12) and includes a leucine at position 384 of the pre-pro-polypeptide. In one embodiment, the sequence of the encoded Factor IX polypeptide has at least 99% identity to FIXp-MP-AA (SEQ ID NO: 12) and includes a leucine at position 384 of the pre-pro-polypeptide. In one embodiment, the sequence of the encoded Factor IX polypeptide has at least 99.5% identity to FIXp-MP-AA (SEQ ID NO: 12) and includes a leucine at position 384 of the pre-pro-polypeptide. In one embodiment, the sequence of the encoded Factor IX polypeptide has at least 99.9% identity to FIXp-MP-AA (SEQ ID NO: 12) and includes a leucine at position 384 of the pre-pro-polypeptide. In one embodiment, the sequence of the encoded Factor IX polypeptide is FIXp-MP-AA (SEQ ID NO: 12).

In one embodiment, a codon-altered polynucleotides provided herein encodes for a single-chain Factor IX polypeptide including a light chain, a heavy chain, and a polypeptide linker joining the C-terminus of the light chain to the N-terminus of the heavy chain. The light chain of the Factor IX polypeptide is encoded by a first nucleotide sequence having high sequence identity to CS06-LC-NA (SEQ ID NO:50), which is the portion of CS06-FL-NA (SEQ ID NO:9) encoding the Factor IX light chain. The heavy chain of the Factor IX polypeptide is encoded by a second nucleotide sequence having high sequence identity to CS06-HC-NA (SEQ ID NO:49), which is the portion of CS06-FL-NA (SEQ ID NO:9) encoding the Factor IX heavy chain. The polypeptide linker includes Factor XI cleavage sites, which allow for maturation in vivo (e.g., after expression of the precursor single-chain Factor IX polypeptide.

In some embodiments, the first and second nucleotide sequences have at least 95% sequence identity to CS06-LC-NA and CS06-HC-NA (SEQ ID NOS:50 and 49), respectively. In some embodiments, the first and second nucleotide sequences have at least 96% sequence identity to CS06-LC-NA and CS06-HC-NA (SEQ ID NOS:50 and 49), respectively. In some embodiments, the first and second nucleotide sequences have at least 97% sequence identity to CS06-LC-NA and CS06-HC-NA (SEQ ID NOS:50 and 49), respectively. In some embodiments, the first and second nucleotide sequences have at least 98% sequence identity to CS06-LC-NA and CS06-HC-NA (SEQ ID NOS:50 and 49), respectively. In some embodiments, the first and second nucleotide sequences have at least 99% sequence identity to CS06-LC-NA and CS06-HC-NA (SEQ ID NOS:50 and 49), respectively, respectively. In some embodiments, the first and second nucleotide sequences have at least 99.5% sequence identity to CS06-LC-NA and CS06-HC-NA (SEQ ID NOS: 50 and 49), respectively. In some embodiments, the first and second nucleotide sequences have at least 99.9% sequence identity to CS06-LC-NA and CS06-HC-NA (SEQ ID NOS: 50 and 49), respectively. In some embodiments, the first and second nucleotide sequences are CS06-LC-NA and CS06-HC-NA (SEQ ID NOS:50 and 49), respectively.

In some embodiments, the polypeptide linker of the Factor IX construct is encoded by a third nucleotide sequence having high sequence identity to CS06-AP-NA (SEQ ID NO:61), which is a codon-altered sequence encoding the wild type Factor IX activation polypeptide, e.g., amino acids 192-226 of FIX-FL-AA (SEQ ID NO:2). In some embodiments, the third nucleotide sequence has at least 80% identity to CS06-AP-NA (SEQ ID NO:61). In some embodiments, the third nucleotide sequence has at least 90% identity to CS06-AP-NA (SEQ ID NO:61). In some embodiments, the third nucleotide sequence has at least 95% identity to CS06-AP-NA (SEQ ID NO:61). In some embodiments, the third nucleotide sequence has at least 96% identity to CS06-AP-NA (SEQ ID NO:61). In some embodiments, the third nucleotide sequence has at least 97% identity to CS06-AP-NA (SEQ ID NO:61). In some embodiments, the third nucleotide sequence has at least 98% identity to CS06-AP-NA (SEQ ID NO:61). In some embodiments, the third nucleotide sequence has at least 99% identity to CS06-AP-NA (SEQ ID NO:61). In some embodiments, the third nucleotide sequence is CS06-AP-NA (SEQ ID NO:61).

In some embodiments, the encoded Factor IX polypeptide also includes a signal peptide (e.g., a Factor IX signal peptide) and/or a pro-peptide (e.g., a Factor IX pro-peptide). In some embodiments, the signal peptide is the wild-type Factor IX signal peptide (FIX-SP-AA (SEQ ID NO:37)). In some embodiments, the signal peptide is encoded by a codon-altered polynucleotide sequence having high sequence identity (e.g., at least 95%, 96%, 97%, 98%, or 99%) to CS06-SP-NA (SEQ ID NO:29). In some embodiments, the pro-peptide is the wild-type Factor IX pro-peptide (FIX-PP-AA (SEQ ID NO:38)). In some embodiments, the pro-peptide peptide is encoded by a codon-altered polynucleotide sequence having high sequence identity (e.g., at least 95%, 96%, 97%, 98%, or 99%) to CS06-PP-NA (SEQ ID NO:35).

In some embodiments, the encoded Factor IX polypeptide, e.g., the polypeptide encoded by the polynucleotide having high sequence homology to CS06-LC-NA (SEQ ID NO:50) and CS06-HC-NA (SEQ ID NO:49), has high sequence identity to the wild type, mature Factor IX single-chain polypeptide sequence FIX-MP-AA (SEQ ID NO:10) and/or the mature Padua (hFIX(R384L)) single-chain sequence FIXp-MP-AA (SEQ ID NO: 12). The encoded Factor IX polypeptide should retain the ability to become activated into a function Factor IXa protein (e.g., by removal of any signal peptide and the pro-peptide, and by excision of the activation polypeptide).

In one embodiment, the sequence of the encoded Factor IX polypeptide has at least 85% identity to FIX-MP-AA (SEQ ID NO: 10). In one embodiment, the sequence of the encoded Factor IX polypeptide has at least 90% identity to FIX-MP-AA (SEQ ID NO:10). In one embodiment, the sequence of the encoded Factor IX polypeptide has at least 95% identity to FIX-MP-AA (SEQ ID NO: 10). In one embodiment, the sequence of the encoded Factor IX polypeptide has at least 96% identity to FIX-MP-AA (SEQ ID NO: 10). In one embodiment, the sequence of the encoded Factor IX polypeptide has at least 97% identity to FIX-MP-AA (SEQ ID NO: 10). In one embodiment, the sequence of the encoded Factor IX polypeptide has at least 98% identity to FIX-MP-AA (SEQ ID NO:10). In one embodiment, the sequence of the encoded Factor IX polypeptide has at least 99% identity to FIX-MP-AA (SEQ ID NO:10). In one embodiment, the sequence of the encoded Factor IX polypeptide has at least 99.5% identity to FIX-MP-AA (SEQ ID NO: 10). In one embodiment, the sequence of the encoded Factor IX polypeptide has at least 99.9% identity to FIX-MP-AA (SEQ ID NO: 10). In one embodiment, the sequence of the encoded Factor IX polypeptide is FIX-MP-AA (SEQ ID NO: 10).

In one embodiment, the sequence of the encoded Factor IX polypeptide has at least 85% identity to FIXp-MP-AA (SEQ ID NO:12) and includes a leucine at position 384 of the pre-pro-polypeptide (e.g., position 338 of the mature Factor IX single-chain polypeptide FIXp-MP-AA (SEQ ID NO: 12)). In one embodiment, the sequence of the encoded Factor IX polypeptide has at least 90% identity to FIXp-MP-AA (SEQ ID NO: 12) and includes a leucine at position 384 of the pre-pro-polypeptide. In one embodiment, the sequence of the encoded Factor IX polypeptide has at least 95% identity to FIXp-MP-AA (SEQ ID NO: 12) and includes a leucine at position 384 of the pre-pro-polypeptide. In one embodiment, the sequence of the encoded Factor IX polypeptide has at least 96% identity to FIXp-MP-AA (SEQ ID NO: 12) and includes a leucine at position 384 of the pre-pro-polypeptide. In one embodiment, the sequence of the encoded Factor IX polypeptide has at least 97% identity FIXp-MP-AA (SEQ ID NO: 12) and includes a leucine at position 384 of the pre-pro-polypeptide. In one embodiment, the sequence of the encoded Factor IX polypeptide has at least 98% identity to FIXp-MP-AA (SEQ ID NO:12) and includes a leucine at position 384 of the pre-pro-polypeptide. In one embodiment, the sequence of the encoded Factor IX polypeptide has at least 99% identity to FIXp-MP-AA (SEQ ID NO: 12) and includes a leucine at position 384 of the pre-pro-polypeptide. In one embodiment, the sequence of the encoded Factor IX polypeptide has at least 99.5% identity to FIXp-MP-AA (SEQ ID NO: 12) and includes a leucine at position 384 of the pre-pro-polypeptide. In one embodiment, the sequence of the encoded Factor IX polypeptide has at least 99.9% identity to FIXp-MP-AA (SEQ ID NO: 12) and includes a leucine at position 384 of the pre-pro-polypeptide. In one embodiment, the sequence of the encoded Factor IX polypeptide is FIXp-MP-AA (SEQ ID NO: 12).

In some embodiments, with reference to FIG. 1, a nucleic acid composition is provided that includes a self-complementary polynucleotide of structure A, where the FIX coding sequence portion of the polynucleotide includes a nucleic acid sequence, encoding a mature Factor IX polypeptide, that has at least 95%, 96%, 97%, 98%, 99%, 99.5%, 99.9%, or 100% identity to CS06-MP-NA (SEQ ID NO: 17). In some embodiments, the FIX coding sequence portion of the polynucleotide also includes a nucleic acid sequence, encoding a Factor IX signal peptide, that has at least 90%, 95%, 96%, 97%, 98%, 99%, or 100% identity to one of FIX-SP-NA (SEQ ID NO:24), CS02-SP-NA (SEQ ID NO:25), CS03-SP-NA (SEQ ID NO:26), CS04-SP-NA (SEQ ID NO:27), CS05-SP-NA (SEQ ID NO:28), and CS06-SP-NA (SEQ ID NO:29). In some embodiments, the FIX coding sequence portion of the polynucleotide also includes a nucleic acid sequence, encoding a Factor IX pro-peptide (optionally in combination with a nucleic acid sequence for a Factor IX signal peptide, as described above), that has at least 90%, 95%, 96%, 97%, 98%, 99%, or 100% identity to one of FIX-PP-NA (SEQ ID NO:30), CS02-PP-NA (SEQ ID NO:31), CS03-PP-NA (SEQ ID NO:32), CS04-PP-NA (SEQ ID NO:33), CS05-PP-NA (SEQ ID NO:34), and CS06-PP-NA (SEQ ID NO:35). In some embodiments, the FIX coding sequence portion of the polynucleotide includes a nucleic acid sequence, encoding a pre-pro-Factor IX polypeptide, that has at least 95%, 96%, 97%, 98%, 99%, 99.5%, 99.9%, or 100% identity to CS06-FL-NA (SEQ ID NO:9).

In some embodiments, with reference to FIG. 1, a nucleic acid composition is provided that includes a self-complementary polynucleotide of structure B, where the FIX coding sequence portion of the polynucleotide includes a nucleic acid sequence, encoding a mature Factor IX polypeptide, that has at least 95%, 96%, 97%, 98%, 99%, 99.5%, 99.9%, or 100% identity to CS06-MP-NA (SEQ ID NO: 17). In some embodiments, the FIX coding sequence portion of the polynucleotide also includes a nucleic acid sequence, encoding a Factor IX signal peptide, that has at least 90%, 95%, 96%, 97%, 98%, 99%, or 100% identity to one of FIX-SP-NA (SEQ ID NO:24), CS02-SP-NA (SEQ ID NO:25), CS03-SP-NA (SEQ ID NO:26), CS04-SP-NA (SEQ ID NO:27), CS05-SP-NA (SEQ ID NO:28), and CS06-SP-NA (SEQ ID NO:29). In some embodiments, the FIX coding sequence portion of the polynucleotide also includes a nucleic acid sequence, encoding a Factor IX pro-peptide (optionally in combination with a nucleic acid sequence for a Factor IX signal peptide, as described above), that has at least 90%, 95%, 96%, 97%, 98%, 99%, or 100% identity to one of FIX-PP-NA (SEQ ID NO:30), CS02-PP-NA (SEQ ID NO:31), CS03-PP-NA (SEQ ID NO:32), CS04-PP-NA (SEQ ID NO:33), CS05-PP-NA (SEQ ID NO:34), and CS06-PP-NA (SEQ ID NO:35). In some embodiments, the FIX coding sequence portion of the polynucleotide includes a nucleic acid sequence, encoding a pre-pro-Factor IX polypeptide, that has at least 95%, 96%, 97%, 98%, 99%, 99.5%, 99.9%, or 100% identity to CS06-FL-NA (SEQ ID NO:9).

In some embodiments, with reference to FIG. 1, a nucleic acid composition is provided that includes a polynucleotide of structure C (e.g., a single-stranded polynucleotide), where the FIX coding sequence portion of the polynucleotide includes a nucleic acid sequence, encoding a mature Factor IX polypeptide, that has at least 95%, 96%, 97%, 98%, 99%, 99.5%, 99.9%, or 100% identity to CS06-MP-NA (SEQ ID NO:17). In some embodiments, the FIX coding sequence portion of the polynucleotide also includes a nucleic acid sequence, encoding a Factor IX signal peptide, that has at least 90%, 95%, 96%, 97%, 98%, 99%, or 100% identity to one of FIX-SP-NA (SEQ ID NO:24), CS02-SP-NA (SEQ ID NO:25), CS03-SP-NA (SEQ ID NO:26), CS04-SP-NA (SEQ ID NO:27), CS05-SP-NA (SEQ ID NO:28), and CS06-SP-NA (SEQ ID NO:29). In some embodiments, the FIX coding sequence portion of the polynucleotide also includes a nucleic acid sequence, encoding a Factor IX pro-peptide (optionally in combination with a nucleic acid sequence for a Factor IX signal peptide, as described above), that has at least 90%, 95%, 96%, 97%, 98%, 99%, or 100% identity to one of FIX-PP-NA (SEQ ID NO:30), CS02-PP-NA (SEQ ID NO:31), CS03-PP-NA (SEQ ID NO:32), CS04-PP-NA (SEQ ID NO:33), CS05-PP-NA (SEQ ID NO:34), and CS06-PP-NA (SEQ ID NO:35). In some embodiments, the FIX coding sequence portion of the polynucleotide includes a nucleic acid sequence, encoding a pre-pro-Factor IX polypeptide, that has at least 95%, 96%, 97%, 98%, 99%, 99.5%, 99.9%, or 100% identity to CS06-FL-NA (SEQ ID NO:9).

In some embodiments, with reference to FIG. 1, a nucleic acid composition is provided that includes a polynucleotide of structure D (e.g., a single-stranded polynucleotide), where the FIX coding sequence portion of the polynucleotide includes a nucleic acid sequence, encoding a mature Factor IX polypeptide, that has at least 95%, 96%, 97%, 98%, 99%, 99.5%, 99.9%, or 100% identity to CS06-MP-NA (SEQ ID NO:17). In some embodiments, the FIX coding sequence portion of the polynucleotide also includes a nucleic acid sequence, encoding a Factor IX signal peptide, that has at least 90%, 95%, 96%, 97%, 98%, 99%, or 100% identity to one of FIX-SP-NA (SEQ ID NO:24), CS02-SP-NA (SEQ ID NO:25), CS03-SP-NA (SEQ ID NO:26), CS04-SP-NA (SEQ ID NO:27), CS05-SP-NA (SEQ ID NO:28), and CS06-SP-NA (SEQ ID NO:29). In some embodiments, the FIX coding sequence portion of the polynucleotide also includes a nucleic acid sequence, encoding a Factor IX pro-peptide (optionally in combination with a nucleic acid sequence for a Factor IX signal peptide, as described above), that has at least 90%, 95%, 96%, 97%, 98%, 99%, or 100% identity to one of FIX-PP-NA (SEQ ID NO:30), CS02-PP-NA (SEQ ID NO:31), CS03-PP-NA (SEQ ID NO:32), CS04-PP-NA (SEQ ID NO:33), CS05-PP-NA (SEQ ID NO:34), and CS06-PP-NA (SEQ ID NO:35). In some embodiments, the FIX coding sequence portion of the polynucleotide includes a nucleic acid sequence, encoding a pre-pro-Factor IX polypeptide, that has at least 95%, 96%, 97%, 98%, 99%, 99.5%, 99.9%, or 100% identity to CS06-FL-NA (SEQ ID NO:9).

C. Codon-Altered Factor IX Signal and Pro-Peptides

In one aspect, the disclosure provides codon-altered polynucleotides encoding Factor IX signal peptides, Factor IX pro-peptides, and both (e.g., Factor IX pre-pro-peptides). These codon-altered polynucleotides improve Factor IX expression and may be placed, e.g., upstream of a polynucleotide, codon-altered or otherwise, encoding a Factor IX single-chain polypeptide (e.g., a Factor IX light chain, activation peptide, and heavy chain). Generally, the encoded peptides are wild-type Factor IX signal peptides (e.g., FIX-SP-AA (SEQ ID NO:37)), pro-peptides (e.g., FIX-PP-AA (SEQ ID NO:38), and pre-pro-peptides (FIX-PPP-AA (SEQ ID NO:36)).

In certain embodiments, the codon-altered polynucleotides encoding Factor IX signal peptides, pro-peptides, and pre-pro-peptides have a sequence with high identity (e.g., at least 90%, 91%, 92%, 93%, 94%, 95%, 96%, 97%, 98%, 99%, or 100%) to one of CS02-SP-NA (SEQ ID NO:25), CS03-SP-NA (SEQ ID NO:26), CS04-SP-NA (SEQ ID NO:27), CS05-SP-NA (SEQ ID NO:28), CS06-SP-NA (SEQ ID NO:29), CS02-PP-NA (SEQ ID NO:31), CS03-PP-NA (SEQ ID NO:32), CS04-PP-NA (SEQ ID NO:33), CS05-PP-NA (SEQ ID NO:34), CS06-PP-NA (SEQ ID NO:35), CS02-PPP-NA (SEQ ID NO: 19), CS03-PPP-NA (SEQ ID NO:20), CS04-PPP-NA (SEQ ID NO:21), CS05-PPP-NA (SEQ ID NO:22), and CS06-PPP-NA (SEQ ID NO:23).

CS02 Signal and Pro-Peptides

In one embodiment, the codon-altered polynucleotide encoding a Factor IX signal peptide has at least 95% sequence identity to CS02-SP-NA (SEQ ID NO:25). In other embodiments, the codon-altered polynucleotide encoding a Factor IX signal peptide has at least 96%, 97%, 98%, 99%, or 100% identity to CS02-SP-NA (SEQ ID NO:25).

In one embodiment, the codon-altered polynucleotide encoding a Factor IX pro-peptide has at least 95% sequence identity to CS02-PP-NA (SEQ ID NO:31). In other embodiments, the codon-altered polynucleotide encoding a Factor IX pro-peptide has at least 96%, 97%, 98%, 99%, or 100% identity to CS02-PP-NA (SEQ ID NO:31).

In one embodiment, the codon-altered polynucleotide encoding a Factor IX pre-pro-peptide has at least 95% sequence identity to CS02-PPP-NA (SEQ ID NO:19). In other embodiments, the codon-altered polynucleotide encoding a Factor IX pre-pro-peptide has at least 96%, 97%, 98%, 99%, or 100% identity to CS02-PPP-NA (SEQ ID NO:19).

CS03 Signal and Pro-Peptides

In one embodiment, the codon-altered polynucleotide encoding a Factor IX signal peptide has at least 95% sequence identity to CS03-SP-NA (SEQ ID NO:26). In other embodiments, the codon-altered polynucleotide encoding a Factor IX signal peptide has at least 96%, 97%, 98%, 99%, or 100% identity to CS03-SP-NA (SEQ ID NO:26).

In one embodiment, the codon-altered polynucleotide encoding a Factor IX pro-peptide has at least 95% sequence identity to CS03-PP-NA (SEQ ID NO:32). In other embodiments, the codon-altered polynucleotide encoding a Factor IX pro-peptide has at least 96%, 97%, 98%, 99%, or 100% identity to CS03-PP-NA (SEQ ID NO:32).

In one embodiment, the codon-altered polynucleotide encoding a Factor IX pre-pro-peptide has at least 95% sequence identity to CS03-PPP-NA (SEQ ID NO:20). In other embodiments, the codon-altered polynucleotide encoding a Factor IX pre-pro-peptide has at least 96%, 97%, 98%, 99%, or 100% identity to CS03-PPP-NA (SEQ ID NO:20).

CS04 Signal and Pro-Peptides

In one embodiment, the codon-altered polynucleotide encoding a Factor IX signal peptide has at least 95% sequence identity to CS04-SP-NA (SEQ ID NO:27). In other embodiments, the codon-altered polynucleotide encoding a Factor IX signal peptide has at least 96%, 97%, 98%, 99%, or 100% identity to CS04-SP-NA (SEQ ID NO:27).

In one embodiment, the codon-altered polynucleotide encoding a Factor IX pro-peptide has at least 95% sequence identity to CS04-PP-NA (SEQ ID NO:33). In other embodiments, the codon-altered polynucleotide encoding a Factor IX pro-peptide has at least 96%, 97%, 98%, 99%, or 100% identity to CS04-PP-NA (SEQ ID NO:33).

In one embodiment, the codon-altered polynucleotide encoding a Factor IX pre-pro-peptide has at least 95% sequence identity to CS04-PPP-NA (SEQ ID NO:21). In other embodiments, the codon-altered polynucleotide encoding a Factor IX pre-pro-peptide has at least 96%, 97%, 98%, 99%, or 100% identity to CS04-PPP-NA (SEQ ID NO:21).

CS05 Signal and Pro-Peptides

In one embodiment, the codon-altered polynucleotide encoding a Factor IX signal peptide has at least 95% sequence identity to CS05-SP-NA (SEQ ID NO:28). In other embodiments, the codon-altered polynucleotide encoding a Factor IX signal peptide has at least 96%, 97%, 98%, 99%, or 100% identity to CS05-SP-NA (SEQ ID NO:28).

In one embodiment, the codon-altered polynucleotide encoding a Factor IX pro-peptide has at least 95% sequence identity to CS05-PP-NA (SEQ ID NO:34). In other embodiments, the codon-altered polynucleotide encoding a Factor IX pro-peptide has at least 96%, 97%, 98%, 99%, or 100% identity to CS05-PP-NA (SEQ ID NO:34).

In one embodiment, the codon-altered polynucleotide encoding a Factor IX pre-pro-peptide has at least 95% sequence identity to CS05-PPP-NA (SEQ ID NO:22). In other embodiments, the codon-altered polynucleotide encoding a Factor IX pre-pro-peptide has at least 96%, 97%, 98%, 99%, or 100% identity to CS05-PPP-NA (SEQ ID NO:22).

CS06 Signal and Pro-Peptides

In one embodiment, the codon-altered polynucleotide encoding a Factor IX signal peptide has at least 95% sequence identity to CS06-SP-NA (SEQ ID NO:29). In other embodiments, the codon-altered polynucleotide encoding a Factor IX signal peptide has at least 96%, 97%, 98%, 99%, or 100% identity to CS06-SP-NA (SEQ ID NO:29).

In one embodiment, the codon-altered polynucleotide encoding a Factor IX pro-peptide has at least 95% sequence identity to CS06-PP-NA (SEQ ID NO:35). In other embodiments, the codon-altered polynucleotide encoding a Factor IX pro-peptide has at least 96%, 97%, 98%, 99%, or 100% identity to CS06-PP-NA (SEQ ID NO:35).

In one embodiment, the codon-altered polynucleotide encoding a Factor IX pre-pro-peptide has at least 95% sequence identity to CS06-PPP-NA (SEQ ID NO:23). In other embodiments, the codon-altered polynucleotide encoding a Factor IX pre-pro-peptide has at least 96%, 97%, 98%, 99%, or 100% identity to CS06-PPP-NA (SEQ ID NO:23).

IV. Factor IX Expression Vectors

In some embodiments, the codon-altered polynucleotides described herein are integrated into expression vectors. As will be appreciated by one of skill in the art, many forms of vectors can be used to effectuate Factor IX gene therapy using the codon-altered Factor IX polynucleotide sequences disclosed herein. Non-limiting examples of expression vectors include viral vectors (e.g., vectors suitable for gene therapy), plasmid vectors, bacteriophage vectors, cosmids, phagemids, artificial chromosomes, and the like.

In some embodiments, the codon-altered polynucleotides described herein are integrated into a viral gene therapy vector. Non-limiting examples of viral vectors include: retrovirus, e.g., Moloney murine leukemia virus (MMLV), Harvey murine sarcoma virus, murine mammary tumor virus, and Rous sarcoma virus; adenoviruses, adeno-associated viruses; SV40-type viruses; polyomaviruses; Epstein-Barr viruses; papilloma viruses; herpes viruses; vaccinia viruses; and polio viruses.

In vivo, Factor IX is synthesized primarily in the liver. As such, hepatocytes have been targeted as suitable host cells for Factor IX gene therapy constructs. Several classes of viral vectors have been shown competent for liver-targeted delivery of a gene therapy construct, including retroviral vectors (see, e.g., Axelrod et al., 1990; Kay et al., 1992; Van den Driessche et al., 1999, and Xu et al., 2003, 2005, the disclosures of which are hereby expressly incorporated by reference, in their entireties, for all purposes), lentiviral (see, e.g., Ward et al., 2011, Brown et al., 2007, and Matrai et al., 2011, the disclosures of which are hereby expressly incorporated by reference, in their entireties, for all purposes), adeno-associated viral (AAV) (see, e.g., Herzog et al., 1999, the disclosure of which is hereby expressly incorporated by reference, in its entirety, for all purposes), and adenoviral vectors (see, e.g., Brown et al., 2004 and Ehrhardt & Kay, 2002, the disclosures of which are hereby expressly incorporated by reference, in their entireties, for all purposes).

In some embodiments, the gene therapy vector is a retrovirus, and particularly a replication-deficient retrovirus. Protocols for the production of replication-deficient retroviruses are known in the art. For review, see Kriegler, M., Gene Transfer and Expression, A Laboratory Manual, W.H. Freeman Co., New York (1990) and Murry, E. J., Methods in Molecular Biology, Vol. 7, Humana Press, Inc., Cliffton, N.J. (1991).

In one embodiment, the gene therapy vector is an adeno-associated virus (AAV) based gene therapy vector. AAV systems have been described previously and are generally well known in the art (Kelleher and Vos, Biotechniques, 17(6):1110-17 (1994); Cotten et al., P.N.A.S. U.S.A., 89(13):6094-98 (1992); Curiel, Nat Immun, 13(2-3):141-64 (1994); Muzyczka, Curr Top Microbiol Immunol, 158:97-129 (1992); and Asokan A, et al., Mol. Ther., 20(4):699-708 (2012), each incorporated herein by reference in their entireties for all purposes). Details concerning the generation and use of rAAV vectors are described, for example, in U.S. Pat. Nos. 5,139,941 and 4,797,368, each incorporated herein by reference in their entireties for all purposes. In a particular embodiment, the AAV vector is an AAV-8 vector.

An exemplary AAV delivery vector for liver-specific Factor IX expression is described in WO 2009/130208, the content of which is expressly incorporated by reference herein, in its entirety, for all purposes. The vector is a single-stranded AAV vector encoding human Factor IX, and includes TTR Serp regulatory sequences driving a factor cDNA. The vector also includes intron I of the human Factor IX gene and a poly-adenylation signal.

In some embodiments, the codon-altered polynucleotides described herein are integrated into a retroviral expression vector. These systems have been described previously, and are generally well known in the art (Mann et al., Cell, 33:153-159, 1983; Nicolas and Rubinstein, In: Vectors: A survey of molecular cloning vectors and their uses, Rodriguez and Denhardt, eds., Stoneham: Butterworth, pp. 494-513, 1988; Temin, In: Gene Transfer, Kucherlapati (ed.), New York: Plenum Press, pp. 149-188, 1986). In a specific embodiment, the retroviral vector is a lentiviral vector (see, for example, Naldini et al., Science, 272(5259):263-267, 1996; Zufferey et al., Nat Biotechnol, 15(9):871-875, 1997; Blomer et al., J Virol., 71(9):6641-6649, 1997; U.S. Pat. Nos. 6,013,516 and 5,994,136).

In some embodiments, the codon-altered polynucleotides described herein can be administered to a subject by a non-viral method. For example, naked DNA can be administered into a cell by electroporation, sonoporation, particle bombarment, or hydrodyamic delivery. DNA can also be encapsulated or coupled with polymers, e.g., liposomes, polysomes, polypleses, dendrimers, and administered to the subject as a complex. Likewise, DNA can be coupled to inorganic nanoparticles, e.g., gold, silica, iron oxide, or calcium phosphate particles, or attached to cell-penetrating peptides for delivery to cells in vivo.

Codon-altered Factor IX coding polynucleotides can also be incorporated into artificial chromosomes, such as Artificial Chromosome Expression (ACEs) (see, e.g., Lindenbaum et al., Nucleic Acids Res., 32(21):e172 (2004)) and mammalian artificial chromosomes (MACs). For review see, e.g., Perez-Luz and Diaz-Nido, J Biomed Biotechnol. 2010: Article ID 642804 (2010).

A wide variety of vectors can be used for the expression of a Factor IX polypeptide from a codon-altered polypeptide in cell culture, including eukaryotic and prokaryotic expression vectors. In certain embodiments, a plasmid vector is contemplated for use in expressing a Factor IX polypeptide in cell culture. In general, plasmid vectors containing replicon and control sequences which are derived from species compatible with the host cell are used in connection with these hosts. The vector can carry a replication site, as well as marking sequences which are capable of providing phenotypic selection in transformed cells. The plasmid will include the codon-altered polynucleotide encoding the Factor IX polypeptide, operably linked to one or more control sequences, for example, a promoter.

Non-limiting examples of vectors for prokaryotic expression include plasmids such as pRSET, pET, pBAD, etc., wherein the promoters used in prokaryotic expression vectors include lac, trc, trp, recA, araBAD, etc. Examples of vectors for eukaryotic expression include: (i) for expression in yeast, vectors such as pAO, pPIC, pYES, pMET, using promoters such as AOX1, GAP, GAL 1, AUG1, etc; (ii) for expression in insect cells, vectors such as pMT, pAc5, pIB, pMIB, pBAC, etc., using promoters such as PH, p10, MT, Ac5, OpIE2, gp64, polh, etc., and (iii) for expression in mammalian cells, vectors such as pSVL, pCMV, pRc/RSV, pcDNA3, pBPV, etc., and vectors derived from viral systems such as vaccinia virus, adeno-associated viruses, herpes viruses, retroviruses, etc., using promoters such as CMV, SV40, EF-1, UbC, RSV, ADV, BPV, and β-actin.

In some embodiments, the disclosure provides an AAV gene therapy vector that includes a codon-altered Factor IX polynucleotide, as described herein, internal terminal repeat (ITR) sequences on the 5' and 3' ends of the vector, one or more promoter and/or enhancer sequences operably-linked to the Factor IX polynucleotide, and a poly-adenylation signal following the 3' end of the Factor IX polynucleotide sequence. In some embodiments, the one or more promoter and/or enhancer sequences include one or more copies of a liver-specific regulatory control element.

FIG. 1 illustrates several exemplary architectures for a Factor IX gene therapy vector, in accordance with some implementations. FIG. 1A illustrates a self-complementary AAV vector having a mutated 5' ITR, truncated TTR enhancer/promoter sequences, an MVM viral intron sequence, a codon-altered Factor IX coding sequence, a poly-adenylation sequence, and a 3'-ITR. FIG. 1B illustrates a self-complementary AAV vector encoding a Factor IX polypeptide similar to FIG. 1A, but further including one or more (e.g., one, two, three, or more) liver-specific regulatory control elements. FIG. 1C illustrates a single-stranded vector having the same elements as FIG. 1A, except that the 5'-ITR is not mutated, preventing self-complementarity. FIG. 1D illustrates a single-stranded AAV vector encoding a Factor IX polypeptide similar to FIG. 1A, but further including one or more (e.g., one, two, three, or more) liver-specific regulatory control elements. Although illustrated with reference to a Factor IX protein that includes an R384L 'Padua' amino acid substitution in FIG. 1, in some embodiments, a Factor IX nucleotide construct having a general structure as depicted in FIG. 1 (e.g., structure A, B, C, or D) encodes a Factor IX protein that does not include an R384L 'Padua' amino acid substitution.

FIG. 25 shows the nucleotide sequence of an AAV Factor IX gene therapy vector CS06-CRM8.3-ssV (SEQ ID NO:40), which exemplifies the gene therapy vector architecture illustrated in FIG. 1D. Nucleotides 1-145 of CS06-CRM8.3-ssV (SEQ ID NO:40) is an AAV2 5'-ITR sequence (SEQ ID NO:51). The 5'-ITR sequence is followed by three copies of a liver-specific CRM8 regulatory control element CRM8 (SEQ ID NO:39) at nucleotides 165-236, 238-309, and 311-382. Following the CRM8 sequence is a truncated TTR enhancer/promoter sequence (SEQ ID NO:52) at nucleotides 383-712. Next, the vector includes a minute virus of mice (MVM) intron (SEQ ID NO:53) at nucleotides 724-800. Nucleotides 814-2199 of the vector are a CS06 codon-altered Factor IX(R384L) coding sequence (CS06-FL-NA (SEQ ID NO:9)). The Factor IX polynucleotide sequence is followed by a BGH poly-adenylation signal at nucleotides 2208-2441 and, finally, an AAV2 3'-ITR sequence (SEQ ID NO:55) at nucleotides 2458-2602.

In some embodiments, the disclosure provides a Factor IX polynucleotide comprising a sequence having at least 95% identity to nucleotides 1-2602 of SEQ ID NO:40. In some embodiments, the disclosure provides a Factor IX polynucleotide comprising a sequence having at least 99% identity to nucleotides 1-2602 of SEQ ID NO:40. In some embodiments, the disclosure provides a Factor IX polynucleotide comprising a sequence having at least 99.5% identity to nucleotides 1-2602 of SEQ ID NO:40. In some embodiments, the disclosure provides a Factor IX polynucleotide comprising the sequence of nucleotides 1-2602 of SEQ ID NO:40.

Several AAV serotypes have been characterized, including AAV1, AAV2, AAV3, AAV4, AAV5, AAV6, AAV7, AAV8, and AAV9. Generally, any AAV serotype may be used for the Factor IX gene therapy constructs described herein. However, the serotypes have different tropisms, e.g., they preferentially infect different tissues. In one embodiment, because Factor IX is produced primarily in the liver, an AAV serotype for the disclosed gene therapy constructs is selected based on a liver tropism, found in at least serotypes AAV7, AAV8, and AAV9. Accordingly, in one embodiment, a Factor IX gene therapy construct is an AAV7 serotype vector. In another embodiment, a Factor IX gene therapy construct is an AAV8 serotype vector. In yet another embodiment, a Factor IX gene therapy construct is an AAV9 serotype vector.

The Factor IX gene therapy constructs described herein may be single-stranded (e.g., a ssAAV vector, as illustrated in FIGS. 1C and 1D) or self-complementary (e.g., a scAAV vector, as illustrated in FIGS. 1A and 1B). Although research and theory has suggested that self-complementary AAV vectors should facilitate better transgene expression, by bypassing the requirement for second-strand synthesis prior to translation, single-stranded AAV vectors promoting better Factor IX expression that comparable self-complementary vector were identified, as reported in Example 5.

Promoters and Enhancers

The Factor IX gene therapy constructs described herein generally include one or more promoter and/or enhancer element that drives gene expression in vivo, e.g., a regulatory element. In some embodiments, a promoter or enhancer element drives expression in a tissue dependent fashion, e.g., predominantly in a specific tissue. Because Factor IX is synthesized primarily in the liver, in some embodiments, the gene therapy vectors described herein include a liver-specific regulatory element, which substantially limit expression of the gene therapy vector to hepatic cells.

Generally, liver-specific regulatory elements can be derived from any gene known to be exclusively expressed in the liver. WO 2009/130208 identifies several genes expressed in a liver-specific fashion, including, serpin peptidase inhibitor, clade A member 1, also known as α-antitrypsin (SERPINA1; GeneID 5265), apolipoprotein C-I (APOC1; GeneID 341), apolipoprotein C-IV (APOC4; GeneID 346), apolipoprotein H (APOH; GeneID 350); transthyretin (TTR; GeneID 7276), albumin (ALB; GeneID 213), aldolase B (ALDOB; GeneID 229), cytochrome P450, family 2, subfamily E, polypeptide 1 (CYP2E1; GeneID 1571), fibrinogen alpha chain (FGA; GeneID 2243), transferrin (TF; GeneID 7018), haptoglobin related protein (HPR; GeneID 3250). In some embodiments, the Factor IX gene therapy constructs described herein include a liver-specific regulatory element derived from the genomic loci of one or more of these proteins. Several examples of such elements are described in WO 2009/130208, the content of which is expressly incorporated herein by reference, in its entirety, for all purposes.

One example of a liver-specific regulatory element is from the transthyretin (TTR) gene, commonly referred to as "TTRe" or "TTREnh." Hsieh J. L., et al., Cancer Sci., 100(3):537-45 (2009), the content of which is expressly incorporated herein by reference, in its entirety, for all purposes. In some embodiments, the Factor IX gene therapy constructs described herein include truncated TTR enhancer and promoter elements. An example of these elements is provided at nucleotides 383-712 of CS06-CRM8.3-ssV (SEQ ID NO:40), provided as FIG. 25. In some embodiments, a truncated TTR enhancer and promoter element has at least 85% sequence identity to nucleotides 383-712 of CS06-CRM8.3-ssV (SEQ ID NO:40). In other embodiments, the truncated TTR enhancer and promoter element have at least 90%, 95%, 96%, 97%, 98%, 99%, 99.5%, or 100% sequence identity to nucleotides 383-712 of CS06-CRM8.3-ssV (SEQ ID NO:40).

Another example of a liver-specific regulatory element is from the SERPINA1 gene, as described in PCT Publication No. WO 2016/146757, the content of which is expressly incorporated herein by reference, in its entirety, for all purposes. An example of such an element is the CRM8 regulatory control element (SEQ ID NO:39) provided at nucleotides 165-236 of CS06-CRM8.3-ssV (SEQ ID NO:40). In some embodiments, a SERPINA1-derived regulatory control element has at least 85% sequence identity to CRM8 (SEQ ID NO:39). In other embodiments, the truncated SERPINA1-derived regulatory control element has at least 90%, 95%, 96%, 97%, 98%, 99%, or 100% sequence identity to CRM8 (SEQ ID NO:39).

In some embodiments, a Factor IX gene therapy construct includes one or more SERPINA1-derived regulatory control element, as exemplified by the constructs illustrated in FIGS. 1B and 1D. In one embodiment, a construct includes one SERPINA1-derived regulatory control element (e.g., CRM8). In another embodiment, a construct includes two SERPINA1-derived regulatory control elements (e.g., CRM8). In another embodiment, a construct includes three SERPINA1-derived regulatory control elements (e.g., CRM8). In yet other embodiments, a construct includes 4, 5, 6, or more SERPINA1-derived regulatory control elements (e.g., CRM8).

In one embodiment, a Factor IX gene therapy construct includes one or more SERPINA1-derived regulatory control element (e.g., CRM8) and a truncated TTR enhancer and promoter element, as exemplified in FIGS. 1B, 1D, and 25.

Introns

In some embodiments, the Factor IX gene therapy constructs described herein include an intron, e.g., a virally-derived intron, to increase expression of the Factor IX gene. Suitable introns for the expression of gene therapy constructs are known in the art. Typically, the intron is positioned 5' of the transgene coding sequence, as exemplified in the Factor IX constructs shown in FIG. 1 and FIG. 25. However, in some embodiments, the intron may be positioned within the transgene coding sequence, e.g., at a natural Factor IX intron junction or otherwise, or 3' of the transgene coding sequence. Non-limiting examples of introns that can be used in the Factor IX gene therapy constructs described herein include introns derived from a Minute Virus of Mice (MVM) intron, a beta-globin intron (betaIVS-ll), a Factor IX (FIX) intron A, a Simian virus 40 (SV40) Small T intron, and a beta-actin intron.

In one embodiment, the Factor IX gene therapy constructs described herein include an MVM-derived intron, e.g., as illustrated in FIG. 1 and exemplified by the MVM intron (SEQ ID NO:53) at nucleotides 724-800 of CS06-CRM8.3-ssV (SEQ ID NO:40) in FIG. 25. In some embodiments, an intron used in the gene therapy constructs described herein has at least 85% sequence identity to MVM (SEQ ID NO:53). In other embodiments, an intron used in the gene therapy constructs described herein has at least 90%, 95%, 96%, 97%, 98%, 99%, or 100% sequence identity to MVM (SEQ ID NO:53).

Poly-Adenylation Signals

In some embodiments, the Factor IX gene therapy constructs described herein include a poly-adenylation signal, e.g., as illustrated in in FIG. 1. The poly-adenylation signal directs synthesis of a poly-A tail on the 3' end of the mRNA transcript generated from the Factor IX transgene. Accordingly, the poly-adenylation signal is positioned 3' to the Factor IX coding sequence. Non-limiting examples of poly-adenylation signals that can be used in the Factor IX gene therapy constructs described herein include poly-adenylation signals derived from a Simian virus 40 (SV40) late gene, a bovine growth hormone (BGH) polyadenylation signal, and a minimal rabbit β-globin (mRBG) gene.

In one embodiment, the Factor IX gene therapy constructs described herein include a poly-adenylation signal derived from the bovine growth hormone (BGH) polyadenylation signal, e.g., as illustrated in FIG. 1 and exemplified by the BGHpA signal (SEQ ID NO:54) at nucleotides 2208-2441 of CS06-CRM8.3-ssV (SEQ ID NO:40) in FIG. 25. In some embodiments, a poly-adenylation signal used in the gene therapy constructs described herein has at least 85% sequence identity to the BGHpA signal (SEQ ID NO:54). In other embodiments, a poly-adenylation signal used in the gene therapy constructs described herein has at least 90%, 95%, 96%, 97%, 98%, 99%, or 100% sequence identity to the BGHpA signal (SEQ ID NO:54).

V. Methods

Production

The codon-altered Factor IX polynucleotides and viral vectors described herein (e.g., the nucleic acid compositions) are produced according to conventional methods for nucleic acid amplification and vector production. Two predominant platforms have developed for large-scale production of recombinant AAV vectors. The first platform is based on replication in mammalian cells, while the second is based on replication in invertebrate cells. For review, see, Kotin R. M., Hum. Mol. Genet., 20(R1):R2-6 (2011), the content of which is expressly incorporated herein by reference, in its entirety, for all purposes.

Accordingly, the disclosure provides methods for producing an adeno-associated virus (AAV) particle. In some embodiments, the methods include introducing a codon-altered Factor IX polynucleotide construct having high nucleotide sequence identity (e.g., at least 95%, 96%, 97%, 98%, 99%, 99.5%, 99.9%, or 100%) to one of a CS02, CS03, CS04, CS05, or CS06 sequence, as described herein, into a host cell where the polynucleotide construct is competent for replication in the host cell.

In some embodiments, the host cell is a mammalian host cell e.g., an HEK, CHO, or BHK cell. In a specific embodiment, the host cell is an HEK 293 cell. In some embodiments, the host cell is an invertebrate cell, e.g., an insect cell. In a specific embodiment, the host cell is an SF9 cell.

Formulations

Compositions for use in treatment of bleeding disorders are provided herein. Such compositions contain a therapeutically effective amount of a codon-altered Factor IX polynucleotide, e.g., an AAV gene therapy vector including a codon-altered polynucleotide encoding for Factor IX, as described herein. Therapeutically effective amounts of the codon-altered FIX polynucleotide (e.g., an AAV gene therapy vector including the codon-altered Factor IX coding sequence) are mixed with a suitable pharmaceutical carrier or vehicle for systemic, topical or local administration. Final formulation of the codon-altered Factor IX polynucleotides disclosed herein will be within the abilities of those skilled in the art.

Dosages

The nucleic acid compositions of the invention are administered to patients in need thereof. The amount or dose of the therapeutic gene therapy agent administered depends on factors such as the particular codon-altered FIX polynucleotide construct, the delivery vector used, the severity of the disease, and the general characteristics of the subject. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). It is within the abilities of the skilled physician to determine a particular dosage and dosing regimen for treatment of a particular subject.

In some embodiments, a gene therapy vector (e.g., an AAV gene therapy vector particle) having a codon-altered Factor IX polynucleotide is administered intravenously at a therapeutically effective dose to a subject in need thereof (e.g., a subject with mild, moderate, or severe hemophilia B). In some embodiments, a therapeutically effective dose is between about 2×10E11 and 2×10E14 vector genomes per kilogram body weight of the subject. In a specific embodiment, a therapeutically effective dose is between about 2×10E12 and 2×10E13 vector genomes per kilogram body weight of the subject. In some embodiments, the subject is administered about 2×10E11, 3×10E11, 4×10E11, 5×10E11, 6×10E11, 7×10E11, 8×10E11, 9×10E11, 1×10E12, 2×10E12, 3×10E12, 4×10E12, 5×10E12, 6×10E12, 7×10E12, 8×10E12, 9×10E12, 1×10E13, 2×10E13, 3×10E13, 4×10E13, 5×10E13, 6×10E13, 7×10E13, 8×10E13, 9×10E13, 1×10E14, or 2×10E14 vector genomes per kilogram body weight of the subject.

Accordingly, the disclosure provides methods for treating a Factor IX deficiency (e.g., hemophilia B). In some embodiments, the methods include administering to a patient in need thereof a codon-altered Factor IX polynucleotide construct having high nucleotide sequence identity (e.g., at least 95%, 96%, 97%, 98%, 99%, 99.5%, 99.9%, or 100%) to one of a CS02, CS03, CS04, CS05, or CS06 sequence, as described herein. In some embodiments, the codon-altered Factor polynucleotide has high sequence identity to a codon-altered Factor IX pre-pro-polypeptide coding sequence, e.g., high sequence identity to one of CS02-FL-NA (SEQ ID NO:5), CS03-FL-NA (SEQ ID NO:6), CS04-FL-NA (SEQ ID NO:7), CS05-FL-NA (SEQ ID NO:8), or CS06-FL-NA (SEQ ID NO:9). In some embodiments, the codon-altered Factor polynucleotide has high sequence identity to a codon-altered mature Factor IX single-chain polypeptide coding sequence, e.g., high sequence identity to one of CS02-MP-NA (SEQ ID NO: 13), CS03-MP-NA (SEQ ID NO: 14), CS04-MP-NA (SEQ ID NO: 15), CS05-MP-NA (SEQ ID NO: 16), or CS06-MP-NA (SEQ ID NO:17).

In some embodiments, treatment includes administering to a patient in need thereof a gene therapy vector including a codon-altered Factor IX polynucleotide construct having high nucleotide sequence identity (e.g., at least 95%, 96%, 97%, 98%, 99%, 99.5%, 99.9%, or 100%) to one of a CS02, CS03, CS04, CS05, or CS06 sequence, as described herein. In one embodiment, the gene therapy vector is a mammalian gene therapy vector. In a specific embodiment, the mammalian gene therapy vector is a viral vector, e.g., a lentivirus, retrovirus, adeno virus, or adeno-associated virus vector.

In one embodiment, the gene therapy vector is an adeno-associated virus (AAV) particle harboring a viral vector encoding the codon-altered Factor IX coding sequence. Generally, the viral vector includes inverted terminal repeats (ITR) at each termini, one or more expression regulatory elements, a codon-altered Factor IX coding sequence, and a poly-A signal sequence. In a specific embodiment, the gene therapy vector includes a liver-specific regulatory control element (e.g., one or more copies of a CRM8 element).

Production

The codon-altered Factor IX polynucleotides and viral vectors described herein (e.g., the nucleic acid compositions) are produced according to conventional methods for nucleic acid amplification and vector production. Two predominant platforms have developed for large-scale production of recombinant AAV vectors. The first platform is based on replication in mammalian cells, while the second is based on replication in invertebrate cells. For review, see, Kotin R. M., Hum. Mol. Genet., 20(R1):R2-6 (2011), the content of which is expressly incorporated herein by reference, in its entirety, for all purposes.

Accordingly, the disclosure provides methods for producing an adeno-associated virus (AAV) particle. In some embodiments, the methods include introducing a codon-altered Factor IX polynucleotide construct having high nucleotide sequence identity (e.g., at least 95%, 96%, 97%, 98%, 99%, 99.5%, 99.9%, or 100%) to one of a CS02, CS03, CS04, CS05, or CS06 sequence, as described herein, into a host cell where the polynucleotide construct is competent for replication in the host cell.

In some embodiments, the host cell is a mammalian host cell e.g., an HEK, CHO, or BHK cell. In a specific embodiment, the host cell is an HEK 293 cell. In some embodiments, the host cell is an invertebrate cell, e.g., an insect cell. In a specific embodiment, the host cell is an SF9 cell.

Treatment

In some embodiments, the nucleic acid compositions (e.g., codon-altered polynucleotides) described herein are administered to a subject in need thereof, in accordance with known administrative methods. Methods for administering gene therapy vectors are well known in the art. These include, without limitation, intravenous administration, intramuscular injection, interstitial injection, and intra-hepatic administration (e.g., intra-hepatic artery or vein). For example, see Chuah M K et al., Hum Gene Ther., 23(6): 557-65 (2012); Chuah M K et al., J Thromb Haemost., 10(8): 1566-69 (2012); Chuah M K et al., J Thromb Haemost. 11 Suppl 1:99-110 (2013); VandenDriessche et al., Hum Gene Ther. 23(1):4-6 (2012); High K A, Blood, 120(23):4482-87 (2012); Matrai et al., Mol Ther., 18(3): 477-90 (2010); and Matrai et al., Curr Opin Hematol., 17(5):387-92 (2010), each of which is hereby incorporated by reference herein, for review.

Assessing Therapeutic Efficacy

The therapeutic efficacy of a hemophilia B treatment can be evaluated, for example, by measuring the Factor IX-dependent coagulation potential of blood from a subject being treated. Metrics for assessing coagulation potential include, without limitation, in vitro activated partial thromboplastin time assay (APPT), Factor IX chromogenic activity assays, blood clotting times, and Factor IX antigen levels (e.g., using a Factor IX-specific ELISA). It should be noted that a therapeutic dose need not result in wild-type levels of FIX in a patient; rather, sufficient expression to decrease symptoms in a meaningful or measurable way is considered therapeutic for the purposes of the invention.

According to the National Hemophilia Foundation, a subject is classified as having mild hemophilia B when their blood plasma contains between 6% and 49% of the Factor IX activity of normal human blood plasma. Subjects with mild hemophilia B typically experience bleeding only after serious injury, trauma or surgery. In many cases, mild hemophilia is not diagnosed until an injury, surgery or tooth extraction results in prolonged bleeding. The first episode may not occur until adulthood. Women with mild hemophilia often experience menorrhagia, heavy menstrual periods, and can hemorrhage after childbirth.

According to the National Hemophilia Foundation, a subject is classified as having moderate hemophilia B when their blood plasma contains between 1% and 5% of the Factor IX activity of normal human blood plasma. Subjects with moderate hemophilia B tend to have bleeding episodes after injuries. Bleeds that occur without obvious cause are called spontaneous bleeding episodes.

According to the National Hemophilia Foundation, a subject is classified as having severe hemophilia B when their blood plasma contains less than 1% of the Factor IX activity of normal human blood plasma. Subjects with severe hemophilia B experience bleeding following an injury and may have frequent spontaneous bleeding episodes, often into their joints and muscles.

In some embodiments, normal human blood plasma is defined as containing 1 IU of Factor IX activity per mL. Thus, in some embodiments, blood plasma from a subject classified with mild hemophilia B contains between 0.06 and 0.49 IU of Factor IX activity per mL. In some embodiments, blood plasma from a subject classified with moderate hemophilia B contains between 0.01 and 0.05 IU of Factor IX activity per mL. In some embodiments, blood plasma from a subject classified with severe hemophilia B contains between 0.01 and 0.05 IU of Factor IX activity per mL.

Accordingly, in some embodiments, hemophilia B therapy is therapeutically effective when it raises the average level of Factor IX activity in the subject's blood/plasma. In some embodiments, a therapeutically affective treatment raises the average level of Factor IX activity in the subject's blood/plasma by at least 1%, 2%, 3%, 4%, 5%, 6%, 7%, 8%, 9%, 10%, 15%, 20%, 25%, 30%, 35%, 40%, 45%, 50%, or more. In a specific embodiment, a therapeutically effective hemophilia therapy increases the average Factor IX activity in the blood/plasma of a subject by at least 5%. In another specific embodiment, a therapeutically effective hemophilia therapy increases the average Factor IX activity in the blood/plasma of a subject by at least 10%. In another specific embodiment, a therapeutically effective hemophilia therapy increases the average Factor IX activity in the blood/plasma of a subject by at least 15%. In another specific embodiment, a therapeutically effective hemophilia therapy increases the average Factor IX activity in the blood/plasma of a subject by at least 20%. In another specific embodiment, a therapeutically effective hemophilia therapy increases the average Factor IX activity in the blood/plasma of a subject by at least 25%. In another specific embodiment, a therapeutically effective hemophilia therapy increases the average Factor IX activity in the blood/plasma of a subject by at least 30%.

In some embodiments, a therapeutically effective treatment raises the average level of Factor IX activity in the subjects blood such that the subject is classified as having a less severe form of hemophilia B. For example, in one embodiment, a subject originally classified with severe hemophilia B is reclassified with moderate hemophilia B or mild hemophilia B after undergoing a therapeutically effective treatment. In another embodiment, a subject originally classified with moderate hemophilia B is reclassified with mild hemophilia B after undergoing a therapeutically effective treatment.

VI. Examples

Example 1—Codon-Altered Factor IX Expression Sequences Enhance FIX Expression Levels In order to generate gene therapy constructs providing improved expression of heterologous Factor IX in vivo, a panel of self-complementary AAV8-based vectors encoding a full-length Factor IX preproprotein with an R384L amino acid substitution (FIXp-FL-AA SEQ ID NO:4)) were constructed. The Factor IX coding sequence of each construct was altered to improve expression in humans through several steps. Each Factor IX coding sequence was modified according to an algorithm designed to account for preferred/disfavored sequence motifs and to skew codon-usage towards preferred human codons. Several algorithms were used for this first step, as reported in Table 2. Intermediate codon-altered sequences, resulting from application of the algorithms reported in Table 2, where then further modified manually to reduce or eliminate CpG dinucleotides, adjust the final GC content, adjust to allow for preferred codon pairs, adjust to avoid disfavored codon pairs, and adjust the final codon usage. For further information on these considerations, see, e.g., Fath S. et al., PLoS. One., 6, e17596 (2011); Haas J. et al., Curr. Biol., 6, 315-324 (1996); Tats A., BMC Genomics. 9:463 (2008), Grote A. et al., Nucleic Acids Research, 33(Web Server issue), W526-W531 (2005), Mirsafian H. et al., Scientific World Journal., 639682 (2014), and Pechmann S. et al., Nat Struct Mol Biol. 20(2):237-43 (2013), the contents of which are expressly incorporated hereinby reference, in their entireties, for all purposes, specifically for their teachings of codon alteration considerations.

Each generated codon-altered coding sequence (e.g., CS02, CS03, CS04, CS05, and CS06, shown in FIGS. 5 through 9, respectively) encoded for an identical FIX (R384L) protein (FIXp-FL-AA (SEQ ID NO:4)). The CS02, CS03, and CS04 constructs contain no CpG motifs, while CS05 and CS06 contain 11 and 3 CpGs, respectively.

To use as controls, vector constructs incorporating wild-type FIX coding sequences, with and without R384L Padua amino acid substitutions, were also generated. The WH01 construct encodes a wild type FIX preproprotein without the R384L Padua mutation, and includes 20 CpG dinucleotides. The WH02 construct encodes a wild type FIX preproprotein with the R384L Padua mutation, and includes 19 CpG dinucleotides.

The WH01 and WH02 constructs include 20 and 19 CpGs in their coding sequences, respectively. In contrast, the CS02, CS03, and CS04 constructs contain no CpG motifs, while the CS05 and CS06 constructs contain 11 and 3 CpGs, respectively.

As shown in FIG. 1A, the codon-altered Factor IX coding sequences were inserted into an Adeno-associated virus ("AAV") transgene cassette containing a mouse transthyrethrin enhancer/promoter (SEQ ID NO:52), a mouse minute virus ("MVM") intron (SEQ ID NO:53), the codon-altered FIX construct including the R384L "Padua" amino acid substitution (U.S. Pat. No. 6,531,298; Simione et al., NEJM 361:1671-75 (2009); the R384L mutation is commonly reported as an R338L mutation, referring to the position of the wild-type arginine in the human single-chain FIX protein lacking the signal and propeptide), followed by a bovine growth hormone polyA element (SEQ ID NO:54). The gene cassette is flanked by AAV2 inverted terminal repeats ("ITR") (SEQ ID NOs:51 and 55). The left ITR repeat includes a mutation in the terminal concatemer resolution site resulting in the self-complementary (sc) phenotype of the vectors. The basic vector design is described in detail in Wu et al., Mol. Ther. 16:280-89 (2008) and in PCT Publication Number WO 2014/064277 A1, the contents of which are incorporated herein by reference, in their entireties, for all purposes.

The CS and WH Factor IX AAV constructs were administered to B6/129P2-F9tm1Dws FIX knockout mice (described in Lin et al., Blood, 90:3962-66 (1997), the content of which is incorporated by reference herein, in its entirety, for all purposes). AAV vector dilutions were injected into animals (4-8 animals per group) via the lateral tail vein based upon the individual animals body weights (4×10E11 vector genomes/kilogram (vg/kg) body weight). Blood samples were collected at defined time intervals by retro-orbital puncture after dosing according to known procedures using glass capillaries. Blood was then transferred to a tube pre-filled with sodium citrate anticoagulant and plasma was obtained by standard procedures and frozen at −20° C.

Expression of the various Factor IX constructs was determined and plasma FIX levels at day 14 in FIX knockout mice were used to judge the potency of the constructs after tail vein injection of the vectors into the mice, as reported in Table 2. By day 14, expression levels in the knockout mouse model have nearly reached the maximum FIX expression. As shown in Table 2, the WH02 FIX(R384L) control construct was expressed at 1.03 units FIX at day 14 after administration of 4×10E11 vector genomes/kilogram (vg/kg) body weight. This expression level was used as a baseline to determine fold-enrichment of the codon-altered Factor IX constructs. As reported in Table 2, the CS codon-altered constructs provided between about 2-fold and 4-fold increased expression, as compared to the WH02 control construct, encoded by a wild-type polynucleotide sequence. Most notably, the CS06 codon-altered construct provided 4.2-fold greater Factor IX activity than the WH002 control construct and 21.6-fold greater Factor IX activity than the WH01 (wild-type Factor IX) control construct.

TABLE 2

Expression of Factor IX from contracts with wild-type codon sequences (WH01 - wtFIX; WH02 - FIX(R384L) and codon-altered sequences (CS02-CS06).

| AAV Construct | Modification of vector genome | Number of CpGs | Day 14 expression levels [% hum FIX] | Fold expression compared to WH01 | Fold expression compared to WH02 |
| --- | --- | --- | --- | --- | --- |
| WH01 | Human FIX wild-type sequence (GeneBank NM000133.3) without R338L (Padua) mutation | 20 | 0.20 | 1.0 | 0.19 |
| WH02 | Human FIX wild-type sequence with R338L (Padua) mutation | 19 | 1.03 | 5.2 | 1.0 |
| CS02 | Human FIX sequence with R338L mutation; Geneart basic algorithm further optimized towards human serum albumin codons. | 0 | 2.12 | 10.6 | 2.1 |
| CS03 | Human FIX sequence with R338L mutation; Geneart basic algorithm further optimized towards most frequently used human codons (Haas et al., 1996. Curr Biol. 6, 315-324). | 0 | 1.98 | 9.9 | 1.9 |
| CS04 | Human FIX sequence with R338L mutation; Geneart basic algorithm further optimized towards liver codon usage as described in Uhlen et al., 2015 Science 347, 6220. | 0 | 2.77 | 13.9 | 2.7 |
| CS05 | Human FIX sequence with R338L mutation; JCAT algorithm modified to reduce CpGs; (Grote et al., 2005. Nucleic Acids Res 1, 33). | 11 | 3.93 | 19.7 | 3.8 |
| CS06 | Human FIX sequence with R338L mutation; Geneart basic algorithm further optimized towards most frequently used human codons (Haas et al., 1996. Curr Biol. 6, 315-324). | 3 | 4.32 | 21.6 | 4.2 |

Example 2—Liver-Specific CRM8 Elements Enhance Expression of FIX in Mice

To further increase Factor IX expression and activity from the codon-altered constructs, one to three copies of a liver-specific cis-regulatory control element (CRM8 (SEQ ID NO:39)), as reported in Nair et al., Blood 123:3195-99 (2014) was incorporated into the gene cassette, creating the construct diagramed in FIG. 1B. AAV vectors harboring the CS02 codon-altered FIX coding sequence with zero (CS02-CRM8.0-V), one (CS02-CRM8.1-V), two (CS02-CRM8.2-V), or three (CS02-CRM8.3-V) CRM8 control elements were injected into wild-type mice by the tail vein route. Human FIX antigen in mouse plasma was then measured over time with a human FIX-specific ELISA assay.

As reported in Table 3, use of CRM8 regulatory elements increased Factor IX expression in vivo by about 2-fold and 4-fold, as compared to expression from the control construct lacking a CRM8 element, 21-days post infection. For example, the CS02-CRM8.1-V vector, containing a single CRM8 element, provided twice the expression of FIX as did the CS02-CRM8.0-V control vector. The inclusion of multiple copies of the CRM8 element further improved this expression. For example, vectors containing 2 copies of the CRM8 element provided three-fold expression and vectors containing 3 copies of the CRM8 element provided 3.4-fold expression, relative to the control vector.

TABLE 3

Factor IX expression levels in the plasma of wild-type mice injected with codon-altered AAV vectors with 0-3 copies of a CRM8 regulatory control element.

| # | AAV construct | # of CRM8 elements | FIX (ng/ml) Day 4 | FIX (ng/ml) Day 11 | FIX (ng/ml) Day 21 | Fold increase Day 21 |
|---|---|---|---|---|---|---|
| 1 | CS02-CRM8.0-scV | 0 | 65.8 | 133.4 | 239.2 | 1.0 |
| 2 | CS02-CRM8.1-scV | 1 | 120.7 | 250.7 | 442.8 | 1.9 |
| 3 | CS02-CRM8.2-scV | 2 | 152.9 | 417.3 | 713.8 | 3.0 |
| 4 | CS02-CRM8.3-scV | 3 | 130.9 | 432.6 | 800.9 | 3.4 |

Example 3—Liver-Specific CRM8 Elements Enhance Expression of FIX in Human Hepatic Cells The CS02 Factor IX gene therapy constructs containing 0-3 copies of the CRM8 liver-specific regulatory control element, as described in Example 2, were further tested by in vitro biopotency assays performed with the human hepatic cell line HepG2. Briefly, HepG2 cells were infected with one of the CS02-CRM8-V AAV vectors, as described in Example 2, and FIX activity was measured by a chromogenic substrate assay three days after infection. Consistent with the results reported in Example, 2, all vectors containing a CRM8 regulatory control element provided higher FIX expression, as reported in Table 4. Striking, the effect of using multiple CRM8 elements was even more pronounced in the human HepG2 cells than in the mouse model. For example, vectors containing 2 copies of the CRM8 element provided 6.7-fold expression and vectors containing 3 copies of the CRM8 element provided 12.8-fold expression, relative to the control vector. This confirms the positive effects that the CRM8 regulatory control element has on FIX expression in these vectors.

TABLE 4

Factor IX expression levels in human hepatic HepG2 cells injected with codon-altered AAV vectors with 0-3 copies of a CRM8 regulatory control element.

| AAV construct | # of CRM8 elements | FIX activity [Biopotency units] | Fold increase |
|---|---|---|---|
| CS02-CRM8.0-scV | 0 | 0.35 | 1 |
| CS02-CRM8.1-scV | 1 | 0.82 | 2.3 |
| CS02-CRM8.2-scV | 2 | 2.36 | 6.7 |
| CS02-CRM8.3-scV | 3 | 4.48 | 12.8 |

Example 4—Single Stranded FIX AAV8 Vectors Provide Similar In Vivo Expression as Comparable Self-Complementary Vectors In some instances, self-complementary (sc) AAV vectors express a transgene cassette more efficiently than a similar single-stranded (ss) AAV vector. This is presumably due to more rapid double strand formation after uncoating of a self-complementary vector genome in the cell nucleus. For review, see, McCarty D., Mol. Ther., (16):1648-56 (2008), the content of which is incorporated herein by reference, in its entirety, for all purposes.

A recent study confirmed this effect using an EGFP vector. Bell et al., Hum. Gene Ther. Methods, (27):228-37 (2016). However, the study also showed that this effect was transgene and dose dependent. For example, a human ornithine transcarbamylase (hOTC) gene cassette in a self-complementary AAV8 vector showed better expression at low dose in the liver of mice as compared to a corresponding single-stranded vector. However, this effect could not be demonstrated at a high dose suggesting that the effect, at least in the non-secreted gene studied, was transgene and dose dependent. Id.

In order to explore the properties of the disclosed codon-altered FIX gene constructs in the context of single-stranded and self-complementary design, single-stranded constructs harboring a CS06 codon-altered FIX(R338L) gene and two intact ITRs were constructed with and without CRM8 regulatory control elements, as diagramed in FIGS. 1D and 1C, respectively. The single-stranded (ss) vectors were produced in an HEK293 cell system, and Factor IX expression was compared to expression of the self-complementary constructs reported in Examples 1-3.

First, the self-complementary (sc) and single-stranded (ss) CS06-CRM8.0-V constructs were tested in vivo following injection into B6/129P2-F9tm1Dws FIX knockout mice, as described above. Surprisingly, as reported in Table 5, the self-complementary (sc) and single-stranded (ss) CS06 vector constructs showed very similar plasma levels of FIX activity, suggesting the reported advantage of sc vectors, as compared to ss vectors, does not hold for the codon-altered Factor IX constructs described herein. Expression is dependent on many parameters including the transgene construct, the stability of transcript, the promoter(s) used in the construct, time, and dose. As shown in Table 5, under the conditions chosen to correct bleeding and obtain long-term expression in FIX ko mice, the corresponding sc and ss vectors provided substantially similar expression levels.

The effects of the liver-specific CRM8 regulatory control element on FIX expression was also investigated in the single-stranded vector background. As reported in Table 5, inclusion of one CRM8 element in the single-stranded vector improved FIX expression in the B6/129P2-F9tm1Dws FIX knockout mice. Inclusion of three CRM8 elements further improved FIX expression from the single-stranded CS06 construct, to levels slightly more than 2-fold above the self-complementary CS06 control, lacking a CRM8 element. As compared to the wild-type WH02 construct, the single-stranded CS06 vectors provided up to 7-fold greater expression, when paired with three CRM8 regulatory control elements.

TABLE 5

Factor IX expression levels in FIX knockout mice injected with various single-stranded (ss) and self-complementary (sc) AAV Factor IX vectors.

| AAV construct | # of CRM8 elements | Expr level[1] (d 7) | Expr level (d 14) | Expr level (d 28) | Fold increase vs CS06 (d 7/d 14/d 28) | Fold increase vs WH02 (d 7/d 14/d 28) |
|---|---|---|---|---|---|---|
| CS06-CRM8.0-ssV | 0 | 1.38 | 2.73 | 2.99 | 0.7/0.9/0.9 | 1.5/2.7/2.7 |

TABLE 5-continued

Factor IX expression levels in FIX knockout mice injected with various single-stranded (ss) and self-complementary (sc) AAV Factor IX vectors.

| AAV construct | # of CRM8 elements | Expr level[1] (d 7) | Expr level (d 14) | Expr level (d 28) | Fold increase vs CS06 (d 7/d 14/d 28) | Fold increase vs WH02 (d 7/d 14/d 28) |
|---|---|---|---|---|---|---|
| CS06-CRM8.1-ssV | 1 | 1.92 | 3.57 | 3.47 | 1.0/1.1/1.0 | 2.1/3.5/3.2 |
| CS06-CRM8.3-ssV (SEQ ID NO: 40) | 3 | 4.43 | 6.65 | 7.78 | 2.3/2.1/2.2 | 4.9/6.5/7.1 |
| CS06-CRM8.0-scV | 0 | 1.89 | 3.17 | 3.50 | 1.0/1.0/1.0 | 2.1/3.1/3.2 |
| WH02-CRM8.0-scV | 0 | 0.90 | 1.03 | 1.10 | 0.5/0.3/0.3 | 1.0 |

[1]FIX activity in International Units (average of 7-8 mice); d, day;

Example 5—Single Stranded FIX AA V8 Vectors Provide Better FIX Expression in Human Hepatic Cells than Comparable Self-Complementary Vectors Factor IX expression from the single-stranded CS06 vectors described in Example 4 was then investigated in human HepG2 cells and compared to similar self-complementary vector constructs. Consistent with the in vivo results reported in Example 4, single-stranded CS06 vectors without a CRM8 element provided FIX expression at slightly lower levels than a comparative self-complementary vector in HepG2 cells. However, inclusion of a single CRM8 element increased FIX expression from the single-stranded CS06 vector to a level 2.6-times greater than expression from the self-complementary CS06 vector, as reported in Table 6.

Most surprisingly, however, inclusion of three CRM8 elements in the single-stranded CS06 vector increased FIX expression to a level 16.8-times greater than expression from the self-complementary CS06 vector. The increased FIX expression was more than 100-times greater than FIX expression from the WH02 control vector. In summary, the single-stranded CS06 vector containing three CRM8 elements provides the highest expression levels in both the in-vivo and the in-vitro biopotency assays.

TABLE 6

Factor IX expression levels from single-stranded (ss) and self-complementary vectors in human hepatic cells.

| AAV construct | # of CRM8 elements | FIX activity [Biopotency units] | Fold increase vs CS06-CRM8.0-scV | Fold increase vs WH02-CRM8.0-scV |
|---|---|---|---|---|
| CS06-CRM8.0-ssV | 0 | 0.24 | 0.6 | 3.9 |
| CS06-CRM8.1-ssV | 1 | 0.95 | 2.6 | 15.9 |
| CS06-CRM8.3-ssV (SEQ ID NO: 40) | 3 | 6.20 | 16.8 | 103.3 |
| CS06-CRM8.0-scV | 0 | 0.37 | 1.0 | 6.2 |
| WH02-CRM8.0-scV | 0 | 0.06 | 0.2 | 1.0 |

Materials and Methods for Examples 1-5

Animal Experiments.

For the experiments in FIX knockout model, the FIX ko mouse strain B6/129P2-F9tm1Dws (developed by Lin et al., 1997. Blood 90:3962-6) were used. In the wild-type mouse model 4-5 week old male C57BL6-J B16 mice were used. Both strains were obtained from commercial breeders. The AAV vector dilutions were injected into animals (4-8 animals per group) via the lateral tail vein based upon the individual animals body weights. Blood sampling was done at defined time intervals by retro-orbital puncture after dosing according to known procedures using glass capillaries. Blood was then transferred to a tube pre-filled with sodium citrate anticoagulant and plasma was obtained by standard procedures and frozen at −20° C.

In Vitro Biopotency Assay in HepG2 Cells Including FIX Chromogenic Substrate Assay.

The in vitro biopotency assay for gene therapy vector preparations was performed in the human hepatic cell line HepG2 (ATCC HB-8065). After treatment with hydroxyurea, cells were infected with AAV8FIX vectors and incubated for approximately 96 hrs. During incubation time, FIX was expressed and released into the cell supernatant and FIX-activity was determined by chromogenic endpoint measurement (Rossix AB, Sweden). Each assay run includes a standard curve of purified AAV-FIX vector material using MOI ranging between 700 and 7000. FIX activity of the standard at MOI 3270 is set as Bio Potency Unit (BPU) of 1.

Human FIX Quantifications in Mouse Plasma.

To quantify human FIX in knock-out mouse plasma FIX coagulation assays were performed using standard FIX coagulation analytics. To quantify human FIX antigen in plasma of the wild-type mice a commercially available ELISA kit (ASSERACHROM IX:AG (cat. nr. 00943 Stago BNL) was used that specifically detects human FIX.

Example 6—Improved Transcriptional Efficacy by Incorporation of CRM8 Elements To address whether improved biopotency of CRM8-containing vectors results from increased transcriptional efficacy, a human liver cell line (HepG2) and mouse liver cells (FIX knock-out mice) were transduced with single-stranded CS06 vectors containing 0, 1, or 3 CRM8 elements. FIX mRNA and DNA levels were determined and presented as ratio between normalized FIX mRNA and DNA levels.

In the in vitro model, inclusion of one CRM8 element (CS06-CRM8.1-ssV) or three CRM8 elements (CS06-CRM8.3-ssV (SEQ ID NO:40)) resulted in 5-fold and 23-fold higher human FIX mRNA levels in transduced human hepatic cells than in cells transduced with vector lacking a CRM8 element (CS06-CRM8.0-ssV) (Table 6), respectively. Similarly, in the in vivo model, FIX expression in murine liver from vectors containing one or three CRM8 elements was 2.0-fold and 2.8-fold higher than FIX expression from vector lacking a CRM8 element (Table 6), respectively. Both models support that CRM8 element(s) provide a beneficial effect in improving transcriptional activity of a FIX construct.

TABLE 7

FIX mRNA levels following AAV8-FIX transduction of a human liver cell line or mouse liver.

| AAV construct | In vitro hepatic cell line (HepG2) | | In vivo mouse liver tissue | |
|---|---|---|---|---|
| | Normalized FIX ratio: mRNA/DNA | Fold increase vs CS06-CRM8.0-ssV | Normalized FIX ratio: mRNA/DNA | Fold increase vs CS06-CRM8.0-ssV |
| CS06-CRM8.0-ssV | 0.025 | 1 | 0.38 | 1 |
| CS06-CRM8.1-ssV | 0.14 | 5.4 | 0.78 | 2.0 |
| CS06-CRM8.3-ssV | 0.58 | 23.4 | 1.09 | 2.8 |

Methods for Example 6

Quantitative real-time polymerase chain reaction including RNA and DNA extraction. Genomic DNA and total RNA were extracted from frozen livers (see animal experiments) or HepG2 cells (see in vitro biopotency assay in HepG2 cells) by standard procedures. For analytics of the in vivo experiments, a subset of three animals per treatment group close to the mean FIX activity of the respective group at day 14 (inside the mean±SD) was selected. cDNA was synthesized using an oligo (dT20) primer, the SuperScript III reverse transcriptase (RT) and DNase-treated total RNA according to the manual (DNeasy Blood & Tissue Kit, Qiagen, Germany; RNeasy mini kit, Qiagen).

FIX-transgene copy numbers in both gDNA and cDNA samples were determined by a fluorescent-based quantitative real-time polymerase chain reaction (qPCR), amplifying a 96 bp sequence of FIX exon 6. Murine β-actin served as endogenous control and was quantified using a commercially available TaqMan assay. qPCR data analysis was performed using the specific device's software, calculating the FIX or β-actin copies per reaction based on the linear regression parameters of the standard curve. Further, the results were normalized to 1 µg of either RNA or DNA and the mRNA:DNA ratio was calculated.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A nucleic acid composition, comprising a Factor IX polynucleotide encoding a Factor IX protein, said Factor IX polynucleotide comprising a nucleic acid sequence that is least 97% identical to the nucleic acid sequence of CS06-MP-NA (SEQ ID NO:17).

2. The nucleic acid composition of claim 1, wherein the Factor IX polynucleotide comprises a nucleic acid sequence that is at least 99% identical to the nucleic acid sequence of CS06-MP-NA (SEQ ID NO:17).

3. The nucleic acid composition of claim 1, wherein the Factor IX polynucleotide has no more than 10 CpG dinucleotides.

4. The nucleic acid composition of claim 1, wherein the Factor IX polynucleotide has no more than 3 CpG dinucleotides.

5. The nucleic acid composition of claim 1, wherein the Factor IX polynucleotide comprises the nucleic acid sequence of CS06-MP-NA (SEQ ID NO:17).

6. The nucleic acid composition of claim 1, wherein the Factor IX polynucleotide encodes for leucine at the amino acid position corresponding to residue 384 of the full-length wild type Factor IX polypeptide (SEQ ID NO:2), which is an arginine in the wild type Factor IX polypeptide.

7. The nucleic acid composition of claim 1, wherein the Factor IX protein encoded by the Factor IX polynucleotide has from 1 to 10 amino acid substitutions as compared to FIXp-MP-AA (SEQ ID NO:12).

8. The nucleic acid composition of claim 1, wherein the Factor IX protein encoded by the Factor IX polynucleotide has the amino acid sequence of FIXp-MP-AA (SEQ ID NO:12).

9. The nucleic acid composition of claim 1, wherein the Factor IX polynucleotide further comprises a pre-pro-leader polynucleotide encoding a pre-pro-leader peptide, said pre-pro-leader peptide comprising the amino acid sequence of FIX-PPP-AA (SEQ ID NO:36).

10. The nucleic acid composition of claim 9, wherein the pre-pro-leader polynucleotide has the nucleic acid sequence of CS06-PPP-NA (SEQ ID NO:23).

11. The nucleic acid composition of claim 1, wherein the Factor IX polynucleotide has a nucleic acid sequence that is at least 99% identical to the nucleic acid sequence of CS06-FL-NA (SEQ ID NO:9).

12. The nucleic acid composition of claim 1, wherein the Factor IX polynucleotide has the nucleic acid sequence of CS06-FL-NA (SEQ ID NO:9).

13. The nucleic acid composition of claim 1, further comprising a liver-specific promoter element operably linked to the Factor IX polynucleotide.

14. The nucleic acid composition of claim 13, wherein the liver-specific promoter element comprises one copy of a promoter polynucleotide, said promoter polynucleotide comprising a nucleic acid sequence that is least 95% identical to CRM8 (SEQ ID NO:39).

15. The nucleic acid composition of claim 13, wherein the liver-specific promoter element comprises three copies of a promoter polynucleotide, said promoter polynucleotide comprising a nucleic acid sequence that is least 95% identical to CRM8 (SEQ ID NO:39).

16. The nucleic acid composition of claim 15, wherein said promoter polynucleotide comprises the nucleic acid sequence of CRM8 (SEQ ID NO:39).

17. The nucleic acid composition of claim 1, further comprising an intron operatively linked to the Factor IX polynucleotide.

18. The nucleic acid composition of claim 17, wherein the intron comprises an MVM intron polynucleotide comprising a nucleic acid sequence that is at least 95% identical to MVMI (SEQ ID NO:53).

19. The nucleic acid composition of claim 18, wherein said MVM intron polynucleotide comprises the nucleic acid sequence of MVMI (SEQ ID NO:53).

20. The nucleic acid composition of claim 19, wherein said intron is positioned between a promoter element and the translation initiation site of the nucleotide sequence encoding a Factor IX polypeptide.

21. The nucleic acid composition of claim 1, comprising the nucleic acid sequence of CS06-CRM8.3-ssV (SEQ ID NO:40).

22. The nucleic acid composition of claim 1, comprising a mammalian gene therapy vector.

23. The nucleic acid composition of claim 22, wherein the mammalian gene therapy vector is an adeno-associated virus (AAV) vector.

24. The nucleic acid composition of claim 23, wherein said adeno-associated virus vector is a serotype 8 adeno-associated virus (AAV-8) vector.

25. The nucleic acid composition of claim 23, wherein the mammalian gene therapy vector comprises a single-stranded polynucleotide encoding the Factor IX protein.

\* \* \* \* \*